United States Patent
von Borstel et al.

(10) Patent No.: US 6,702,705 B1
(45) Date of Patent: Mar. 9, 2004

(54) PRODRUGS ACTIVATED BY TARGETED CATALYTIC PROTEINS

(75) Inventors: Reid von Borstel, Potomac, MD (US); Jan M. Casadei, Bethesda, MD (US); Balreddy Kamireddy, Rockville, MD (US); John Kenten, Gaithersburg, MD (US); Mark T. Martin, Germantown, MD (US); Richard J. Massey, Rockville, MD (US); Andrew D. Napper, Natick, MA (US); David M. Simpson, Adelphia, MD (US); Rodger Smith, Jefferson, MD (US); Richard C. Titmas, Rockville, MD (US); Richard O. Williams, Potomac, MD (US)

(73) Assignee: IGEN International, Inc., Gaithersburg, MD (US)

( * ) Notice: Subject to any disclaimer, the term of this patent is extended or adjusted under 35 U.S.C. 154(b) by 1,532 days.

(21) Appl. No.: 08/392,407

(22) Filed: Feb. 22, 1995

Related U.S. Application Data

(63) Continuation of application No. 07/740,501, filed on Aug. 5, 1991, now abandoned, which is a continuation-in-part of application No. PCT/US89/01951, filed on May 4, 1989, and a continuation-in-part of application No. 07/190,271, filed on May 4, 1988, now abandoned, application No. 08/392, 407, which is a continuation-in-part of application No. 07/700,210, filed on Jun. 12, 1991, now abandoned, and a continuation-in-part of application No. 07/498,225, filed on Mar. 23, 1990, now Pat. No. 5,229,272, and a continuation-in-part of application No. PCT/US89/01950, filed on May 4, 1989.

(51) Int. Cl.$^7$ ................................ C12N 9/00
(52) U.S. Cl. ................................... 475/188.5
(58) Field of Search ....................... 475/188.8

(56) References Cited

U.S. PATENT DOCUMENTS

| 3,975,367 A |   | 8/1976  | Gish et al.        |         |
|-------------|---|---------|--------------------|---------|
| 4,196,265 A |   | 4/1980  | Koprowski et al.   | 435/2   |
| 4,376,110 A |   | 3/1983  | David et al.       | 436/513 |
| 4,486,530 A |   | 12/1984 | David et al.       | 435/7   |
| 4,492,751 A |   | 1/1985  | Boguslaski et al.  | 435/7   |
| 4,493,890 A |   | 1/1985  | Morris             | 435/7   |
| 4,659,567 A |   | 4/1987  | Tramontano et al.  | 424/85  |
| 4,661,586 A |   | 4/1987  | Levy et al.        | 530/387 |
| 4,792,446 A |   | 12/1988 | Kim et al.         | 424/85.8|
| 4,888,281 A |   | 12/1989 | Schochetman et al. | 435/72  |
| 4,900,674 A |   | 2/1990  | Benkovic et al.    | 435/232 |
| 4,963,355 A |   | 10/1990 | Kim et al.         | 424/85.8|
| 5,030,717 A | * | 7/1991  | Tramontano et al.  | 530/387 |
| 5,190,865 A | * | 3/1993  | Schultz            | 435/108 |
| 5,411,984 A |   | 5/1995  | Kingston et al.    | 514/449 |

FOREIGN PATENT DOCUMENTS

| EP | A-0 170 090    | 2/1986  |
|----|----------------|---------|
| EP | A-0 221 506    | 5/1987  |
| EP | A-0 308 977    | 3/1988  |
| EP | 89 109613.3    | 12/1989 |
| FR | A-2 135 221    | 12/1972 |
| GB | A-2 218 417    | 11/1989 |
| WO | PCT/US89/01950 | 11/1989 |
| WO | 91/00507       | 8/1991  |

OTHER PUBLICATIONS

Schultz, P. G., (1989) Acc. Chem. Res 22, 287–294.*
Paul, S, et. al. (1992) J. Biol. Chem. 19, 13142–13145.*
Janda, K. D., et al. (1991) Tetrahedron 47 (14/15), 2503–2506.*
B.D. Bagshawe et al., Br. J. Cancer, "A Cytotoxic Agent can be Generated Selectively at Cancer Sites", 1988, vol. 58, No. 6, pp. 700–703.
J.E.F. Reynolds & A.B. Prasad, The Pharmaceutical Press, London, GB, "Martindale, the Extra Pharmacopeia", 1982, pp. 246–247, item No. 2611–e.
Ajito K et al., J. Antibiot, "Inhibition of Human immuno-deficiency virus–associated reverse transcriptase by 14–00 acyladriamycins", 1989, vol. 42, No. 4, pp. 611–619.
Reznikova M I et al., Chemical Abstracts, "Semisynthetic derivatives of daunorubicin and carminymycin. Inhibition of DNA synthesis after intravenous administration to mice", 1988, vol. 109, pp. 18–19, 109:221921X.
Arcamone et al., J. Med. Chem., "Synthesis and biological evaluation of some 14–0–acyl derivatives of adriamycin", 1974, vol. 17, No. 3, pp. 335–337.
Akiyama T et al., Chem. Lett., "5–Fluorouracil derivatives. XVIII. p–Methoxybenzyl as a new N3–imide protecting group of 5–fluorouridine and its application to the synthesis of 5'0–acryloyl–5–fluorouridine", 1990, No. 3, pp. 339–343.
Ajmera S et al., J. Med. Chem., "Synthesis and interaction with uridine phosphorylase of 5'–deoxy–4", 1988, vol. 31, No. 6, pp. 1094–1098.
Weckbecker G et al., Methods Enzym. Anal., (3rd Ed.), "5–fluoro–UDP glucose and 5–Fluoro–UDP galactose", 1985, vol. 7, pp. 545–550.
Nio Y et al., Anti–Cancer Drugs, "A comparative study of the antitumor activities of 5'–deoxy–5–fluorouridine and its prodrug trimethoxy benzoyl–5'–deoxy–5–fluorocytidine (Ro09–1390) on human digestive organ cancer xenograft lines transplanted into nude mice", 1992, vol. 3, No. 4, pp. 387–393.
Lal, R., et al., "Selective Elimination of Lymphocyte Sub-populations by Monoclonal Antibody–Enzyme Conjugates" *Journal of Immunological Methods*, 79 (1985) 307–318.
Bolis, G. et al., *J. Med. Chem.* 30 (1987):1729–37.

(List continued on next page.)

*Primary Examiner*—Charles L. Patterson, Jr.
(74) *Attorney, Agent, or Firm*—Barry Evans, Esq.; Kramer Levin Naftalis and Frankel LLP

(57) ABSTRACT

Catalytic antibodies are disclosed. The catalytic antibodies are specific for prodrug compounds. The catalytic antibodies enhance cleavage of an active drug moiety from a prodrug residue, thereby activating the drug.

71 Claims, 45 Drawing Sheets

OTHER PUBLICATIONS

Burd, J.K., Carrico, R.J., et al., "Specific protein–binding reactions monitored by enzymatic hydrolysis of ligands–fluorescent dye conjugates," *Analytical Biochemistry* 77:56–67 (1975).

Cochran, et al., *J. Am. Chem. Soc.* 110 (1988):7888–7890.

David, et al., *Clinchem*, vol. 27, pp. 1580–1585 (1981).

Durfor, et al., *J. Am. Chem. Soc.* 110 (1988):8713.

Gish, et al., *J. Med. Chem.* 14 (1971):1159–1162.

Green et al., (1989) TIBTECH 7:304–310.

Hiller, S., *A Better Way to Make Medicine Go Down*, Science 253, 1095–1096.

Hilvert, et al., *Proc. Natl. Acad. Sci.* USA 85 (1988):4953–4955.

Iverson, et al., *Science* 243 (1989):1184–1188.

Jackson, et al., *J. Am. Chem. Soc.* 110 (1988):4841–4842.

Jacobs, et al., *J. Am. Chem. Soc.* 109 (1987):2174–2176.

Janda, et al., *Science* 241 (1988):1188–1191.

Jencks, W.P., *Mol. Biol. Biochem. and Biophysics*, F. Chapeville and A.L. Haeoni, editors, 32, 3–25 (Springer Verlag, New York 1980).

Jencks, W.P., *Adv. Enzymol.*, 43, 219–410 (1975).

Kohen, F. et al., "Monoclonal immunoglobulin G augments hydrolysis of an ester of the homologous hapten,"*FEBS Letters* 111:427–431 (1980).

Kohen, F. et al., "Antibody–enhanced hydrolysis of steroid esters," *Biochimica et Biophysica Acta* 629:328–337 (1980).

Kohen, F., et al., "nonradioisotopic homogeneous steroid immunoassays," *J. Steroid Biochemistry* 11:161–167 (1979).

Kohen, F., et al., "A steroid immunoassay based on antibody–enhanced hydrolysis of a steroid umbelliferone conjugate," *FEBS Letters* 100:137–140 (1979).

Lerner et al. (1987) TIBS 12:427–430.

Maniatis, T., et al., *Molecular Cloning: A Laboratory Manual*, 1982, 150–160, New York: Cold Spring Harbor Laboratory.

Melcners et al., *Biochem. Biophys. Res Comm.*, vol. 40(3), p. 570, 575 (1970).

Paul et al., *Science* 244 (1989):1158–1162.

Pollack, et al., *J. Am. Chem. Soc.* 111 (1989):5961–5962.

Sacks D. et al., *J. Experimental Med.*, vol. 155, pp. 1108–1119 (1982).

Schultz et al. (1990) C&EN May 28th issue pp. 26–40.

Skerra, A., et al., *Science* 240 (1988):1038–1040.

Slobin, L., "Preparation and some properties of antibodies with specificity towards p–nitrophenyl esters," *Biochemistry* 5: 2836–2844 (1966).

Stinson (1987) C&EN Oct. 19th issue pp. 30–33.

Altschuh, D. et al., "Localization of Antigenic Determinants of a Viral Protein by Inhibition of Enzyme–Linked Immunosorbent Assay (ELISA) with Tryptic Peptides", *J. Immunology Methods*, v.50, p. 99 (1982).

Amit, A. G. et al., "Three–Dimensional Structure of an Antigen–Antibody Complex at 2.8 A Resolution", *Science* 233: 747 (1986).

Amzel, L. M. et al., "Three–Dimensional Structure of Immunoglobulins", *Ann. Rev. Biochem.* 48:961 (1979) (Cover page only).

Aruffo, A. et al., "Molecular Cloning of a CD38 cDNA by a high–efficiency COS cell expression system", *Proc. Natl. Acad. Sci.*, 84: 8573–8577 (1987).

Atassi, M. Z., "Surface–Simulation Synthesis and Its Application in Protein Molecular Recognition", *Protein Engineering—Applications in Science, Medicine and Industry*, pp. 125–153 Edited by Inouye, M. and Sarma, R., Academic Press (1986).

Azuma, T. et al., "Diversity of the Variable–Joining Region Boundary of $\gamma$ Light Chains has a Pronounced Effect on Immunoglobulin Ligand–Binding Activity", *Proc. Natl. Acad. Sci. USA*, v. 81, p. 6139, (Oct. 1984).

Barrett, A. J., *Proteinase Inhibitors* (Editors A. J. Barrett and G. Salvesen), pp 3–22, Elsevier, London, (1986).

Benjamin, E. et al., "Immunochemical Studies on the Tobacco Mosaic Virus Protein. VI. Characterization of Antibody Population Following Immunization with TMV Protein", *Biochemistry*, v.7, No. 4, pp. 1253–1260 (1968).

Benjamini, E. et al., "Immunochemical Studies on the Tobacco Mosaic Virus Protein. VII. The Binding of Octanoylated Peptides of the TMV Protein with Antibodies to the Whole Protein", *Biochemistry*, v.7, No. 4, pp. 1261–1264 (1968).

Better, M. et al., "*Escherichia coli* Secretion of an Active Chimeric Antibody Fragment", *Science*, 240: 1041–1043 (1988).

Blackburn, G. M. et al., "Catalytic Antibodies", *Biochem. J.* 262: 381 (1989).

Bloom, S. R. et al., "Autoimmunity in Diabetics Induced by Hormonal Contaminants of Insulin", *Lancet* i:14–17 (1979).

Chalufour, A. et al., "Rare Sequence Motifs are Common Constituents of Hypervariable Antibody Regions", *Ann. Inst. Pasteur/Immunology*, 138:671, Elsevier, Paris (1987).

Chaudhary, V. J. et al., "A recombinant immunotoxin consisting of two antibody variable domains fused to *Psuedomonas* exotoxin", *Nature* 339: 394 (1989).

Chothia, C. et al., "Canonical Structures for the Hypervariable Regions of Immunoglobulins", *J. Mol. Biol.* 196: 901 (1987).

Chothia, C. et al., "The Predicted Structure of Immunoglobulin D1.3 and Its Comparison with the Crystal Structure", *Science* 755 (Aug. 1986).

Colman, P. M. et al., "Three–Dimensional Structure of a Complex of Antibody with Influenza Virus Neuraminidase", *Nature* 326: 358 (Mar. 1987).

Corey, D. R. et al., "Generation of a Hybrid Sequence–Specific Single–Stranded Deoxyribonuclease", *Science* 1401 (Dec. 1987).

de la Paz, P. et al., "Modelling of the Combining Sites of Three Anti–Lysozyme Monoclonal Antibodies and of the Complex Between One of the Antibodies and its Epitope", *EMBO J.*, 5:2, 415 (1986).

Dimaline, R. et al., "A novel VIP from elasmobranch intestine has full affinity for mammalian pancreatic VIP receptors", *Biochimica et Biophysica Acta*, 930, 97–100 (1987).

Dimaline, R. et al., "Purification and Characterization of VIP from Two Species of Dogfish", *Peptides*, 7(Suppl. 1): 21–25 (1986).

Dixon, M. et al., *Enzymes*, Third Edition, London, (1979) (Index only).

Edelman, G. M. et al., "Reconstitution of Immunologic Activity by Interaction of Polypeptide Chains of Antibodies", *Proc. Natl. Acad. Sci.*, 50: 753–761 (1963).

Emr, S. D. et al., "Sequence analysis of mutations that prevent export of $\gamma$ receptor, an *Escherichia coli* outer membrane protein", *Nature*, 285: 82–85 (1980).

Erhan, S. et al., "Do immunoglobulins have proteolytic activity?", *Nature*, v.251, pp. 353–355 (Sep. 27, 1974).

Frackelton, Jr., A. R., et al., "Functional Diversity of Antibodies Elicited by Bacterial β–D Galactosidase", *J. Bio. Chem.*, 255 (*11*), 5286–5290 (1980).

Franek, F. and Nezlin, R. S., *Biokhimiya*, 28: 193 (1963).

Franke, F. and Nezlin, R. S., "Recovery of Antibody Combining Activity By Interaction of Different Peptide Chains Isolated from Purified Horse Antitoxins", *Folia Microbiol.*, 8: 128–130 (1963).

Geysen, H. M. et al., "*A Priori* Delineation of a Peptide Which Mimics a Discontinuous Antigenic Determinant", *Molecular Immunology*, 23:7 p. 709 (1986).

Giam, C. Z. et al., "In Vivo and In Vitro Autoprocessing of Human Immunodeficiency Virus Protease Expressed in *Escherichia coli*", *J. Biol. Chem.*, 263: 14617–14620 (1985).

Gish et al., *J. Med. Chem.*, 14: 1159–1162, (1971).

Hansen, D., "Antibodies with Some Bite", *Nature*, 325, 304 (1987).

Hendershot, L. M. et al., "Identity of the Immunoglobulin Heavy–Chain–Binding Protein with the 78,000–Dalton Glucose–Regulated Protein and the Role of Posttranslational Modifications in Its Binding Function", *Mol. and Cellular Bio.*, 8(10), 4250–4256, (1988).

Highfeld, R., "AIDS Drug A Step Nearer", *The Daily Telegraph*, 9, (Aug. 4, 1987).

Hochman, J. et al., "An Activity Antibody Fragment (Fv) Composed of the Variable Portions of Heavy and Light Chains", *Biochemistry 12*: 1130 (1973).

Huse, W. D. et al., "Generation of a Large Combinatorial Library of the Immunoglobulin Repertoire in Phage Lambda", *Science*, 246: 1275–1281 (1989).

Inbar, D. et al., "Localization of Antibody–Combining Sites within the Variable Portions of Heavy and Light Chains", *Proc. Natl. Acad. Sci. USA*, 69: 2659 (1972).

Inbar, D. et al., "Crystallization with Hapten of the Fab Fragment from a Mouse IgA Myeloma Protein with Antidinitrophenyl Activity", *J. of Biol. Chem.* 246: 6272 (1971).

Itoh, N. et al., "Human Preprovasoactive Intestinal Polypeptide Contains A Novel PHI–27–Like Peptide, PHM–27", *Nature* 304: 547–549 (1983).

Iverson, B. L. et al., "Sequence–Specific Peptide Cleavage Catalyzed by an Antibody", *Science* 243:1184 (1989).

Jacobs, J. et al., "Catalytic Antibodies", *J. Am. Chem. Soc.*, 109, 2174–2176 (1987).

Janda, K. D. et al., "Induction of an Antibody that Catalyzes the Hydrolysis of an Amide Bond", *Science 241*, 1188–1191 (1988).

Jaton, J. C. et al., "Recovery of Antibody Activity upon Reoxidation of Completely Reduced Polyalanyl Heavy Chains and Its Fd Fragment Derived from Anti–2,4–dinitrophenyl Antibody", *Biochemistry*, 7: 4185–4195 (1968).

Jencks, W. P., "Catalysis in Chemistry and Ezymology", 282–320, 288 (McGraw Hill, New York) (1969).

Jerne, N. K. et al., "Recurrent Idiotopes and Internal Images", *EMBO J.*, v.1, No. 2, 243–247 (1982).

Knisley, K. A. et al., "Affinity Immunoblotting. High Resolution Isoelectric Focusing Analysis of Antibody Clonotype Distribution", *J. Immunological Methods*, 95, 79–87, Elsevier (1986).

Koerner and Nieman, "High Performance Liquid Chromatographic Determination of Glucosides", *J. Chromatography 449*, 217–228, (1988).

Kohler, G. et al., "Continuous Cultures of Fused Cells Secreting Antibody of Predefined Specificity", *Nature*, 256: 495–497 (1975).

Kozbor, D. et al., "The Production of Monoclonal Antibodies from Human Lymphocytes", *Immunology Today* 4:72–79, (1983).

Kozbor, D. et al., "Establishment of Anti–TNP Antibody–Producing Human Lymphoid Lines by Preselection for Hapten Binding Followed by EBV Transformation", *Scand. J. Immunol.*, 10:187–194, (1979).

Kwan, S. et al., "Production of Monoclonal Antibodies", *Genetic Engineering*, 2, 31–46, (1980).

Lee, F. et al., "Isolation and Characterization of a mouse interleukin cDNA clone that expresses B–cell stimulatory factor 1 activities and T–cell and mast–cell stimulating activities", *Proc. Natl. Acad. Sci. U.S.A.* 83: 2061–2065 (1986).

Lerner, R. A. et al., "At the Crossroads of Chemistry and Immunology: Catalytic Antibodies", *Science*, 252, 659–667 (May 1991).

Lerner, R. A. et al., "Antibodies as Enzymes", *Trends Biochem. Science*, 12(*11*), 427–430 (1987).

Lerner, R. A., "Antibodies of Predetermined Specificity in Biology and Medicine", *Adv. In Immun.*, 36, 1–40 (1984).

Lorberboum–Galski, H. et al., "Cytotoxic Activity of an Interleukin 2–*Pseumomonas* Exotoxin Chimeric Protein Produced in *Escherichia coli*", *Proc. Natl. Acad. Sci. U.S.A.*, 85: 1922–1926 (1988).

Loh, E. Y. et al., "Polymerase Chain Reaction with Single–Sided Specificity: Analysis of T Cell Receptor Δ Chain", *Science*, 243: 217–220 (1989).

MacDonald, R. J. et al., "Isolation of RNA Using Guanidinium Salts", *Meth. Enzymol.*, 152: 219–226 (1987).

Mariuzza, R. A. et al., "The Structure Basis of Antigen–Antibody Recognition", *Ann. Rev. Biophys. Chem.*, 16: 139 (1987) (Cover sheet only).

Marx, J., "Making Antibodies Work Like Enzymes", *Science 234*, 1497–1498 (1986).

Massey, R., "Catalytic Antibodies Catching On", *Nature*, 328, No. 6129, 457–458 (1987).

Meek, T. D. et al., "Inhibition of HIV–1 Protease in Infected T–Lymphocytes by Synthetic Analogues", *Nature*, 343: 90–92 (1990).

Mierendorf, R. C. et al., "Direct Sequencing of Denatured Plasmid DNA", *Meth. Enzymol.*, 152: 556–562 (1987).

Milstein, C., "Monoclonal Antibodies", *Scientific American*, 243(*4*), 66–74 (1980).

Moe, K., "Scripps, UC Create 'Killer' Antibodies", *S. D. Union*, (Dec. 12, 1986).

Mutter, M., "The Construction of New Proteins and Enzymes—A Prospect for the Future?", *Agnew. Chem. Int. Ed. Engl.* 24, p. 639 (1985).

Napper, A. "A Stereospecific Cyclization Catalyzed by an Antibody", *Science*, 237, 1041–1043 (1987).

Nilsson, A., "Structure of the Vasoactive Intestinal Peptide from Chicken Intestine. The Amino Acid Sequence", *FEBS Letters*, 60: 322–326 (1975).

Nishi, N. et al., "Apparent Autolysis of the N–Terminal Tetrapeptide of VIP", *Chem. Pharm. Bull.* 31(3), p. 1067 (1983).

Offord, R. E., "REVIEW Protein Engineering by Chemical Means?", *Protein Engineering*, v.1, No. 5, p. 151 (1987).

Opstad, K., "The Plasma VIP Response to Exercise is Increased After Prolonged Strain, Sleep and Energy Deficiency and Extinguished by Glucose Infusion", *Peptides, 8*, 175–178 (1986).

Orlandi, R. et al., "Cloning Immunoglobulin variable domains for expression by the polymerase chain reaction", *Proc. Natl. Acad. Sci. U.S.A., 86*: 3833–3837 (1989).

Paul, S. et al., "Affinity Chromatography of Catalytic Autoantibody to Vasoactive Intestinal Peptide", *J, Immunology*, v.145, No. 4, pp. 1196–1199 (Aug. 1990).

Paul, S. et al., "Catalytic Hydrolysis of Vasoactive Intestinal Peptide by Human Autoantibody", *Science, 244*: 1158–1162 (1989).

Paul, S. et al., "Characterization of Autoantibodies to VIP in Asthma", *J. Neuroimmunology, 23*: 133–142 (1989).

Paul, S., "A New Effector Mechanism for Antibodies: Catalytic Cleavage of Peptide Bonds", *Cold Spring Harbor Symposium on Immunological Research*, v.54 (1989).

Paul, S. et al., "Autoabzyme Catalyzed Cleavage of Vasoactive Intestinal Peptide", *Progress in Immunology*, v.VIII, pp. 833–836 (editors F. Melchers et al.) Springer Verlag, Berlin (1989).

Paul, S. et al., "Human Autoantibody to Vasoactive Intestinal Peptide: Increased Incidence in Muscular Exercise", *Life Sciences 43*: 1079–1084 (1988).

Paul, S. et al., "Regulatory Aspects of the VIP Receptor in Lung", *Annals of New York Academy of Science*, v.527, pp. 282–295 (Jun. 1988).

Paul, S. et al., "Elevated Levels of Atrial Natriuretic Peptide and Vasoactive Intestinal Peptide in Exercising Man", Abstract, *Clin. Res., 35*: 112A (1987).

Paul, S. et al., "Characterization of Receptors for Vasoactive Intestinal Peptide from the Lung", *J. Biol. Chem. 262*: 158–162 (1987).

Paul, S. et al., "High Affinity Peptide Histidine Isoleucine–Preferring Receptors in Rat Liver", *Life Sciences*, v.41, pp. 2373–2380 (1987).

Paul, S. et al., "Autoantibody to Vasoactive Intestinal Peptide in Human Circulation", *Biochem. Biophys. Res. Commun. 130*: 479–485 (1985).

Paul S. et al., "Purification of [$^{125}$I]—Vasoactive Intestinal Peptide by Reverse–Phase HPLC", *Peptides 5*: 1085, 1087 (1987).

Pauling, L., "Nature of Forces Between Large Molecules of Biological Interest" *Nature, 161*: 707 (1948).

Pollack, S. J. et al., "Antibody Catalysis by Transition State Stabilization", *Cold Spring Harbor Symposium on Quantitative Biology, 52*, 97–104 (1987).

Pollack, S. J. et al., "Selective Chemical Catalysis by an Antibody", *Science, 234*, 1570–1573 (1986).

Porter, R. R. et al., "Subunits of Immunoglobulins and their relationship to Antibody Specificity", *J. Cell Physiol., 67* (Suppl. 1): 51–64 (1966).

Raso, V. et al., "The Antibody–Enzyme Analogy. Comparison of Enzymes and Antibodies Specific for Phosphopyridoxyltyrosine", *Biochemistry, 14*, 591–599 (1975).

Raso, V. et al., "Antibodies Specific for Conformationally Distinct Coenzyme Substrate Transition State Analogs.", *J. Am. Chem. Soc., 95*(5), 1621–1628 (1973).

Rees, A. R. et al., "Investigating Antibody Specificity Using Computer Graphics And Protein Engineering", *Trends in Biochemical Sciences, 11*: 144 (Mar. 1986).

Rich, D. H., "Inhibitors of Aspartic Proteinases", *Proteinase Inhibitors* (Editors A. J. Barrett and G. Salvesen), Elsevier, pp. 179–217 (1986).

Roberts, R. J., "Directory of Restriction Endonuclease", *Methods In Enzymology, 68*, 27–31 (Academic Press, New York, R. Wu, Editor) (1979).

Roder, J. et al., "The EBV–Hybridoma Technique", *Methods In Enzymology, 121*: 140–167 (1986).

Roholt, O. et al., "Specific Combination of H and L Chains of Rabbit γ–Globulins", *Proc. Natl. Acad. Sci., 51*: 173–178 (1964).

Rosselin, G., "The Receptors for the VIP Family Peptides (VIP, Secretin, GRF, PHI, PHM, GIP, Glucagon and Oxyntomodulin). Specificities and Identity.", *Peptides*, 7(Suppl. 1): 89–100 (1986).

Royer, G. P., "Enzyme–Like Synthetic Catalysts (Synzymes)", *Advances In Catalysis, 29*: 197–227 (1980).

Ruff, M. R. et al., "CD4 Receptor Binding Peptides that Block HIV Infectivity cause Human Monocyte Chemotaxis", *FEBS Letters, 211*: 17–22 (1987).

Sacerdote, P. et al., "Vasoactive Intestinal Peptide 1–12: A Ligand for the CD4 (T4)/Human Immunodeficiency Virus Receptor", *J. of Neuroscience Res., 18*: 102–107 (1987).

Sastry, L., et al., "Cloning of the immunological repertoire in *Escherichia coli* for generation of monclonal catalytic antibodies", *Proc. Natl. Acad. Sci. U.S.A., 86*: 5728–5732 (1989).

Schultz, P. G., "Catalytic Antibodies", *Acc. Chem. Res., 22*: 287 (1989).

Schultz, P. G., "The Interplay Between Chemistry and Biology in the Design of Enzymatic Catalysts", *Science, 240*: 426 (1988).

Shenkin, P. S. et al., "Predicting Antibody Hypervariable Loop Conformation. I. Ensembles of Random Conformations for Ringlike Structures", *Biopolymers 26*: 2053 (1987).

Sheriff, S. et al., "Three–Dimensional Structure of an Antibody–Antigen Complex", *Proc. Natl. Acad. Sci. U.S.A., 84*: 8075 (1987).

Shokat, K. M. et al., " A New Strategy for the Generation of Catalytic Antibodies", *Nature*, v.338, P. 269–271 (Mar. 1989).

Shokat, K. et al., "An Antibody–Mediated Redox Reaction", *Agnew. Chem. Int. Ed. Engl. 27*: 1172 (1988).

Skerra, A. et al., "Assembly of a Functional Immunoglobulin $F_v$ Fragment in *Escherichia coli*", *Science, 240*: 1038–1043 (1988).

Smith–Gill, S. J. et al., "Contributions of Immunoglobulin Heavy and Light Chains to Antibody Specificity for Lysozyme and Two Haptens", *J. Immunology, 139*: 4135 (1987).

Steinitz, M. et al., "Continuous Production of Monoclonal Rheumatoid Factor by EBV–Transformed Lymphocytes", *Nature, 287*: 443–445, (1980).

Steinitz, M. et al., "Establishment of a Human Lymphoblastoid Cell Line with Specific Antibody Production Against Group A Streptococcal Carbohydrate", *Immunobiology, 156*: 41–47 (1979).

Steinitz, M. et al., "EB Virus–Induced B Lymphocyte Cell Lines Producing Specific Antibody", *Nature* 269: 420–422 (1977).

Stewart, J. M. et al., "Solid Phase Peptide Synthesis", Pierce Chemical Co., Rockford, Illinois (1984) (Index Only).

Summers, Jr., J. B., "Catalytic Principles of Enzyme Chemistry: Antibody Models and Stereo Electronic Control", Harvard University Ph.D. Thesis, 22–101 (1983).

Sun, L. K. et al., *Proc. Natl. Acad. Sci. U.S.A*, 84: 214–218 (1987).

Tramontono, A. et al., "Antibody Catalysis Approaching the Activity of Enzymes", *J. Am. Chem. Soc. 110*: 2282 (1988).

Tramontono, A. et al., "Specificity and Mechanism of Esterolytic Antibodies", *J. of Cellular Biochemistry*, Supp. 11C, Abstract N 417, p. 238 (1987).

Tramontono, A. et al., "Antibodies as Enzymic Catalysts", *J. Cellular Biochemistry*, Supp. 11C, p. 199, Abstract N 022 (1987).

Tramontono, A. et al., "Catalytic Antibodies", *Science 234*: 1566–1570 (1986).

Tramontono, A. et al., "Chemical Reactivity at an Antibody Binding Site Elicited by Mechanistic Design of a Synthetic Antigen", *Proc. Natl. Acad. Sci. U.S.A., 83*: 6736–6740 (1986).

Turner, J. T. et al., "Characterization of the VIP Receptor in Rat Submandibular Bland: Radioligand Binding Assay in Membrane Preparations", *J. Pharmacol. Exp. Therap. 242*: 873–881 (1987).

Unkeless, J. C. et al., "Structure and Function of Human and Murine Receptors for IgG", *Ann. Rev. Immunology, 6*: 251–281 (1988).

Van Brunt, J., "Antibodies Find a New Role—As Enzymes", *Biotechnology, 5*: 767 (1987).

Van der Eb, A. J. et al., "Assay of Transforming Activity of Tumor Virus DNA", *Meth. Enzymol., 65*: 826–839 (1980).

Van Regenmortel, R. H. V., *Synthetic Peptides as Antigens*, Laboratory Techniques in Biochemistry and Molecular Biology Series (Editors R. H. Burdon and P. H. van Knippenberg), 19: 1–39 (1988).

Ward, E. S. et al., "Binding activities of a repertoire of single immunoglobulin variable domains secreted from *Escherichia coli*", *Nature, 341*: 544–546 (1989).

White, A. et al., *Principles of Biochemistry*, 200, 201, 217–221, 573, 575 and 585 (McGraw Hill Book Company, New York, Fourth Edition) (1968).

Winter, G. P., "Antibody Engineering", *Phil Trans. R. Soc. Lond.*, B 324, 537–547 (1989).

Woie, L. et al., "Increase in Plasma VIP in Muscular Exercise", *Gen. Pharmacol., 17*: 321–326 (1987).

Wong, G. C. et al., "Human GM–CSF: Molecular Cloning of the Complementary DNA and Purification of the Natural and Recombinant Proteins", *Science, 228*: 810–815 (1985).

Yang, Y. C. et al., "Human IL–3 (Multi–CSF): Identification by Expression Cloning of a Novel Hematopoietic Growth Factor Related to Murine IL–3", *Cell, 47*: 3–10 (1986).

Yokota, T. et al., "Isolation and characterization of a human interleukin cDNA clone, homologous to mouse B–cell stimulatory factor 1, that expresses B–cell and T–cell stimulatory activities", *Proc. Natl. Acad. Sci. U.S.A., 83*: 5894–5896 (1986).

"Abzylutely Spot On", *The Economist*, 80–81 (Feb. 7, 1987).

"Abzymes", *Scientific American, 256*, No. 2, 84–85 (1987).

*Affinity Chromatography Principles and Methods*, Pharmacia, pp. 12–18, Uppsala Sweden (1986).

"Antibody Catalyzes Stereospecific Reaction", Science/Technology Concentrates, *C&EN*, 15 (Aug. 31, 1987).

Bulletin Office Of Public Information, Berkeley Campus, University of California (Dec. 9, 1986).

"Cancer Breakthrough Seen—IGEN Discovers New Protein Class", *Rockville Gazette* (Jan. 21, 1987).

Baum, R., "Catalytic Antibodies Open Up New Strategy For Protein Engineering", Science, *C&EN*, 30–33 (Apr. 6, 1987).

*FPLC™ Ion Exchange and Chromatofocusing—Principles and Methods*, Pharmacia, pp. 59–105, Uppsala, Sweden (1987).

"Making Antibodies Act Like Enzymes", *Science News, 130*, Nos. 25 & 26 (Dec. 20 & 27, 1986).

*PhastGel Silver Kit Instruction Manual*, Pharmacia, Uppsala, Sweden (1987).

* cited by examiner

PRODRUGS ACTIVATED BY TARGETED CATALYTIC PROTEINS

This application is a continuation of application Ser. No. 07/740,501, filed Aug. 5, 1991, now abandoned, which is a continuation-in-part of U.S. application Ser. No. 07/190,271, filed May 4, 1988, abandoned, a continuation-in-part of PCT/US89/01951, filed May 4, 1989, which corresponds to U.S. application Ser. No. 07/700,210, filed Jun. 12, 1991, a continuation-in-part of PCT/US89/01950, filed May 4, 1989, and a continuation-in-part of U.S. application Ser. No. 07/498,225, filed Mar. 23, 1990.

FIELD OF THE INVENTION

The present invention provides methods and compounds for providing suitable prodrugs of cytotoxic agents that are activated by enzymes or catalytic antibodies.

BACKGROUND OF THE INVENTION

Many pharmaceutical compounds such as antiviral, immunosuppresive, and cytotoxic cancer chemotherapy agents generally have undesirable toxic effects on normal tissues. Such effects, which include damage to bone marrow (with consequent impairment of blood cell production) and gastrointestinal mucosa, alopecia, and nausea, limit the dose of pharmaceutical compound that can be safely administered and thereby reduce the potential efficacy.

Prodrugs of Antineoplastic Agents a. Nucleoside Analogs

A number of nucleoside analogs have utility as antitumor. agents, including fluorouracil, fluorodeoxyuridine, fluorouridine, arabinosyl cytosine, mercaptopurine riboside, thioguanosine, arabinosyl fluorouracil, azauridine, azacytidine, fluorcytidine, fludarabine. Such drugs generally act by conversion to nucleotide analogs that either inhibit biosynthesis of important nucleotides or that are incorporated into nucleic acids, resulting in defective RNA or DNA. 5-Fluorouracil (5-FU) is a major antineoplastic drug with clinical activity in a variety of solid tumors, such as cancers of the colon and rectum, head and neck, liver, breast, and pancreas. 5-FU has a low therapeutic index. The size of the dose that may be administered is limited by toxicity, reducing the potential efficacy that would be obtained if higher concentrations could be attained near tumor cells.

5-FU must be anabolized to the level of nucleotides (e.g., fluorouridine- or fluorodeoxyuridine-5'-phosphates) in order to exert its potential cytotoxicity. The nucleosides corresponding to these nucleotides (5-fluorouridine and 5-fluoro-2'-deoxyuridine) are also active antineoplastic agents, and in some model systems are substantially more potent than 5-FU, probably because they are more readily converted to nucleotides than is 5-FU.

AraC, also called arabinosylcytosine, 1-b-D-arabinofuranosylcytosine, cytarabine, cytosine-b-D-arabinofuranoside and b-cytosine arabinoside, is a widely used anti-cancer drug, albeit with some major disadvantages (see below). Currently AraC is used to treat both myelogenous and lymphocytic leukemias and non-Hodgkin's lymphomas. Used alone it has resulted in a 20–40% remission of acute leukemia and, in combination with other chemotherapeutic agents, has yielded greater than 50% remission (Calabresi, et al., "In The Pharmacological Basis of Therapeutics". Eds. Gilman, A. G., et al., New York: Macmillian Publishing Company, (1985):1272).

One of the disadvantages of AraC as a cancer drug is its rapid catabolism by deaminases. Human liver contains high levels of deoxycytidine deaminase which converts AraC to Ara-Uracil, an inactive metabolite. This rapid catabolism results in a $t_{1/2}$ in humans of 3–9 minutes following parenteral administration (Baguley, et al., Cancer Chemotherapy Reports 55 (1971):291–298). Compounding this problem, only cells undergoing DNA synthesis are susceptible to the drug's effect and therefore, one must maintain a toxic concentration until all cells of an asynchronously growing tumor pass through S-phase. Unfortunately, this means that the optimum dose schedule of AraC involves a slow intravenous infusion over many hours on each of 5 days, thus requiring a hospital stay. Prolonged application leads to the major problem of general toxicity amongst rapidly dividing normal cells, leading to bone marrow suppression, infection, and hemorrhage. Another problem encountered using this drug is the resistance to AraC eventually developed by cells, presumably due to selection of cells with low kinase activity, or an expanded pool of deoxy CTP.

Prodrug derivatives of AraC have been synthesized in order to: 1) protect AraC from rapid degradation by cytidine deaminase; 2) act as molecular depots of AraC and thereby simplify drug dose schedules; 3) act as carrier molecules for transport on serum proteins and facilitate cellular uptake; or 4) overcome resistance of cells with low kinase activity. AraC derivatives substituted at the 5' position of the arabinose or the N4 position of the cytidine ring have been found to be cytidine deaminase-resistant. Acting as carrier molecules that protect AraC from degradation by cytidine deaminase, lipophilic 5'-ester derivatives (Neil, et al., Biochem. Pharmacol. 21 (1971):465–475; Gish, et al., J. Med. Chem. 14 (1971):1159–1162) and N4-acyl derivatives (Aoshima, et al., Cancer Res. 36 (1976):2726–2732) of AraC have been shown to possess higher anti-tumor activity than AraC in leukemic mice.

All of the above prodrug derivatives are designed to be administered systemically as the parent drug itself is administered. The side effects of the prodrug arising out of the non-tumor-specific toxicity are very similar, if not identical to the systemic application of the parent drug, Ara-C. These prodrugs are presumably acting as molecular depots of Ara-C and thus prolonging the time of drug availability.

Like 5FU and Ara-C, the size of the dose of other antineoplastic nucleoside analogs, including but not limited to: fluorouracil arabinoside, mercaptopurine riboside, arabinosyl adenine, or fluorodeoxyuridine, that may be administered is limited by toxicity, reducing the potential efficacy that would be obtained if higher concentrations could be attained near tumor cells.

Most antineoplastic nucleoside analogs are rapidly catabolized, limiting the duration of their action. Some prodrugs of antineoplastic nucleoside analogs are known. Such prodrugs are generally acyl derivatives of the nucleoside analogs; the acyl groups are removed by endogenous esterase activity following administration. Some of these prodrugs of arabinosyl cytosine (Neil, et al., Cancer Research 30 (1970):1047–1054; Neil, et al., Biochem Pharmacol. 20 (1971):3295–3308; Gish, et. al., J. Med. Chem. 14 (1971):1159–1162; Aoshima, et al., Cancer Research (1976) :2762–2732 or fluorodeoxyuridine (Schwendener, et al., Biochem. Biophys. Res. Comm. 126 (1985):660–666) provide active drug for a period longer than would occur after administration of the parent drug.

However, such prodrugs do not selectively deliver the drug to tumor tissue; enhanced toxicity often accompanies enhanced antitumor efficacy (Schwendener, et al., Biochem. Biophysi. Res. Comm. 126 (1985):660–666).

Previous suggestions for targeted prodrugs of antineoplastic nucleoside analogs are unsatisfactory. Bagshawe, et al., Patent Application WO 88/07378, proposed that the corresponding nucleotides of antineoplastic nucleosides could be converted back to the nucleoside with an appropriate enzyme; Senter, et al., Patent Application EP 88112646, similarly suggest the use of fluorouridine monophosphate to be activated by the enzyme alkaline phosphatase conjugated to an antibody that binds to a tumor cell surface antigen. These proposals fail to take into account the high and ubiquitous activity of enzymes which convert nucleotides to nucleosides (e.g., 5'nucleotidase) in blood and tissues. Nucleotides (nucleoside phosphates) are therefore not useful for targeted delivery of antineoplastic nucleoside analogs.

b. Alkylating Agents

Nitrogen mustard alkylating agents are an important class of antineoplastic drugs. Examples of antineoplastic alkylating agents with clinical utility are: cyclophosphamide, melphalan, chlorambucil, or mechlorethamine. These agents share, as a common structural feature, a bis-(2-chloroethyl) grouping on a nitrogen which can alkylate and thereby damage nucleic acids, proteins, or other important cellular structures. The cytotoxic activity of alkylating agents is less dependent upon the cell cycle status of their targets than is the case for antimetabolites that affect nucleic acid synthesis. For this reason, the cytotoxicity of alkylating agents can be less selective for rapidly dividing cells (e.g., many tumors) relative to normal tissues, but on the other hand, it may be more completely effective against populations of cells that are not synchronized in their cell cycles.

Previous attempts at designing targeted prodrugs of nitrogen mustard compounds have been unsuccessful. Bagshawe, et al., Patent Application WO 88/078378, disclose benzoic acid nitrogen mustard glutamides as prodrugs which are only 5 to 10 fold lower in toxicity than the corresponding activated drugs; these authors state that drugs for clinical use require that the prodrug be at least 100 times less toxic than the drug.

Kerr, et al., *Cancer Immunol. Immunother.* 31 (1990):202–206, disclose melphalan-N-p-hydroxyphenoxyacetamide (an amide derivative of melphalan) as a potential prodrug to be activated with the enzyme penicillin-V-amidase (PVA). While this prodrug was in fact more than 100 fold less toxic than melphelan to particular cell lines in culture, pretreatment of cells with an antibody-PVA conjugate failed to enhance the toxicity of the prodrug because PVA hydrolyzed the phenoxyacetamide bond of the prodrug too slowly to generate a toxic level of drug.

c. Other Antineoplastic Agents

The anthracyclines, daunorubicin and doxorubicin are widely used antitumor agents that exert a number of biochemical effects that contribute to both therapeutic and toxic effects of the drugs. One of the primary mechanisms of the drugs is to intercalate DNA and to destroy gene replication in dividing cells. Doxorubicin is effective in acute leukemias and malignant lymphomas. It is very active in a number of solid tumors. Together with cyclophosphamide and cisplatin, doxorubicin has considerable activity against carcinoma of the ovary. It has been used effectively in the treatment of osteogenic sarcoma, metastatic adenocarcinoma of the breast, carcinoma of the bladder, neuroblastoma and metastatic thyroid carcinoma. The myocardial toxicity of doxorubicin limits the dose of this drug that a patient may receive.

Catalytic Proteins a. Enzymes

The prior art discloses the use of non-mammalian enzymes conjugated to targeting antibodies in order to activate the prodrug selectively at tumor sites (e.g., carboxypeptidases described in Bagshawe, et al., Patent Application WO 88/078378; Penicillin-V amidase described in Kerr, et al., *Cancer Immunol. Immunother.*, 31 (1990):202–6; and beta-lactamase described in Eaton, et al., Patent Application EP 90303681.2). Non-mammalian enzymes will generally be antigenic, and will thus be useful only for short term use or perhaps only a single use, due to the formation of neutralizing antibodies or the induction of undesirable immune responses.

In the cases where mammalian enzymes have been proposed (Senter, et al., Patent Application EP 88112646) no provision has been made to obviate the problem of endogenous human enzymes from activating the prodrug. Enzymes from different species of mammals will also present problems due to antigenicity. In addition, some proposed prodrug-activating enzymes, e.g., neuraminidase (Senter, et al., Patent Application EP 88/112646) could cause serious damage to the organism to which they are administered; neuraminidase removes the sialic acid residue at the terminus of oligosaccharides on glycoproteins (important components of erythrocyte membranes, for example), exposing galactose residues which mark such glycoproteins for rapid degradation in the liver. Due consideration of the situation in vivo is necessary for practical implementation of the strategy of targeted activation of prodrugs of antineoplastic agents in embodiments suitable for use in humans.

b. Catalytic Antibodies

The manner in which catalytic antibodies carry out chemical reactions on substrates (or antigens) is essentially governed by the same theoretical principles that describe how enzymes carry out chemical reactions. See U.S. Pat. No. 4,888,281, hereby incorporated by reference, which describes the catalysis of chemical reactions by antibodies. For most chemical transformations to occur, substantial activation energy is required to overcome the energy barrier that exists between reactant and product. Enzymes catalyze chemical reactions by lowering the activation energy required to form the short-lived unstable chemical species found at the top of the energy barrier, known as the transition state (Pauling, L., *Am.Sci.* 36 (1948):51; Jencks, W. P., *Adv. Enzymol.* 43 (1975):219). Four basic mechanisms are employed in enzymatic catalysis to stabilize the transition state, thereby reducing the free energy of activation. First, general acid and base residues are often found optimally positioned for participation in catalysis within catalytic active sites. A second mechanism involves the formation of covalent enzyme-substrate intermediates. Third, model systems have shown that binding reactants in the proper orientation for reaction can increase the "effective concentration" of reactants by at least seven orders of magnitude (Fersht, A. R., et al., *Am. Chem.* Soc. 90 (1968):5833) and therefore greatly reduce the entropy of a chemical reaction. Finally, enzymes can convert the energy obtained upon substrate binding to distort the reaction towards a structure resembling the transition state.

Drawing upon this understanding of enzymatic catalysis, several antibodies with catalytic activity have been induced by immunization and isolated (Powell, M. J., et al., *Protein Engineering* 3 (1989):69–75). One approach for inducing acid or base residues into the antigen binding site is to use a complementary charged molecule in the immunogen. This technique proved successful for elicitation of antibodies with a hapten containing a positively-charged ammonium ion (Shokat, et al., *Chem. Int. Ed. Engl.* 27 (1988):269–271). Several of these monoclonal antibodies catalyzed a beta-elimination reaction.

In another approach, antibodies are elicited to stable compounds that resemble the size, shape, and charge of the transition state of a desired reaction (i.e., transition state analogs). See U.S. Pat. Nos. 4,792,446 and 4,963,355 which describe the use of transition state analogues to immunize animals and the production of catalytic antibodies. Both of these patents are hereby incorporated by reference.

Examples of catalytic antibodies that are able to accelerate reactions by stabilizing the transition state structure and/or enhancing the "effective concentration" of reactants are discussed below.

1. Esterases

The mechanism of ester hydrolysis involves a charged transition state whose electrostatic and shape characteristics can be mimicked by a phosphonate structure. Immunization of a mouse with a nitrophenyl phosphonate ester hapten-protein conjugate led to the isolation of monoclonal antibodies with hydrolytic activity on methyl-p-nitrophenyl carbonate (Jacobs, et al., *J. Am. Chem. Soc.* 109 (1987):2174–2176). An antibody against a similar transition state analog could hydrolyze its ester substrate in an organic matrix (Durfor, et al., *J. Am. Chem. Soc.* 110 (1988):8713–8714). A substantial catalytic rate increase was reported for an antibody raised by immunization with a dipicolinic phosphonate ester (Tramontano, et al., *J. Am. Chem. Soc.* 110 (1988):2282). The antibody hydrolyzed 4-acetamidophenyl esters with a kcat of 20 $s^{-1}$, which was 6 million times faster than the rate constant for uncatalyzed ester decomposition. A recent report on the stereospecific cleavage of alkyl esters containing D-phenylalanine versus L-phenylalanine by monoclonal antibodies raised against phosphonate esters adds further credence to the use of phosphonate esters to elicit catalytic esterase monoclonal antibodies (Pollack, et al., *J. Am. Chem. Soc.* 111 (1989):5961–5962).

2. Peptidases/Amidases

Several ways of designing a transition state analog to mimic the transition state for a peptidase or amidase have been described. One report discussed the use of an aryl phosphonamidate transition state analog to produce an antibody that could cleave an aryl carboxamide (Janda, et al., *Science* 241 (1988):1188–1191). Another scheme for production of peptidases utilized a metal complex cofactor linked to a peptide (Iverson, et al., *Science* 243 (1989):1184–1188). Although the site of cleavage was not predicted by this method, further studies may allow for site-directed cleavage. Naturally occuring proteolytic antibodies have been found in humans (Paul, et al., *Science* 244 (1989):1158–1162). The antibodies were originally discovered in a subpopulation of asthma patients. One antiserum preparation cleaved a 28 amino acid polypeptide, vasoactive intestinal peptide (VIP) at one specific cleavage site.

3. Other Catalytic Antibodies

Other reactions which monoclonal antibodies have catalyzed are: a Claisen rearrangement (Jackson, et al., *J. Am. Chem. Soc.* 110 (1988):4841–4842; Hilvert, et al., *Proc. Natl. Acad. Sci.* USA 85 (1988):4953–4955; Hilvert, et al., *J. Am. Chem. Soc.* 110 (1988):5593–5594), redox reactions (Shokat, et al., *Angew. Chem. Int. Ed. Engl.* 27 (1989):269–271), photochemical cleavage of a thymine dimer (Cochran, et al., *J. Am. Chem. Soc.* 110 (1988):7888–7890) stereospecific transesterification rearrangements (Napper, et al., *Science* 237 (1987):1041–1043) and a bimolecular amide synthesis (Benkovic, et al., *Proc. Natl. Acad. Sci.* USA 85 (1988):5355–5358,; Janda, et al., *Science* 241 (1988):1188–1191).

OBJECTS OF THE INVENTION

It is an object of the invention to provide novel prodrugs of cytotoxic chemotherapeutic agents.

It is an object of the invention to provide methods for localizing formation or delivery of cytotoxic chemotherapeutic agents to or near tumors.

It is an object of the invention to provide prodrugs with a high drug/prodrug cytotoxicity ratio, which are essentially stable to endogenous mammalian enzymes and which are activated by targeted catalytic proteins of the invention.

It is an object of the invention to provide methods for localizing formation or delivery of cytotoxic chemotherapeutic agents to or near tumors to overcome the problems of 1) toxicity toward normal tissues and 2) reduced antitumor efficacy due to utilization or inactivation of the drugs at non-tumor sites.

It is an object of the invention to provide methods for selective targeting of active alkylating species to tumor cells.

It is an object of the invention to reduce systemic drug toxicity through specific tumor site activation of prodrugs using tumor-specific antibody binding and prodrug activation.

It is an object of the invention to provide prodrugs that are stable to mammalian enzymes, ensuring minimal drug activation or degradation outside the targeted tumor cells.

SUMMARY OF THE INVENTION

These and other objects of the invention are achieved by compounds of the formula

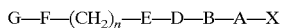

Compounds of the formula are prodrug compounds and are haptens which can be used to produce antibodies capable of cleaving the protective groups from the drugs. The substituent X is a drug, e.g. a nucleoside analog joined at the 5' and/or 3' position of the aldose ring, an alkylating agent such as cyclophosphamide, melphalan or daunomycin.

In the prodrug compounds D is C=O and the remainder of the compound is a protective moiety. The protective moiety lends stability to the compound, i.e. compounds of the invention have a half life in serum of at least one hour and preferably longer and substantially reduce the toxicity of the prodrug relative to the drug by at least one hundred fold.

The haptens of the formula are capable of producing catalytic antibodies by in vitro techniques followed by protein engineering of the antibodies found to be specific for the haptens, e.g. by random or site-directed mutagenesis, or by eliciting immune responses in mice or other hosts. The antibodies so-produced are capable of cleaving the protective moiety from the drug by esterase, amidase or hydrolase activity.

In the preferred embodiments of the invention, prodrug compounds are identified having the general formula which meet the desired stability and toxicity characteristics and haptens are identified which have the same or substantially the same formula, and are capable of producing antibodies which catalytically cleave the drug X from the residue of the formula.

The invention also includes methods for treating various disease conditions by delivering a drug to a specific cell population such as a tumor. A targeting compound, e.g. an antibody, to which a catalytic antibody of the invention or fragment thereof is conjugated, is administered and permitted to become localized at the cell population. Thereafter the prodrug is administered and is cleaved at the cell population to deliver the drug.

Figure 1A:
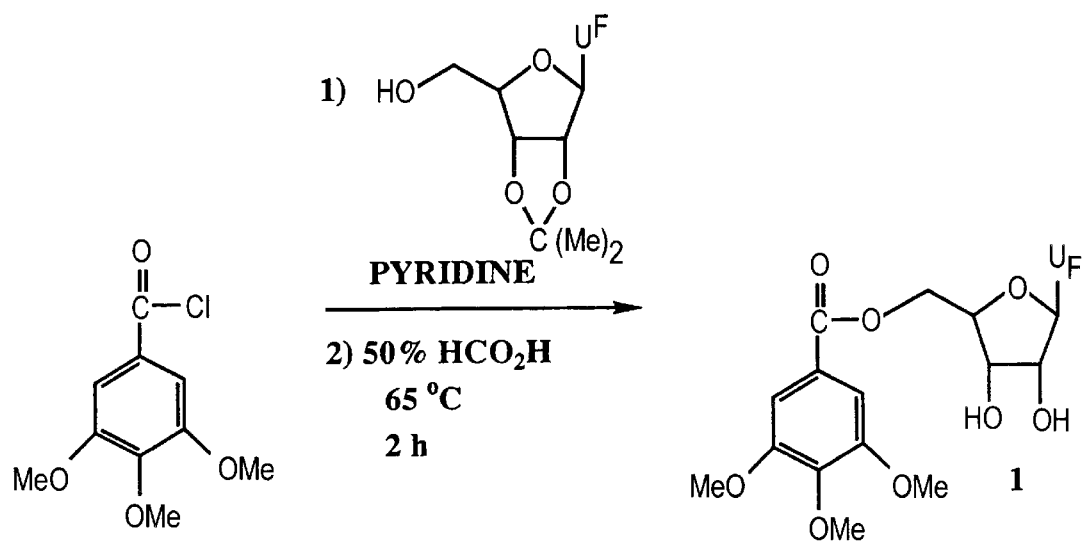
FIG. 1a shows the preparation of linear trimethoxybenzoate-5-fluorouridine prodrug, Compound 1.

The invention, as well as other objects, features and advantages thereof will be understood more clearly and fully from the following detailed description, when read with reference to the accompanying figures which illustrate the results of the experiments discussed in the examples below.

DETAILED DESCRIPTION OF THE INVENTION

The invention provides specific methods for converting a variety of cancer chemotherapy drugs to substantially nontoxic prodrugs which are stable to endogenous enzymes, but which can be activated in or near tumors by prior administration of a tumor-selective agents such as receptor-binding ligands, analogs which bind to tumor associated enzymes, and antibodies conjugated to, or otherwise physically connected to a protein catalyst which converts the prodrugs to active cytotoxic agents. The protein catalyst is 1) an exogenous (or non-mammalian) enzyme, 2) an endogenous (or mammalian) enzyme, or 3) a catalytic antibody. Such a system permits formation of relatively high concentrations of active agent localized at the tumor site(s) while also reducing systemic exposure to the drugs.

The invention provides prodrugs with a high drug/prodrug cytotoxicity ratio, which are essentially stable to endogenous mammalian enzymes and which are activated by targeted catalytic proteins of the invention.

The invention provides methods and compounds for providing suitable prodrugs of antineoplastic nucleoside analogs that are substantially non-toxic in vivo until activated by a catalytic protein of the invention. In designing prodrugs of cytotoxic agents for targeted activation, it is important that the prodrug substituents impart two properties to the drug: (1) that they are pharmaceutically stable, i.e. have a half life in serum of at least one hour, and (2) that they are specifically activatable.

In the invention, prodrugs of antineoplastic agents are made by attaching appropriate substituents, described below, to antineoplastic drugs. Substituents are chosen which render the parent drug relatively nontoxic and which are relatively resistant to removal by endogenous enzyme activity, but which are removed (yielding active drug) by the catalytic proteins of the invention.

Catalytic proteins, and especially catalytic antibodies, most easily catalyze reactions with relatively low activation energies. Reactions that are known to be catalyzed or accelerated by antibodies include ester cleavage, Claisen rearrangement, redox reactions, stereospecific transesterification rearrangements, and amide or peptide cleavage.

Catalytic antibodies, as well as enzymes, catalyze chemical reactions by lowering the activation energy required to form the short-lived, unstable transition state. Catalytic antibodies which stabilize or enhance the formation of the transition state are produced by generating antibodies to stable analogs of the prodrugs that resemble the size, shape, and charge of the transition state of the substituent-cleavage reaction. For example, transition state analogs of ester-cleavage reactions are prepared by substituting a stable phosphonate or sulfonate group for the normal carbonyl group.

Substantial esterase activity is present and ubiquitous in mammalian tissues. This activity is relatively nonspecific, cleaving ester bonds in a large variety of compounds. However, some classes of prodrugs of the invention, e.g., substituted aromatic esters of nucleoside analogs, have ester substituents which are relatively resistant to endogenous mammalian esterase activity.

Similar substituted aromatic esters and other prodrug substituents of the invention are useful for preparing prodrugs of a variety of classes of antineoplastic agents with appropriate functional groups, including but not limited to nucleoside analogs and other antimetabolites, alkylating agents such as cyclophosphamide derivatives, intercalating agents such as doxorubicin or etoposide, spindle poisons such as vinca alkaloids, or other classes of cytotoxic drugs.

The prodrugs of the invention, which are relatively resistant to activation by endogenous mammalian enzymes, are activated by the catalytic proteins of the invention, e.g., catalytic antibodies prepared by raising antibodies to analogs of the transition states of the prodrug activation reactions.

The catalytic proteins of the invention are conjugated to, or otherwise physically associated with, a tumor-selective antibody, antibody fragment, or binding protein or analogs to tumor associated enzymes or tumor-selective receptor ligands. This complex is typically administered prior to the prodrug, so that it is localized in or near cancer cells. The prodrug is then administered and cleaved by the catalytic protein, forming active antineoplastic drugs in or near tumors.

Below are described various prodrugs of the invention as well as transition state analogs corresponding to such prodrugs. Additionally described are the haptens which can be used to produce antibodies capable of cleaving the protective groups from the prodrugs.

Novel Prodrugs and Haptens

The novel compounds in accordance with the invention, which may be prodrugs or haptens include compounds of the formula

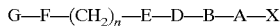

wherein

X is (a) a nucleoside analog joined at the 5' and/or 3' position of the aldose ring wherein the unsubstituted hydroxyl groups on the sugar moiety of the nucleoside analog are optionally and independently substituted with acyl, phosphate and alkyl radicals, and are optionally replaced with H, halogen or azide, and wherein the O of the nucleoside by which it is attached is optionally replaced by S, NH, and $CH_2$, (b) $QP(O)(NH_2)NR^1R^2$, wherein Q is O or $CH_2$ and Q can be omitted and $R^1$ and $R^2$ are the same or different but both cannot be H and each is haloalkyl, alkyl, alkyl with heteroatoms, cycloalkyl, phenyl (optionally substituted), alkylphosphonate, alkylsulfonate, alkylcarboxylate, alkylammonium or alkene or $R^1$ and $R^2$ are optionally connected to each other in a ring structure such as morpholino or piperidino, (c) melphalan joined to the remainder of the compound at the primary amino group and optionally the amino group can be replaced by $CH_2$ or S, or (d) daunomycin or other drug joined to the remainder of the compound at a hydroxy, amino or thio group which can be replaced by $CH_2$, S or O;

A, which may be omitted, is ethylene or any isomer of propenyl;

B, which may be omitted, is O, S, $CH_2$, or $NR^3$, wherein $R^3$ is H, alkyl, alkyl with heteroatoms, cycloalkyl, phenyl (optionally substituted), alkylphosphonate, alkylsulfonate, alkylcarboxylate, alkylammonium and alkene;

D, which may be omitted, is (a) C=O, (b) $C=NR^4$ or $R^5R^6N—C=NR^4$, where $R^4$ is H, alkyl, alkyl with heteroatoms, cycloalkyl, phenyl (optionally substituted), alkylphosphate, alkylsulfonate, alkylcarboxylate, alkylammonium and alkene and $R^4$ and $R^5$ or $R^5$ and $R^6$ are optionally connected to each other in a ring structure such as morpholino or piperidino and $R^5$ and $R^6$ can be haloalkyl, alkyl, alkyl with heteroatoms, cycloalkyl, phenyl (optionally substituted), alkylphosphonate, alkylsulfonate, alkylcarboxylate, alkylammonium, and alkene,
(c) SO or CHOH with any stereochemistry,
(d) $SO_2$, or
(e) $P(T)(TR^7)$ wherein T is O, N, S or $CH_2$ and $R^7$ is H, alkyl, alkyl with heteroatoms, cycloalkyl, phenyl (optionally substituted), alkylphosphonate, alkylsulfonate, alkylcarboxylate, alkylammonium and alkene and is optionally attached to E at $R^8$, $R^{11}$ or $R^{13}$;

E, which may be omitted, is the radical

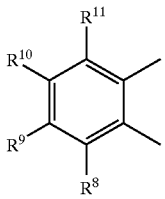

or $R^{12}R^{13}C$ where $R^{8-13}$ are the same or different and are H or alkyl with 1–10 carbon atoms, phenyl (optionally substituted), alkene with 1–10 carbon atoms, hydroxyalkyl, alkoxy, aminoalkyl, alkylthio, thioalkyl, amino, alkylamino, alkylphosphonate, alkylsulfonate, alkylcarboxylate, alkylammonium, carboxylate, sulfate, phosphate, or hydroxyl, and wherein $R^{12}$ and $R^{13}$ are the same or different and are O substituted with alkyl, alkyl with heteroatoms, cycloalkyl, phenyl (optionally substituted), alkylphosphonate, alkylsulfonate, alkylcarboxylate, alkylammonium or alkene, and are optionally connected to each other in a ring structure such as a five-membered or six-membered acetal ring where the diol is derived from a sugar, cycloalkyl or phenyl moiety, and is optionally attached to the radical D at $R^7$ through $R^8$ or $R^{11}$ or $R^{13}$;

n is an integer from 0 to 3;

F, which may be omitted, is an oxygen, carbonyloxy, or oxycarbonyl radical; and

G, which may be omitted, is
(a) H or alkyl with 1–10 carbon atoms, alkoxy with 1–10 carbon atoms, phenyl (optionally substituted), alkene with 1–10 carbon atoms, hydroxyalkyl, aminoalkyl, thioalkyl, amino, alkylamino, alkylphosphonate, alkylsulfonate, alkylcarboxylate, alkylammonium, carboxylate, sulfate, phosphate, or hydroxyl, or
(b) the radical

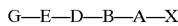

where Y is $C=O$, $SO_2$, or CHOH or SO with any stereochemistry, Z is O, N, CH with any stereochemistry, or S, and $R^{14}$, $R^{15}$, $R^{16}$, $R^{17}$ or $R^{18}$ is the site of attachment to the remainder of the compound, provided that where $R^{14}$ is the site of attachment, then $R^{15}$, $R^{16}$, $R^{17}$ and $R^{18}$ are the same or different and are hydrogen, alkyl with 1–10 carbon atoms, alkenyl with 1–10 carbon atoms, phenyl (optionally substituted), carboxyalkyl with 1–10 carbon atoms and with or without heterocyclic or phenyl substitution (optionally substituted on the heterocyclic or phenyl group), alkoxy with 1–10 carbon atoms, alkylamino with 1–10 carbon atoms, aminoalkyl with 1–10 carbon atoms, acyloxy with 1–10 carbon atoms, with or without heterocyclic or phenyl substitution (optionally substituted on the heterocycle or phenyl group) or acylamino with 1–10 carbon atoms, with or without heterocyclic or phenyl substitution (optionally substituted on the heterocyclic or phenyl group), and further provided that where one of $R^{15}$, $R^{16}$, $R^{17}$, or $R^{18}$ is the site of attachment then $R^{14}$ and the remainder of $R^{15}$, $R^{16}$, $R^{17}$, and $R^{18}$ are the same or different and are as defined for $R^{15}$–$R^{18}$ when $R^{14}$ is the site of attachment and, $R^{14}$ is optionally $SO_3H$ or $SO_4H$.

Depending upon the mechanism by which the specific compound works, each compound of the invention relates to and affects enzymatic catalysis differently. In particular, the compounds of the invention may effect esterase, amidase, glycosidase or hydrolase catalysis.

Esterase Catalysis

Novel compounds in accordance with the invention which have been found to effect esterase catalysis include compounds of the formula $$G-E-D-B-A-X$$

wherein

B, which may be omitted, is O, S or $CH_2$;

D is
(a) $C=O$,
(b) SO or CHOH with any stereochemistry,
(c) $SO_2$, or
(d) $P(T)(TR^7)$ wherein T is O, N, S or $CH_2$ and $R^7$ may be H, alkyl, alkyl with heteroatoms, cycloalkyl, phenyl (optionally substituted), alkylphosphonate, alkylsulfonate, alkylcarboxylate, alkylammonium and alkene and is optionally attached to E at $R^8$, $R^{11}$ or $R^{13}$;

E is the radical

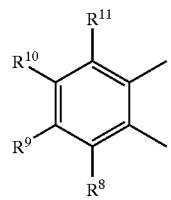

or $R^{12}R^{13}C$ where $R^{8-13}$ may be the same or different and are H or alkyl with 1–10 carbon atoms, phenyl (optionally substituted), alkene with 1–10 carbon atoms, hydroxyalkyl, alkoxy, aminoalkyl, alkylthio, thioalkyl, amino, alkylamino, alkylphosphonate, alkylsulfonate, alkylcarboxylate, alkylammonium, carboxylate, sulfate, phosphate, or hydroxyl, and is optionally attached to the radical D at $R^7$ through $R^8$ or $R^{11}$ or $R^{13}$; and G is H or alkyl with 1–10 carbon atoms, alkoxy with 1–10 carbon atoms, phenyl (optionally substituted), alkene with 1–10 carbon atoms, hydroxyalkyl, aminoalkyl, thioalkyl, amino, alkylamino, alkylphosphonate, alkylsulfonate, alkylcarboxylate, alkylammonium, carboxylate, sulfate, phosphate, or hydroxyl, and A and X A are as already defined.

More specifically, the following compounds effect esterase catalysis

Prodrug Group 1: Substituted Aromatic Carboxylic Acid Esters of Nucleoside Analogs

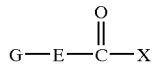

wherein

X is a nucleoside analog joined at the 3' and/or 5' position of the aldose ring, E is a substituted phenyl group and G is H, alkyl, alkoxy, phenyl (optionally substituted), alkene or alkylthio.

Hapten Group 1: Transition State Analogs for Substituted Aromatic Carboxylic Acid Esters of Nucleoside Analogs

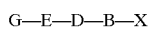

wherein

X is a nucleoside analog joined at the 3' and/or 5' position of the aldose ring wherein the O of the nucleoside by which it is attached is replaced by B, B is O, S, NH or $CH_2$, D is P(O)OH, $SO_2$ or CHOH, E is a substituted phenyl group and G is H, alkyl, alkoxy, phenyl (optionally substituted), alkene or alkylthio.

Prodrug Group 2: Ortho Substituted Aromatic Carboxylic Acid Esters of Nucleoside Analogs

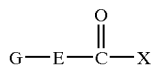

wherein

X is a nucleoside analog joined at the 3' and/or 5' position of the aldose ring and E is a substituted phenyl group with an ortho substituent to (C=O)X which is hydroxyalkyl, aminoalkyl, thioalkyl, alkylcarboxylate, alkylammonium, alkylamine or carboxylate and G is H, alkyl, alkoxy, phenyl (optionally substituted), alkene or alkylthio.

Hapten Group 2: Transition State Analogs for Ortho Substituted Aromatic Carboxylic Acid Esters of Nucleoside Analogs

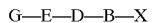

wherein

X is a nucleoside analog joined at the 3' and/or 5' position of the aldose ring wherein the O of the nucleoside by which it is attached is replaced by B, B is O, S, NH or $CH_2$, D is $P(T)(TR^7)$ wherein T is O, N, S, or $CH_2$ and $R^7$ is alkyl, alkyl with heteroatoms, cycloalkyl, phenyl (optionally substituted), or alkene, and is attached to radical E at $R^8$ or $R^{11}$, E is a substituted phenyl group where $R^8$ or $R^{11}$ is attached to the radical D at $R^7$, $R^{8-11}$ are optionally the same or different and are H or alkyl with 1–10 carbon atoms, phenyl (optionally substituted), alkene with 1–10 carbon atoms, hydroxyalkyl, aminoalkyl, alkoxy, alkylthio, thioalkyl, amino, alkylamino, alkylphosphonate, alkylsulfonate, alkylcarboxylate, alkylammonium, carboxylate, sulfate, phosphate or hydroxyl and G is H, alkyl, alkoxy, phenyl (optionally substituted), alkene and alkylthio.

Prodrug Group 3: Di- or Tri-substituted Acetic Acid Esters of Nucleoside Analogs

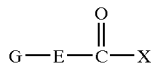

wherein

X is a nucleoside analog joined at the 3' and/or 5' position of the aldose ring, E is $R^{12}R^{13}C$ and G is H.

Hapten Group 3: Transition State Analogs for Di- or Tri-substituted Acetic Acid Esters of Nucleoside Analogs

wherein

X is an antineoplastic nucleoside analog joined at the 3' and/or 5' position of the aldose ring, B is O, S, NH or $CH_2$, D is P(O)OH, $SO_2$ or CHOH and E is $R^{12}R^{13}C$.

Prodrug Group 4: Di-substituted Acetic Acid Esters of Nucleoside Analogs Where One or Both of the Substituents Contains a Heteroatom

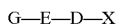

wherein

X is a nucleoside analog joined at the 3' and/or 5' position of the aldose ring, D is C=O, E is $R^{12}R^{13}C$ where $R^{12}$ is hydroxyalkyl, aminoalkyl, thioalkyl, alkylcarboxylate, alkylammonium, alkylamino or carboxylate, $R^{13}$ is optionally the same as $R^{12}$ or alkyl, phenyl (optionally substituted), alkene, alkylphosphonate, alkylsulfonate or hydroxyl, and G is H, alkyl, alkoxy, phenyl (optionally substituted), alkene or and alkylthio.

Hapten Group 4: Transition State Analogs for Disubstituted Acetic Acid Esters of Nucleoside Analogs Where One or Both of the Substituents Contains a Heteroatom

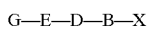

wherein

X is a nucleoside analog joined at the 3' and/or 5' position of the aldose ring wherein the O of the nucleoside by which it is attached is replaced by B, B is O, S, NH or $CH_2$, D is $P(T)(TR^7)$ wherein T is O, N, S, or $CH_2$ and $R^7$ is alkyl, alkyl with heteroatoms, cycloalkyl, phenyl (optionally substituted), or alkene, and D is attached to radical E at $R^{12}$ or $R^{13}$, E is $R^{12}R^{13}C$, where $R^{12}$ or $R^{13}$ is attached to radical D at $R^7$, and the other of $R^{12}$ or $R^{13}$ is alkyl, alkyl with hereroatoms, cycloalkyl, phenyl (optionally substituted) or alkene, and G is H, alkyl, alkoxy, phenyl (optionally substituted), alkene or alkylthio.

Prodrug Group 10

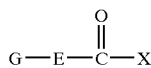

where

X is

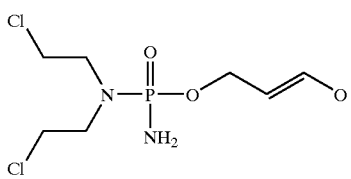

and

G—E is a substituted phenyl radical.

Hapten Group 10

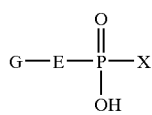

where

X is

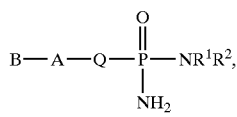

Q is O or CH$_2$ and R$^1$ and R$^2$ are the same or different but both cannot be H, R$^1$ and R$^2$ may be connected to each other in a ring structure such as morpholino or piperidino moieties, R$^1$ and R$^2$ can be haloalkyl, alkyl, alkyl with heteroatoms, cycloalkyl, phenyl (optionally substituted), alkylphosphonate, alkylsulfonate, alkylcarboxylate, alkylammonium, and alkene;

A is any isomer of propenyl,

B is O, S, or CH$_2$,

D is P(T)(TR$^7$) wherein T is O, N, S, or CH$_2$ and R$_7$ is alkyl, alkyl with heteroatoms, cycloalkyl, phenyl (optionally substituted), or alkene, and is attached to radical E at R$^8$ or R$^{11}$, E is a substituted phenyl group where R$^8$ or R$^{11}$ is attached to the radical D at R$^7$, R$^{8-11}$ are optionally the same or different and are H or alkyl with 1–10 carbon atoms, phenyl (optionally substituted), alkene with 1–10 carbon atoms, hydroxyalkyl, aminoalkyl, alkoxy, alkylthio, thioalkyl, amino, alkylamino, alkylphosphonate, alkylsulfonate, alkylcarboxylate, alkylammonium, carboxylate, sulfate, phosphate or hydroxyl and G is H, alkyl, alkoxy, phenyl (optionally substituted), alkene and alkylthio.

Prodrug Group 11

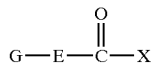

where

X is

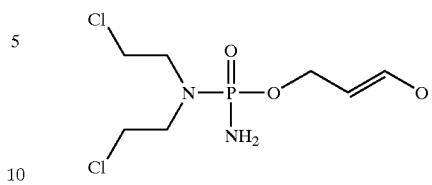

E is is a substituted phenyl group with an ortho substituent to (C=O)X which is hydroxyalkyl, aminoalkyl, thioalkyl, alkylcarboxylate, alkylammonium, alkylamine or carboxylate and G is H, alkyl, alkoxy, phenyl (optionally substituted), alkene or alkylthio.

Hapten Group 11

G—E——X where

X is

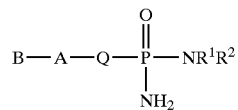

where

Q is O or CH$_2$ and R$^1$ and R$^2$ are the same or different but both cannot be H, R$^1$ and R$^2$ may be connected to each other in a ring structure such as morpholino or piperidino moieties, R$^1$ and R$^2$ can be haloalkyl, alkyl, alkyl with heteroatoms, cycloalkyl, phenyl (optionally substituted), alkylphosphonate, alkylsulfonate, alkylcarboxylate, alkylammonium, and alkene;

A is any isomer of propenyl,

B is O, S, or CH$_2$,

D is P(T)(TR$^7$) wherein T is O, N, S, or CH$_2$ and R$^7$ is alkyl, alkyl with heteroatoms, cycloalkyl, phenyl (optionally substituted), or alkene, and is attached to radical E at R$^8$ or R$^{11}$, E is a substituted phenyl group where R$^8$ or R$^{11}$ is attached to the radical D at R$^7$, R$^{8-11}$ are optionally the same or different and are H or alkyl with 1–10 carbon atoms, phenyl (optionally substituted), alkene with 1–10 carbon atoms, hydroxyalkyl, aminoalkyl, alkoxy, alkylthio, thioalkyl, amino, alkylamino, alkylphosphonate, alkylsulfonate, alkylcarboxylate, alkylammonium, carboxylate, sulfate, phosphate or hydroxyl and G is H, alkyl, alkoxy, phenyl (optionally substituted), alkene and alkylthio.

Prodrug Groups 14

A prodrug of the formula:

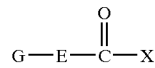

wherein x is an anthracycline antineoplastic agent joined via the oxygen atom of a free hydroxyl group on either the anthracycline moiety or the aglycone moiety and E is a substituted phenyl radical or a prodrug as defined wherein the anthracycline antineoplastic agent is selected from the group consisting of doxorubicin, daunorubicin, or epirubicin.

Hapten Group 14

A hapten compound of the formula:

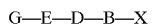

wherein x is an anthracycline agent joined via the oxygen atom of a free hydroxyl group on either the anthracyline moiety or the aglycone moiety, B is O, S, NH or $CH_2$, D is $P(O)OH$, $SO_2$, or CHOH and E is a substituted phenyl radical or a hapten compound as in recited wherein the anthracycline is selected from the group consisting of doxorubicin, daunorubicin, or epirubicin.

Amidase Catalysis

Novel compounds in accordance with the invention which have been found to effect amidase catalysis include compounds of the formula:

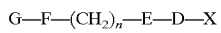

wherein

X is
(a) a nucleoside analog joined at the 5' and/or 3' position of the aldose ring wherein the unsubstituted hydroxyl groups on the sugar moiety of the nucleoside analog are optionally and independently substituted with acyl, phosphate and alkyl radicals, and are optionally replaced with H, halogen or azide, and wherein the O of the nucleoside by which it is attached can be replaced by S, NH, and $CH_2$,
(b) melphalan joined to the remainder of the compound at the primary amino group and optionally the amino group can be replaced by $CH_2$ or S, or
(c) daunomycin or other drug joined to the remainder of the compound at a hydroxy, amino or thio group which may be replaced by $CH_2$, S or O;

D, which may be omitted, is
(a) C=O,
(b) SO or CHOH with any stereochemistry,
(c) $SO_2$, or
(d) $P(T)(TR^7)$ wherein T is O, N, S or $CH_2$ and $R^7$ may be H, alkyl, alkyl with heteroatoms, cycloalkyl, phenyl (optionally substituted), alkylphosphonate, alkylsulfonate, alkylcarboxylate, alkylammonium and alkene and is attached to E at $R^8$, $R^{11}$ or $R^{13}$;

E, which may be omitted, is the radical

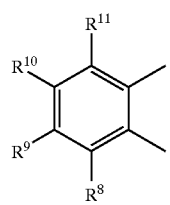

or $R^{12}R^{13}C$ where $R^{8-13}$ are the same or different and are H or alkyl with 1–10 carbon atoms, phenyl (optionally substituted), alkene with 1–10 carbon atoms, hydroxyalkyl, aminoalkyl, thioalkyl, amino, alkylamino, alkylphosphonate, alkylsulfonate, alkylcarboxylate, alkylammonium, carboxylate, sulfate, phosphate, or hydroxyl, and is optionally attached to the radical D at $R^7$ through $R^8$ or $R^{11}$ or $R^{13}$;

n is an integer from 0 to 3;

F, which may be omitted, is an oxygen, carbonyloxy, or oxycarbonyl radical; and

G, which may be omitted, is H or the radical

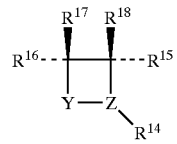

where Y is C=O, $SO_2$, or CHOH or SO with any stereochemistry, Z is O, N, CH with any stereochemistry, or S, and $R^{14}$, $R^{15}$, $R^{16}$, $R^{17}$ or $R^{18}$ is the site of attachment to the remainder of the compound, provided that where $R^{14}$ is the site of attachment, then $R^{15}$, $R^{16}$, $R^{17}$ and $R^{18}$ are the same or different and are hydrogen, alkyl with 1–10 carbon atoms, alkenyl with 1–10 carbon atoms, phenyl (optionally substituted), carboxyalkyl with 1–10 carbon atoms and with or without heterocyclic or phenyl substitution (optionally substituted on the heterocyclic or phenyl group), alkoxy with 1–10 carbon atoms, alkylamino with 1–10 carbon atoms, aminoalkyl with 1–10 carbon atoms, acyloxy with 1–10 carbon atoms, with or without heterocyclic or phenyl substitution (optionally substituted on the heterocycle or phenyl group) or acylamino with 1–10 carbon atoms, with or without heterocyclic or phenyl substitution (optionally substituted on the heterocyclic or phenyl group), and further provided that where one of $R^{15}$, $R^{16}$, $R^{17}$, or $R^{18}$ is the site of attachment then $R^{14}$ and the remainder of $R^{15}$, $R^{16}$, $R^{17}$, and $R^{18}$ are the same or different and are as defined for $R^{15}$–$R^{18}$ when $R^{14}$ is the site of attachment and, $R^{14}$ is optionally $SO_3H$ or $SO_4H$, but may be omitted.

Overview of Hapten Strategies for Raising b-Lactamase Antibodies

It is necessary to design strategies and prepare haptens for immunization to elicit antibodies capable of monocyclic b-lactam hydrolysis. Some possibilities of design are shown below.

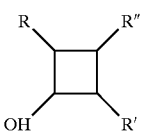

1

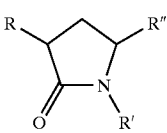

2

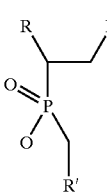

3

The strategy of Compound 1 which differs from the b-lactam substrate in that the b-lactam ring has been replaced with cyclobutanol (such that a secondary alcohol replaces the b-lactam carbonyl). Alcohol transition state analogs have been successfully designed and are well known as transition state inhibitors in enzymology (Bolis, G., et al., *J. Med. Chem.* 30(1987):1729–37) and have been used to raised hydrolytic catalytic antibodies (Shokat, K. M., et al., *Chem. Int. Ed. Engl.* 29 (1990):1296–1303).

The strategy of Compound 2 involves the addition of a methylene group to the b-lactam ring to form a g-lactam ring. Because of the difference in ring size (four-versus five-membered), the bond angle of the carbonyls will differ with respect to their respective rings. The carbonyl of the g-lactam will be more out of plane of the ring (more tetrahedral) than the b-lactam carbonyl (Baldwin, J. E., et al., *Tetrahedron* 42 (1986):4879). This difference will cause subtrate destabilization of the b-lactam to a g-lactam-elicited antibody, contributing to catalysis.

Non-cyclic hapten 3 utilizes a combination of substrate destabilization and transition state complementarity to induce an antibody with b-lactamase activity. This or similar compounds will be a linear analogs of the b-lactam in which the scissile bond has been replaced by the transition state-like dialkylphosphinate (shown here), or similar phosphorous-based group. The combination of transition state analogy and ground state destabilization may result in efficient catalytic antibodies.

In all strategies, the structure of the substituents will depend on the drug (occupying R') conjugation to an immunogenic carrier protein including but not limited to KLH or BSA (through R, R', or R") and the structure of the antibiotic (R and R") used in screening mutants.

The following compounds which effect amidase catalysis
Prodrug Group 6: Substituted Aromatic Carboxylic Acid Ester Protected Nucleoside Analogs

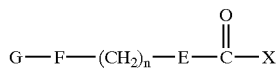

where
  X is a nucleoside analog esterified in the 5' and/or 3' position, E is a substituted phenyl radical and G is said azetidinone radical.

Hapten Group 6: Transition State Analogs of Substituted Aromatic Carboxylic Acid Ester Protected Nucleoside Analogs G—F—(CH$_2$)$_n$—E—D—X where
  X is a nucleoside analog esterified in the 5' and/or 3' position, D is C=O and G is said azetidinone radical wherein Y is SO$_2$ or CHOH or SO with any stereochemistry and Z is CH.

Prodrug Group 7: Substituted Aliphatic Carboxylic Acid ster-protected Nucleoside Analogs

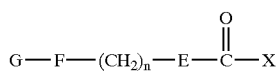

where
  E is R$^{12}$R$^{13}$C.

Hapten Group 7: Transition State Analogs of Substituted Aliphatic Carboxylic Acid Ester-protected Nucleoside Analogs

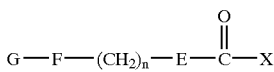

wherein
  D is C=O, E is R$^{12}$R$^{13}$C and G is said azetidinone radical where Y is SO$_2$ or CHOH or SO with any stereochemistry and Z is CH.

Prodrug Group 8: (S)-3-acylamino-2-azetidinone Alkylated Analogs of nucleoside Analogs

G—X where
  X is a nucleoside alkylated in the 5' and/or 3' position, and G is a 2-azetidinone radical.

Hapten Group 8: Transition State Analogs of (S)-3-acylamino-2-azetidinone Alkylated Analogs of Nucleoside Analogs

G—X where
  X is a nucleoside analog alkylated in the 5' and/or 3' position and where the hydroxyl at the point of attachment is optionally replaced by CH$_2$ and G is a 2-azetidinone radical where Y is SO$_2$ or CHOH or SO with any stereochemistry and Z is CH.

Prodrug Group 13

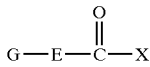

where
  X is melphalan bound at its free amino group and E is a substituted phenyl group or R$^{12}$R$^{13}$C and G is H, alkyl, alkoxy, phenyl (optionally substituted), alkene and alkylthio.

Hapten Group 13

E—D—B—X where
  X is melphalan whose free amino group is replaced by B, and B is O, S, NH or CH$_2$, D is P(O)(OH), SO$_2$ or CHOH and E is a substituted phenyl group.

Hydrolase Catalysis

Novel compounds in accordance with the invention which have been found to effect hydrolase catalysis include compounds of the formula:

G—E—D—B—A—X wherein
  X is
    (a) a nucleoside analog joined at the 5' and/or 3' position of the aldose ring wherein the unsubstituted hydroxyl groups on the sugar moiety of the nucleoside analog are independently substituted with acyl, phosphate and alkyl radicals, and are optionally replaced with H, halogen or azide, and wherein the O of the nucleoside by which it is attached can be replaced by S, NH, and CH$_2$,
    (b) QP(O)(NH$_2$)NR$^1$R$^1$, wherein Q is O or CH$_2$ and Q can be omitted and R$^1$ and R$^2$ are the same or different but both cannot be H and each is haloalkyl, alkyl, alkyl with heteroatoms, cycloalkyl, phenyl (optionally substituted), alkylphosphonate, alkylsulfonate, alkylcarboxylate, alkylammonium or alkene or $R^1$ and $R^2$ are optionally connected to each other in a ring structure such as morpholino or piperidino, (c) melphalan joined to the remainder of the compound at the primary amino group and optionally the amino group can be replaced by $CH_2$ or S, or (d) daunomycin or other drug joined to the remainder of the compound at a hydroxy, amino or thio group which can be replaced by $CH_2$, S, or O;

A, which may be omitted, is ethylene or any isomer of propenyl;

B, which may be omitted, is $NR^3$, wherein $R^3$ may be H, alkyl, alkyl with heteroatoms, cycloalkyl, phenyl (optionally substituted), alkylphosphonate, alkylsulfonate, alkylcarboxylate, alkylammonium and alkene;

D, which may be omitted, is $C=NR^4$ or $R^5R^6N—C=NR^4$, where $R^4$ is H, alkyl, alkyl with heteroatoms, cycloalkyl, phenyl (optionally substituted), alkylphosphate, alkylsulfonate, alkylcarboxylate, alkylammonium and alkene and $R^4$ and $R^5$ or $R^5$ and $R^6$ may be connected to each other in a ring structure such as morpholino or piperidino and $R^5$ and $R^6$ can be haloalkyl, alkyl, alkyl with heteroatoms, cycloalkyl, phenyl (optionally substituted), alkylphosphonate, alkylsulfonate, alkylcarboxylate, alkylammonium, and alkene;

E, which may be omitted, is $R^{12}R^{13}C$ where $R^{12}$ and $R^{13}$ may be the same or different and are O substituted with alkyl, alkyl with heteroatoms, cycloalkyl, phenyl (optionally substituted), alkylphosphonate, alkylsulfonate, alkylcarboxylate, alkylammonium or alkene, and are optionally connected to each other in a ring structure such as a five-membered or six-membered acetal ring where the diol is derived from a sugar, cycloalkyl or phenyl moiety; and G, which may be omitted, is H or alkyl with 1–10 carbon atoms, phenyl (optionally substituted), alkylphosphonate, alkylsulfonate or alkylcarboxylate.

The following compounds effect hydrolase catalysis.

Prodrug Group 5: Orthoester-group-protected Nucleoside Analogs

A prodrug compound of the formula:

wherein

X is a nucleoside analog joined at the 5' or 3' position of the aldose ring and E is $R^{12}R^{13}C$ wherein $R^{12}$ and $R^{13}$ are the same or different and are alkoxy radicals and G is H. Preferably $R^{12}$ and $R^{13}$ are ethoxy.

Hapten Group 5: Transition State Analogs of Orthoester-group-protected Nucleoside Analogs A hapten compound of formula:

wherein

X is a nucleotide analog joined at the 5' or 3' position of the aldose ring and D is $R^5R^6N—C=NR^4$ wherein $R^4$ and $R^5$ are alkyl and $R^6$ is H. Preferably $R^4$ and $R^5$ are ethyl.

Prodrug Group 12

A prodrug compound of the formula:

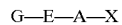

where

X is $QP(O)(NH_2)NR^1R^2$, Q is O, $R^1$ and $R^2$ are —$CH_2$—$CH_2$—Cl, A is ethylene, E is $R^{12}R^3C$ and G is H or a prodrug compound as defined wherein $R^{12}$ and $R^{13}$ are the same or different and are alkoxy radicals and G is H or $R^{12}$ and $R^{13}$ are the same or different and are ethoxy radicals and G is H.

Hapten Group 12

A hapten compound of the formula:

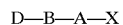

wherein $X=QP(O)(NH_2)NR^1R^2$, Q is omitted, $R^1$ and $R^2$ are ethylene groups joined with an NH to form a piperazino moiety, A is ethylene, B is $NR^3$ wherein $R^3$ is H, D is $R^5R^6N—C=NR^4$ wherein $R^4$ and $R^5$ are alkyl and $R^6$ is H. Preferably $R^4$ and $R^5$ are ethyl.

Another hapten compound is of the formula:

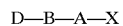

wherein

X is $QP(O)(NH_2)NR^1R^2$, Q is $CH_2$, $R^1$ and $R^2$ are ethylene groups joined with an NH to form a piperazino moiety, A is ethylene, D is $R^5R^6N—C=NR^4$ wherein $R^4$ and $R^5$ are alkyl and $R^6$ is H. Preferably $R^4$ and $R^5$ are ethyl.

Glycosidases

Novel compounds in accordance with the invention are prodrugs of an antineoplastic nucleotide analog comprising a monosaccharide hexopyranose or hexofuranose covalently attached via the anomeric position to the 3' or 5' oxyten of the nucleotide analog, in particular such prodrugs wherein said hexopyranose or hexofuranose is selected from the group consisting of glucose, glucosamine, D-quinovopyranose, galaetose, galactosamine, L-fucopyranose, L-rhamnopyranose, D-glucopyranuronic acid, D-galactopyranuronic acid, D-mannopyranuronic acid, or D-iodopyranuronic acid.

The haptens for a glycosyl prodrug of an antineoplastic nucleoside analog comprise an amidine analog of a monosaccharide hexopyranose or hexofuranose in which the nucleoside oxygen of attachment is replaced by $NR^1$ and the furanose or pyranose ring oxygen is replaced by $NR^2$. Such haptens include amidine analogs of a monosaccharide hexopyranose or hexofuranose which is a structural analog of a sugar selected from the group consisting of glucose, glucosamine, D-quinovopyranose, galactose, galactosamine, L-galactopyranuronic acid, D-mannopyranuronic acid, or D-iodopyranuronic acid.

The compounds include compounds of the formula:

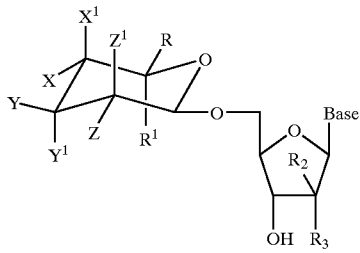

The preferred coupling reaction to make b-glycosylated nucleosides from hexopyranoses and nucleosides is the direct treatment of the peracetylated hexoses and the 5' hydroxy nucleosides in the presence of a Lewis acids such as TMS triflate, $BF_3EtO$ etc. in the solvent, acetonitrile. This method can be extended to the sugars listed below to make the corresponding b-glycosylated nucleosides.

The coupling reaction can be accomplished also by activation of the anomeric position by converting to SPh, F and immidate groups and subsequent treatment of the 5' hydroxy nucleoside will make the corresponding glycosylated nucleosides.

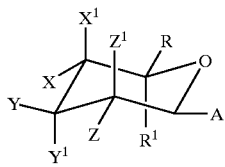

The coupling reaction of hexofuranoses at their anomeric position to the nucleoside 5' position to make furanosylated nucleoside can be accomplished by the method described above.

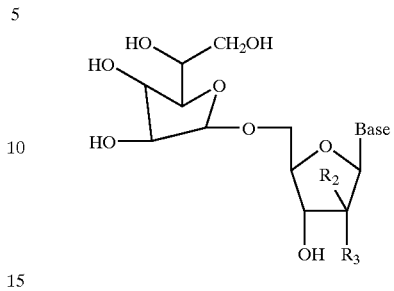

Coupling of hexofuranoses to nucleosides will make a mixture of anomers, because of the ring size.

Hapten Group 9

Amidine haptens are prepared as transition-state analogs for eliciting an immune response to make catalytic antibodies. The amidine hapten mimics the transition state for the hydrolysis of the glycosidic bond. Because of the sofa/chair conformation of the hapten, antibodies raised to these haptens may cleave a wide variety of monosaccharide hexopyranoses.

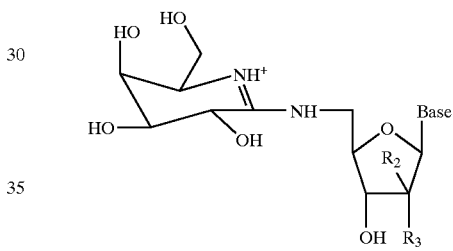

The synthesis of the haptens is accomplished by the coupling reaction of the appropriate lactam and the corre-

| | A = OAc, SPh, F, Immidate | | | | | | | |
|---|---|---|---|---|---|---|---|---|
| Name of the sugar | X1 | X | Y1 | Y | Z1 | Z | R | R1 |
| Glucose | H | OH | H | OH | H | OH | $CH_2OH$ | H |
| Glucosamine | H | OH | H | OH | H | NH2 | $CH_2OH$ | H |
| D-Quinovopyranose | H | OH | H | OH | H | OH | $CH_3$ | H |
| Galactose | OH | H | H | OH | H | OH | $CH_2OH$ | H |
| Galactosamine | OH | H | H | OH | H | NH2 | $CH_2OH$ | H |
| L-Fucopyranose | OH | H | H | OH | H | OH | $CH_3$ | H |
| L-Rhamnopyranose | H | OH | H | OH | H | OH | $CH_3$ | H |
| Hexuronic Acids: | | | | | | | | |
| D Glucopyranuronic acid | H | OH | H | OH | H | OH | COOH | H |
| D Galactopyranuronic acid | OH | H | H | OH | H | OH | COOH | H |
| D manopyranuronic acid | H | OH | H | OH | OH | H | COOH | H |
| D Iodopyranuronic acid | H | OH | H | OH | H | OH | H | COOH | sponding 5 amino nucleoside in the presence of triethoxy tetrafluoroborate in methylene chloride as the solvent.

A hapten (amidine TS analog) for galactose or equivalent sugar for the cleavable of glycosidic bond to liberate drug, said hapten having the formula:

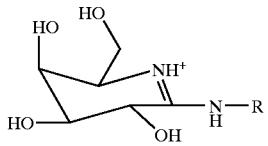

Definitions

Monosaccharide: A nonreducible naturally occurring sugars having the empirical formula $C_6H_{12}O_6$.

Hexopyranoses: Monosaccharides having six membered ring conformation.

Prodrug Group 14

Included in the invention are prodrugs comprising doxorubicin protected with aromatic carboxilic acid (substituted or unsubstituted) at the amino functionality of daunosamine (sugar portion) or esterified at primary hydroxy position of aglycone or esterified to hydroxy group of daunosamine.

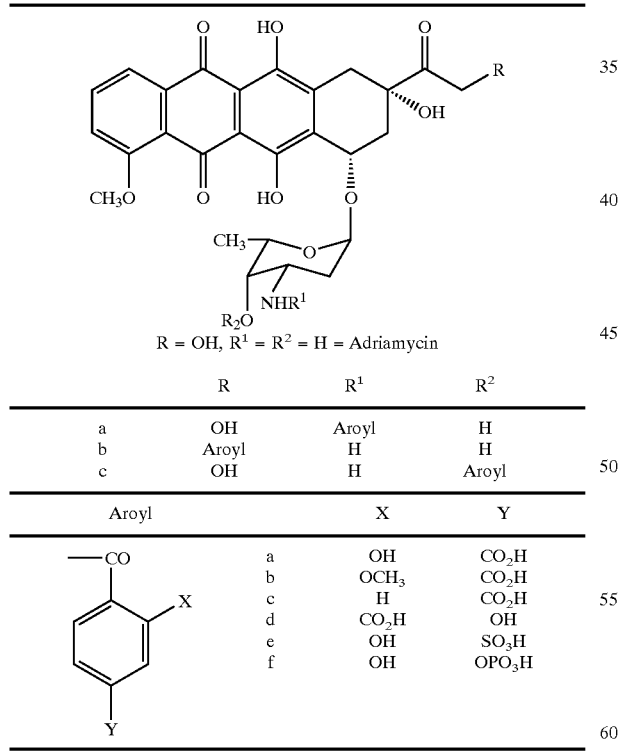

R = OH, $R^1$ = $R^2$ = H = Adriamycin

|   | R | $R^1$ | $R^2$ |
|---|---|---|---|
| a | OH | Aroyl | H |
| b | Aroyl | H | H |
| c | OH | H | Aroyl |

| Aroyl | X | Y |
|---|---|---|
|  | a  OH | $CO_2H$ |
|  | b  $OCH_3$ | $CO_2H$ |
|  | c  H | $CO_2H$ |
|  | d  $CO_2H$ | OH |
|  | e  OH | $SO_3H$ |
|  | f  OH | $OPO_3H$ |

Hapten Group 14

Haptens for the adriamycin and their analogs protected at amino group of daunosamine or primary hydroxyl group of aglycone or hydroxyl group of daunosamine.

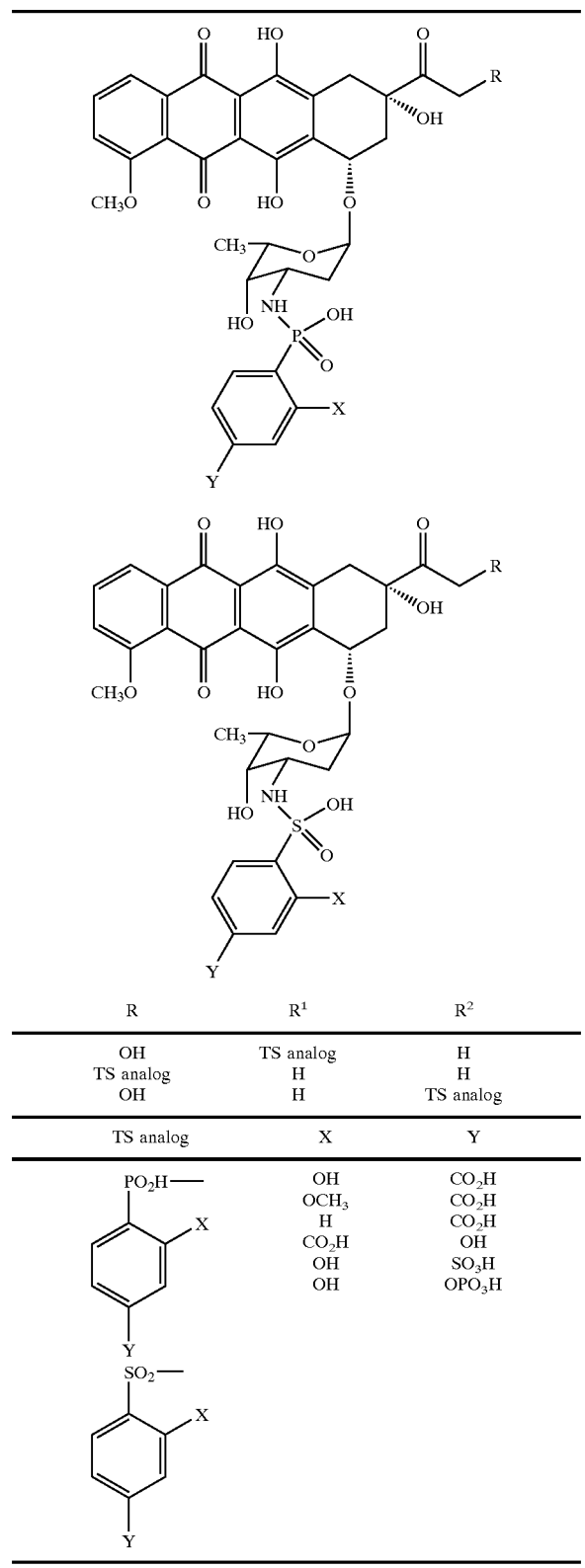

| R | $R^1$ | $R^2$ |
|---|---|---|
| OH | TS analog | H |
| TS analog | H | H |
| OH | H | TS analog |

| TS analog | X | Y |
|---|---|---|
| $PO_2H$— | OH | $CO_2H$ |
|  | $OCH_3$ | $CO_2H$ |
|  | H | $CO_2H$ |
|  | $CO_2H$ | OH |
|  | OH | $SO_3H$ |
|  | OH | $OPO_3H$ |
| $SO_2$— |  |  |

Prodrugs of Nucleoside Analogs

A number of cytotoxic nucleoside analogs have utility as antitumor agents, though there is often a low margin of safety. Effective antineoplastic doses of these drugs can have serious side effects, generally related to their toxicity toward normal tissues such as bone marrow or gastrointestinal mucosa.

5-Fluorouracil (5-FU) is a major antineoplastic drug with clinical activity in a variety of solid tumors, such as cancers of the colon and rectum, head and neck, liver, breast, and pancreas. 5-FU has a low therapeutic index. The size of the dose that may be administered is limited by toxicity, reducing the potential efficacy that would be obtained if higher concentrations could be attained near tumor cells.

5-FU must be anabolized to the level of nucleotides (e.g., fluorouridine- or fluorodeoxyuridine-5'-phosphates in order to exert its potential cytotoxicity. The nucleosides corresponding to these nucleotides (5-fluorouridine and 5-fluoro-2'-deoxyuridine) are also active antineoplastic agents, and in some model systems are substantially more potent than 5-FU, probably because they are more readily converted to nucleotides than is 5-FU.

The methods for localized delivery of fluorouridine to tumor cells of the subject invention have the advantage of providing high concentrations at the tumor site(s) with minimal systemic exposure. Another degree of tumor selectively is obtained through the rapid catabolism of fluorouridine (to form, initially, the less toxic 5-FU) that is not immediately taken up by tumor cells.

Similarly, arabinosylcytosine (Ara-C) is widely used in treating leukemias and lympohomas. Ara-C is rabidly degraded by cytidine deaminase, producing the inactive metabolite arabinosyluracil. Therapeutic use of Ara-C often results in side effects related to bone marrow suppression or damage to gastrointestinal mucosa. Targeted delivery of Ara-C, e.g., into lymphomas, results in increased therapeutic efficacy with minimized side effects.

A similar argument and rationale hold true for other antineoplastic nucleoside analogs, including but not limited to: fluorouracil arabinoside, mercaptopurine riboside, 5-aza-2'-deoxycytidine, arabinosyl 5-azacytosine, 6-azauridine, azaribine, 6-azacytidine, trifluoro-methyl-2'-deoxyuridine, thymidine, thioguanosine, 3-deazauridine.

In the present invention, prodrugs of antineoplastic nucleoside analogs are made by attaching an appropriate substituent to the 5' position of the aldose ring. A substituent in this position reduces toxicity of the drug, since cytotoxic nucleoside analogs must typically be phosphorylated (yielding a nucleotide analog) in order to manifest their toxicity. Substituents on the 5' position also render nucleoside analogs stable to the nucleoside-degrading enzymes uridine phosphorylase (which degrades uridine and analogs thereof) and cytidine deaminase (which degrades cytidine and analogs thereof). Prodrugs with substituents on the 3' position of the aldose ring of antineoplastic nucleoside analogs are also useful for targeted delivery of antineoplastic nucleoside analogs.

Prodrugs of Alkylating Agents

The present invention also provides novel methods and compounds for achieving localized delivery and formation of active alkylating agents.

Prodrug substituents of the invention, attached to certain cyclophosphamide metabolites (e.g., 4-hydroxycyclophosphamide or aldophosphamide) prevents their enzymatic and chemical breakdown to cytotoxic products. An appropriate protein catalyst, conjugated to a tumor-selective reagent, is administered prior to the prodrug; the catalyst thereupon produces active alkylating species in the vicinity of tumor cells after subsequent administration of the prodrug.

The present invention utilizes prodrugs related to cyclophosphamide, which is the most widely used alkylating agent in clinical practice, with utility in treating cancers of breast, endometrium, lung, as well as in treating leukemias and lymphomas. Cyclophosphamide, as such, is inactive and is converted primarily in the liver to 4-hydroxycyclophosphamide, which then breaks down further into cytotoxic metabolites. Thus, after cyclophosphamide administration, the active metabolites of cyclophosphamide are spread systemically via the circulation following release from the liver and cannot be concentrated in the area of tumor cells by; for example, localized injection. The active cytotoxic metabolites of cyclophosphamide are unstable or very toxic and thus, cannot be administered directly. Side effects of cyclophosphamide treatment include leukopenia, bladder damage, and alopecia. The present invention provides methods and compounds for providing suitable prodrugs of cytotoxic cyclophosphamide metabolites that are activated in one embodiment of the invention by catalytic antibodies.

Similar prodrugs and haptens related to other alkylating agents are within the scope of the invention. Other antineoplastic alkylating agents include but are not limited to alkyl sulfates such as busulfan, aziridines such as benzodepa or meturadepa, nitrosoureas such as carmustine, and nitrogen mustards such as chlorambucil, melphalan, ifosfamide or mechlorethamine.

Catalytic Proteins for Activating Prodrugs and Targeting the Prodrugs

Catalytic Proteins for Activating Prodrugs

In addition to the development of suitable prodrugs, a critical element in this therapeutic strategy is the choice of an appropriate catalytic protein for activation of these prodrugs.

a. Enzymes for Activating Prodrugs

The enzymes used in conjunction with the prodrugs of the prior art can be used with the novel prodrugs of the subject invention. The enzyme and catalytic activities used in the constructs of the subject invention are selected from: glycosidase, peptidase, lipase, hydrolase, oxido-reductase, transferase, isomerase, lyase or ligase. The preferred class comes from those enzymes and catalytic antibodies with glycosidase, peptidase, lipase, and other hydrolase activities. Specific examples are beta galactosidase, beta gulcosidases, inulinases, alpha-L-arabinofuranosidases and agarases. The primary aim is to select an enzyme activity not normally present in the serum or other body compartments to which the drug is exposed.

b. Antibodies for Activating Prodrugs

The catalytic antibodies of the subject invention are made using the novel haptens described herein with the techniques known to those skilled in the art for making catalytic antibodies.

Target Reagents

The targeting component of the targeting and activating compounds of the invention includes any agent which selectively binds or concentrates on or in the vicinity of a specific cell population for example, any antibody or other compound which binds specifically to a tumor-associated antigen. (Other examples include hormones, growth factor, substrates, or analogs of enzymes, etc. Examples of such antibodies include, but are not limited to, those which bind specifically to antigens found on carcinomas, melanomas, lymphomas and bone and soft tissue sarcomas as well as other tumors. Antibodies that remain bound to the cell surface for extended periods or that are internalized very slowly are preferred. These antibodies may be polyclonal or preferably, monoclonal, may be intact antibody molecules or fragments containing the active binding region of the antibody.

The system, according to the invention, may be used for delivering a drug at any host target site where treatment is required, providing the target site has one or more targetable components, for example, epitopes that are substantially unique to that site and which can be recognized and bound by the immunoconjugate. Particular target sites include those regions in a host arising from a pathogenic state induced by, for example, a tumor, a bacterium, a fungus or a virus; or as a result of a malfunction of a normal host system, for example, in cariovascular diseases, such as the formation of the thrombus, in inflammatory diseases, and in diseases of the central nervous system.

The use of genetic cloning and engineering methods have revolutionized the potential to generate reagents able to target an enzyme or catalytic antibody. This has been exemplified by the progress which has occurred in the area of immunology.

a. Antibodies which Bind Tumor Cells

Advantageously, antibodies which bind antigens that are expressed in high density on tumor cells and that do not shed from the tumor are used in the subject invention. These prerequisites are identical to those used in the related field of tumor imaging, and treatment using radiolabelled monoclonal antibodies.

A large number of monoclonal antibodies labelled with a variety of radionuclides, including $125_I$, $131_I$, $111_{In}$, $99_{mTc}$, $186_{Re}$, $90_Y$ have been used to visualize tumors. This work has shown that a variety of tumors can be successfully visualized by radio-immunoscintigraphic techniques. The tumor types that have been successfully targeted are listed in the table below. Antibodies to the listed antigens for example, will be used to target the prodrug activation embodied in this patent.

| Tumor Type | Tissue | Mab | Antigen | Reference |
|---|---|---|---|---|
| Carcinoma | G.I. tract with hepatic metastasis | NR-LU-10 | 40 kD glycoprotein | Goldrosen, M., et al., Cancer Research 50 (1990):7973–7978 |
| Adenocarcinoma | G.I. tract and other tissues | FO23C5 | Carcino-embryonic antigen (CEA) | Siccardi, A., Cancer Research 50 (1990):899s–903s |
| Carcinoma | Lung | KC-4G3 | Milk fat globule glyco-protein expressed as cytoplasmic (490 kD) and membrane (438 kD) antigen in tumors | Dienhart, D., et al., Cancer Research 50 (1990):7068–7076 |
| Carcinoma | Head/Neck and Vulva | E48 | Peptide epitope within 22 kD surface antigen | Gerretsen, M., et al., British Journal of Cancer 63 (1991):37–44 |
| Carcinoma | Larynx, pharynx and parotid gland | | CEA | Kairemo, K., et al., Acta Oncologica 29 (1990):539–543 |
| Carcinoma | Liver | NP-4 | CEA | Wang, Z., et al., Cancer Research 50 (1990): 869s–872s |
| Carcinoma | Breast | | CEA | Kairemo, K., et al., Acta Oncologica 29 (1990):533–538 |
| Carcinoma | Bladder | BW 431/26 | CEA | Boeckmann, W., et al., British Journal of Cancer 62 (1990):81–84 |
| Carcinoma | Ovary | HMFG1 | Milk fat globule glyco-protein (>200 kD) | Hird, V., et al., British Journal of Cancer 50 (1990):48–51 |
| Carcinoma | Pancreas | DU-PAN1 | Glycoprotein expressed in >50% of pancreatic tumors | Worlock, A., et al., Cancer Research 50 (1990):7246–7251 |
| Melanoma | Xenograft in nude mouse | G7A5 | High molecular weight-melanoma associated antigen (HMW-MAA). Gp 220 core protein of chondroitin sulfate proteoglycan (250–280 kD) | Le Doussal, J. M., et al., Cancer Research 50 (1990):3445–3452 |
| Melanoma | Lymph node | 225.28S and 763.24T | HMW-MAA (different epitopes) | Wahl, R., et al., Cancer Research 50 (1990):941s–948s |

-continued

| Tumor Type | Tissue | Mab | Antigen | Reference |
|---|---|---|---|---|
| Melanoma | Skin, lymph node | 225.28S | HMW-MAA | Siccardi, A., Cancer Research 50 (1990):899s–903s |
| Glioma | Brain | | | Williams, J., et al., Cancer Research 50 (1990):974s–979s |
| Glioma | Brain | EGFR1 | External domain of human and rat epidermal growth factor receptor | Kalofanos, H., et al., J. Nuc Med 30 (1989):1638–1645 |
| | | H17E2 | Placental alkaline phosphatase (67 kD) | |
| Germ-cell (seminoma and non-seminoma) | Testis | H17E2 | Placental alkaline phosphatase (67 kD) | Pectasides, D., et al., British Journal of Cancer 62 (1990):74–77 |

In some cases the use of subfragments of antibodies e.g., F(ab')2 has yielded enhanced specificity of tumor imaging when there has been shown to be a lower actual antigen concentration at the tumor site (Worlock, A., et al., *Cancer Research* 50 (1990):7246–7251; Gerretsen, M., et al., *British Journal of Cancer* 63 (1991):37–44). Successful imaging has been possible even in patients with significant serum concentration of antigens shed from the tumor (CEA, Boeckmann, W., et al., *British Journal of Cancer* 62 (1990): 81–84).

b. Other Targeting Proteins

In addition to the use of antibodies, any binding species can be used for binding a catalytic protein (be it enzyme or catalytic antibody) to the site of action. Growth factors have been used to deliver toxin molecules (Siegall, et al., *Proc. Natl. Acad. Sci. USA* 85 (1985):9738–9742; Chaudhary, et al., *Proc. Natl. Acad. Sci. USA* 84 (1987):4538–4542; Kondo J., et al., *Biol. Chem.* 263 (1988):9470–9475). Generation of analogous fusions using the growth factors interleukin 6, interleukin 2, transforming growth factor alpha, and others are made by linking enzymes or abzymes using the methods described in the above references. The incorporation of catalytic antibodies into these can be done via the fusion of these growth factors to the end of antibody single chain gene constructs (Patent Application WO 88/01649) or alternatively the growth factors could be fused to the front end of such gene constructs (at the 5' end of the gene or amino terminus of the protein). The use of constructs as described in Patent Application EP A 0,194,276 (Neuberger) could also be used to combine catalytic antibody activity and the binding properties of growth factors.

The use of human CD4-Pseudomonas exotoxin fusion has proved effective in the killing of HIV infected cells. The use of such a binding activity from CD4 linked to an enzyme or catalytic antibody allows the use of prodrug therapy directed at treatment of AIDS. The CD4 binds to the gp120 expressed on HIV1 infected cells. The converse of such a construct makes use of gp120-enzyme (or catalytic antibody) fusion to develop an immunosuppression reagent system (Moore et al., *Science,* 250, (1990):1139). Other binding species which are useable in the subject invention are the integrin family i.e., LAF-1, which can be used to modulate the immune system (Inghirami et al., *Science,* 250, (1990):682) and the selectinn family i.e., ELAM, which can be used to target tumors and immune cells (Walz, et al., *Science* 250 (1990): 1132).

Production of Bispecific Proteins a. Production of Bispecific Proteins by Chemical Linkage of Enzymes or Catalytic Antibodies to Targeting Proteins The enzymes of this invention can be covalently bound to the targeting proteins of this invention by techniques well known in the art such as the use of the heterobifunctional cross-linking reagents SPDP (N-succinimidyl-3(2-pyridyldithio)proprionate) or SMCC (succinimidyl 4-(N-maleimidomethyl)cyclohexane-1-carboxylate [see, e.g., Thorpe, P. E., et al., "The Preparation And Cytotoxic Properties Of Antibody-Toxin Conjugates." *Immunological Rev.,* 62 (1982):119–58; Lambert, J. M., et al., supra at p. 12038; Rowland, G. F., et al., supra, at pp. 183–84 and Gallego, J., et al., supra, at pp. 737–38].

b. Production of Bispecific Proteins by Recombinant DNA

Fusion proteins comprising at least the antigen binding region of the targeting protein of the invention linked to at least a functionally active portion of an enzyme or catalytic antibody of the invention can be constructed using recombinant DNA techniques well known in the art [see, e.g., Neuberger, M. S., et al., *Nature* 312, (1984):604–608 (1984)]. These fusion proteins act in essentially the same manner as the antibody-enzyme conjugates described herein.

Recombinant DNA methods have been used to express antibody genes in mammalian systems (Oi, V. T., et al., *Proc. Natl. Acad. Sci. USA* 80 (1983):825–829; Neuberger, M. S., *EMBO* 2 (1983):1373–1378). Further expression and recovery of biologically active immunoglobulin proteins (human IgE Fc fragment) from *E. coli* has been demonstrated (Kenten, J. H., et al., *Proc. Natl. Acad. Sci. USA* 81 (1984): 2955–2960) and expression and recovery of whole active antibody has been demonstrated (Boss, M. A., et al., *Nucleic Acids Res.* 12 (1984):3791–3799). This was followed by other groups demonstrating the generality of the potential to generate both immunoglobulin binding and effector function activities in *E. coli* (Cabilly, S., et al., *Proc Natl. Acad Sci USA* 81 (1984):3273–3277; Skerra, A., et al., *Science* 240 (1988):1038–1040; Better, M., et al., *Science* 240 (1988): 1041–1043). These skills and abilities have also been applied to manipulation of many other genes.

The following are examples of the prodrug targeting reagents. Most of these depend on the ability to clone, manipulate and express genes as described above.

The use of genetically engineered antibodies as outlined above provide a route to a well-defined and reproducible reagent which allow the rapid analysis of the effectiveness of the various prodrugs. These methods of antibody engineering are exemplified in European Patent Application EP A 0,194,276 (Neuberger) in which the heavy chain gene is truncated by removal of the CH2 and CH3 domains, followed by the addition of various genes. Introduction of the required enzymatic activity follows these basic procedures. To achieve the optimized level of enzyme activity, manipulation of the sequences between the antibody and enzyme may be needed. Addition of linker sequences and/or alteration of the fusion site may be needed for this optimization. In addition, to the advantage of a defined antibody-enzyme reagent, the reduced size possible by the removal of the CH2 CH3, and the CH4 in the case if IgE and IgM heavy chains, is valuable.

Generation of antibodies which are bispecific is well-known to the art (Shawler, et_al., Immunol. 135 (1985): 1530–1535; Kurokawa, T., et al., Bio/Technology 7 (1989): 1163–1167). Examples of the functionality of such bispecific antibodies are the tumor specific antibodies which also bind to metal chelates for use in tumor therapy, and also the bispecific antibodies which bind to tumor cells and T cells (Johnson, M. J., et al., Patent Application EP 369566A, 1990; and Gilliland L. K., et al., Patent Application GB2197323, 1986). Methods for generation of bispecific antibodies consist of chemical methods of separation and recombination of the antibody chains or by the fusion of the two hybridomas to generate so called quadromas. These methods are effective but are prone to generate mixed species and require purification to isolate the desired products.

Generation of smaller binding species has been the goal of much research in antibody engineering. This has led to the development of single chain antibodies, in which the variable (V) region of the two antibody chains are combined into a single molecule using a linker sequence (Patent Application WO 88/01649, Ladner and Bird). This combination of V regions results in expression of a protein which has one of the V regions at the amino terminus and the other V region attached at its COOH terminus via the linker to its amino terminus. This head to tail, head to tail linkage of V regions has been described with both V light chain—V heavy chain and V heavy chain—V light chain orientations. The utility of these systems has been developed with the addition to single chain antibodies of other proteins (Vijay, et al., Nature 339 (1989):394–397). This format, for the addition of other proteins to the end of single chain antibodies, is used for the production of similar molecules making use of desired enzyme genes to affect these constructions. This results in the production of molecules having the desired properties of antibody binding and enzymatic activity in a small molecule ideally suited for therapy.

To engineer the production of two antibody activities into a bispecific molecule in a single chain or equivalent small molecule follows the outline below using methods well known to those skilled in the art.

The construct would consist of: the V Heavy chain region (VH) linked to the V Light chain region (VL); specific for the tumor cell or antigen via the linkers described for single chain antibodies (Vijay, et al., Nature 339 (1989):394–397; Patent Application WO 88/01649, Ladner and Bird); these sequences would be linked directly to the catalytic antibody VL which would, in turn, be linked to its VH partner via a linker sequence. The V region combinations can also follow VL-VH-VH-VL or VL-VH-VL-VH or VH-VL-VH-VL sequences. The linker sequences used in these constructions are those described above for single chain antibody construction. This combination allows the expression of a single chain bispecific antibody previously unknown. Such a molecule allows the production of large amounts of such a bispecific activity without the purification and characterization problems encountered with other methods. This molecule also has the low molecular weight desirable for such a reagent. Another species based on similar construction would describe a previously unknown molecule as follows. The VH region specific for the tumor or antigen linked directly to the VL region of the catalytic antibody; this molecule is advantageously expressed separately or together with the other construct of VL specific for the tumor or antigen linked directly to the VH of the catalytic antibody. The expression of these two molecules together, or by post expression mixing, would associate to form a bispecific antibody. Other combinations of V regions lead to similar molecules. This molecular species is favored over the molecule above as it has a lower molecular weight. The use of single domain binding proteins is also valuable to explore in the form of direct fusions to enzymes or catalytic antibodies (Patent Application WO 90/05144, Winter).

Humanization of Antibodies

It will be appreciated that the humanization of antibodies and other reagents is valuable to reduce the immune response. Reagent antigenicity has been a problem in early mouse antibody treatments which have been made ineffective by patients mounting a significant antibody response to the mouse antibodies (Patent Application EP A 0 194 276, Neuberger; Patent Application EP A 0 239 400; LoBuglio, A. F., et al., Proc Natl Acad Sci USA 86 (1989):4220–4224). The immune response is not only associated with the constant regions of the antibody but is also with the variable region domains giving rise to a strong anti-idiotypic response (Bruggemann, M., et al., J. Exp. Med. 170 (1989): 2153–2157; Shawler, D. L., et al., Immunol. 135 (1985): 1530–1535).

The value of humanization methods for the generation of therapeutically valuable proteins has been demonstrated by humanization of mouse antibodies by replacement of the V-region framework. This humanization method makes use of the basic structure of the binding site with its antigen-binding loops which are fairly well determined (Kabat, E. A., et al., U. S. Dept. of Health and Human Services, U. S. Government Printing Office, 1987). The replacement of the framework with human sequences while retaining the loops from the original antibody effectively transfers the antigen binding from a mouse to a human structural context (Riechmann, L., et al., Nature 332 (1988):323–327; Jones, P. T., et al., Nature 321 (1986):522–524,; Verhoeyen, M., et al., Science 239 (1988):1534–1536; Queen, C., et al., Proc Natl Acad Sci USA 86 (1989):10029–10033). With this humanization technology certain assumptions have been made; A) the contribution of the hypervariable loops to binding; B) the conservation of framework structure, and that C) the loops all interact with the framework in similar ways. With the use of basic molecular modelling, the humanization can be optimized improving the degree of success (Riechmann, L., et al., Nature 332 (1988):323–327).

These methods aimed at humanization are applicable to enzyme activities. The use of structural analysis allows grafting of homologous outer loop regions in order to camouflage the antigenicity, if enzymes with similar structures to a human protein can be found. Problems of antigenicity can also be obviated by the use of covalent modification i.e., polyethylene glycol modification of the surface of the protein.

Antibody Expression Vectors

Recent advances in the application of PCR cloning of immunoglobulin genes has led to the ability to produce antibody expression libraries in *E. coli.* (Huse, W. D., et al., *Science* 246 (1989):1275–1281). The phage lambda based system generates a library of phage plaques that secrete Fab which can then be screened by a filter binding assay using radiolabeled hapten (Caton, A. J., et al., *PNAS*, USA 87 (1990):6450–6454). Although potentially valuable for isolating plaques with a desired binding activity, each clone must be individually screened if one is attempting to isolate an antibody mediated catalytic activity.

An alternative approach, not previously described, is to use a plasmid based rather than phage lambda based system for production of the antibody expression library. In this system, rather than having the VH and VL genes as separate transcription units, they are covalently linked by a short peptide to produce a single chain antibody as defined by Bird, E., et al., *Science* 242 (1988):423–426). Using appropriate PCR primers, a combinatorial single chain antibody library consisiting of essentially random associations of VH and VL is generated by a single step PCR methodology previously described (Davis, G. T., et al., *Bio/Technology* (1991) in press.). The single-chain PCR product is cloned into a suitable *E. coli* expression vector containing an inducible promotor such as Ptac. A signal sequence, such as pelB, is added 5' of the cloned single-chain to allow secretion of the expressed antibody protein (Better, M., et al., *Science* 240 (1988):1041–1043). Unlike the phage lambda expression system in which the *E. coli* are lysed, the plasmid based expression system described allows the possibility of directly screening an *E. coli* library for catalytic antibodies using direct selection. One possible selection method, inactivation of a beta-lactam or beta-lactam derivative, is described in the section "Screening for Catalytic Antibodies", part A2, p.41 of this patent. Other possible selection methods include antibody catalyzed release of a nutrient, vitamin or cofactor essential for the growth of the *E. coli.* One such selection procedure utilizing thymidine requiring auxotrophs is described in section Screening for Catalytic Activation of Nucleoside Analogue Prodrugs, part A2, herein.

Mutagenesis

VH and VL domains from *E. coli* clones that express antibody with a desired binding or catalytic activity can be mutagenized to alter or enhance antibody function. The specific CDR amino acid residue(s) to be targeted for mutagenesis can be identified by molecular modelling of the antibody active site. Mutagenesis is accomplished by one of a variety of previously described site-directed mutagenesis procedures using mutagenic oligonucleotides (Maniatis, T., et al., *Molecular Cloning: A Laboratory Manual,* (1989): 15.51–15.65, New York: Cold Spring Harbor Laboratory).

If selective mutagenesis is not able to produce the desired result, more wholesale alterations of the active site are made. One useful methodology is replacement of one, few or several CDRs with sets or partial sets of random amino acids. This random mutagenesis procedure was successfully used to alter the activity of a beta-lactamase enzyme (Dube, D. K., et al., *Biochemistry* 28 (1989):5703–5707; Oliphant, A. R., et al., *PNAS*, USA 86 (1989):9094–9098). The method described involved introduction of random amino acids into the enzyme active site by replacement of the DNA sequence encoding that portion of the active site with a random oligonucleotide.

Random mutagenesis of an antibody CDR region is accomplished by any of a number of different methods. One example of a protocol that is used to randomly mutagenize CDR1 VH of an anti-fluorescein monoclonal antibody (Mab 4-4-20, Bedzyk, W. D., et al., *JBC* 264 (1989):1565–1569) is presented in detail below.

1. An oligonucleotide of the following sequence (SEQ ID NO:1) shown below is synthesized on an automated DNA synthesizer. The number above certain nucleotide triplets corresponds to the amino acid position within 4-4-20 VH as designated by Bedzyk, et al., 1989.

5'-TCCTGTGTTGCCTCTGGATTCACTTT-
   TAGT(NNKNNKNNKNNK)AACTGGGTCCGC-
   CAGTCTCCAGAGAAAGGA-3"

In the sequence above, VH CDR1 (amino acids 31–34) is replaced with a random nucleoide sequence where N is A, C, G, r T (equimolar) and K is G or T (equimmolar). Excluding A or C at the the third position in each triplet will reduce the number of potential termination codons by two thirds as reported by Cwirla, S. E., et al., *PNAS*, USA 87 (1990): 6378–6382.

2. A second oligonucleotide is synthesized which is complimentary to the last 20 base pairs at the 3' end of the oligonucleotide from Step 1. Following phosporylation with T4 kinase, oligonucleotides are annealed and then added to a primer extension reaction containing deoxynucleotides and Klenow fragment. The resulting full length double stranded random oligonucleotide is purified by polyacrylamide gel electrophoresis or reverse phase HPLC.

3. Double stranded random oligonucleotide from Step 2 can serve as a "sticky foot" primer in the "sticky foot" mutagenesis procedure described by Clackson, T., et al., *NAR* 17 (1989):10163–10170. This procedure will result in replacement of the wild type VH CDR1 present in the template strand with a random CDR1 sequence specified by the random oligonucleotide described in Step 1.

4. Following sticky foot mutagenesis the DNA from step 3 is used to transform *E. coli* resulting in an antibody library in which VH CDR1 is replaced with a random sequence.

5. The resulting library can be screened by binding assays with appropriate hapten or selection assays as described herein.

Additional CDR regions of either VH or VL can be randomly mutagenized in a similar fashion. In addition, one, two, or all three CDR regions within a VH or VL chain can be mutagenized simultaneously. Due to limitations on the length of an oligonucleotide that can be synthesized on an automated machine, 3 separate random oligonucleotides corresponding to each of the 3 CDR regions can be made as described in Step 1 above. During oligonucleotide synthesis, restriction sites are incorporated at appropriate positions within framework regions that flank each of the CDRs. Following conversion into double stranded DNA as in Step 2 above, each oligonucleotide is digested with the appropriate restriction enzyme and the oligonucleotides are ligated together to produce a complete VH or VL. The final ligated product is then used as a "sticky foot" primer as in Step 3 above.

An alternative approach to the method described above is to engineer restriction enzyme sites into the framework regions on each side of the CDR VH or VL to be mutagenized. During synthesis of the random oligonucleotide as in Step 1 above, compatible restriction sites are then added to the framework flanking regions. Restriction sites are chosen so as to best preserve the wild type coding sequence within the framework region. The wild type CDR region is then removed by digesting with the appropriate restriction enzyme and replaced with the double stranded random oligonucleotide digested with compatible restriction enzymes.

Selection of New Binding Activities Using Mutagenesis and Selection in Filamentous Phage Selection of mutant antibodies by selection for growth under selective conditions has been illustrated (see the section entitled, "Screening of Mutant Catalytic Antibodies in *E. coli*). In concert with these methods for selection and mutagenesis, the use of methods described by Cwirla S., et al., *PNAS*, 87 (1990):6378–6382; and McCafferty J., et al., *Nature*, 348 (1991):552–554 help generate/improve catalytic antibodies for prodrug activation.

These methods have allowed for the generation of vast libraries of peptides and the screening via the binding of the resultant mutants. By taking the mutant single chain antibodies generated in the protocol as outlined above and inserting these into the adsorption protein (gene III) of the filamentous bacteriophage, fd. The site for the introduction of the PCR cloned and mutagenized single chain antibody is 5–6 amino acids from the N terminus of the adsorption protein (gene III). This allows for the presentation of the antibody for binding to antigen. The vector (fd-CAT1) after insertion of the single chain antibody gene is then used to electrotransform *E. coli* TG1 (K12, (lac-pro), supE, thi, hsdD5/F' traD36, proA+B+ lacIq, lacZM15) or similar host.

The transformed *E.coli* are then subjected to selection using the tetracycline resistance of the vector. This phage library is cultured on plates allowing its amplification and the estimation of the library size (library sizes in the range of $10^{12}$ allow the screening of random mutants at 9 sites in the antibody).

This library is then subjected to amplification in liquid culture the resultant phage in the supernatant are concentrated using polyethylene glycol precipitation and dissolved in PBS with 2% skimmed milk powder. These phage are then mixed with, for example 100 $\mu l$ of solid phase-antigen, such as epoxy activated Sepharose CL-6B (Sigma Ltd) reacted with a suitable antigen, for the selection of the desired binding activity. The candidate compounds for use in this selection would include those described in FIGS. 1*b*, 2*b*, 3*b*, 5*b*, 5*c*, 7, 8*c*, 30, 34, 36, 37, 39, 40. These antigens used for the raising of antibodies can also be coupled indirectly to a solid phase, such as epoxy activated Sepharose CL-6B, via coupling to a protein carrier. The choice of carrier protein is made such that the protein used for immunization would not be used, preventing the potential of isolating non-specific antibodies to the carrier protein.

Ensuing the binding, adsorbed phage is then separated by centrifugation followed by a series of wash steps removing the non-specific or weakly binding activities. The nature of the wash steps is such as to select for the type and nature of the interactions with the antigen of choice, i.e. selection of high salt washes would reduce the binding due to ionic interactions, or use of ethylene glycol would enable the reduction of hydrophobic interactions in favor of other binding affinities for example. An enhanced selection based on these wash conditions is not restricted to these broad based wash conditions but would also encompass the use of specific wash protocols based on the use of related antigens or substrates for the desired reaction. The elution of pools of phage is also based on the same set of criteria as used for the washes. The results of the combination of these approaches allowed selection of a vast matrix of related binding activities.

The desired pool(s) of binding activity is then amplified and subjected to detailed analysis of their binding and catalytic properties. The application of these types of selective washes and elutions enables the selection of desired properties. This need not be the final step in the process of mutagenesis and selection but is a stage on the route the desired structures with catalytic activity. Thus, this protocol would allow successive rounds of selections to mature the binding site.

The isolated potential candidate antibodies with or without catalytic activity are then introduced in the expression systems described above for the selection of activity based on the further selection directly for catalytic activity using antibiotic or auxotrophic selection (see Section B, part 2, p. 77). Also, these candidate molecules are selected for further rounds of mutagenesis and selection using this phage system. The technical details of this phage library approach are described in the publications by Cwirla, S., et al., *PNAS*, 87 (1990):6378–6387; and McCafferty, J., et al., *Nature*, 348 (1991):552–554.

Screening for Catalytic Antibodies

A. Selection of Antibodies for Beta-Lactamase Activity

Selection of catalytic activation of monolactam-based prodrugs can be done using antibodies produced by hybridomas or by mutating antibodies in *E. coli* to improve catalytic efficiency of existing antibodies.

1. Screening Hybridoma-based Antibodies for Beta-Lactamase Activity

In vitro detection of catalytic hydrolysis of monolactam prodrugs can be carried out with either hybridoma supernatant antibodies immobilized to plastic 96 well plates (by a method described below) or in solution with antibodies purified from ascites fluid.

Immobilization: Those hybridomas producing antibodies binding to hapten in an ELISA assay were selected for screening. Supernatants were pooled from exhausted 5 mL cultures, and the pH adjusted to 7–7.5 with 2N NaOH (20 $\mu L$). Cell debris was removed by centrifugation for 30 minutes at 2700 rpm, and supernatants (4 mL) were decanted into clean polypropylene tubes. Anti-mouse immunoglobulin affinity gel (Calbiochem, binding capacity 0.5–2 mg of immunoglobulin per mL of gel) was added as a 50% slurry in PBS (140 $\mu L$, containing 70 $\mu L$ of gel) and the resulting suspensions were mixed gently for 16 hours at 25° C. A 96 well Millititer GV filtration plate (Millipore) was pre-wetted and washed in PBS containing 0.05% Tween-20. The affinity gel suspensions were spun in a centrifuge at 2500 rpm for 15 min, the bulk of the supernatant was removed, and the residual slurries (250 $\mu L$) from each polypropylene tube were each transferred to separate wells in the 96 well filter plate. Residual supernatant was removed by aspiration through the filter plate and the immobilized antibody was washed at 4° C. with PBS/Tween (5×200 $\mu L$), PBS (3×200 $\mu L$), and 25 mM HEPES, pH 7.2 (3×200 $\mu L$).

Following appropriate incubation of antibody with prodrug, separation of drug from unhydrolyzed prodrug can be accomplished by standard HPLC procedures. Hydrolysis of the prodrugs will result in liberation of an aromatic drug that can be easily detected by absorbance spectroscopy. Detection and quantitation of drug produced can be quantitated by an online spectral detector.

2. Screening Antibodies in *E. coli* for Beta-Lactamase Activity

Efficiencies of catalytic antibodies are often substantially below those of natural enzymes. If current technologies are used to raise catalytic antibodies, many will be unsuitable for effective commercial use without improvement by chemical or genetic alteration. Catalytic antibodies with b-lactamase activity will be particularly amenable for improvement by genetic mutation because their catalytic activity provides a rapid and convenient means by which host colonies of E. coli expressing antibody can be screened for activity. Because E. coli (especially certain hypersensitive strains (Imada, A., et al., Nature 289 (1981):590–591; Dalbadie-McFarland, G., et al., Proc. Natl. Acad. Sci. USA 79 (1982):6409–6413) is killed by b-lactam antibiotics, a secreted antibody with b-lactamase activity will confer resistance to b-lactam toxicity. The more catalytically efficient the mutant antibody, the higher the minimum inhibitory concentration (MIC) of antibiotic for the host E. coli. Methods such as random mutagenesis of the genes for mildly catalytic antibodies will result in large numbers of E. coli colonies, creating large numbers of unique antibodies. Increased resistance to an appropriate b-lactam antibiotic will provide a rapid and efficient basis for screening enormous numbers of mutants and signal those antibodies with efficiencies above those of wild type antibodies.

Prodrug Strategy: Elimination of an Active Drug from the b-Lactam Ring

An active drug can be generated from an inactive prodrug as a consequence of hydrolysis of a substituted monocyclic b-lactam ring:

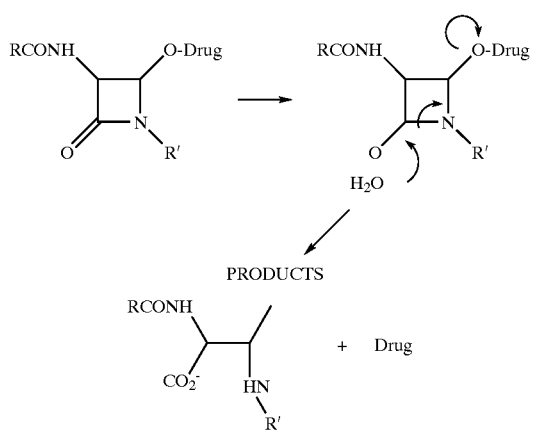

The substituents (R and R') will specifically depend on what is required to make the b-lactam an effective agent for disrupting the cell wall of a b-lactamase enzyme-deficient E. coli causing death or impaired growth. In addition, these substituents may be used in coupling a carrier protein (KLH or BSA) during immunization.

Cloning and Mutation of Antibodies to Improve Catalytic Activity

Antibody genes producing catalytic antibodies will be cloned and expressed in E. coli. It will be critical to use a strain of E. coli that is hypersensitive to b-lactam antibiotics (i.e., one that lacks natural defenses against b-lactam antibiotics). Such strains exist that lack b-lactamase enzymes and/or penicillin binding proteins (Imada, A., et al., Nature 289 (1981):590–591; Dalbadie-McFarland, G., et al., Proc. Natl. Acad. Sci. USA 79 (1982):6409–6413). E. coli colonies will contain plasmid DNA encoding antibody genes mutated by either site-directed or random mutagenesis. The organisms will express and secrete altered antibody. Because many clones will be generated, each clone secreting antibodies of a different amino acid sequence, a rapid and labor-unintensive method of determining which mutants have increased catalytic activity will be used.

Screening of Mutant Catalytic Antibodies in E. coli

A sensitive and convenient method to screen E. coli mutants producing antibodies with b-lactamase activity is to detect the altered ability of the mutant to resist toxicity of a b-lactam antibiotic that resembles the prodrug. A critical feature of this method is that the structures of the hapten, the prodrug, and the effective antibiotic used in screening must all be similar enough to be recognized by the antibody. The hapten must elicit antibodies that not only bind and hydrolyze the prodrug but also an antibiotic (prodrug minus the drug) used to challenge the host organism, E. coli. An additional feature to be considered in the design of the prodrug is that upon hydrolysis it must expel the active drug. Based on these criteria, a number of different structures can be used for the prodrug as described elsewhere herein. One attractive example is to have a prodrug derivative of the monobactam antibiotic, aztreonam (Koster, W. H., et al., Frontiers of Antibiotic Research, ed. H. Umezawa., (1987) :211–226 Orlando, Academic Press).

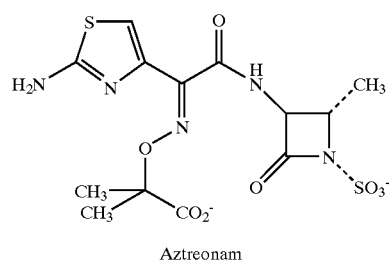

Aztreonam

Aztreonam is an effective antibiotic against E. coli (MIC= 0.1 mg/mL) and is not degraded by human enzymes in the bloodstream. Haptens can be designed and prepared that will hydrolyze the b-lactam ring of modified aztreonam to give elimination of an active drug.

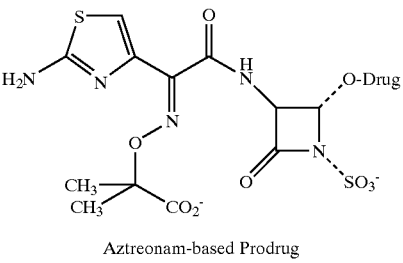

Aztreonam-based Prodrug

Screening (in hypersensitive strains of E. coli) for efficient catalytic antibody-producing mutants is accomplished by challenging the host antibody-secreting colonies with aztreonam itself rather than with the actual prodrug. This is done because aztreonam (or a similar antibiotic) itself is an effective antibiotic against E. coli although it is not clear what effect the addition of the drug (modified aztreonam) will have on aztreonam's antibiotic properties. The presence of the drug portion may abolish or diminish the antibiotic action of aztreonam on E. coli. Screening with aztreonam rather than with the larger aztreonam-drug conjugate is acceptable because the antibodies are raised to a hapten that included the drug or an analog thereof and mutant antibodies will retain the capability to bind the drug. Screening is done by standard methods such as agar dilution (Sigal, I. S., et al., Natl. Acad. Sci. USA 79 (1982):7157–7160; Sowek, J. A., et al., Biochemistry 30 (1991):3179–88) or by using concentration gradients of aztreonam (Schultz, S. C., et al., J. Proteins 2 (1987):290–297).

Characterization of Mutants

E. coli colonies found to be resistant to aztreonam are grown in larger quantities so that milligrams of antibody can be expressed and purified for further in vitro characterization. At this stage, antibodies will be purified and characterized in a buffered solution. A critical kinetic property is the ability to efficiently hydrolyze the b-lactam prodrug resulting in elimination of the active drug species. Lack of strong product inhibition by the prodrug (substrate), hydrolyzed aztreonam, or by the activated drug is required as well as efficient hydrolysis in human serum.

B. Isolation of Catalytic Antibodies that Activate Nucleoside Analog Prodrugs

Catalytic antibodies that activate nucleoside analog prodrugs can be isolated by either of two general principles; in vivo by selection methods or screening hybridoma-produced antibodies by physicochemical methods (screening methods). The in vivo isolating method described below can be applied to screening antibodies for all of the nucleoside analog prodrugs. The screening methods are divided into two types based on the two kinds of inactivating groups claimed. One type of screening methods detects esterase activity and the other detects glycosidase activity. Screening can either be applied to antibodies purified from mouse ascites fluid, or at an earlier stage, to antibodies present in hybridoma supernatants. The methods listed here are specifically described for early screening of hybridoma supernatants for catalytic activity but can easily be adapted for the screening and assay of monoclonal antibodies purified from ascites.

1. Screening of Catalytic Activation of Nucleoside Analog Prodrugs

Screening is either carried out at an early stage in hybridoma supernatants using the immobilization procedures described in section A, or at a later stage using antibodies puried from mouse ascites.

Screening Antibodies for Galactosidase Catalytic Activity

To either antibody free in solution or antibody washed and immobilized, a solution of the prodrug in the appropriate assay buffer is added. Following incubation at 25° C. for a time dependent on the uncatalyzed rate of prodrug activation, formation of activated drug is measured. The substrate solution is either removed from the well (in the immobilization method) to determine the extent of product formation or the product is measured in situ (as in the case of antibody free solution).

Detection of prodrug activation is carried out by colorometric or fluorometric determination of the generation of galactose, which accompanies prodrug activation.

One of a number of possible galactose detection methods is employed. Some sensitive and specific detection methods follow:

1. Radiolabelling of Free Galactose with $^{32}$P-phosphate a) Galactokinase (E.C. 2.7.1.6) is commercially available (Sigma Chemical Co., St. Louis, USA) and catalyzes the following reaction;

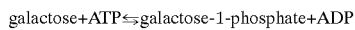

galactose+ATP⇌galactose-1-phosphate+ADP

If the ATP (adenosine triphosphate) used has $^{32}$P in the gamma phosphate position, free galactose generated by catalytic antibodies becomes radioactively-labelled. Labelled galactose-1-phosphate is separated from the other constituents in the reaction mixture by thin layer chromatography (TLC) or high performance liquid chromatography (HPLC) and quantitated by scintillation counting.

2. Detection of Catalysis Using Fluorescent or Chromophoric Aldehyde-reactive Reagents In this type of detection method, galactose is non-catalytically reacted with commercially available (from, for example, Molecular Probes, Inc., Eugene, Oreg.) aldehyde-reactive reagents to yield a colored or fluorescent derivative. The product of the reaction with galactose is isolated by HPLC or by TLC and detected by absorbance or by fluorescence by standard means.

One potential reagent is dansyl hydrazine (Molecular Probes, Inc.). Dansyl hydrazine reacts under mild conditions with aldehydes to give a fluorescent product (Eggert, F. M., et al., J. Chromatogr. 333 (1985):123; Avigad, G., J. Chromatogr. 139 (1977):343) that is detectable at low concentrations upon TLC or HPLC of the reaction mixture. Other potential reagents that are more useful than dansyl hydrazine because of possible lower detection limits, greater reaction specificity, or milder reaction conditions are other fluorescent hydrazides that are commercially available such as coumarin hydrazide, fluorescein thiosemicarbazide (Molecular Probes, Inc.). These reagents are compared to see which best suits the specific requirements.

3. Detection of Galactose with Color-generating Specific Enzymes a) One enzyme that can be used to detect galactose is galactose dehydrogenase (E.C. 1.1.1.48) (Sigma Chemical Company, St. Louis, Mo., USA) which catalyzes the following oxidation-reduction reaction;

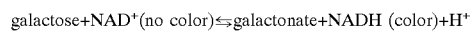

galactose+NAD$^+$(no color)⇌galactonate+NADH (color)+H$^+$

The oxidation of galactose is accompanied by the reduction of nicotinamide adenine dinucleotide (NAD$^+$). The oxidized form of NAD$^+$, NADH, is colored and its appearance is monitored spectrophotometrically at 340 nm.

b) An alternative enzyme that is useful in detecting galactose is galactose oxidase, (E.C. 1.1.3.9) which, used in combination with peroxidase and o-tolidine, will cause a color change in response to the presence of free galactose generated by a catalytic antibody. The coupled reactions are as follows. The first reaction is catalyzed by galactose oxidase and the second by peroxidase, both available from Sigma Chem. Company;

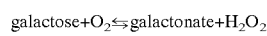

galactose+O$_2$⇌galactonate+H$_2$O$_2$   1.

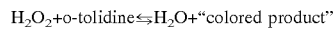

H$_2$O$_2$+o-tolidine⇌H$_2$O+"colored product"   2.

The colored product generated can be measured spectrophotometrically.

Screening Antibodies for Esterase Catalytic Activity

To immobilized washed antibody or antibody free in solution, a solution of the prodrug (unless otherwise indicated) in the appropriate assay buffer is added. Following incubation at a suitable temperature such as 25° C. for a time dependent on the uncatalyzed rate of prodrug activation, formation of activated drug is measured as described.

Detection of prodrug formation can be detected by pH change that accompanies ester hydrolysis in weakly buffered solutions. Changes in pH can be detected by including an acid-base indicator in the solution, such as phenol red (Benkovic, P. A., et al., Biochemistry 18 (1979):830), which changes color with pH change. Alternatively, a method that is more sensitive is to use a pH stat or pH meter equipped with a fine-tipped electrode that can be inserted into the wells (Lazar Research Laboratories, Los Angeles, Calif.) to measure pH changes. For screens involving measuring changes in pH, it may be necessary during the incubation to keep the wells under nitrogen gas to prevent pH changes from atmospheric carbon dioxide.

Hydrolysis of aromatic ester-protected prodrugs results in the liberation of an acidic aromatic group which can easily be separated by conventional chromatographic means on an HPLC (anion exchange or reverse phase columns). Furthermore, detection of the aromatic ring eluting from the HPLC can be easily accomplished using an online UV absorbance detector.

A third method for in vitro detection of hydrolysis of aromatic ester nucleoside analogs is to use an enzyme-linked assay. One inexpensive commercially-available enzyme (Sigma Chemical Company, St. Louis, Mo.) that could be used for this purpose is thymidine phosphorylase (E.C. 2.4.2.4). This enzyme converts the substrates thymidine and orthophosphate to the products thymine and 2-deoxy-D-ribose-1-phosphate. Rather than the prodrug being screened here, a conjugate of the inactivating ester with thymidine will be used (the same types of compounds that will be used in biological screening with auxotrophic bacterial mutants). This enzyme will not catalyze the phosphorylation of the aromatic ester protected thymidine, but only free thymidine produced by the catalytic antibody. To the wells will be added the thymidine phosphorylase, the thymidine version of the prodrug, and $^{32}$P-labelled orthophosphate. After incubation of the buffered components with the immobilized antibodies, aliquots are run on TLC to separate radiolabelled orthophosphate and 2-deoxy-D-ribose-1-phosphate. The $^{32}$P can then be detected on the TLC plates by autoradiography.

2. Thymidine Auxotrophic Selection for Isolation of Catalytic Antibodies with Esterase Activity for Nucleoside Analogue Prodrugs Bacterial expression of antibodies promises to provide large numbers of different antibodies to screen for catalytic activity. However, the usefulness of this methodology is dependent on the availability of effective methods of selecting those colonies producing active antibody. A powerful approach is to use biological selection, in which only those colonies producing catalytic antibody are able to survive. One way in which this selection can be carried out is for the catalytic antibody to supply a particular nutrient in which the bacteria are deficient; survival is dependent on the antibody cleaving a substrate which releases the required nutrient. This type of selection to obtain prodrug-cleaving catalytic antibodies, is described below.

To produce a catalytic antibody capable of cleaving a prodrug, thereby releasing a nucleoside analogue (e.g., fluorouridine, fluorodeoxyuridine, fluorouridine arabinoside, cytosine arabinoside, adenine arabinoside, guanine arabinoside, hypoxanthine arabinoside, 6-mercaptopurineriboside, theoguanosine riboside, nebularine, 5-iodouridine, 5-iododeoxyuridine, 5-bromodeoxyuridine, 5-vinyldeoxyuridine, 9-[(2-hydroxy) ethoxy]methylguaine (acyclovir), 9-[(2-hydroxy-1-hydroxymethyl)-ethoxy]methylguanine (DHPG), azauridien, azacytidine, azidothymidine, dideoxyadenosine, dideoxycytidine, dideoxyinosine, dideoxyguanosine, dideoxythymidine, 3'deoxyadenosine, 3'-deoxycytidine, 3'-deoxyinosine, 3'deoxyguanosine, 3'deoxythymidine), prodrug activating antibodies are produced by bacterial expression, and those able to supply thymidine to otherwise thymidine-deficient bacteria are selected. Thymidine bears a close structural resemblance to fluorouridine and the other nucleoside analogues listed above; therefore, a catalytic antibody able to release fluorouridine (or any of the other nucleoside analogues listed above) from a prodrug is able to release thymidine from the equivalent substrate in which fluorouridine (or any other nucleoside analogue of interest) has been replaced by thymidine.

This is illustrated below for a fluorouridine-based prodrug. Thymidine-deficient bacteria are applied with substrate thymidine derivatized by the same promoiety as the fluorouridine prodrug; colonies producing a catalytic antibody able to cleave the pronutrient can utilize released thymidine and therefore survive. Antibody from these surviving colonies is then screened for cleavage of the prodrug to give fluorouridine.

Blocking thymidine production is a potent method of arresting bacterial cell growth. Thymidine is essential for DNA synthesis, and it is obtained only by enzymatic methylation of deoxyuridine. As the base thymine is not found in RNA, there is no possibility of supplementing the thymidine pool by degradation of RNA blocking the conversion of deoxyuridine to thymidine rapidly shuts down DNA synthesis. Therefore, one way of blocking thymidine synthesis is to inhibit the enzymes thymidylate synthetase or dihydrofolate reductase (DHFR). Fluorodeoxyuridylate is an irreversible inhibitor of thymidylatesynthetase, but it also gives rise to synthesis of defective RNA, so that antibody-mediated release of thymidine may not be sufficient to prevent cell death. Methotrexate is a highly specific inhibitor of DHFR; however, tetrahydrofolate, the product of the enzymatic reduction, is also required for the biosynthesis of purines and certain amino acids. Nevertheless, the purine pool may be maintained by supplementing the growth medium with hypoxanthine so that the methotrexate-treated bacteria would then have a unique requirement for thymidine. (Another folate analogue, trimethoprim, is an even more potent inhibitor of bacterial DHFR than methotrexate, and may be used if necessary; Gilman, A. G., et al. *The Pharmacological Basis of Therapeutics* (1985):1263–1268).

An alternative way of selecting for cleavage of thymidine-based prodrug would be to use a strain of *E. coli* deficient in thymidylate synthetase (Neihardt, F. C., *Escherichia coli and Salmonella typhimurium: Cellular and Molecular Biology* (1987). Use of a strain in which expression of the enzyme is temperature sensitive allows all the colonies initially to be grown with the enzyme fully expressed. Raising the temperature then shuts down enzyme expression, and only those colonies producing an antibody able to cleave the thymidine-based prodrug are able to survive.

C. Screening of Catalytic Activation of Cyclophosphamide Prodrug

Immobilization and Screening of Catalytic Monoclonal Antibodies

Immobilization

Immobilization is carried out as described in Section A. Alternatively, screening is carried out with antibody free in solution.

Screening Antibodies for Catalytic Activity

To antibody in solution or immobilized washed antibody, a solution of the prodrug in the appropriate assay buffer is added. Following incubation at 25° C. for a time dependent on the uncatalyzed rate of prodrug activation, formation of activated drug is measured. The substrate solution is either removed from the solution to determine the extent of product formation or the product is measured in situ.

Detection of prodrug activation is carried out by colorometric or fluorometric determination of a byproduct that accompanies prodrug activation—allyl aldehyde;

One of a number of possible allyl aldehyde detection methods is employed. So potentially sensitive and specific detection methods follow:

1. Detection of Allyl Aldehyde using Enzymes that Catalyze Allyl Aldehyde
   a) One enzyme that can be used to detect allyl aldehyde formation is alcohol dehydrogenase (E.C. 1.1.1.1) Alcohol dehydrogenase is commercially available (Sigma Chemical Company) and catalyzes the following reaction (where, for example, the aldehyde is acetaldehyde and the alcohol is ethanol);

aldehyde+NADH (colored)+H$^+$⇌alcohol+NAD$^+$ (no color)

The oxidation of NADH to NAD$^+$ is accompanied by a color change centered at 340 nm. This color change is a commonly used with this enzyme to monitor its activity. The compound, allyl aldehyde, will be accepted as the aldehyde substrate by alcohol dehydrogenase since it closely resembles acetaldehyde, and the enzyme is not particularly strict with the exact structure of its substrates. There are different types of alcohol dehydrogenase commercially available from different species (yeast and equine, for example) and the enzymes from different Species differ somewhat in their substrate specificities so that if the enzyme from one species does not oxidize allyl aldehyde, another may.
   b) The reaction catalyzed by aldehyde dehydrogenase (E.C. 1.12.1.5), also commercially available from Sigma Chemical Company, is similar in that aldehyde substrates are accepted and a color change occurs with the reaction. In this reaction, the aldehyde is oxidized to a carboxylic acid (acetaldehyde to acetic acid, for example);

aldehyde+NAD$^+$ (no color)⇌acid+NADH (color)+H$^+$

In this case a disappearance of color at 340 nm will accompany the transformation of substrate since NAD$^+$ is converted to NADH, rather than the other way around as with alcohol dehydrogenase.
   c) A third possible enzyme-coupled detection method employs both alcohol oxidase (E.C. 1.1.3.13) and peroxidase (E.C. 1.11.1.7). Alcohol oxidase can convert an aldehyde to a carboxylic acid using molecular oxygen and creating hydrogen peroxide;

aldehyde+O$_2$⇌acid+H$_2$O$_2$

Alcohol oxidase is commercially available (Sigma Chemical Company) and on the basis of published literature will accept allyl aldehyde as a substrate (Guibault, G. G., *Handbook Of Enzymatic Methods Of Analysis* (1976):244–248, New York: Marcel Dekker). The formation of hydrogen peroxide by alcohol oxidase is monitored by adding peroxidase (Sigma Chemical Company) to the reaction mixture along with the chromophoric peroxidase substrate, o-dianisidine. Peroxidase will catalyze the following reaction;

H$_2$O$_2$+o-dianisidine⇌H$_2$O+"colored product" The colored product is spectrophotometrically observable at 456 nm.

2. Detection of Catalysis Using Fluorescent or Chromophoric Aldehyde-reactive Reagents In this type of detection method, allyl aldehyde is non-catalytically reacted with commercially available aldehyde-reactive reagents (from, for example, Molecular Probes, Inc., Eugene, Oreg., USA) to yield a colored or fluorescent derivative. The product of the reaction with allyl aldehyde is isolated by high performance liquid chromatography (HPLC) or by thin layer chromatography (TLC) and detected by absorbance or by fluorescence by standard means.

One potential reagent is dansyl hydrazine (Molecular. Probes, Inc.).

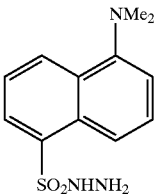

Dansyl hydrazine reacts under mild conditions with aldehydes to give a fluorescent product (Eggert, F. M., et al., *J. Chromatogr.* 333 (1985):123; Avigad, G., *J. Chromatogr.* 139 (1977):343) that is detectable at low concentrations upon TLC or HPLC of the reaction mixture.

Other reagents that are more useful than dansyl hydrazine because of lower detection limits, greater reaction specificity, or milder reaction conditions are other fluorescent hydrazides that are commercially available such as coumarin hydrazide, fluorescein thiosemicarbazide (Molecular Probes, Inc.). These reagents are compared to see which best suits the specific requirements.

D. Screening for Antibody Catalyzed Liberation of Doxorubicin from Prodrugs
   1. Background. Doxorubicin prodrug activation can be detected in either of two basic ways; in vitro detection by observing the inherent physical changes that accompany the chemical transformation of prodrug to active drug, or in vivo detection by biological screening for the toxic effects of the activated drug.
   2. Screening. Screening of antibodies in monoclonal cell line supernatants using the immobization method described in Section A or of antibodies purified from ascites is done by standard methods of either thin layer chromatography (TLC) or high performance liquid chromatography (HPLC). Typically, the reaction mixture contains 200 micromolar prodrug, approximately 1 micromolar antibody, 140 mM sodium chloride, and is buffered at pH 7.4 in 10 mM HEPES buffer. Changes in component concentrations and in pH are also tested. Typical alternative pH values are pH 5.0 in which MES buffer replaces HEPES, and pH 9.0 in which Tris buffer replaces HEPES. The temperature is typically at 25° C. but is raised if the background (uncatalyzed) hydrolysis of the prodrug is not dramatically increased at higher temperatures.

Doxorubicin, its prodrug forms, and the cleaved inactivating pro moiety can all be detected by absorbance or fluorescence. Doxorubicin, and presumably the doxorubicin prodrug both absorb strongly in ultraviolet and visible light (Absorption max (methanol): 233, 252, 288, 479, 496, 529 nm). The aromatic inactivating pro moiety absorbs strongly in the ultraviolet at 260–280 nm as well as 220 nm.

Observation of antibody-catalyzed prodrug activation by TLC is carried out with either purified antibodies or, using the 96-well plate early screening detection method described herein, with impure antibodies in cell culture supernant. TLC of doxorubicin prodrug activation is carried out by standard methods resulting from separation of drug and prodrug on the TLC plate. When the doxorubicin prodrug is hydrolyzed to form free doxorubicin, a primary amino group is exposed on the drug. With proper choice of TLC matrix and solvent systems, separation of pro form from active drug is readily accomplished. Detection of TLC-separated drug and prodrug is either visible inspection of orange-red color or by the natural fluorescence of doxorubicin using an ultraviolet-emitting light. Also, when prodrug activation occurs, a free carboxyl group is formed in the leaving aromatic pro moiety which gives this newly formed compound properties that allow separation by TLC from both prodrug and doxrubicin.

Screening of active drug formation is also carried out by HPLC under standard conditions. Visible and ultraviolet detection of prodrug depletion or drug or pro moiety formation is used with an on-line absorbance or fluorescence detector. Prodrug, drug, and liberated pro moiety is separated in on a reverse phase column using common solvent systems which is optimized for best separation. Conditions that is optimized are; type of reverse phase column, solvent flow rate, solvent mixture components, and elution profile (isocratic elution or gradient elution).

3. Selection. Doxorubicin is a general cytotoxin that is toxic to both bacterial and mammalian cells. Screening for the biological effects of antibody-liberated doxorubicin permits identification of cell lines (bacterial or hybridoma) producing large amounts of catalytically active prodrug-activating antibody. If the prodrug is not cytotoxic, only those cell lines producing prodrug-activating antibody are killed by the prodrug. This idea is analogous to that delineated herein for biological selection of cell lines by screening for increased resistance to β-lactam antibiotics and by ability of catalytic antibody cell lines deficient in thymidine synthetase to produce thymidine by prodrug cleavage. In the case of doxorubicin prodrugs, screening differs in that selection is for cell death by suicide caused by prodrug activation (rather than for catalytic antibody-conferred enhanced survival abilities). Thus, in the case of biological screening for doxorubicin production, an aliquot of each cell line is kept aside and not used in the screening so that the catalytic antibody producing cell lines is not lost during selection. In practice, a series of colonies of monoclonal cells (hybridoma or bacterial) producing antibody are exposed to serial dilutions of the prodrug. Those cell lines that show increased susceptibility to death in a dose-dependent manner are studied further; those antibodies are isolated and further characterized in a pure state. Alternatively, instead of serial dilutions of prodrug administered to a series of colonies of the same cell line, a single dose of prodrug is administered in a concentration calculated to bring about death by an arbitrarily-decided minimally satisfactory kinetic rate of antibody catalysis in the time of the experiment.

E. Screening of Antibodies for Catalytic Activation of Melphalan Prodrugs

Antibodies are either screened at an early stage in hybridoma supernatants by the 96 well plate immobilization technique (described in Section A) or at later stage from mouse ascites. In either case catalysis can be detected by normal methods of HPLC separation of substrates and products. The substrate (prodrug) and products (drug and pro moiety) are all aromatic and can be detected at low levels using a UV detector online with the HPLC apparatus. In the case of the early screen, aliquots from the wells following a suitable incubation time with antibody are withdrawn and injected into the HPLC. Likewise with antibody from ascites, reaction aliquots are injected onto the HPLC and separation of substrate and products as well as detection and quantitation are carried out.

Formulation and Administration

The present invention also encompasses pharmaceutical compositions, combinations and methods for treating cancers and other tumors. More particularly, the invention includes combinations comprising the targeting compounds conjugates catalytic protein antibody-catalytic protein conjugates or bispecific antibodies of the invention and the corresponding prodrug or prodrugs for use in a method for treating tumors wherein a mamalian host is treated in a pharmaceutically acceptable manner with a pharmaceutically effective amount of a targeting protein catalytic protein conjugate or conjugates or bispecific antibody or antibodies and a pharmaceutically effective amount of a prodrug or prodrugs. The combination and methods of this invention are useful in treating humans and animals.

In an advantageous embodiment, the antibody catalytic protein conjugate or bispecific antibody is administered prior to the introduction of the prodrug into the host. Sufficient time is then allowed between administration of the conjugate or bispecific antibody and the prodrug to allow the antibody of the conjugate or the bispecific antibody to target and localize at the tumor site. Such sufficient time may range from 4 hours to one week depending upon the conjugate or bispecific antibody used. The period of time between the end of administration of the immunoconjugate or bispecific antibody and the beginning of administration of prodrug varyies depending on the site to be targeted and the nature of the immunoconjugate or bispecific antibody and prodrug, together with other factors such as the age and condition of patient. More than one administration of prodrug may be necessary to achieve the desired therapeutic effect. Thus, the exact regime will usually need to be determined empirically, with the aim of achieving a maximal concentration of immunoconjugate or bispecific antibody at the target site and a minimal concentration elsewhere in patient, before the prodrug is administered. In this way, an optimum selective therapeutic effect can be achieved.

The immunoconjugate or bispecific antibody may be administered by any suitable route, preferably parenterally., e.g., by injection or infusion. These compounds are administered using conventional modes of administration including, but not limited to, intravenous, intraperitioneal, oral, intralymphatic, or administration directly into the tumor. Intravenous administration is particularly advantageous.

The compositions of the invention—comprising the immunoconjugates or bispecific antibodies or prodrugs—may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application. For example, oral administration of the antibody-enzyme conjugate or bispecific antibody may be disfavored because the conjugate proteins tend to be degraded in the stomach if taken orally, e.g., in tablet form.

Suitable formulations of the immunoconjugate or bispecific antibody or prodrug for parenteral administration include suspensions, solutions or emulsions of each component in oily or aqueous vehicles and optionally contain formulatory agents such as suspending, establishing and/or dispersing agents. Alternatively, the immunoconjugate or bispecific antibody or prodrug may be in powder form for reconstituting with a suitable vehicle, e.g., sterile pyrogen-free water before use. If desired, the immunoconjugate or bispecific antibody and/or prodrug may be presented in unit dosage form. Formulations are conveniently prepared in isotonic saline for injection.

The most effective mode of administration and dosage regimen for the compositions of this invention depends upon the severity and course of the disease, the patient's health and response to treatment and the judgement of the treating physician. Accordingly, the dosages of the immunoconjugates or bispecific antibodies and prodrugs should be titrated to the individual patient.

Nevertheless, an effective dose of the antibody-catalytic protein conjugate or bispecific antibody of this invention may be in the range of from about 1.0 to about 100 mg/m$^2$. An effective dose of the prodrug of the invention will depend upon the particular prodrug used and the parent drug from which it is derived. The precise doses at which the immunoconjugate or bispecific antibody and prodrug will be administered will depend on the route of administration, body weight, and pathology of the patient, the nature of the prodrug, and the catalytic properties of the immunoconjugate or bispecific antibody. Since the prodrug is less cytotoxic than the parent drug, dosages in excess of those recognized in the art for the parent drug may be used.

The prodrug may be administered at doses in general use for the administration of the drug itself but will preferably be administered at lower doses, for example, or around 0.001 to 0.5 times the normally administered dose of drug alone.

Another embodiment of this invention of this invention provides a method of combination chemotherapy using several prodrugs and only a single antibody-enzyme conjugate. According to this embodiment, as number of prodrugs are used that are all substrates for the same enzyme in an immunoconjugate. Thus, a particular antibody-enzyme conjugate or bispecific antibody converts a number of prodrugs into cytotoxic form, resulting in increased antitumor activity at the tumor site.

Still another embodiment of this invention involves the use of a number of immunoconjugates or bispecific antibodies wherein the specificity of the antibody varies, i.e., a number of immunconjugates or bispecific antibodies are used, each one having an antibody that binds specifically to a different antigen on the tumor of interest. The enzyme component of these immunoconjugates may be the same or may vary. This embodiment may be especially useful in situations where the amounts of the various antigens on the surface of a tumor is unknown and one wants to be certain that sufficient enzyme is targeted to the tumor site. The use of a number of conjugates bearing different antigenic specificities for the tumor increases the likelihood of obtaining sufficient enzyme at the tumor site for conversion of a prodrug or series of prodrugs. Additionally, this embodiment is important for achieving a high degree of specificity for the tumor because the likelihood that normal tissue will possess all of the same tumor-associated antigens is small [cf., I. Hellstrom, et al., "Monoclonal Antibodies To Two Determinants Of Melanoma-Antigen p97 Act Synergistically In Complement-Dependent Cytotoxicity", *J. Immunol.* 127 (No. 1), (1981):157–160].

In some patients with multiple metastatic lesions, tumor imaging has proven difficult due to the heterogeneity of the tumor cells wherein only some of the cells express the targeted antigens. In such tumors, where intra or inter-tumor heterogeneity is known to exist, a cocktail of monoclonal antibodies recognizing different tumor antigens are used to activate the prodrug. This approach offers the potential of achieving a higher total concentration of drug at the tumor site in the cases where antigen heterogeneity exists (Wahl, R., *Cancer Research,* Suppl., (1990):941s–948s).

The following examples are illustrative, but not limiting of the methods and compositions of the present invention. Other suitable modifications and adaptations of a variety of conditions and parameters normally encountered in clinical therapy which are obvious to those skilled in the art are within the spirit and scope of this invention.

Experimentals

EXAMPLE 1a

Preparation of the Experimental Prodrug, Linear trimethoxybenzoate-5-fluorouridine, Compound 1

5'-O-(3,4,5-Trimethoxybenzoyl)-5-fluorouridine 1 (For individual reference, compound numbers in bold in the following text refer to the compounds in the synthetic schemes shown in the figures.) Refer to FIG. 1a for the bold numbered compounds in this Example.

The preparation of 5'-O-(3,4,5-trimethoxybenzoyl)-5-fluorouridine 1 is achieved with the reaction of 3,4,5-trimethoxybenzoyl chloride with 2',3'-isopropylidene-5-fluorouridine in pyridine followed by acid hydrolysis with 50% formic acid at 65° C.

In detail, the synthesis is as follows:

5'-O-(3,4,5-Trimethoxybenzoyl)-5-fluorouridine 1

0.604 g of 2',3'-isopropylidene-5-fluorouridine was, after azeotropic removal of moisture from pyridine, dissolved in 4 mL of dry pyridine and cooled to 0° C. Added dropwise a solution of 0.92 g of 3,4,5-trimethoxybenzoyl chloride in 4 mL of dichloromethane over 1 hour period at 0° C. After stirring for a further 1 hour at 0° C., the resulting mixture was quenched by the addition of 7.5 mL of methanol. The mixture was evaporated to a syrup, redissolved in ethyl acetate (75 mL) and washed with saturated sodium hydrogen carbonate (2×75 mL) and water (50 mL). The crude mixture was then purified by flash chromatography using ethyl acetate/hexane to give 0.30 g of 5'-O-(3,4,5-trimethoxybenzoyl)-2',3'-isopropylidene-5-fluorouridine.

0.30 g of 5'-O-(3,4,5-trimethoxybenzoyl)-2',3'-isopropylidene-5-fluorouridine was dissolved in 4.2 mL of 50% aqueous formic acid and was heated with stirring at 65° C. for 2 hours. The mixture was concentrated in vacuo and was then purified by flash chromatography using ethyl acetate to give 0.24 g of 5'-O-(3,4,5-trimethoxybenzoyl)-5-fluorouridine 1.

EXAMPLE 1b

Preparation of the Hapten of the Prodrug in Example 1a, the Linear Phosphonate of trimethoxybenzoate-5-fluorouridine, Compound 4

Figure 1B:
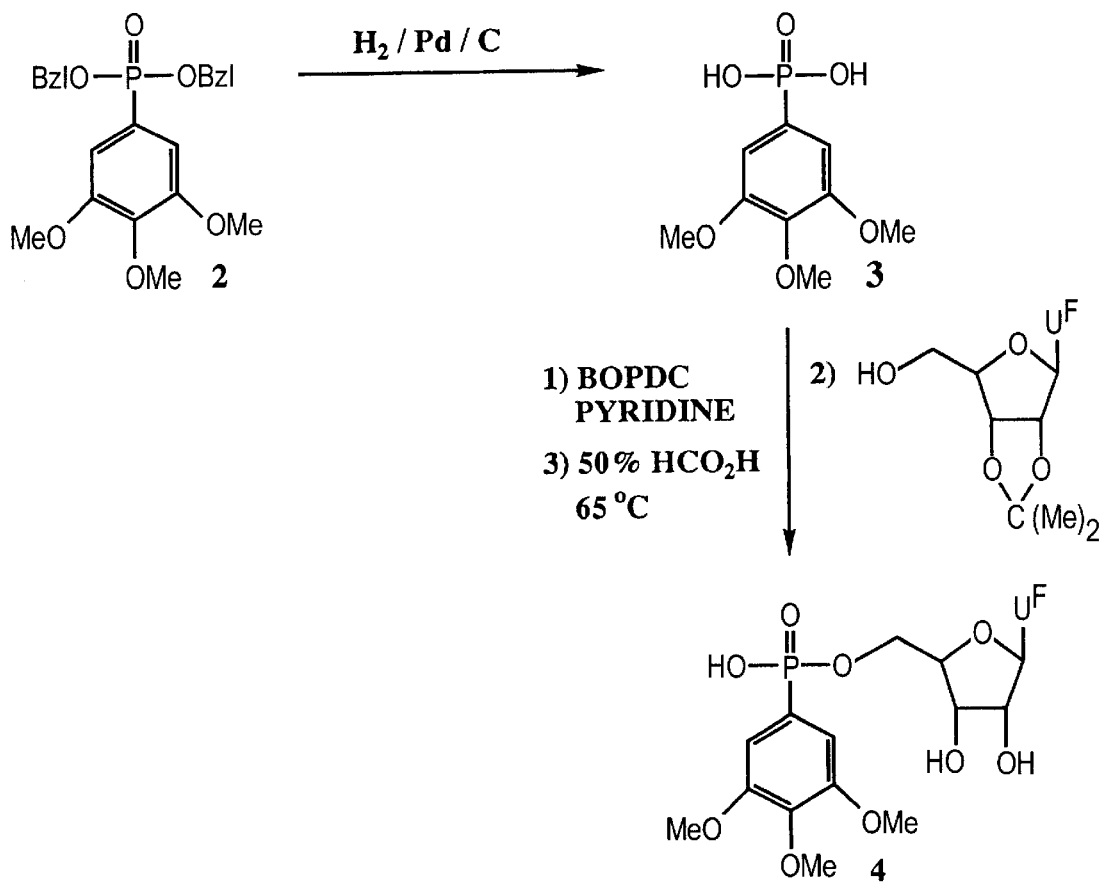
FIG. 1b shows the preparation of the hapten of the Prodrug in Example 1a, the linear phosphonate of trimethoxybenzoate-5-fluorouridine, Compound 4.

Refer to FIG. 1b for the bold numbered compounds in this Example.

Dibenzyl 3,4,5-trimethoxyphenylphosphate 2 can be prepared from the reaction of 3,4,5-trimethoxybromobenzene with dibenzyl phosphite at high temperature in the presence of tetrakis(triphenylphosphine)palladium (0), triethylamine and toluene following the procedure of *J. Med. Chem.* 32 (1989):1580–1590. Removal of the benzyl groups occurs on hydrogenation with 10% Pd on carbon to give the phosphonic acid 3. Subsequent reaction with 2',3'-isopropylidene-5-fluorouridine in the presence of BOPDC in pyridine, followed by acid hydrolysis with 50% formic acid at 65° C. yields 5'-O-(3,4,5-trimethoxyphenylphosphonyl)-5-fluorouridine 4.

In detail, the synthesis is as follows:

Dibenzyl 3,4,5-trimethoxyphenyl phosphonate 2

3,4,5-Trimethoxybromobenzene is prepared following the procedure of *Tetrahedron Lett.* 26 (1985):5939–5942. Dibenzyl phosphite is heated in the presence of tetrakis (triphenylphosphine)palladium (0), triethylamine and toluene with 3,4,5-trimethoxybromobenzene to give Dibenzyl 3,4,5-trimethoxyphenylphosphonate 2 following the procedure of *J. Med. Chem.* 32 (1989):1580–1590.

3,4,5-Trimethoxyphenylphosphonic Acid 3

To a solution of dibenzyl 3,4,5-trimethoxyphenylphosphonate 2 (1 mmol) in 30 mL of ethyl acetate is added 10% Pd on carbon (0.10 g). The mixture is stirred under an atmosphere of hydrogen for 16 hours. Mixture is filtered through celite and washed with methanol (3×10 mL). All washings and filtrate are combined and concentrated to give 3,4,5-trimethoxyphenylphosphonic acid 3.

5'-O-(3,4,5-Trimethoxyphenylphosphonyl)-5-fluorouridine 4

A solution of 3,4,5-trimethoxyphenylphosphonic acid 3 (2.25 mmol) and 2',3'-isopropylidene-5-fluorouridine (1.5 mmol) in 30 mL of dry pyridine is evaporated three times to half volume. To the final solution (15 mL), N,N-bis-(2-oxo-oxazolidin-3-yl)phosphorodiamidic chloride (4.5 mmol) is added. When the reaction is complete, the mixture is diluted with 100 mL of ethyl acetate and extracted with 1M potassium carbonate (2×50 mL). The aqueous phase is acidified to pH 1 with concentrated HCl and extracted with ethyl acetate (4×75 mL). Organic phases are dried over anhydrous $MgSO_4$ and concentrated in vacuo. Product is purified by flash chromatography to give 5'-O-(3,4,5-trimethoxyphenylphosphonyl)-2',3'-isopropylidene-5-fluorouridine which is then dissolved in 5 mL of 50% aqueous formic acid and is heated with stirring at 65° C. for 2 hours. The mixture is concentrated in vacuo to give 5'-O-(3,4,5-trimethoxyphenylphosphonyl)-5-fluorouridine 4.

EXAMPLE 2a
Preparation of Experimental Prodrug, Intramolecular trimethoxybenzoate-5-fluorouridine, Compound 10

Figure 2A:
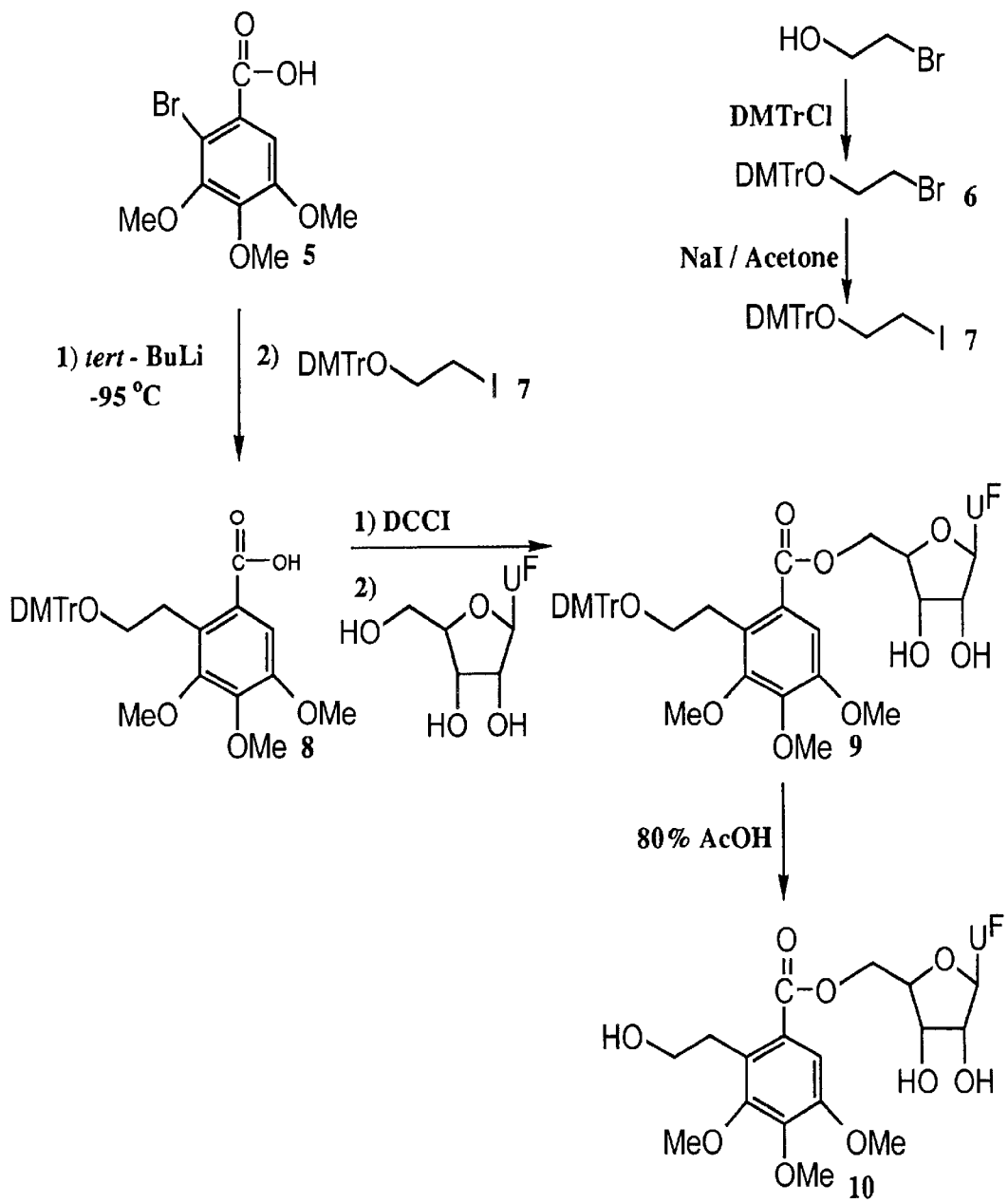
FIG. 2a shows the preparation of the prodrug, intramolecular trimethoxybenzoate-5-fluorouridine, Compound 10.

Refer to FIG. 2a for the bold numbered compounds in this Example.

The bromobenzoic acid 5, whose preparation is described in Example 12, undergoes lithium-halogen exchange and is alkylated with protected iodoethanol 7 (see FIG. 2a). The product 8 is dehydrated to form the symmetric anhydride, which is reacted with 5-fluorouridine to form a stable prodrug precursor, 9. The protecting group of the precursor can be removed rapidly to give the prodrug 10.

In detail, the synthesis is as follows:

2-Bromoethyl 4,4'-dimethoxytriphenylmethyl ether 6

DMAP (100 mmol) is added to a solution of 2-bromoethanol (100 mmol) and 4,4'-dimethoxytriphenylmethyl chloride (100 mmol) in DMF (100 mL) at room temperature. After 16 hours, the mixture is poured into water (300 mL) and extracted with ethyl acetate (3×100 mL). The organic phases are washed with water (100 mL), dried over anhydrous $Na_2SO_4$, and concentrated in vacuo. The mixture is purified by flash chromatography to give the product as a colorless solid.

4,4'-Dimethoxytriphenylmethyl 2-iodoethyl ether 7

A solution of bromide 6 (10 mmol) and NaI (10 mmol) in 100 mL of acetone is heated at reflux with the exclusion of light for 2 hours. The resulting mixture is cooled to room temperature, the solid is removed by filtration, and the solvent is evaporated from the filtrate in vacuo. The resulting yellow oil is used without further purification.

2-[2-(4,4'-Dimethoxytriphenylmethoxy)ethyl]-3,4,5-trimethoxybenzoic Acid 8 tert-Butyllithium (1.7 M solution in pentane, 15 mmol) is added to a solution of bromide 5 (5 mmol) in 50 mL of THF, while maintaining the temperature of the mixture below −95° C. After the addition is completed, the mixture is allowed to warm to −78°C. After 30 minutes, iodide 7 is added in one portion, and the mixture is allowed to warm to 0° C. Water (50 mL) is added, and then the pH of the mixture is carefully adjusted to 3 using 0.1 M HCl. The mixture is extracted with ethyl acetate (3×100 mL). The organic phases are dried over anhydrous $Na_2SO_4$ and concentrated in vacuo. The mixture is purified by flash chromatography to give the product as a colorless oil.

5'-O-{2-[2-(4,4'-Dimethoxytriphenylmethoxy)ethyl]-3,4,5-trimethoxybenzoyl}-5-fluorouridine 9

A solution of DCC (2.5 mmol) in 10 mL of $CH_2Cl_2$ is added to a solution of acid 8 (5 mmol) in 10 mL of $CH_2Cl_2$ at room temperature. After 1 hour, the solid is removed from the mixture by filtration, the solid is washed with 5 mL of $CH_2Cl_2$, and a mixture of 5-fluorouridine (2.5 mmol), and 1-hydroxybenzotriazole (0.25 mmol) in 10 mL of $CH_2Cl_2$ is added to the combined organic phases. When the reaction is completed as observed by TLC, the mixture is concentrated in vacuo. Purification of the mixture by flash chromatography gives the product as a colorless solid.

5'-O-[2-(2-Hydroxyethyl)-3,4,5-trimethoxybenzoyl]-5-fluorouridine 10

Ether 9 (0.1 mmol) is added in one portion to 80% aqueous acetic acid (10 mL) at room temperature. After 15 minutes, the mixture is poured into saturated $NaHCO_3$ (100 mL) and extracted with ether (3×100 mL). The combined organic phases are washed with 100 mL portions of 5% $NaHCO_3$ until no further gas evolution is apparent. The organic phases are then washed with brine (100 mL), dried over anhydrous $Na_2SO_4$, and concentrated in vacuo . The mixture is purified by flash chromatography to give the product.

EXAMPLE 2b
Preparation of the Hapten of Prodrug in Example 2a: The Cyclic Phosphonate of trimethoxybenzoate-5-fluorouridine, Compound 15

Figure 2B:
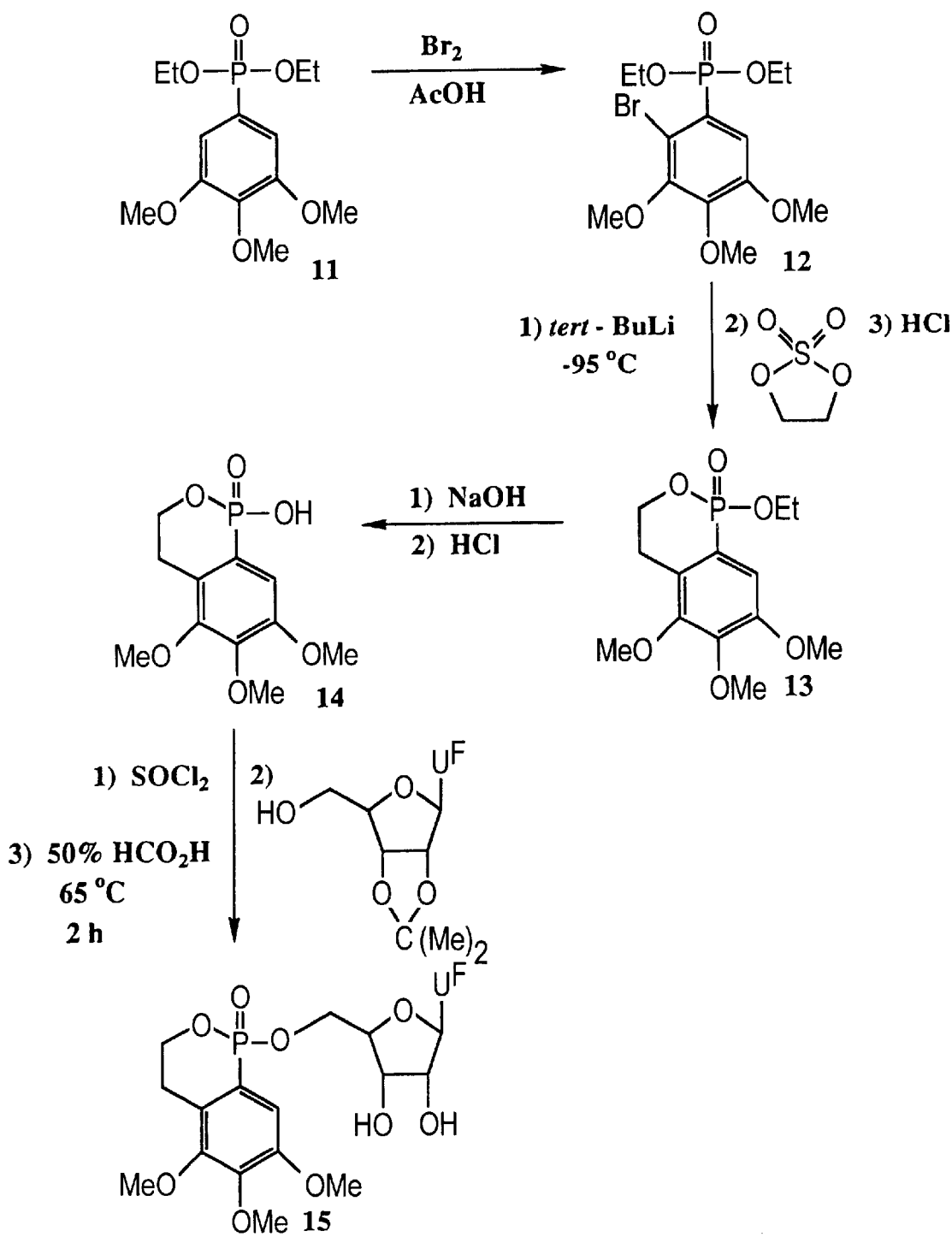
FIG. 2b shows the preparation of the hapten of prodrug in Example 2a: the cyclic phosphonate of trimethoxybenzoate-5-fluorouridine, Compound 15.

Refer to FIG. 2b for the bold numbered compounds in this Example.

The cyclic phosphonate 13 is synthesized following a typical strategy: bromination, lithiation, hydroxyalkylation, and cyclization of an aryl phosphonate 11. Saponification of the phosphonate ester, chlorination, and reaction with 2',3'-isopropylidene-5-fluorouridine followed by acid hydrolysis with 50% formic acid at 65° C. gives the hapten 15.

In detail, the synthesis is as follows:

Diethyl 3,4,5-trimethoxyphenylphosphonate 11

Diethyl 2-bromo-3,4,5-trimethoxyphenylphosphonate 12

A solution of bromine (10 mmol) in 10 mL of acetic acid is added dropwise to a solution of ester 11 (10 mmol) in 10 mL of acetic acid cooled by an ice water bath. After the red color of the resulting mixture is discharged, the mixture is poured into saturated NaHCO$_3$ (100 mL) and extracted with ethyl acetate (3×100 mL). The combined organic phases are washed with 100 mL portions of 5% NaHCO$_3$ until no further gas evolution is apparent. The organic phases are then washed with brine (100 mL), dried over anhydrous MgSO$_4$, and concentrated in vacuo. The mixture is purified by flash chromatography to give the product as a pale yellow solid.

Ethyl 2,3-(3,4,5-trimethoxybenzo)butylphostonate 13 tert-Butyllithium (1.7 M solution in pentane, 10 mmol) is added to a solution of bromide 12 (5 mmol) in 50 mL of THF, while maintaining the temperature of the mixture below −95° C. After the addition is completed, the mixture is allowed to warm to −78° C. After 30 minutes, ethylene sulfonate (5 mmol) is added in one portion, and the mixture is allowed to warm to room temperature. After 1 hour, 1 M HCl (50 mL) is added. After an additional 1 hour, the mixture is extracted with ethyl acetate (3×100 mL). The organic phases are dried over anhydrous MgSO$_4$ and concentrated in vacuo. The mixture is purified by flash chromatography to give the product as a colorless oil.

2,3-(3,4,5-Trimethoxybenzo)butylphostonic Acid 14

A solution of ester 13 (5 mmol) in 50 mL of methanol at room temperature is maintained at pH 12 with 1 M NaOH until the starting material is consumed, as observed by TLC. The pH is then adjusted to 2 with 1 M HCl and the methanol is evaporated in vacuo. The aqueous mixture is extracted with ethyl acetate (3×100 mL), and the organic phases are dried over anhydrous MgSO$_4$ and concentrated in vacuo. The mixture is purified by flash chromatography to give the product as a colorless oil.

5'-O-[2,3-(3,4,5-Trimethoxybenzo)butylphostonyl]-5-fluorouridine 15

Thionyl chloride (5 mmol) is added to a solution of acid 14 (5 mmol) in 50 mL of CH$_2$Cl$_2$ cooled by an ice water bath. After 1 hour, the volatile components are evaporated in vacuo, and the residue is taken up in 10 mL of CH$_2$Cl$_2$ and added to a solution of 2',3'-isopropylidene-5-fluorouridine (5 mmol) and triethylamine (15 mmol) in 25 mL of CH$_2$Cl$_2$ cooled by an ice water bath. After 4 hours, the mixture is poured into 0.1 M HCl (50 mL), the phases are separated, and the aqueous phase is extracted with ethyl acetate (2×50 mL). The combined organic phases are dried over anhydrous MgSO$_4$ and concentrated in vacuo. The mixture is purified by flash chromatography to give the isopropylidene protected intermediate which on treatment with 50% aqueous formic acid (10 mL) at 65° C. for 2 hours and concentration in vacuo yields 5'-O-[2,3-(3,4,5-Trimethoxybenzo)-butylphostonyl]-5-fluorouridine 15.

EXAMPLE 3

Preparation of Experimental Prodrug, galactosyl cytosine b-D-arabinofuranoside, Compound 19

Figure 3:
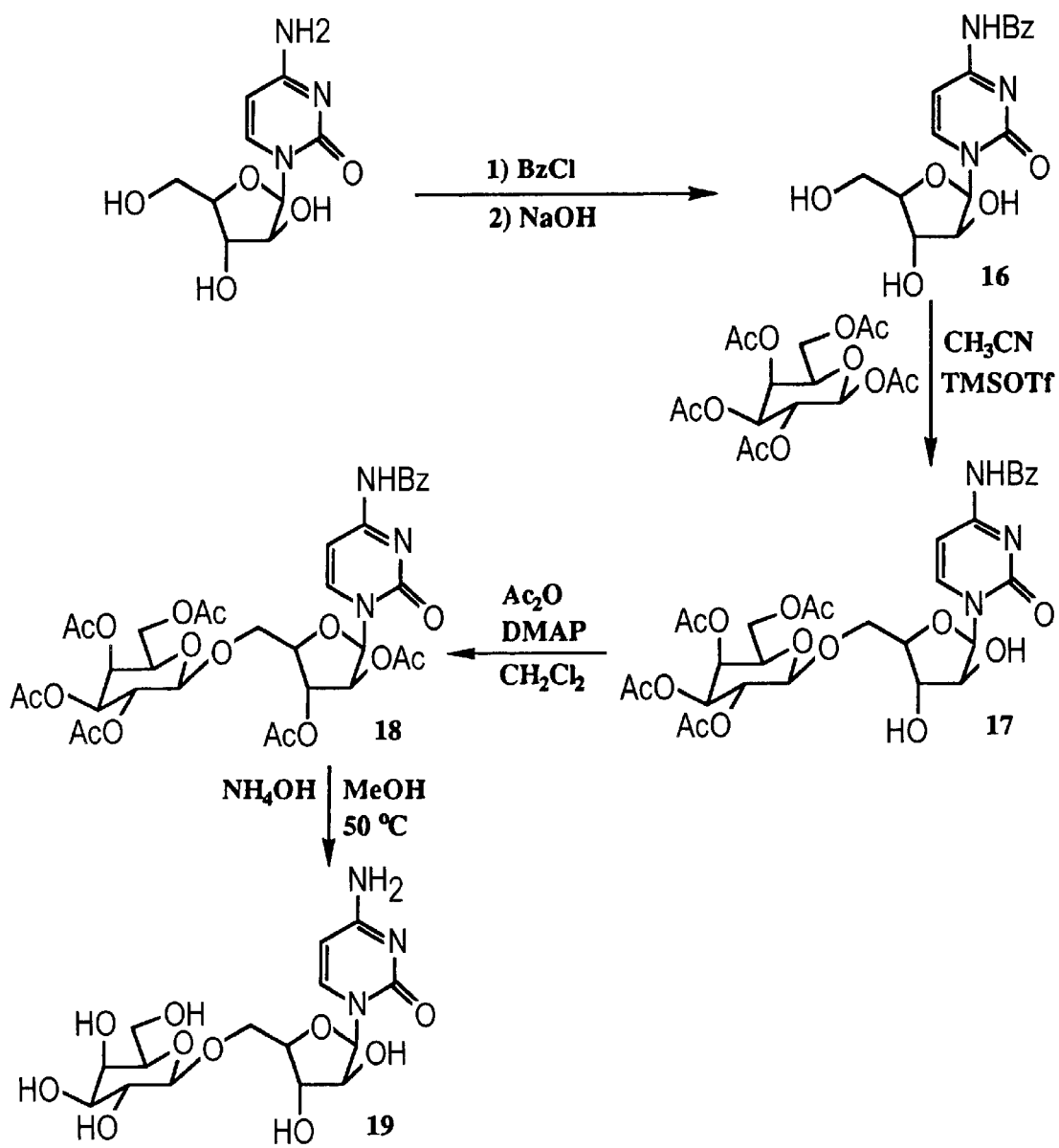
FIG. 3 shows the preparation of experimental prodrug, galactosyl cytosine b-D-arabinofuranoside, Compound 19.

Refer to FIG. 3 for the bold numbered compounds in this Example.

Cytosine b-D-arabinofuranoside was first perbenzoylated and then O-debenzoylated with benzoyl chloride and sodium hydroxide, respectively, to give N$^4$-benzoyl ara-C 16. Subsequent coupling with b-galactose pentacetate in the presence of trimethylsilyl trifluoromethanesulfonate in acetonitrile yielded the partially protected compound 17. Acetylation with acetic anhydride and DMAP in dichloromethane afforded the fully protected compound 18, which on complete deprotection using ammonia in methanol at 50° C. gave the final product, b-gal ara-C 19.

In detail, the synthesis is as follows:

N$^4$-Benzoylcytosine-b-D-arabinofuranoside 16

A suspension of 1.22 g of cytosine-b-D-arabinofuranoside in 50 mL of dry pyridine was cooled to 0° C. 10 mL of benzoyl chloride was added and the mixture was stirred at room temperature for 16 hours. The mixture was poured into 75 mL of 5% aq sodium bicarbonate solution and extracted with CH$_2$CL$_2$ (2×150 mL). The organic phases were washed with water (50 mL), dried over anhydrous MgSO$_4$ and concentrated in vacuo. The mixture was dissolved in 50 mL of pyridine/methanol/water (5:3:2 v/v) and cooled in an ice bath. To this solution was added cold 50 mL of 2M sodium hydroxide in pyridine/methanol/water (5:3:2 v/v). The reaction mixture was stirred at 0° C. for 15 minutes and then the pH was adjusted to 7 with the addition of ammonium chloride. The mixture was concentrated in vacuo and 20 mL of methanol was added. The mixture was filtered and the solid washed with more methanol (3×20 mL). All washings and filtrate were collected, combined and concentrated in vacuo . Redissolved in 50 mL of methanol/CH$_2$CL$_2$ (2:8 v/v) and the mixture was purified by flash chromatography using methanol/CH$_2$CL$_2$ (1:9–2:8 v/v). A second flash chromatography as described above was needed to remove all impurities to give 1.5 g of N$^4$-Benzoylcytosine-b-D-arabinofuranoside 16.

$^1$H NMR (D$_2$O+DMSO-d$_6$, 2:8 v/v) d 8.2 (1H, d, J$_{5,6}$ 7 Hz, H-6), 7.95 (2H, d, J 7 Hz, o-Ph proton×2), 7.75–7.35 (4H, m, H-5 and Ph proton×3), 6.1 (1H, d, J$_{1',2'}$ 4 Hz, H-1'), 4.2–3.9 (3H, m, H-2', H-3' and H-4'), and 3.68 (2H, d, J$_{4',5'}$ 4 Hz, H-5').

Coupling Reaction: Preparation of Compound 17

To a solution of galactose penta acetate (1.17 g, 3 mmol and compound 16 (2 mmol) in dry acetonitrile (5 mL), a solution of trimethylsilyl trifluromethane sulfonate (TMS tf, 354 mg, 1.5 mmol) in dry acetonitrile (2.5 mL) was added through a syringe under argon atmosphere for 2 minutes. Then the reaction mixture was stirred at room temperature for 1 hour and TLC analysis indicated the disappearance of the starting material with the formation of two new compounds (TLC, Ethyl acetate). Then the reaction mixture was quenched with aq. sodium bicarbonate and extracted with ethyl acetate (50 mL). Organic layer was separated, dried and concentrated to give the colorless solid containing mixture of compounds. The mixture was subjected to flash chromatography to afford compound 17 (Rf, 0.36 10% methanol in chloroform, 59%).

NMR (CDCl$_3$): 9.60 (bs, 1 H, NH), 8.16 (d, 1 H, 7.86–7.42 (m, 6H aromatic and 1 H heterocyclic), 6.20 (d, 1 H), 5.32 (m, 3H, CHO of acetate), 4.62 (d, 1 H, J=7.6 Hz, anomeric), 4.20–3.78 (m, 8H) 3.20 (bs, 1 H), 2.62 (bs, 1 H, 2×OH, exchanged with D$_2$O), 2.18 (s, 3 H), 2.04 (s, 6 H), 2.01 (s, 3 H, all CH$_3$ of acetates).

Compound 17 was peracetylated by using acetic anhydride DMAP in methylene chloride to give the compound 18 (Rf, 0.28, Ethyl acetate twice run, 86%). The product was purified by flash chromatography.

NMR (CDCl$_3$): 8.18 (d, 1 H, J=7.5 Hz), 7.82–7.42 (m, 6 H, aromatic, 1 H heterocyclic), 6.42 (d, 1 H, J=5.1 Hz), 5.62–5.08 (m, 5 H, OCH of acetate), 4.60 (d, 1 H, J=7.8 Hz, anomeric), 4.28–3.82 (m, 6 H, OCH), 2.18 (s, 3H), 2.14 (s, 3 H), 2.10 (s, 6 H), 2.06 (s, 3 H), 2.00 (s, 3 H, all are CH$_3$ of acetates ).

NMR (D$_2$O): 7.80 (d, 1 H), 6.22 (d, 1 H), 6.02 (d, 1 H), 4.48 (d, 1 H, J=8.1 Hz, anomeric), 4.40 (t, 1 H), 4.24 (m, 2 H), 3.92 (m, 2 H), 3.80–3.60 (m, 6 H).

EXAMPLE 4
Preparation of Experimental Prodrug galactosyl 5-Flurouridine, Compound 24

Figure 4:
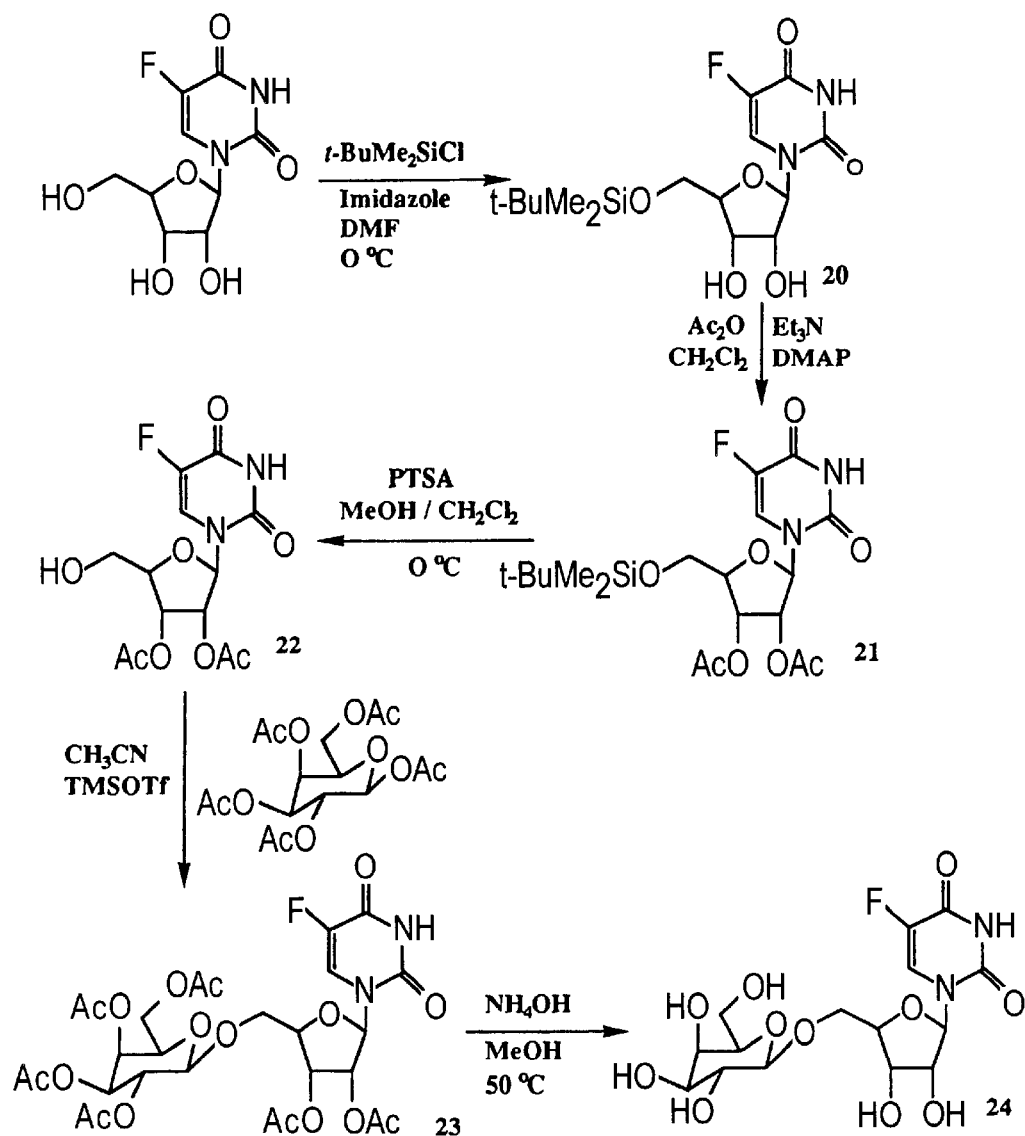
FIG. 4 shows the preparation of experimental prodrug, galactosyl 5-fluorouridine, Compound 24.

Refer to FIG. 4 for the bold numbered compounds in this Example.

The synthesis of b-gal 5-fluorouridine 24 follows a similar strategy. 5-Fluorouridine was treated with t-butyl dimethylchlorosilane in the prescence of imidazole in DMF at 0° C. to give the partially protected compound 20. Subsequent reaction with acetic anhydride in the prescence of DMAP and triethylamine gave the fully protected nucleoside 21. Deprotection of the silyl group was achieved using p toluene sulphonic acid at 0° C., and the resultant product 22 was coupled with b-galactose pentacetate in the presence of trimethylsilyl trifluoromethanesulfonate in acetonitrile to give the fully protected compound 23. Complete deprotection with ammonia in methanol at 50° C. afforded the final product, b-gal 5-fluorouridine 24.

In detail, the synthesis is as follows:

Preparation of Compound 21: To a cooled solution of 5-Flurouridine (1.31 g, 5 mmol) in DMF sequentially added imidazole (0.816 g, 12 mmol) and t-butyldimethylchlorosilane (0.90 g, 6 mmol) and contents were stirred at 0° C. for 2 hours. After completion of the reaction (TLC, 10% Methanol in chloroform) contents were transferred into a separating funnel containing ethyl acetate (100 mL), washed with water (3 times, 25 mL each) and organic layer was separated, dried (MgSO4) and concentrated to give monosilylated product 20 as an oily compound (Rf, 0.44, 10% methanol in chloroform).

The above obtained product 20 (1.80 g, crude, 5 mmol) was dissolved in methylene chloride (20 mL) and added sequentially DMAP (1.34 g, 11 mmol) and acetic anhydride (1.22 g, 12 mmol) and reaction mixture was stirred at room temperature for 1.5 hours. TLC analysis (1:1 Ethyl acetate:Hexane) indicated the completion of reaction. Then the reaction mixture was transferred into a separating funnel and washed with water, dried, concentrated and the product was purified by flash chromatography to afford compound 21 in pure form (Rf, 0.48, 1:1 EtOAc and Hexane, 1.90 g, 83%).

NMR (CDCl$_3$); 8.02 (d, 1 H), 6.26 (d, 1 H), 5.34 (m, 2 H, CHO of acetate), 4.22 (m, 1 H), 3.86 (AB q, 2 H), 2.08, 2.04, (2×s, 3 H, each, CH$_3$ of acetate), 0.92 (s, 9 H, t-bu si), 0.12 (s, 6 H, CH$_3$ of silyl).

$^{13}$C NMR (CDCl$_3$): 169.99, 169.72, 157.06, 156.71, 149.61, 142.51, 139.35, 85.46, 84.12, 73.25, 71.94, 63.28, 25.74, 20.70, 20.68, 20.37, 18.37, −5.70.

Preparation of compound 22: To a cooled solution (0° C. of compound 21 (1.69 g, 3.5 mmol) in methanol (6 mL) and methylene chloride (12 mL), catalytic amount of PTSA (100 mg) was added and reaction mixture was stirred at 0° C. for 30 minutes. After completion of reaction (TLC) it was quenched with triethylamine (0.5 mL) and removed the solvents to give crude compound 22 as an oil. It was then chromatographed to give compound 22 in pure form (Rf, 0.22, 1:1 EtOAc and Hexane, 920 mg 76%).

NMR (CDCl$_3$): 8.09 (d, 1 H J=6.3 Hz), 6.14 (d, 1 H), 5.43 (m 2 H, CHO of acetate), 4.21 (m, 1 H), 3.86 (AB q, 2 H), 2.08, 2.04 (2×s, 3 H each, CH$_3$ of acetate).

$^{13}$C NMR (CDCl$_3$): 170.34, 170.08, 157.56, 149.55, 139.17, 86.61, 83.72, 73.21, 71.48, 61.65, 20.65, 20.38.

Preparation of Coupling compound 23: Coupling reaction between galactose penta acetate and compound 22 was accomplished by the method as mentioned above to give coupling product 23 (Rf, 0.20, 1:1 EtOAC:Hexane, 59%).

NMR (CDCl$_3$): 9.60 (bs, 1 H, NH), 8.18 (d, 1 H, J=6.6 Hz), 6.34 (m, 1 H), 5.46–5.08 (m, 5 H, OCH of acetates), 4.61 (d, 1 H, J=8.1 Hz, anomeric), 4.30–3.72 (m, 6 H), 2.16, 2.13, 2.11, 2.09, 2.05, 2.01 (6×s, each 3 H, CH$_3$ of acetate).

$^{13}$C NMR: 170.37, 170.10, 169.34, 157.00, 156.64, 149.43, 142.52, 139.37, 100.44, 85.83, 82,35, 73.35, 71.63, 70.35, 70.34, 68.57, 68.11, 66.74, 61.13, 20.34, 20.07, 20.29.

Preparation of Prodrug b-D-Gal Fluorouridine 24: Compound 23 was converted to prodrug, compound 24 via the same method (ammonia) as described above (92%).

NMR (D$_2$O): 8.12 (d, 1 H), 5.88 (d, 1 H), 4.44 (d, 1 H, J=7 Hz anomeric), 4.36–3.62 (m, 11 H).

EXAMPLE 5a
Preparation of the Precursor to the Hapten of the Prodrugs in Examples 3 and 4, Compound 25

Figure 5A:
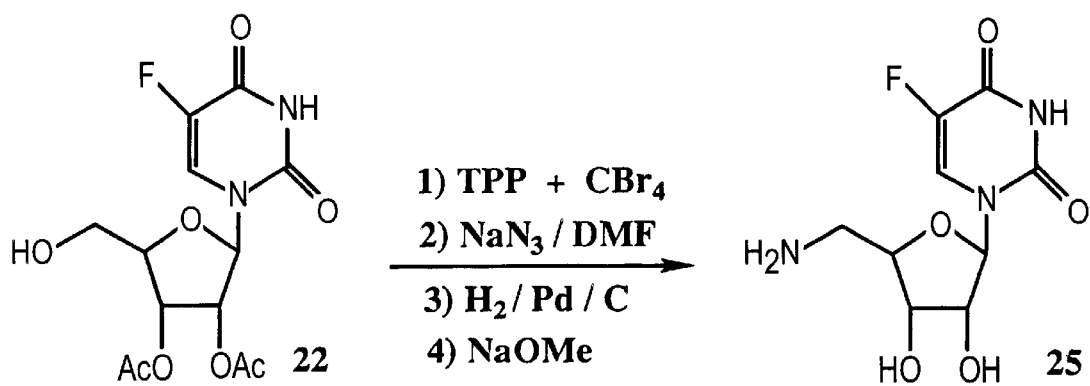
FIG. 5a shows the prepartation of the precursor to the Hapten of the Prodrugs in Examples 3 and 4, Compound 25.

Refer to FIG. 5a for the bold numbered compounds in this Example.

The aminonucleoside 25 is prepared from 5-fluorouridine according to Scheme in FIG. 5. Compound 22 (FIG. 4) is activated with triphenylphosphine and carbontetrabromide, and is then subsequently treated with sodium azide to form an azide intermediate. This intermediate is then hydrogenated with 10% Pd to an amine which is then deprotected with sodium methoxide in methanol to give the aminonucleoside 25. This aminonucleoside is used in subsequent coupling reactions to give the amidine compound 30b (R=5-fluorouridine).

In detail, the synthesis is as follows:

Preparation of 5'-Amino-5-fluororidine 25

To a solution of 5'-hydroxy 2',3' diacetoxy-5-fluorouridine 22 (1 eq) in methylene chloride (0.2 M) are added sequentially triphenyl phosphine (1.1 eq), and carbon tetrabromide (1.2 eq) and the mixture is stirred at 0° C. After completion of the reaction the product is ready for the next step.

Figure 5B:
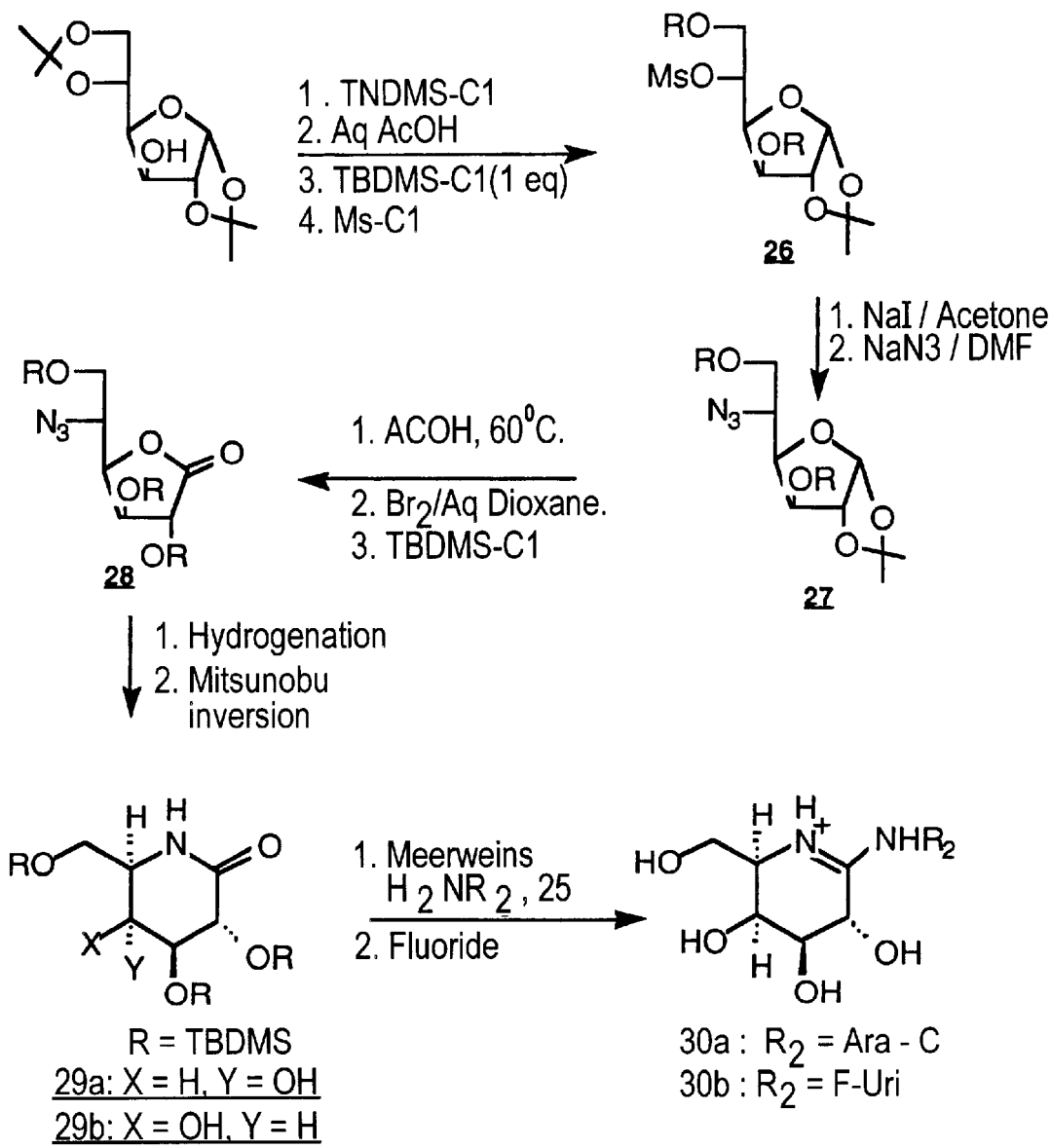
FIG. 5b shows the preparation of the hapten of the prodrugs in examples 3 and 4, Compounds 30a and 30b.
Figure 5C:
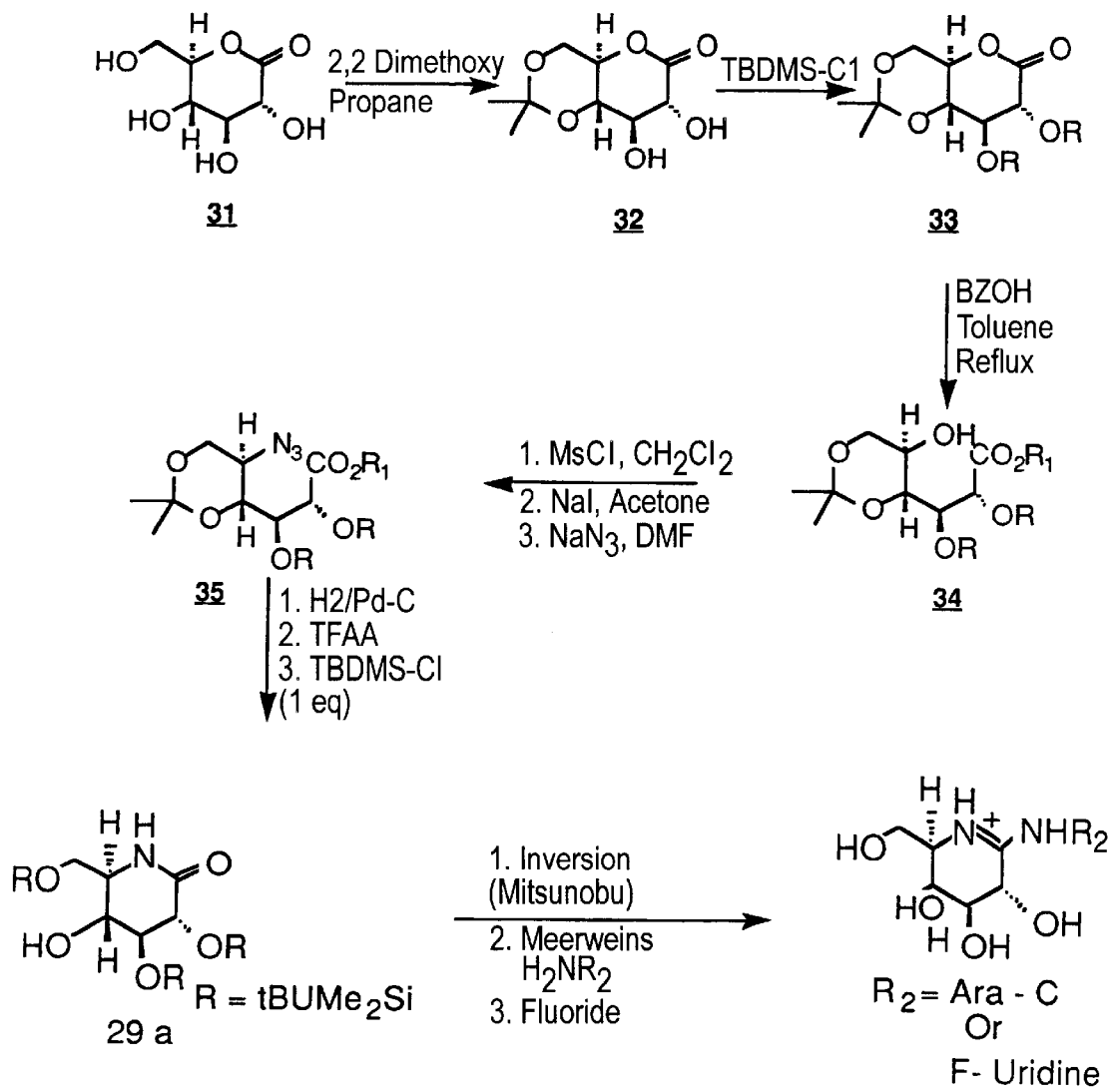
FIG. 5c shows the alternative preparation of the Hapten of the Prodrugs in Examples 3 and 4, Compounds 30a and 30b.

EXAMPLE 5b
Preparation of the Hapten of the Prodrugs in Examples 3 and 4, Compounds 30a and 30b Refer to FIG. 5b and 5c for the bold numbered compounds in this Example.

The preparation of the amidine compound 30a and/or 30b (R=ara C or 5-fluorouridine) can be accomplished by two different synthetic routes. One synthetic route starts with the commercially available diacetone D glucose (FIG. 5b, described here in Example 5b) whilst the other starts from glucospyranose (FIG. 5c, described here in Example 5c).

Starting from diacetone D glucose, the first step involves silylation of the hydroxy group with t-butyl dimethylchlorosilane in the prescence of imidazole in DMF. Subsequent treatment with aqueous acetic acid affords the 5,6 diol which is then silylated at the primary hydroxy position with t-butyl dimethylchlorosilane and the remaining secondary hydroxy group is converted to a mesylate on treatment with MsCl in the prescence of triethylamine. The resultant mesylate compound 26 is then converted to the azide compound 27 by first reacting it with sodium iodide in acetone and then treating the iodide derivative with sodium azide in DMF. Hydrolysis of the acetonide group is accomplished by treating compound 27 with aqueous acetic acid at 60° C. The resultant diol is then oxidised at the anomeric position with bromine in aqueous dioxane to give a lactone derivative which is subsequently silylated with t-butyldimethylchlorosilane to give the lactone compound 28. The azide group of compound 28 is converted to an amino group when subjected to hydrogenation using 10% Pd on carbon, and as a result, rearranges to a glucolactam 29a derivative. Inversion of the secondary hydroxy group using the Mitsunobu reaction procedure gives the galactolactam 29b derivative. Activation with Meerweins reagent and subsequent coupling with the amino nucleoside 25 (Example 7) followed by desilylation with fluoride gives the final amidine compound 30b (R=5-fluorouridine).

In detail, the synthesis is as follows:

Preparation of Compound 26

To a mixture of diacetone D-glucose (5.2 g, 20 mmol) in dry DMF (50 ml), sequentially added imidazole (3.26 g, 48 mmol) t-butyl dimethylchlorosilane (3.60 g, 24 mmol) and contents are stirred at room temperature for 4 hours. After completion of the reaction, the reaction mixture is transferred to a separatory funnel containing ethyl acetate (250 mL) and washed with water, dried, concentrated and product is purified by flash chromatography.

The silylated compound (6.73 g, 17.9 mmol) obtained is dissolved in THF (50 mL) and stirred with aq acetic acid (6 mL) for 6 hours. After completion of the reaction (TLC) solvent was removed and the product is purified by flash chromatography.

The above obtained diol (5.38 g, 16.1 mmol) is dissolved in dry DMF (60 mL) and sequentially added imidazole (2.62 g, 2.4 eq) and tbutyl dimethylchlorosilane (1.2 Eq) and stirred at 0° C. for 2 hours. After completion of the reaction, it is dissolved in ethyl acetate (200 mL) and washed with water, dried, concentrated and the product is purified by chromatography.

The monosilylated hydroxy compound (5.6 g, 12.5 mmol) is dissolved in methylene chloride (40 mL) and cooled to 0° C. and sequentially added triethylamine (2.7 mL) and MsCl (1.85 g, 1.3 eq) and contents are stirred at 0° C. for 3 hours. After completion of the reaction, it is transferred into a separatory funnel and washed with water, dried, and concentrated to give the corresponding mesylate Compound 26.

Preparation of azide 27: A mixture of mesylate 26 (5.26 g, 10 mmol), sodium iodide (1.93 g, 13 mmol) in acetone (50 mL) is heated at reflux for 4 hours. After completion of the reaction, solvent is removed and the resulting material is dissolved in ethyl acetate (100 mL) and washed with water, dried, and the product is purified by chromatography.

A mixture of iodide (4.54 g, 8 mmol), sodium azide (1.30 g, 20 mmol) in dry DMF was heated at 60° C. for 6 hours. After completion of the reaction, it is diluted with ethyl acetate (200 mL) and washed with water dried and concentrated and product is purified by chromatography to obtain azide 27 as a pure compound.

Preparation of Lactone 28: The obtained azide 27 (2.89 g, 6 mmol) is dissolved in THF (30 mL) and aq acetic acid (10 mL) and contents are heated at 60° C. for 6 hours. After completion of the reaction solvent is removed and the resulting material is dissolved in ethyl acetate dried and concentrated to give the diol.

A bromine (1 eq) solution in dioxane was added to the above obtained diol (1.77 g, 4 mmol) in aq dioxane (10%, 20 mL) and the resulting mixture is stirred at room temperature for 2 hours. After completion of reaction, it is diluted with ethyl acetate (50 mL) and washed with aq sodium thiosulfate, dried and concentrated to give hydroxy lactone.

The hydroxyl group in the above lactone is protected as t-butyldimethyl silyl ether as described previously to obtain the lactone 28.

Preparation of Lactam 29a: A suspension of azide 28 (1.10 g, 2 mmol) in methanol (10 mL) and Pd-C (10%, 110 mg) is hydrogenated using hydrogen balloon for 4 hours. After completion of reaction, catalyst was filtered through celite and solvent is removed to give lactam 29a.

Preparation of Lactam having Galacto Configuration 29b: The above obtained lactam 29a was converted to the galacto lactam 29b as mentioned below. To a solution of lactam 29a (0.86 g, 1.6 mmol) and acetic acid (2 mL) in methylene chloride (8 mL) are added sequentially triphenyl phosphine (0.419 g, 1.6 mmol) and diethyl azodicarboxylate (0.295 g 1.7 mmol) at 0° C. and the reaction mixture is stirred for 2 hours. After completion of reaction the solvent is removed and the product is isolated by chromatography. The obtained acetate is hydrolysed by sodium methoxide to obtain the galacto lactam 29b.

EXAMPLE 5c

The Alternative Preparation of the Hapten of the Prodrugs in Examples 3 and 4, Compounds 30a and 30b Refer to FIG. 5c for the bold numbered compounds in this Example.

Preparation of the galactose-b-5-fluorouridine amidine using 5-fluorouridine starts with commercially available glucopyranose 31. Treatment with 2,2 dimethoxypropane in acetone in the presence of catalytic amount of p toluenesufonic acid gives the protected compound 32. Further protection of the remaining hydroxy groups with t-butyldimethylchlorosilane affords the fully protected compound 33. Heating to reflux with benzyl alcohol opens the lactone and the resultant hydroxy compound 34 is mesylated with MsCl. Subsequent conversion to the azide compound 35 is achieved in two steps by first reacting the mesylate group with sodium iodide in acetone and then displacing the iodide group with an azide group using sodium azide in DMF. Hydrogenation using 10% Pd on carbon converts the azide group to an amino which then cyclises to a lactam. Deprotection of the acetonide to a diol on treatment with trifluoroacetic acid and subsequent protection of the primary alcohol with t-butyl dimethylchlorosilane yields the glucolactam compound 29a. The secondary hydroxy group is inverted using the Mitsunobu reaction procedure and the subsequent activation and coupling of the amide is accomplished using Meerweins reagent and the aminonucleside 25 (Example 5a) respectively. Final deprotection using fluoride yields the amidine compound 30b ($R_2$=5-fluorouridine).

In detail, the synthesis is as follows:

Preparation of lactone 32: A mixture of hydroxy compound 31 (8.90 g, 50 mmol), 2,2 dimethoxy propane (4 eq) and PTSA (0.5 g) in methylene chloride (400 mL) and acetone (100 mL) is stirred for 4 hours. After completion of the reaction, it is quenched with triethylamine (3 mL) and the solvent is removed and resulting crude compound is purified by chromatography to obtain Compound 32.

Preparation of Silyl Compound 33: A mixture of Compound 32 (8.72 g, 40 mmol), imidazole (4.4 eq) and t-butyl dimethylchlorosilane (2.2 eq) in dry DMF is stirred for 6 hours. After completion of the reaction, it is diluted with ethyl acetate (500 mL), and washed with water (100 mL×2), dried concentrated and the product is isolated by chromatography to obtain Compound 33.

Preparation of Compound 34: A solution of Compound 33 (13.38 g, 30 mmol) in a mixture of methanol (100 mL) and chloroform (300 mL) is heated at 60° C. until the reaction is completed. After completion of the reaction, solvents are removed and the product is isolated by chromatography to give Compound 34. When benzyl alcohol is used it gives the corresponding hydroxy benzylester.

Preparation of azido ester 35: Conversion of hydroxy Compound 34 to azido. Compound 35 is achieved by the same sequence of reactions as used for the preparation of hydroxy Compound 26 to Compound 27, to obtain azido Compound 35.

Preparation of Lactam 29a and Lactam 29b: Hydrogenation of Compound 35 (under previously described conditions) and deprotection using trifluoro acetic acid (vide supra) and primary alcoholic protection gave lactam 29a. Lactam 29a was inverted to galacto lactam 29b using Mitsunobu reaction condition (vide supra).

EXAMPLE 6

Preparation of the Experimental Prodrug, Aliphatic Diethyl Acetal Protected Aldophosphamide, Compound 38

Figure 6:
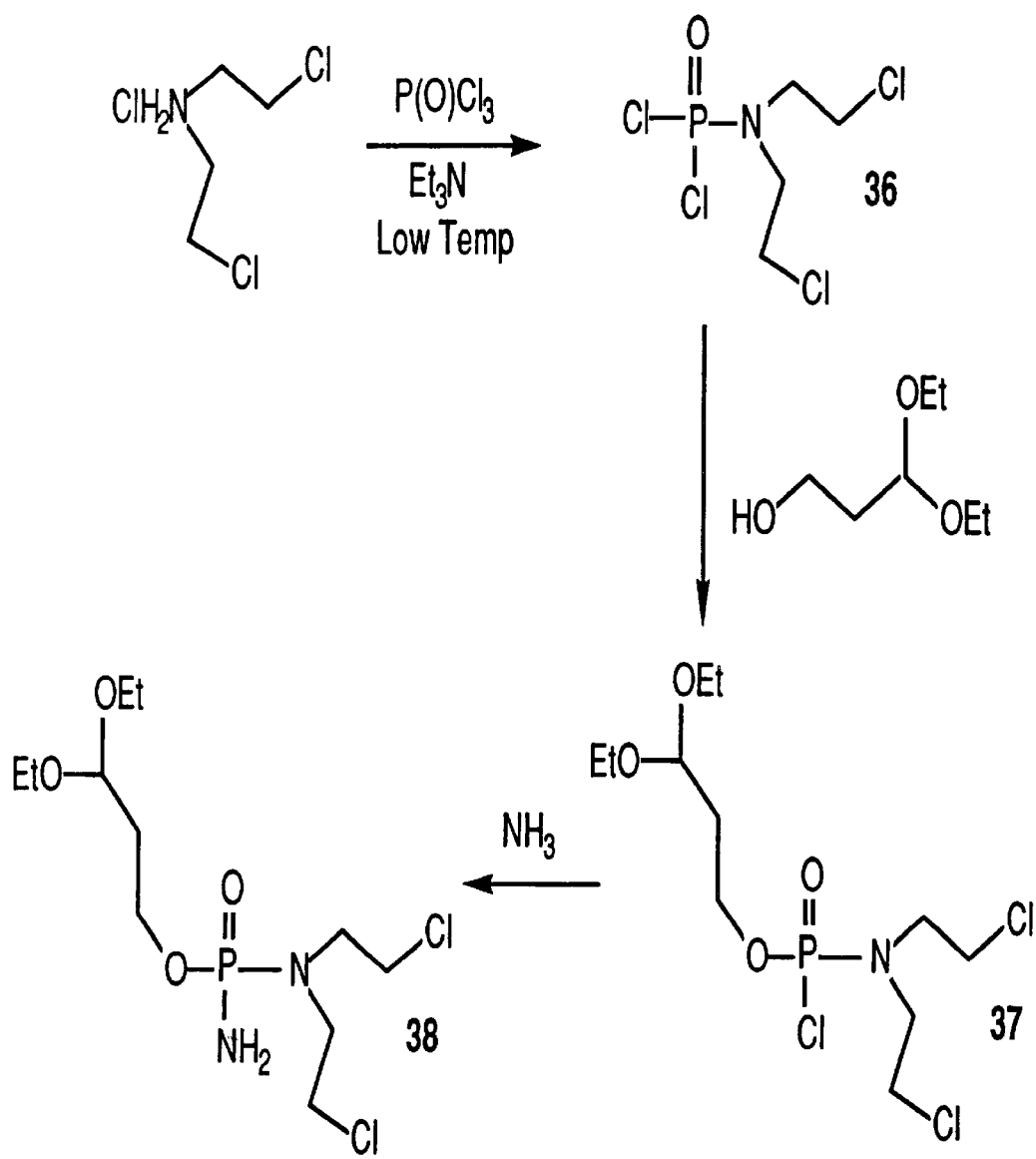
FIG. 6 shows the preparation of the experimental Prodrug, aliphatic diethyl acetal protected aldophosphamide, Compound 37.

Refer to FIG. 6 for the bold numbered compounds in this Example.

When bis(2-chloroethyl)amine hydrochloride was heated with an excess of phosphorus oxychloride (see Example 10 below), the dichlorophosphamide 36 was obtained after distillation as a crystalline solid in good yield. Reaction of the dichlorophosphamide 36 in benzene with one molar equivalent of 3-hydroxypropionaldehyde diethyl acetal gives monochlorophosphamide 37 which on treatment with ammonia affords 3,3-diethoxypropionyl N,N-bis(2-chloroethyl)phosphoric diamide 38.

In detail, the synthesis is as follows:

N,N-Bis(2-chloroethyl)phosphoramidic dichloride 36

A suspension of 50 g of bis(2-chloroethyl)amine hydrochloride in 130 mL of distilled phosphorus oxychloride, bp 105.5–107.5° C., was heated under reflux for 12 hours until complete solution resulted. The excess phosphorus oxychloride was removed by distillation and the residue was distilled under reduced pressure. The fraction, bp 123–125°C./0.6 mm Hg, was collected as a water-clear fluid which crystallised as a solid mass on cooling, 58 g, mp 54–56°C. The product crystallised from acetone-petroleum ether, after standing in the cold, in large prisms, mp 54–56° C.

3,3-Diethoxypropionyl N,N-bis(2-chloroethyl) phosphoramidic chloride 37

To a solution of 52 g of the dichlorophosphamide 36 in 200 mL of dry benzene heated to reflux is added dropwise over a period of 45 minutes a mixture of 32 mL of dry triethylamine and 34.5 g of 3-hydroxypropionaldehyde diethyl acetal in 200 mL of dry benzene. Reflux is maintained by heat for 3 hours after the addition is complete. After several hours at room temperature to complete precipitation, triethylamine hydrochloride is separated from the mixture by filtration. The benzene is distilled from the filtrate, and the residue fractionated at reduced pressure to give 3,3-diethoxypropionyl N,N-bis(2-chloroethyl) phosphoramidic chloride 37.

3,3-Diethoxypropionyl N,N-bis(2-chloroethyl) phosphoric diamide 38

Ammonia gas is bubbled through a solution of 1.05 g of 3,3-diethoxypropionyl N,N-bis(2-chloroethyl) phosphoramidic chloride 37 in 20 mL of dry benzene for 20 minutes, until the precipitation of ammonium chloride is complete. The ammonium chloride is separated by filtration. The benzene filtrate is concentrated to a volume of 10 mL and diluted to cloudiness with petroleum ether to give 3,3-diethoxypropionyl N,N-bis(2-chloroethyl)phosphoric diamide 38.

EXAMPLE 7

Preparation of the Guanyl Hapten of the Experimental Prodrug, Aliphatic Diethyl Acetal Protected Aldophosphamide, Compound 43

Figure 7:
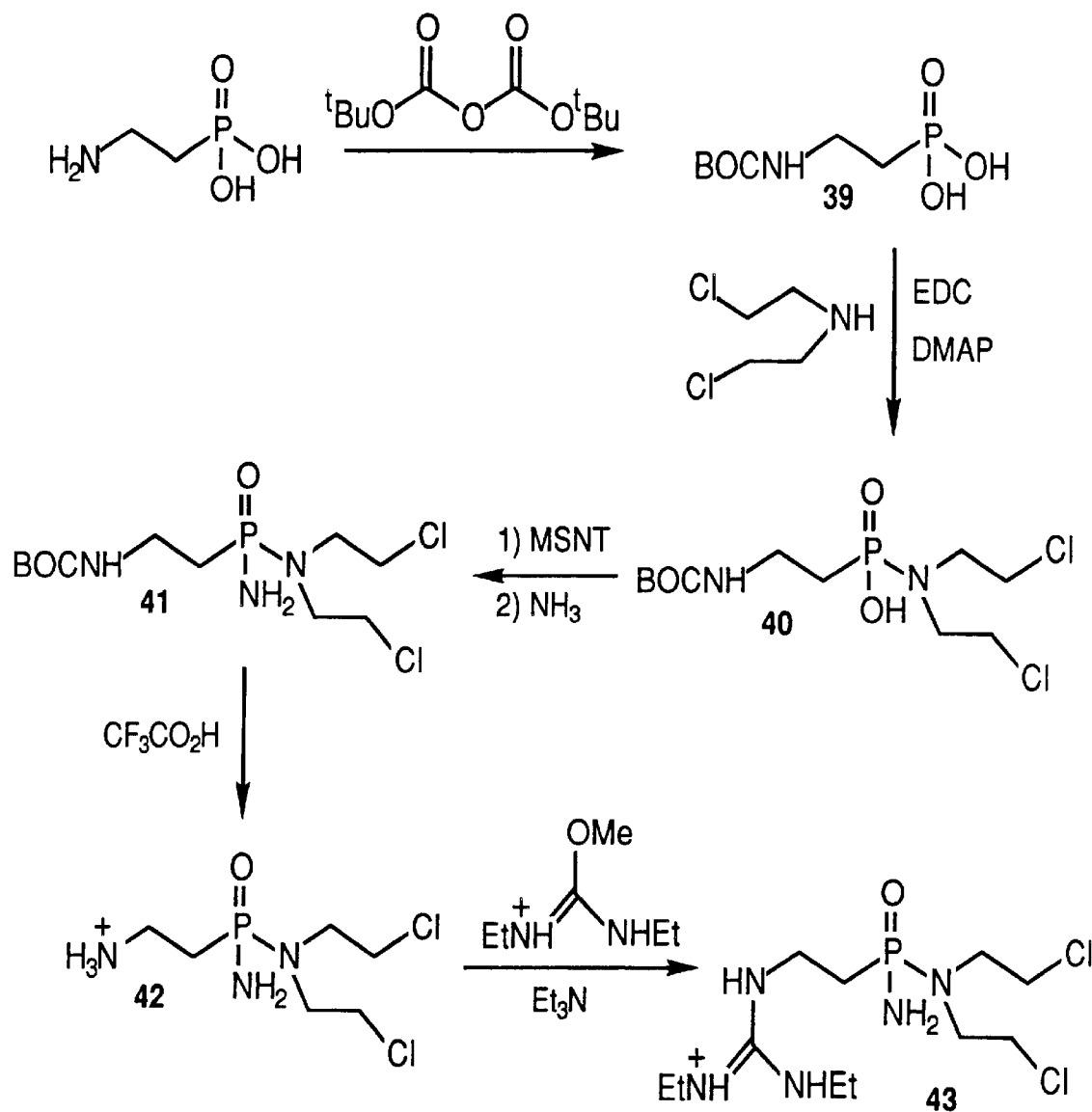
FIG. 7 shows the preparation of the guanyl Hapten of the experimental Prodrug, aliphatic diethyl acetal protected aldophosphamide, Compound 43.

Refer to FIG. 7 for the bold numbered compounds in this Example.

N-t-Boc-aminoethylphosphonic acid 39 is prepared by the reaction of 2-aminophosphonic acid with di-tert-butyl dicarbonate (see Example 11 below). Subsequent reaction with bis(2-chloroethyl)amine hydrochloride in the presence of triethylamine, 4-dimethylaminopyridine and 1-(3-dimethylaminopropyl)-3-ethylcarbodiimide hydrochloride affords the phosphoramidic acid 40. Conversion to the phosphoric diamide 41 is achieved by first activating with 1-(2-mesitylenesulfonyl)-3-nitro-1,2,4-triazole and then reacting with ammonia. Deprotection with trifluoroacetic acid gives 42, which reacts with N,N-diethyl-O-methylisourea tetrafluoroborate to yield the final guanidinium product 43.

In detail, the synthesis is as follows:

N-t-Boc-2-aminoethylphosphonic Acid 39

1.25 g of 2-aminoethylphosphonic acid and 4.2 mL of triethylamine are dissolved in 10 mL of water and a solution of 2.62 g of di-tert-butyl dicarbonate in 10 mL of dry acetonitrile is added. The pH is kept at 9 by addition of triethylamine. After the addition is complete, the mixture is stirred for 2 hours and then concentrated in vacuo. The residue is redissolved in 0.01 M $NaHCO_3$ (100 mL) and washed with ethyl acetate (2×50 mL). The aqueous phase is adjusted to pH 1 by addition of 0.1 M HCl and extracted with ethyl acetate (2×100 mL). The organic phases are dried over anhydrous $MgSO_4$ and concentrated in vacuo to give N-t-Boc-2-aminoethylphosphonic acid 39.

N,N-Bis(2-chloroethyl)-P-[N'-(t-Boc)-2-aminoethyl] phosphonamidic Acid 40

A mixture of 2.25 g of N-t-Boc-2-aminoethylphosphonic acid 39, 2.14 g of bis(2-chloroethyl)amine hydrochloride, 4.2 mL of triethylamine and 0.146 g of 4-dimethylaminopyridine are dissolved in 20 mL of DMF/$CH_2Cl_2$ (1:1 v/v). 2,3 g of 1-(3-dimethylaminopropyl)-3-ethylcarbodiimide hydrochloride is added and the mixture is stirred at room temperature for 16 hours. The mixture is poured into 1 M NaOAc, pH 5 (75 mL) and washed with ether (2×75 mL). The aqueous phase to pH 1 with 1 M HCl and immediately extracted with ethyl acetate (2×100 mL). The organic phases are washed with water (20 mL), dried over anhydrous $MgSO_4$ and concentrated in vacuo. The mixture is purified by flash chromatography to give N,N-bis(2-chloroethyl)-P-[N'-(t-Boc)-2-aminoethyl] phosphonamidic acid 40.

N,N-Bis(2-chloroethyl)-P-[N'-(t-Boc)-2-aminoethyl] phosphonic diamide 41

1.75 g of N,N-bis(2-chloroethyl)-P-[N'-(t-Boc)-2-aminoethyl]phosphonamidic acid 40 is dissolved in dry pyridine (50 mL) and concentrated in vacuo. This process is repeated once more with more pyridine (50 mL). The residue is dissolved in dry pyridine (25 mL) and 2.96 g of 1-(2-mesitylenesulfonyl)-3-nitro-1,2,4-triazole is added. Ammonia gas is bubbled through for 60 minutes. The reaction mixture is concentrated in vacuo, redissolved in ethyl acetate (100 mL) and washed with saturated $NaHCO_3$ (2×100 mL) and saturated NaCl (75 mL). The organic phase is dried over anhydrous $MgSO_4$, concentrated in vacuo and purified by flash chromatography to yield N,N-bis(2-chloroethyl)-P-[N'-(t-Boc)-2-aminoethyl]phosphonic diamide 41.

N,N-Bis(2-chloroethyl)-P-[2-(2,3-diethylguanidyl) ethyl]phosphonic diamide 43

0.873 g of N,N-bis(2-chloroethyl)-P-[N'-(t-Boc)-2-aminoethyl]phosphonic diamide 41 is dissolved in 10 mL of dichloromethane and 10 mL of trifluoroacetic acid is added. After 60 minutes the reaction mixture is concentrated in vacuo to give 42. The residue is redissolved in a mixture of 1 mL of triethylamine and 20 mL of water. The pH is adjusted to 8.5 with more triethylamine and 0.872 g of N,N'-diethyl-O-methylisourea tetrafluoroborate is added while keeping the pH at 8.5 with triethylamine. After 16 hours the reaction mixture is adjusted to pH 7 with acetic acid and concentrated in vacuo. The residue is redissolved in 5 mL of water and purified using reverse phase ODS chromatography to give N,N-bis(2-chloroethyl)-P-[2-(2,3-diethylguanidyl)ethyl]phosphonic diamide 43.

EXAMPLE 8a

Figure 8A:
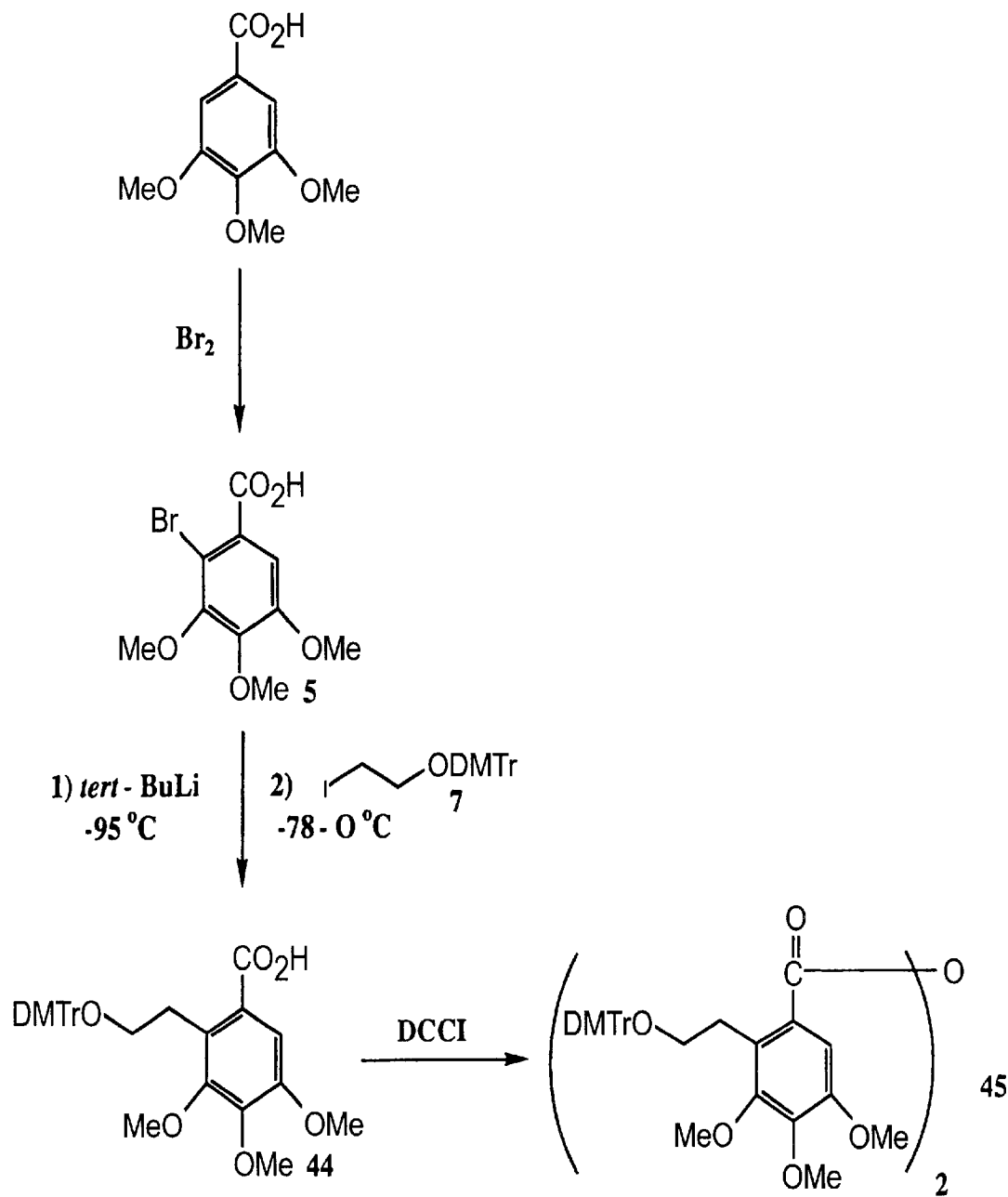
FIG. 8a shows the preparation of the anhydride intermediate, Compound 45, for the synthesis of intramolecular enol trimethoxybenzoate phosphamide prodrug.

Preparation of the Anhydride Intermediate, Compound 45, for the Synthesis of Intramolecular Enol Trimethoxybenzoate Phosphamide Prodrug Refer to FIG. 8a for the bold numbered compounds in this Example.

Commercially available trimethoxybenzoic acid is brominated and the product 5 undergoes low temperature lithium-halogen exchange to produce the aryllithium intermediate. The reactive intermediate is alkylated by a protected iodoethanol 7, and the product 44 is dehydrated to form the symmetric anhydride 45.

In detail, the synthesis is as follows:

2-Bromo-3,4,5-trimethoxybenzoic Acid 5

A solution of bromine (100 mmol) in 100 mL of acetic acid is added dropwise to a solution of 3,4,5-trimethoxybenzoic acid (100 mmol) in 100 mL of acetic acid cooled by an ice water bath. After the red color of the resulting mixture is discharged, the mixture is poured onto 500 g of crushed ice. The resulting solid is collected by filtration, dried over $P_2O_5$ in vacuo, and recrystallized from $Et_2O$ to give the product as a pale yellow solid.

2-[2-(4,4'-Dimethoxytriphenylmethoxy)ethyl]-3,4,5-trimethoxybenzoic Acid (44)

tert-Butyllithium (1.7 M solution in pentane, 15 mmol) is added to a solution of bromide 5 (5 mmol) in 50 mL of THF, while maintaining the temperature of the mixture below −95° C. After the addition is completed, the mixture is allowed to warm to −78° C. After 30 minutes, iodide 7 is added in one portion, and the mixture is allowed to warm to 0° C. Water (50 mL) is added, and then the pH of the mixture is carefully adjusted to 3 using 0.1 M HCl. The mixture is extracted with ethyl acetate (3×100 mL). The organic phases are dried over anhydrous $Na_2SO_4$ and concentrated in vacuo. The mixture is purified by flash chromatography to give the product as a colorless oil.

2-[2-(4,4'-Dimethoxytriphenylmethoxy)ethyl]-3,4,5-trimethoxybenzoic anhydride (45)

A solution of DCC (5.5 mmol) in 10 mL of $CH_2Cl_2$ is added to a solution of acid 44 (10 mmol) in 25 mL of $CH_2Cl_2$ at room temperature. After 1 hour, the resulting solid is removed by filtration and washed with 25 mL of $CH_2Cl_2$, and the solvent is evaporated from the filtrate in vacuo. The product is used without further purification. This anhydride is used in Example 8b to synthesis the aldophosphamide Prodrug Compound 52 FIG. 11.

EXAMPLE 8b

Preparation of the Prodrug, Intramolecular Enol Trimethoxybenzoate Phosphamide, Compound 50

Figure 8B:
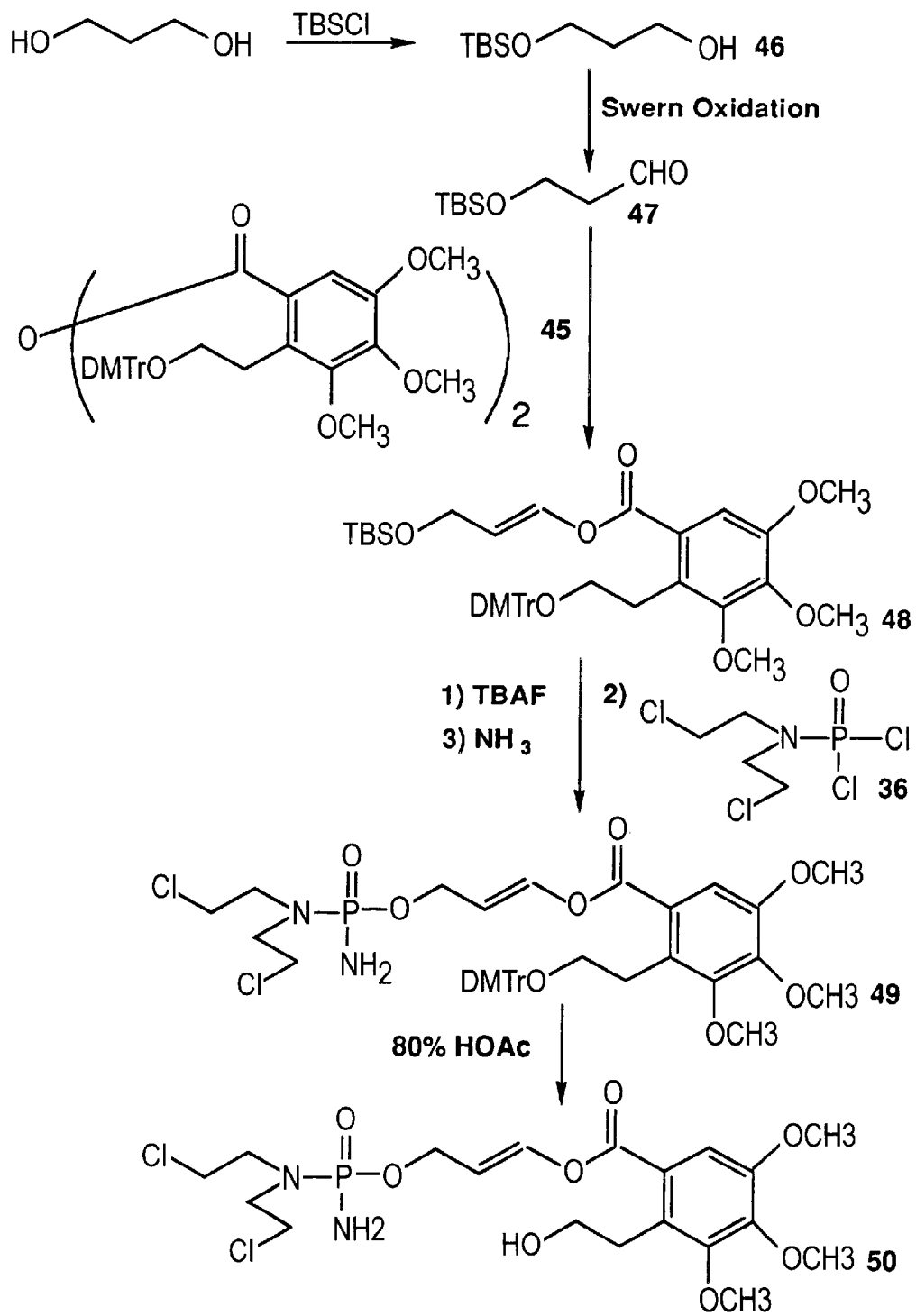
FIG. 8b shows the preparation of the Prodrug, intramolecular enol trimethoxybenzoate phosphamide, Compound 50.

Refer to FIG. 8b for the bold numbered compounds in this Example.

The previously prepared symmetic anhydride 45 (Example 8c) is reacted with a b-siloxy propanal enolate to form the enol benzoate 48 (see Example 13 below). The silyl protecting group is removed, and the alcohol thus revealed is reacted with a phosphoramide dichloridate followed by ammonia to form a relatively stable prodrug precursor 49. This precursor 49 can be rapidly transformed into the more reactive prodrug 50, as needed.

In detail, the synthesis is as follows:

3-(tert-Butyldimethylsiloxy)-1-propanol (46)

A mixture of 1,3-propanediol (10 mmol), tert-butyldimethylchlorosilane (11 mmol), and imidazole (22 mmol) dissolved in 5 mL of DMF was stirred at room temperature for 16 hours. The mixture was poured into 0.1 M HCl (100 mL) and extracted with ether (3×100 mL). The organic phases were washed with brine (100 mL), dried over anhydrous $MgSO_4$, and concentrated in vacuo. The mixture was purified by flash chromatography to give the product as a colorless oil.

3-(tert-Butyldimethylsiloxy)propanal (47)

DMSO (24 mmol) is added to oxalyl chloride (11 mmol) in 40 mL of $CH_2Cl_2$ cooled to −78° C. After 15 minutes, alcohol 46 (10 mmol) is added. After an additional 15 minutes, triethylamine (50 mmol) is added. The mixture is allowed to warm to 0° C. and then poured into 0.1 M HCl (100 mL). The phases are separated, and the aqueous phase is extracted with ethyl acetate (2×100 mL). The organic phases are washed with water (100 mL), dried over anhydrous $MgSO_4$, and concentrated in vacuo. The mixture is purified by flash chromatography to give the product as a colorless oil.

3-tert-Butyldimethylsiloxyprop-1-enyl 2-[2-(4,4'-dimethoxytriphenylmethoxy)ethyl]-3,4,5-trimethoxybenzoate (48)

NaH (60% dispersion in mineral oil, 11 mmol) is washed with hexane (2×10 mL). Ether (20 mL) is added, followed by the dropwise addition of a solution of aldehyde 47 (10 mmol) in 20 mL of ether. Fifteen minutes after the addition is completed, a solution of anhydride 45 (20 mmol) in 20 mL of ether is added in one portion. After an additional 0.5 hour, the reaction mixture is poured into saturated $NH_4Cl$ (20 mL) and the phases are separated. The aqueous phase is extracted with ether (3×40 mL). The combined organic phases are extracted with brine (40 mL), dried over anhydrous $Na_2SO_4$, and concentrated in vacuo. The mixture is purified by flash chromatography to give the product as a colorless oil.

3-{2-[2-(4,4'-Dimethoxytriphenylmethoxy)ethyl]-3,4,5-trimethoxybenzoyloxy}prop-2-enyl N,N-bis(2-chloroethyl)phosphoric diamide (49)

Tetrabutylammonium fluoride (1.0 M solution in THF, 2 mmol) is added to a solution of silyl ether 48 (2 mmol) in 50 mL of THF cooled to −23° C. After 5 minutes, triethylamine (2 mmol) is added, followed by 36 (2 mmol). After an additional 3 hours, NH$_3$ is added. After a further 2 hours, the reaction mixture is poured into ice-cold brine and extracted with ether (4×100 mL). The combined organic phases are dried over anhydrous Na$_2$SO$_4$, and concentrated in vacuo. Purification by flash chromatography gave the product as a colorless oil.

3-[2-(2-Hydroxyethyl)-3,4,5-trimethoxybenzoyloxy] prop-2-enyl N,N-bis(2-chloroethyl)phosphoric diamide (50)

Trityl ether 49 (0.1 mmol) is added in one portion to 80% aqueous acetic acid (10 mL) at room temperature. After 15 minutes, the mixture is poured into saturated NaHCO$_3$ (100 mL) and extracted with ether (3×100 mL). The combined organic phases are washed with 100 mL portions of 5% NaHCO$_3$ until no further gas evolution is apparent. The organic phases are then washed with brine (100 mL), dried over anhydrous Na$_2$SO$_4$, and concentrated in vacuo. The mixture is purified by flash chromatography to give the product as colorless solid.

EXAMPLE 8c

Preparation of the Intramolecular Enol Trimethoxybenzoate Phosphamide Hapten, Compound 57

Figure 8C:
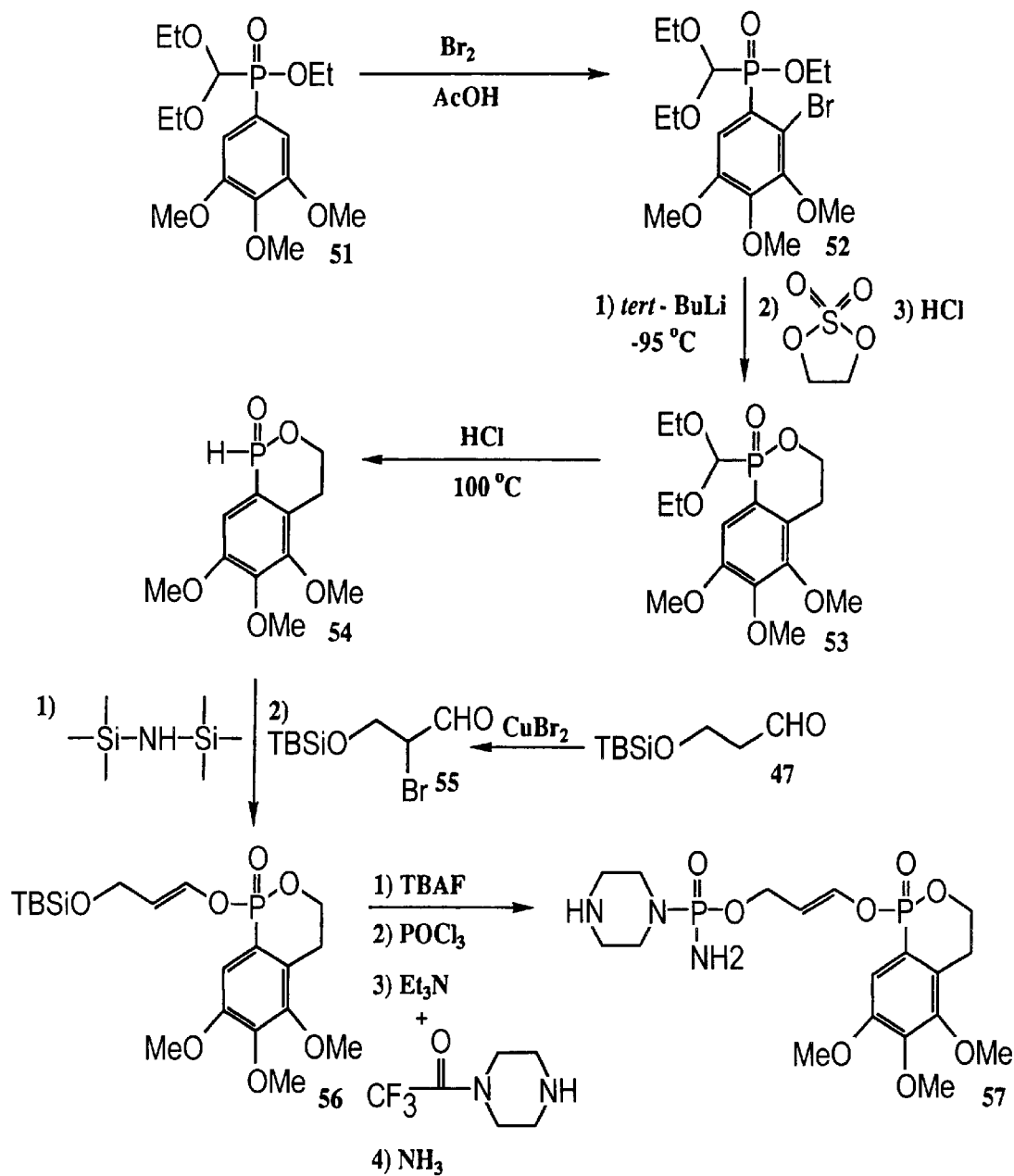
FIG. 8c shows the preparation of the intramolecular enol trimethoxybenzoate phosphamide hapten, Compound 57.

Refer to FIG. 8c for the bold numbered compounds in this Example.

The protected aryl phosphite 51 is synthesized following literature precedent. The aromatic ring is brominated, the bromide 52 undergoes lithium-halogen exchange, and the aryllithium so produced is hydroxyethylated to give 53. After workup and deprotection, the cyclic phosphite 54 is obtained. The phosphite 54 undergoes the Perkow reaction with the a-bromo aldehyde 55 to produce the enol phosphonate 56. Deprotection and reaction with phosphorus oxychloride, followed by N-trifluoroacetylpiperazine and then ammonia gives the hapten 57, which can be linked to a carrier protein through the piperazine ring.

In detail, the synthesis is as follows:

Ethyl P-(3,4,5-trimethoxyphenyl)-P-(diethoxymethyl)phosphinate (51)

3,4,5-Trimethoxybromobenzene is prepared following the procedure of *Tetrahedron Lett.* 26 (1985): 5939–5942. Ethyl (diethoxymethyl)phosphonite is prepared following the procedure of *Tetrahedron* 45 (1989):3787–3808, and reacted with 3,4,5-trimethoxybromobenzene following the procedure of *J. Med. Chem.* 32 (1989):1580–1590.

Ethyl P-(2-bromo-3,4,5-trimethoxyphenyl)-P-(diethoxymethyl)phosphinate (52)

A solution of bromine (10 mmol) in 10 mL of acetic acid is added dropwise to a solution of ester 51 (10 mmol) in 10 mL of acetic acid cooled by an ice water bath. After the red color of the resulting mixture is discharged, the mixture is poured into saturated NaHCO$_3$ (100 mL) and extracted with ethyl acetate (3×100 mL). The combined organic phases are washed with 100 mL portions of 5% NaHCO$_3$ until no further gas evolution is apparent. The organic phases are then washed with brine (100 mL), dried over anhydrous MgSO$_4$, and concentrated in vacuo. The mixture is purified by flash chromatography to give the product as a pale yellow solid.

P-Diethoxymethyl-2,3-(3,4,5-trimethoxybenzo) butylphostinate (53)

tert-Butyllithium (1.7 M solution in pentane, 10 mmol) is added to a solution of bromide 52 (5 mmol) in 50 mL of THF, while maintaining the temperature of the mixture below −95° C. After the addition is completed, the mixture is allowed to warm to −78° C. After 30 minutes, ethylene sulfonate (5 mmol) is added in one portion, and the mixture is allowed to warm to room temperature. After 1 hour, 1 M HCl (50 mL) is added. After an additional 1 hour, the mixture is extracted with ethyl acetate (3×100 mL). The organic phases are dried over anhydrous MgSO$_4$ and concentrated in vacuo. The mixture is purified by flash chromatography to give the product as a colorless oil.

2,3-(3,4,5-Trimethoxybenzo)butylphostinic Acid (54)

A mixture of compound 53 (5 mmol) in 20 mL of 36% aqueous HCl is heated at 100° C. for 2 hours. After cooling to room temperature, the reaction mixture is diluted with 200 mL of water and extracted with ethyl acetate (4×100 mL), and the organic phases are dried over anhydrous MgSO$_4$ and concentrated in vacuo. The mixture is purified by flash chromatography to give the product as a colorless oil.

2-Bromo-3-tert-butyldimethylsiloxypropanal (55)

A mixture of CuBr$_2$ (10 mmol) and aldehyde 47 (10 mmol) in ethyl acetate (50 mL) and chloroform (50 mL) is heated at reflux for 6 hours with the exclusion of light. The mixture is cooled to room temperature, the solid is removed by filtration and washed with ethyl acetate (50 mL), and the combined organic phases are dried over MgSO$_4$ and concentrated in vacuo. Purification of the mixture by flash chromatography gave the product as a pale yellow oil.

3-tert-Butyldimethylsiloxy-1-propenyl 2,3-(3,4,5-trimethoxybenzo)butylphostonate (56)

Acid 54 (1 mmol) is dissolved in hexamethyldisilazane (1 mL) and heated at reflux for 3 hours. The mixture is cooled to room temperature and the volatile components are evaporated in vacuo. Aldehyde 55 (1 mmol) is added to the resulting oil and the mixture is heated at 100° C. under a slow stream of nitrogen for 4 hours. After cooling, the mixture is purified by flash chromatography.

3-[P-amino-P-(N-piperazino) phosphoroxy]-1-propenyl 2,3-(3,4,5-trimethoxybenzo) butylphostonate (57)

Tetrabutylammonium fluoride (1.0 M solution in THF, 2 mmol) is added to a solution of silyl ether 56 (2 mmol) in 50 mL of THF cooled to −23° C. After 5 minutes, triethylamine (2 mmol) is added, followed by POCl$_3$ (2 mmol). After 4 hours, a mixture of N-trifluoroacetylpiperazine (2 mmol) and triethylamine (2 mmol) is added in one portion. After an additional 3 hours, NH$_3$ is added. After a further 2 hours, the reaction mixture is poured into ice-cold brine and extracted with ether (4×100 mL). The combined organic phases are dried over anhydrous Na$_2$SO$_4$, and concentrated in vacuo. Purification by flash chromatography gave the product as a colorless oil.

EXAMPLE 9

Prodrug Activity of Galactosyl-cytosine Arabinoside

The prodrug galactsyl-cytosine arabinoside (galAraC) has been prepared as outlined in Example 3 and has been tested in vitro and in vivo for toxicity and activation by the bacterial enzyme, b-glactosidase.

Figure 9:
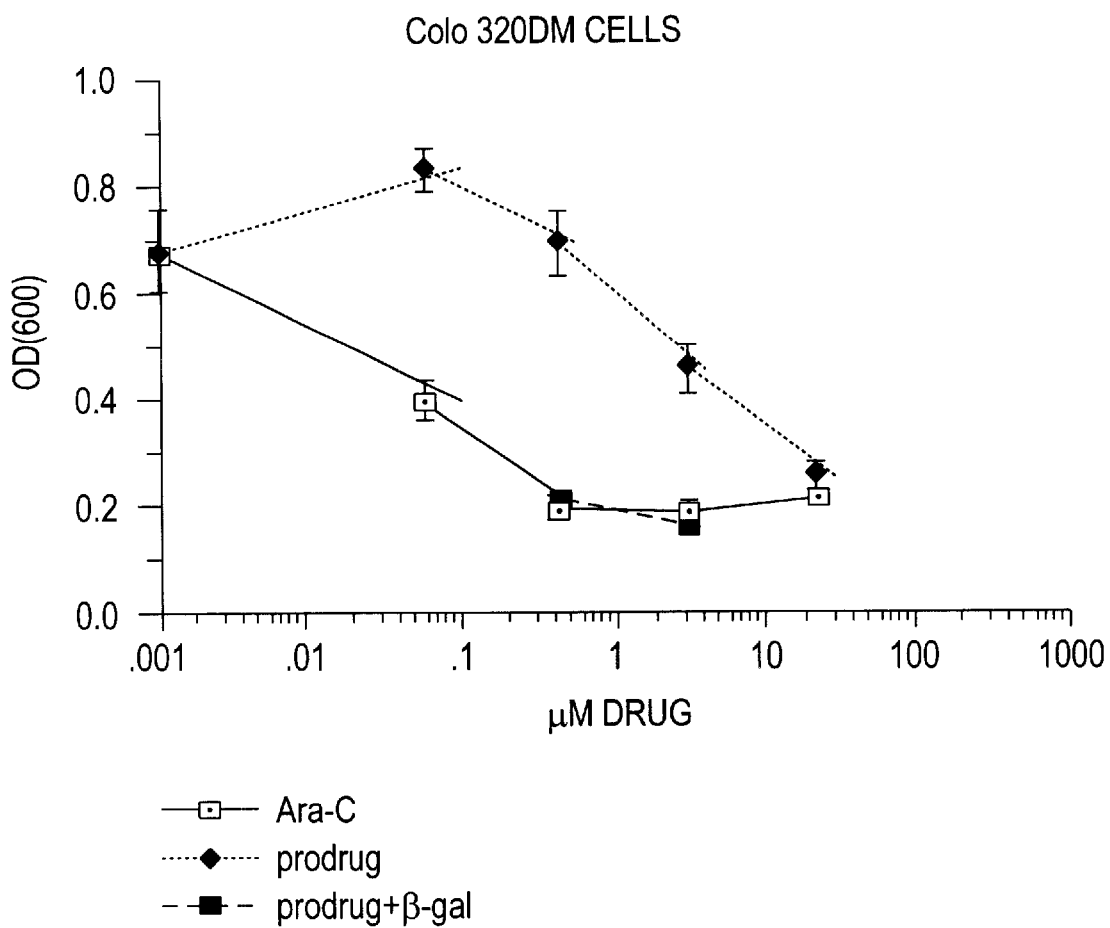
FIG. 9 shows the comparison of AraC and galactosyl-AraC Prodrug on Colo cells.
Figure 10:
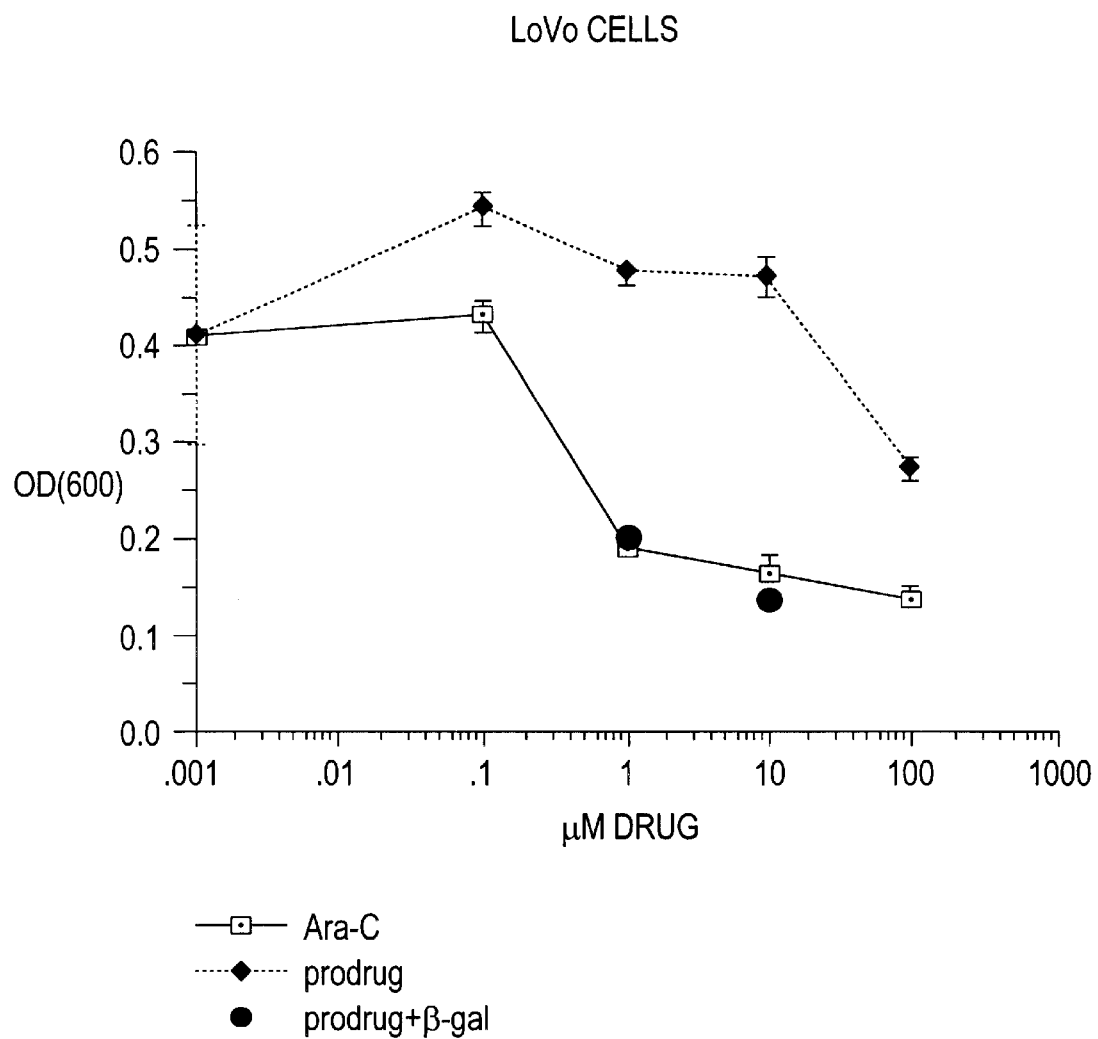
FIG. 10 shows the comparison of AraC and galactosyl-AraC Prodrug on Lovo cells.

Different concentrations of the prodrug galAraC were added to the two different tissue cultures cell lines, Colo 320 DM and Lovo. The cells were grown for four days after which the culture medium was removed and the cells were washed in PBS. After the cells were stained with Giemsa stain, the optical density of the stained cultures bound to the culture well surface was measured at 600 nm. The reduction of the optical density indicates a reduction of cell density adhering to the culture well. The same procedure was used to test the toxicity of AraC itself on the two cell lines. The comparison of the toxicity between prodrug and drug on the Colo 320 DM cell line is shown in FIG. 9. By comparing the concentration of prodrug and drug at the concentrations used to give an OD (600) of 0.5 it can be seen that the galAraC is at least 800-fold less toxic than the AraC. That is, one must use 800-fold higher concentration of galAraC to achieve the equivalent toxicity as AraC itself. Similar results can be seen in FIG. 10 using the cell line Lovo where the prodrug is again at least 800 times less toxic than the drug AraC. Both FIGS. 9 and 10 show that when the prodrug is activated by the enzyme b-galactosidase the toxicity is equivalent to that of the pure drug at the same concentration.

Figure 11:
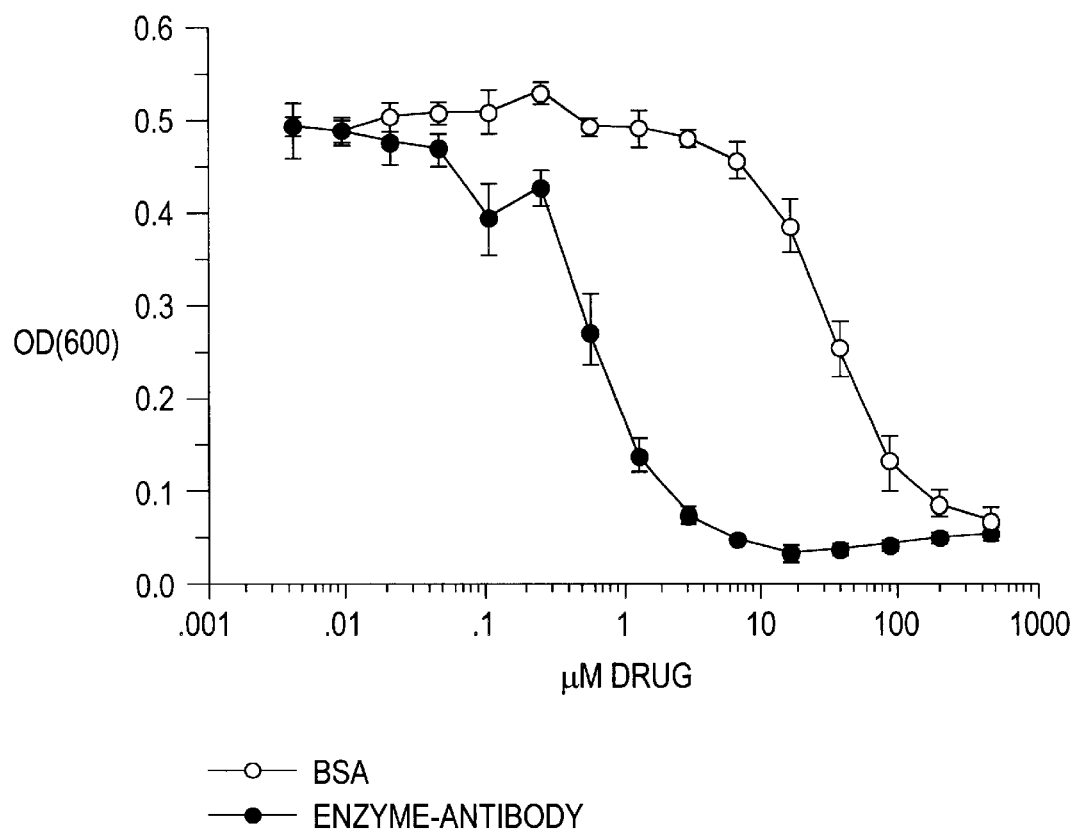
FIG. 11 shows the site specific activation of galactosyl-AraC Prodrug on CEA antigen positive cells.
Figure 12:
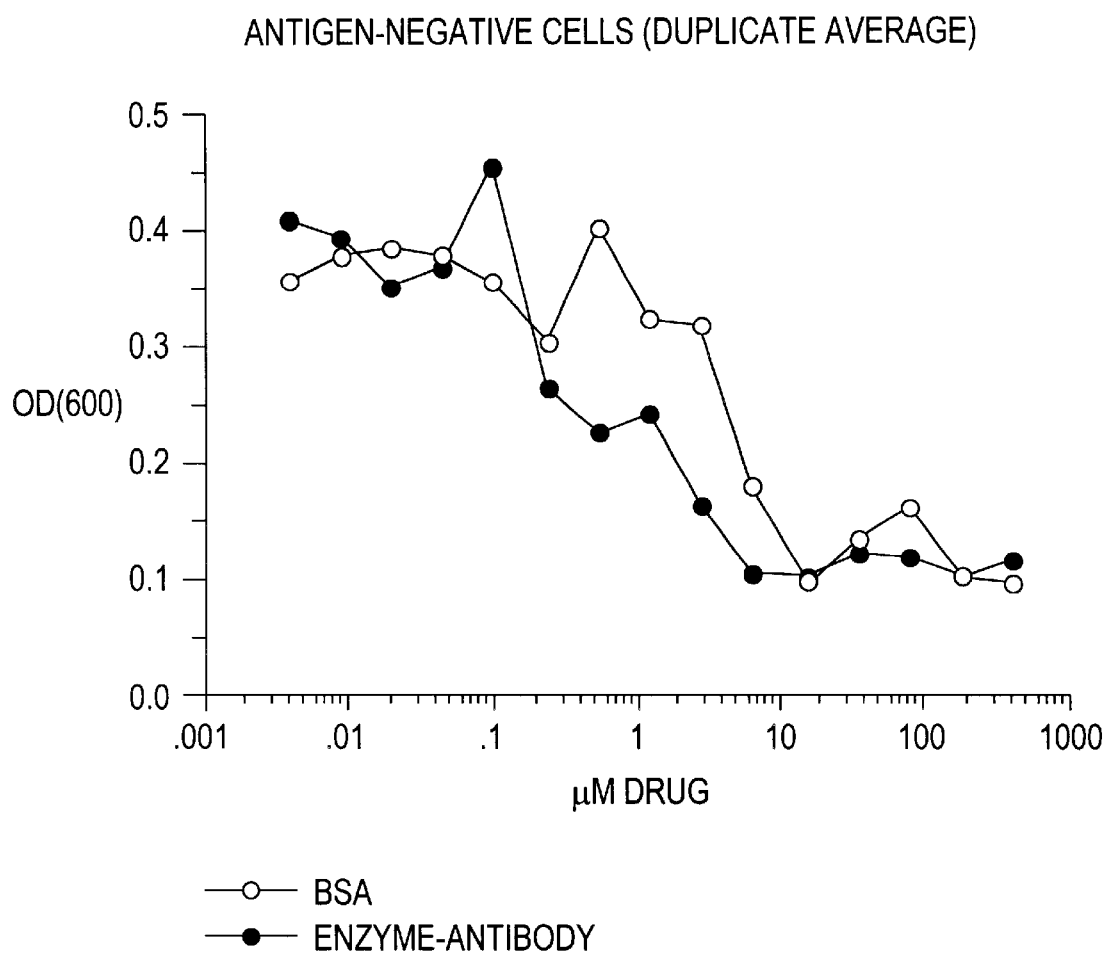
FIG. 12 shows the activity of galactosyl-AraC Prodrug on CEA antigen negative cells.

To test if the prodrug could be activated by b-glactosidase, the enzyme was conjugated to an antibody that was directed against Carcino Embryonic Antigen (CEA) a specific tumor antigen on the surface of the Lovo culture cells. The Colo 320 DM cells lack this surface antigen and were used as controls. The b-galactosidase conjugated antibody was added to the cultures and allowed to bind the antigen. The prodrug, at different concentrations, was then added to the cultures, which were then grown for three days. As controls, BSA without enzyme was added to the cultures and the same range of prodrug concentrations was added to the cultures. FIG. 11 displays the results of this experiment which shows that the prodrug can be activated by the antibody-enzyme conjugate. By comparing FIG. 11 with FIG. 12, it is clear that the prodrug was not only activated by the conjugated antibody but also that the Lovo cells, carrying the CEA tumor marker are specifically killed when compared to the cultures where BSA was added with prodrug. The above results show that the prodrug is approximately 200-fold less toxic than the drug in an antigen localization experiment, and that it can be activated by a bacterial enzyme specifically at the surface of a tumor cell when bound by antibody at the cell surface.

To assess the ability of surface-bound conjugate to generate cytotoxic levels of active drug, the rate of product formation was measured using ONPG as a substrate. Conjugate specifically bound to LoVo cells was found to generate 1.2×10 molecules of product/min/cell. In our particular assay format, this rate is equivalent to 1.6 mM product formed per minute. Since 1.5 mM AraC is reported to inhibit cellular proliferation by 50% (Gish, D., et al., *J. Med. Chem.* 14 (1971):1159) the experimentally obtained rate appears to be sufficient to generate cytotoxicity in vitro assay.

Both AraC and galAraC have been tested for toxicity and activation in the mouse. In separate experiments, mice were given (at a concentration of 100 mg/kg), AraC, galAraC and galAraC followed by b-galactosidase. After five days, a complete blood count was made on all the mice. By comparing the drug with the prodrug (see bars in FIG. 13), it is clear that the prodrug is substantially less toxic than the drug in vivo.

Figure 13:
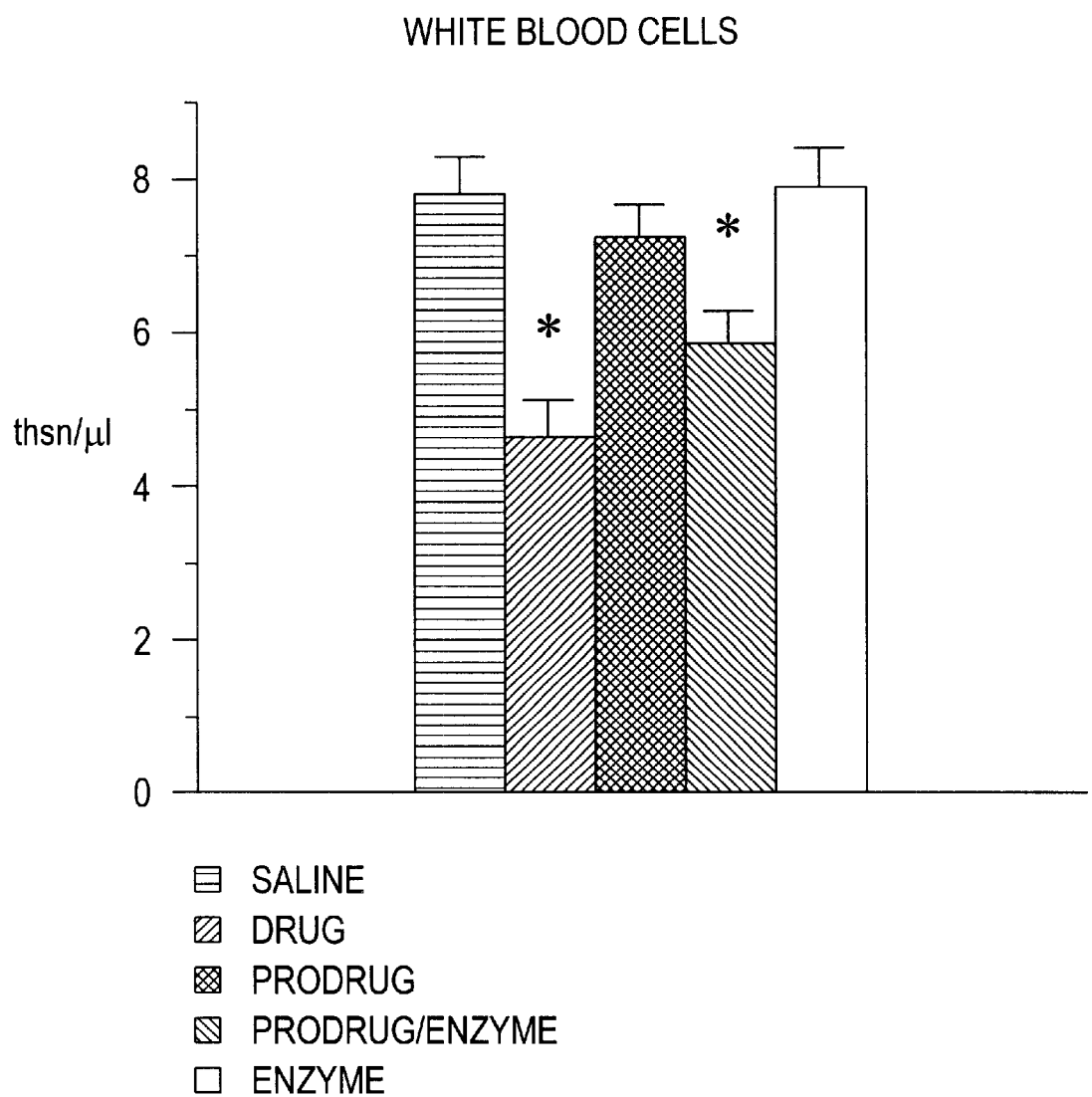
FIG. 13 shows the white blood cell response to drug and prodrug.
Figure 14:
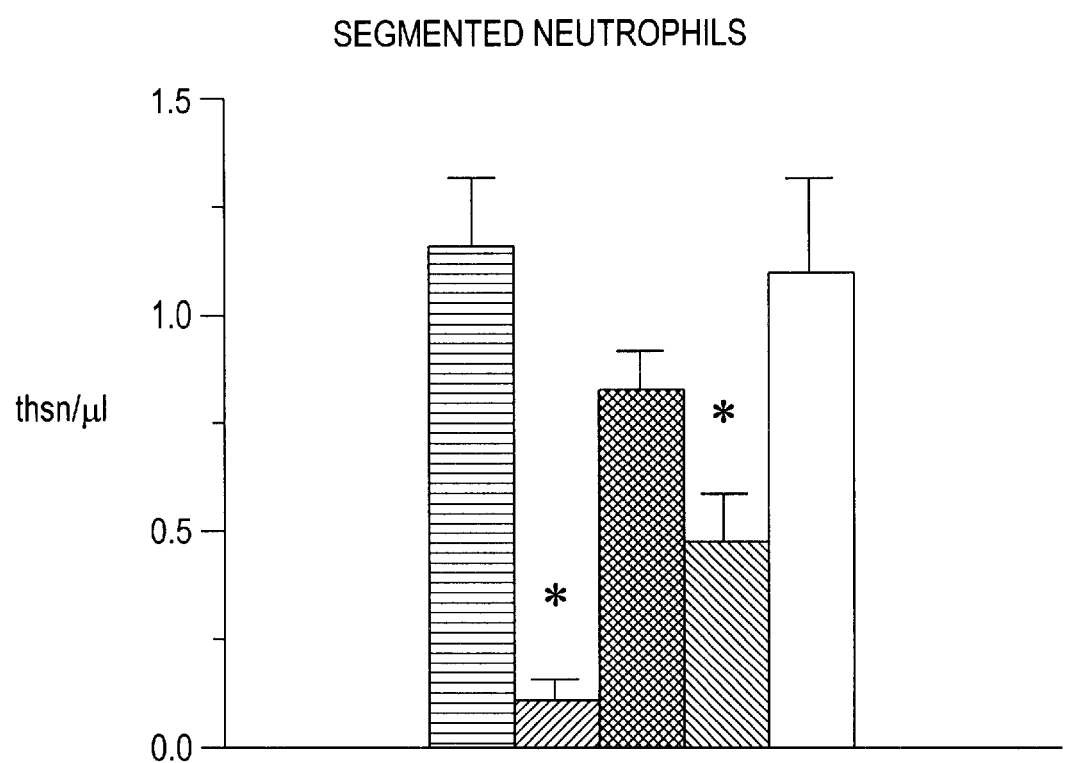
FIG. 14 shows the segmented neutrophil response to drug and prodrug.
Figure 15:
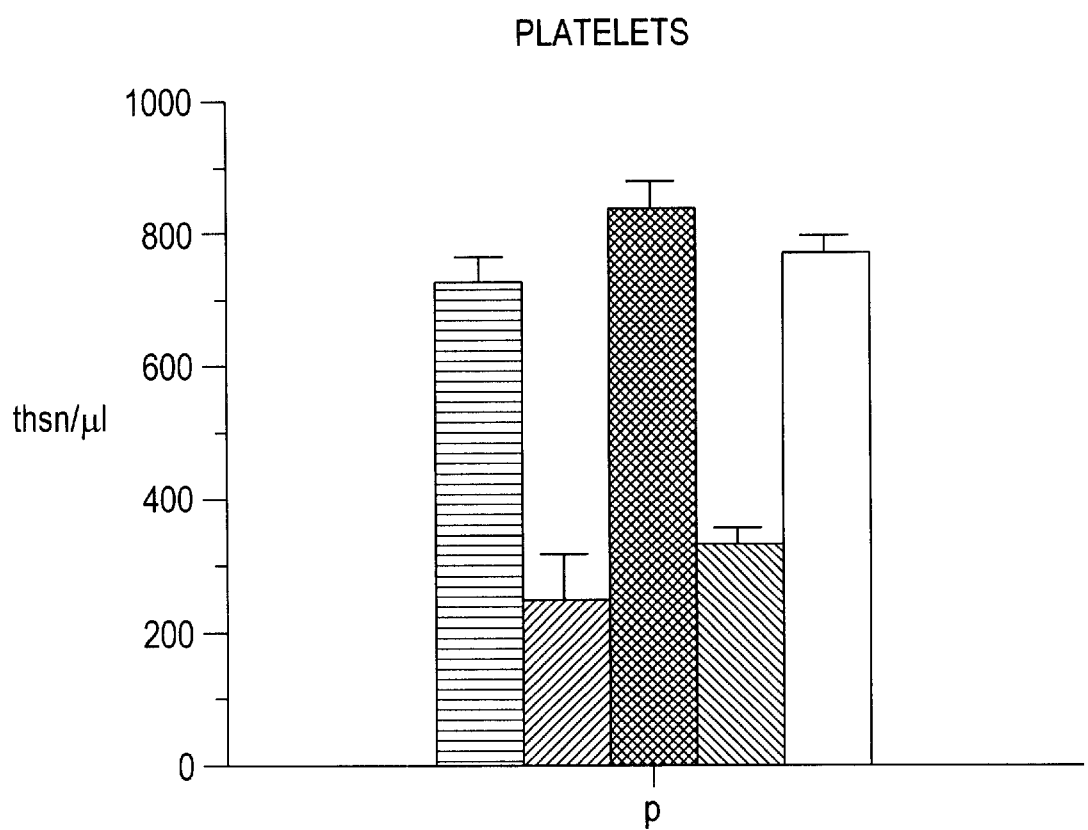
FIG. 15 shows the platelet response to drug and prodrug.
Figure 16:
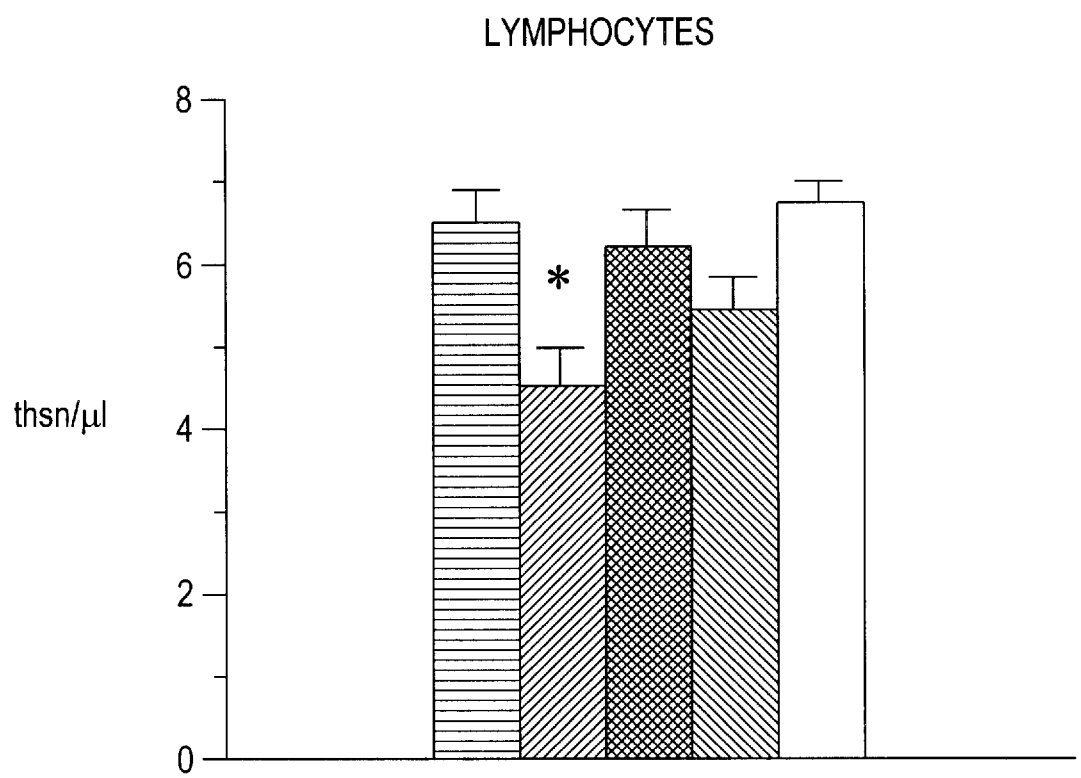
FIG. 16 shows the lymphocyte response to drug and prodrug.
Figure 17:
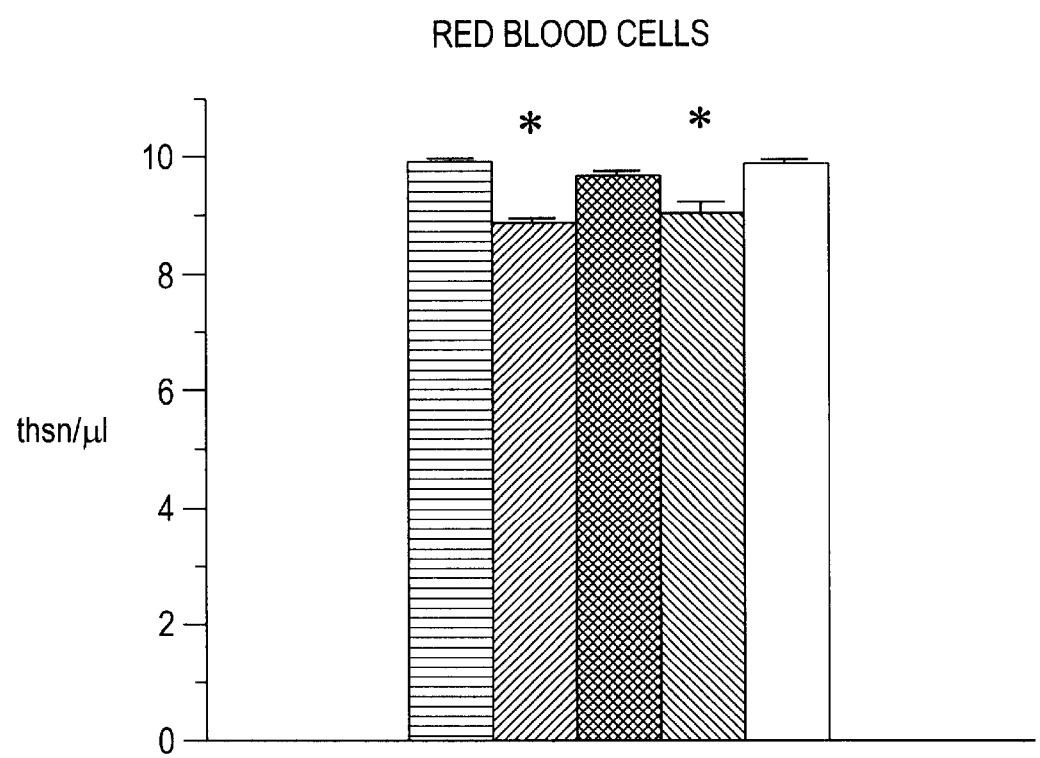
FIG. 17 shows the red blood cell response to drug and prodrug.

Similarly, the data in FIGS. 14 to 17 (the key in FIG. 13 is the same for FIGS. 14 to 17) show that in the presence of b-galactosidase, the prodrug can be activated to create a toxicity much like the drug itself. This effect is quite pronounced in segmented neutrophils and is less so in red blood cells which probably reflects the different kinetics of cell synthesis in the different cell populations.

In summary, these data show that the prodrug, galAraC, has a significantly reduced toxicity in vivo and in vitro and that when activated by an enzyme, the activated prodrug is released creating very simliar toxicity as Arac in vivo and in vitro.

EXAMPLE 10
Prodrug Activity of Galactosyl-5-fluorouridine

Figure 18:
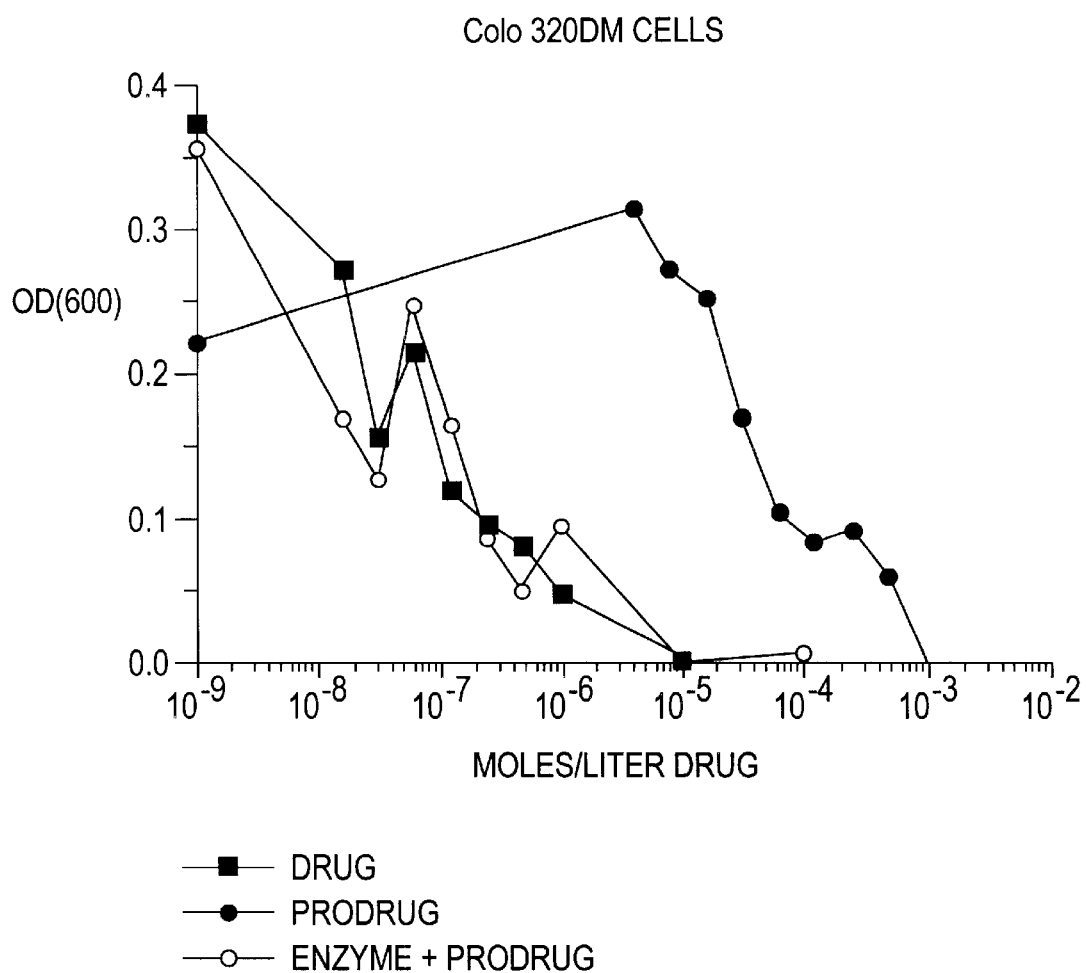
FIG. 18 shows the comparison of 5' fluorouridine and galactosyl-5' fluorouridine Prodrug on CEA antigen negative Colo cells.

In a similar set of experiments the prodrug galactosyl-5-fluorouridine (gal5FU) has been synthesized as described in Example 4 and tested as described above for galAraC. The results of toxicity studies of the prodrug and the drug are shown in FIG. 18. It can be seen that there is over a 500-fold increase in the concentration of the prodrug required to cause a similar degree of toxicity as the drug 5-Fluorouridine. As with galAraC the prodrug gal5FU can be activated in vitro to produce levels of the drug similar to the pure drug itself. Thus, the addition of the galactose moiety onto the drug reduces the toxicity substantially and to a level that makes it an excellent candidate for a prodrug.

Galactosyl-5-fluorouridine has been tested for targeted activation by b-galactosidase conjugated to an antibody with the same CEA antigen tumor surface specificity as was done with the galAraC prodrug. The antibody was allowed to react with antigen-carrying cells (LoVo) and control cells without the CEA antigen marker. The prodrug was then added to different cultures at different concentrations.

Figure 19:
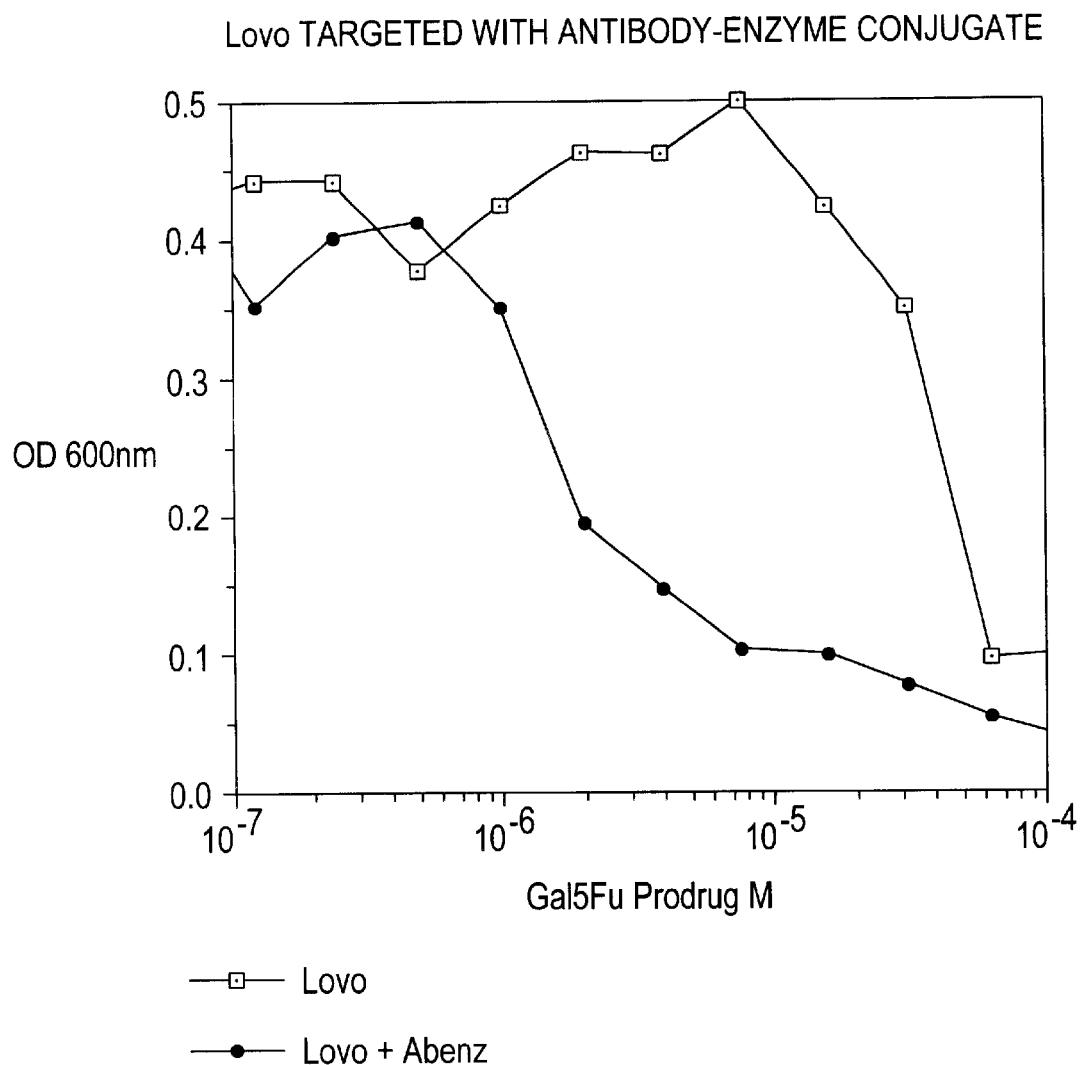
FIG. 19 shows the site specific activation of 5' fluorouridine Prodrug on CEA antigen positive Lovo cells.
Figure 20:
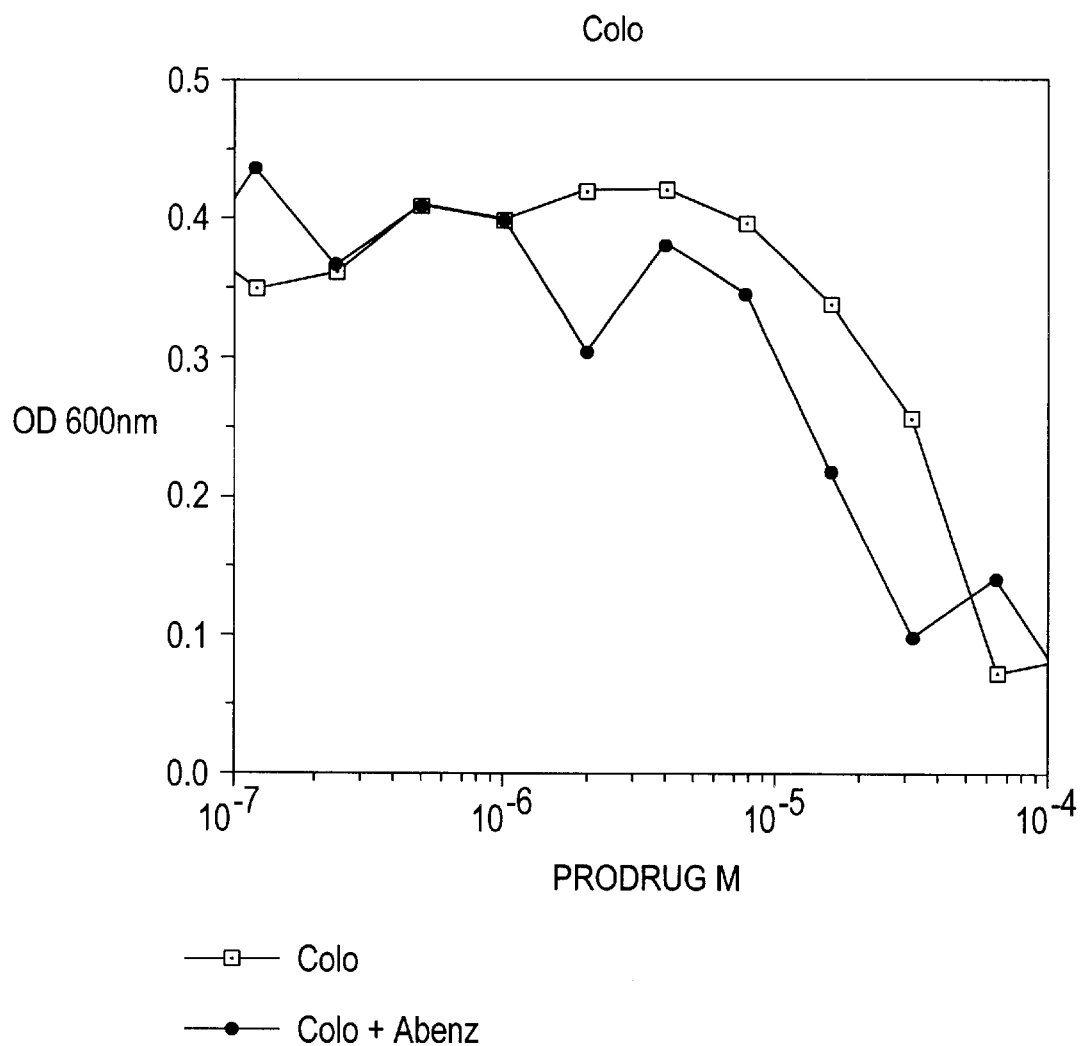
FIG. 20 shows the activity of 5' fluorouridine Prodrug on CEA antigen negative Colo cells.

FIG. 19 displays the results of this experiment which shows that the antibody localized on the surface of the LoVo cells releases a toxic amount of 5-FU from the prodrug at a twenty- to thirty-fold lower concentration than in the control Colo cells (see FIG. 20). Thus site specific activation of the prodrug increases the efficacy of the drug at a significantly lower concentration.

Figure 21:
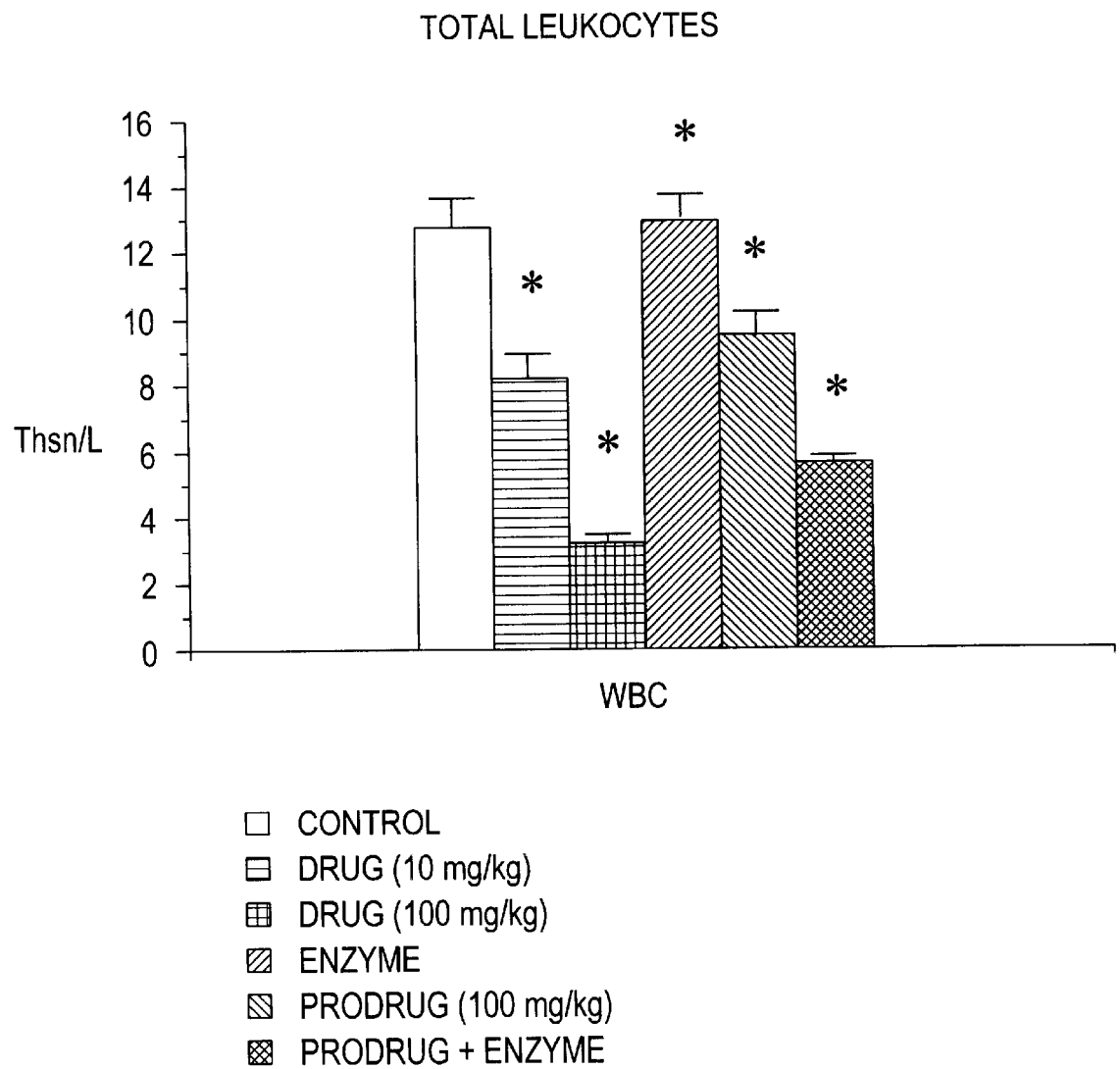
FIG. 21 shows the comparison of 5' fluorouridine and galactosyl-5' fluorouridine Prodrug on total leukocytes in mice.
Figure 22:
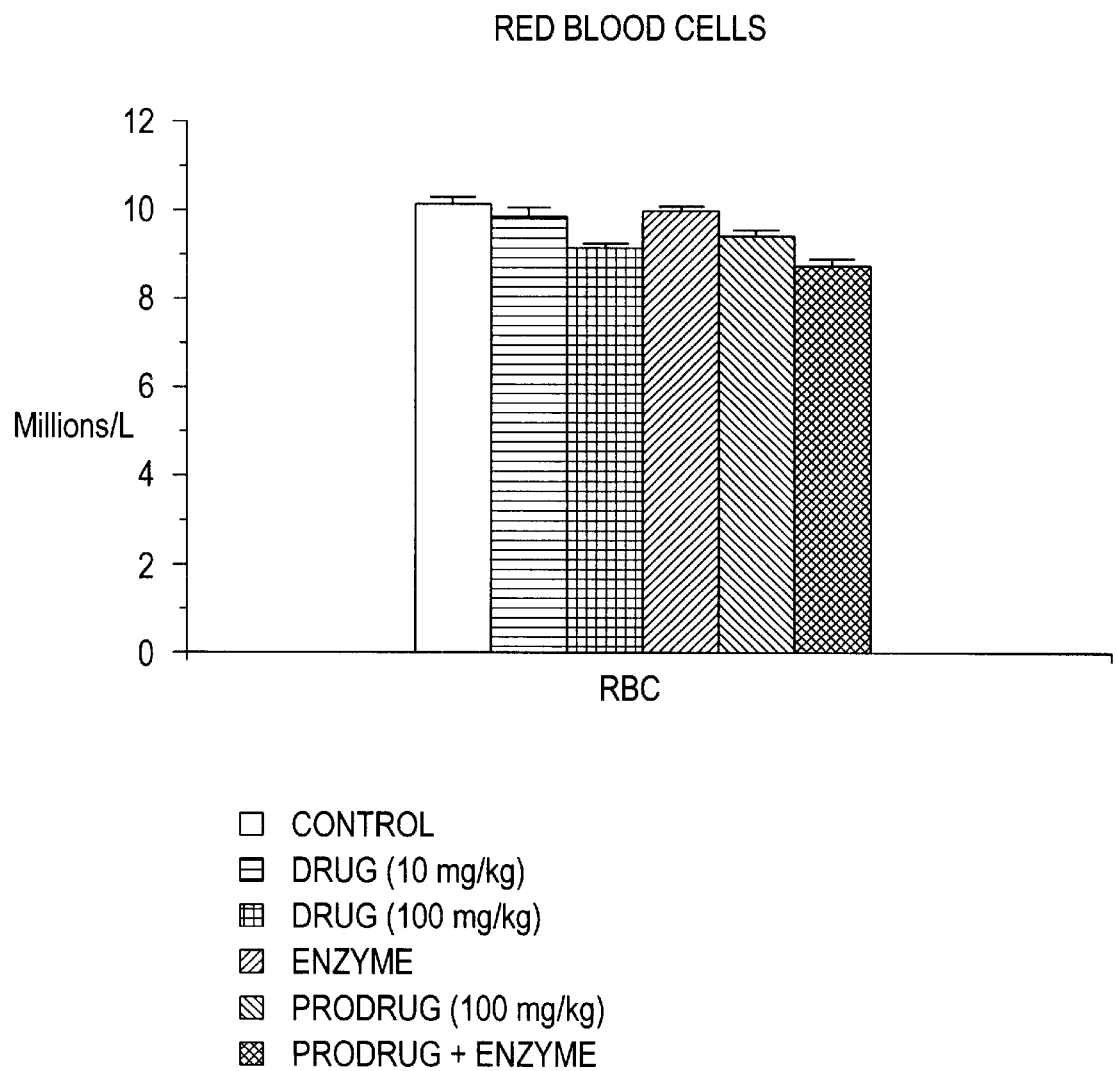
FIG. 22 shows the comparison of 5' fluorouridine and galactosyl-5' fluorouridine Prodrug on Red blood cells in mice.
Figure 23:
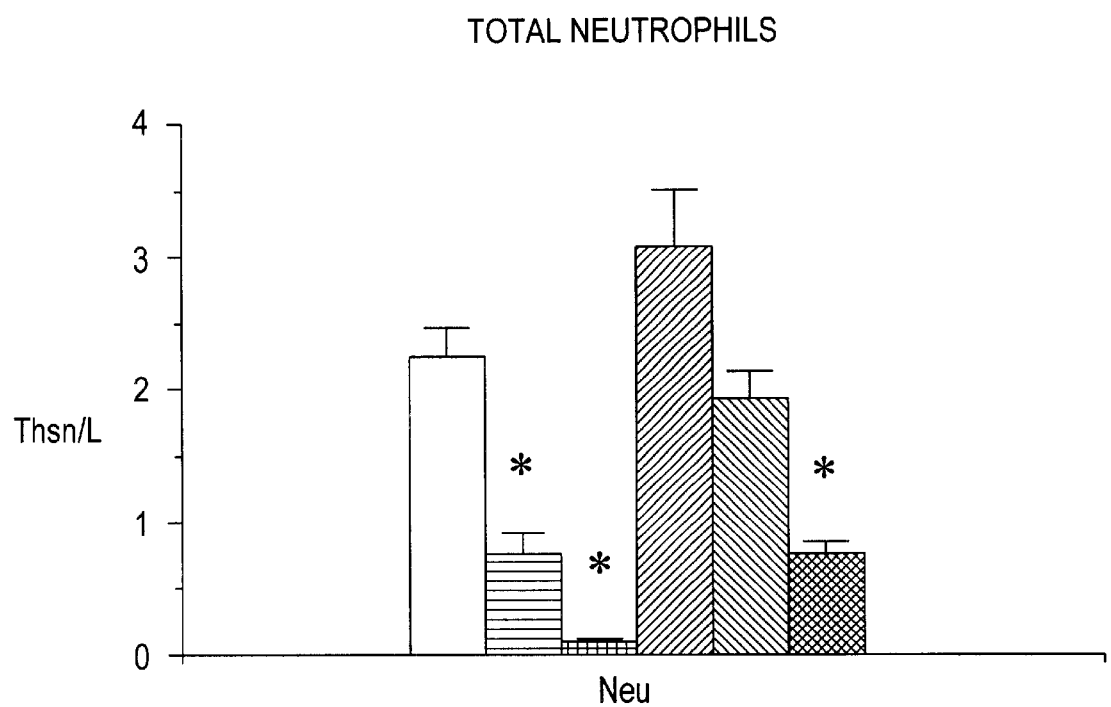
FIG. 23 shows the comparison of 5' fluorouridine and galactosyl-5' fluorouridine Prodrug on total neutrophils in mice.
Figure 24:
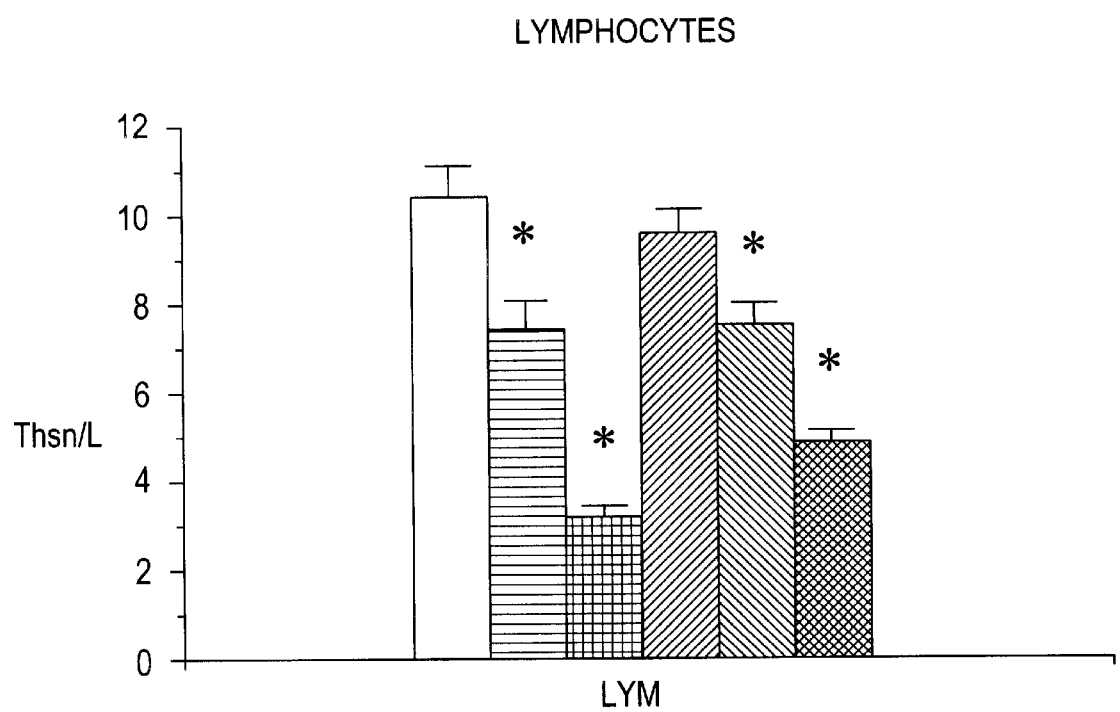
FIG. 24 shows the comparison of 5' fluorouridine and galactosyl-5' fluorouridine Prodrug on total lymphocytes in mice.
Figure 25:
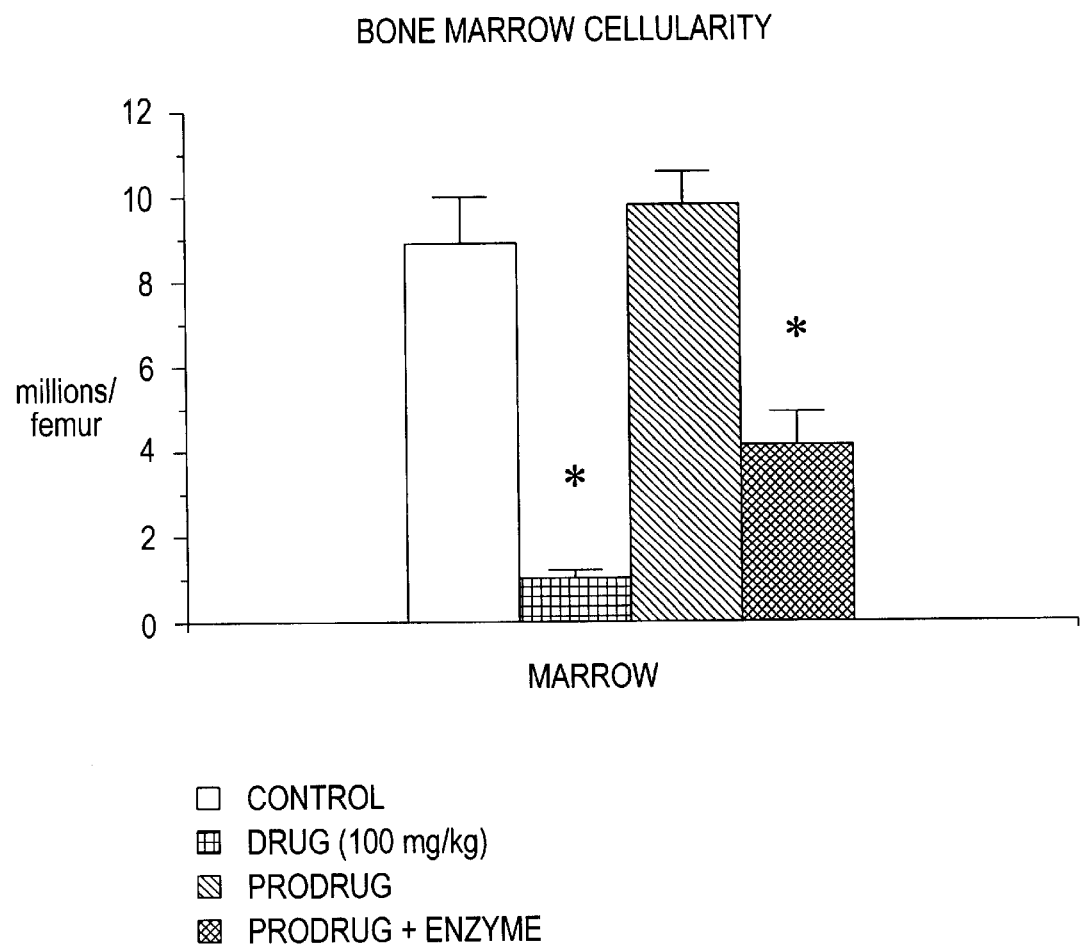
FIG. 25 shows the comparison of 5' fluorouridine and galactosyl-5' fluorouridine Prodrug on total bone marrow cellularity in mice.

Both gal5FU and 5FU have been tested and compared in mice. The in vivo studies were performed as described for the in vivo galAraC experiments. The drug and prodrug were administered and blood white counts along with total bone marrow cellularity were measured six (6) days following injection. The results of this experiment are displayed in FIGS. 21 through 25. The figure key in FIGS. 23 and 24 are the same as for FIG. 21.

In a pattern similar to the results of the galAraC experiments, the prodrug showed reduced toxicity when compared to the drug itself. This is particularly evident in the neutrophil (see FIG. 23) and lymphocyte (see FIG. 24) cell populations. Total leukocytes (see FIG. 21) show the same marked effect while the red cell population is not severly depleated in this six (6) day experiment. The overall difference between the effect of the drug and the less toxic nature of the prodrug are most clearly seen in the measurements of total bone marrow cellularity. These results are displayed in FIG. 25.

Not only is there no effect of the prodrug, it is also clear that it can be actived with b-galactosidase. Thus, the concept of galactosyl-AraC and galactosyl-5-fluoro-uracil to be used as prodrugs is not only a reasonable approach but from these data should stand a reasonable chance of success.

EXAMPLE 15
Preparation of the Intermediate of the Prodrugs in Examples 16 and 20 and of the Haptens of the Prodrugs in Examples 18 and 22, the (thiazolyl)iminoacetic Ester, Compound 60

Figure 26:
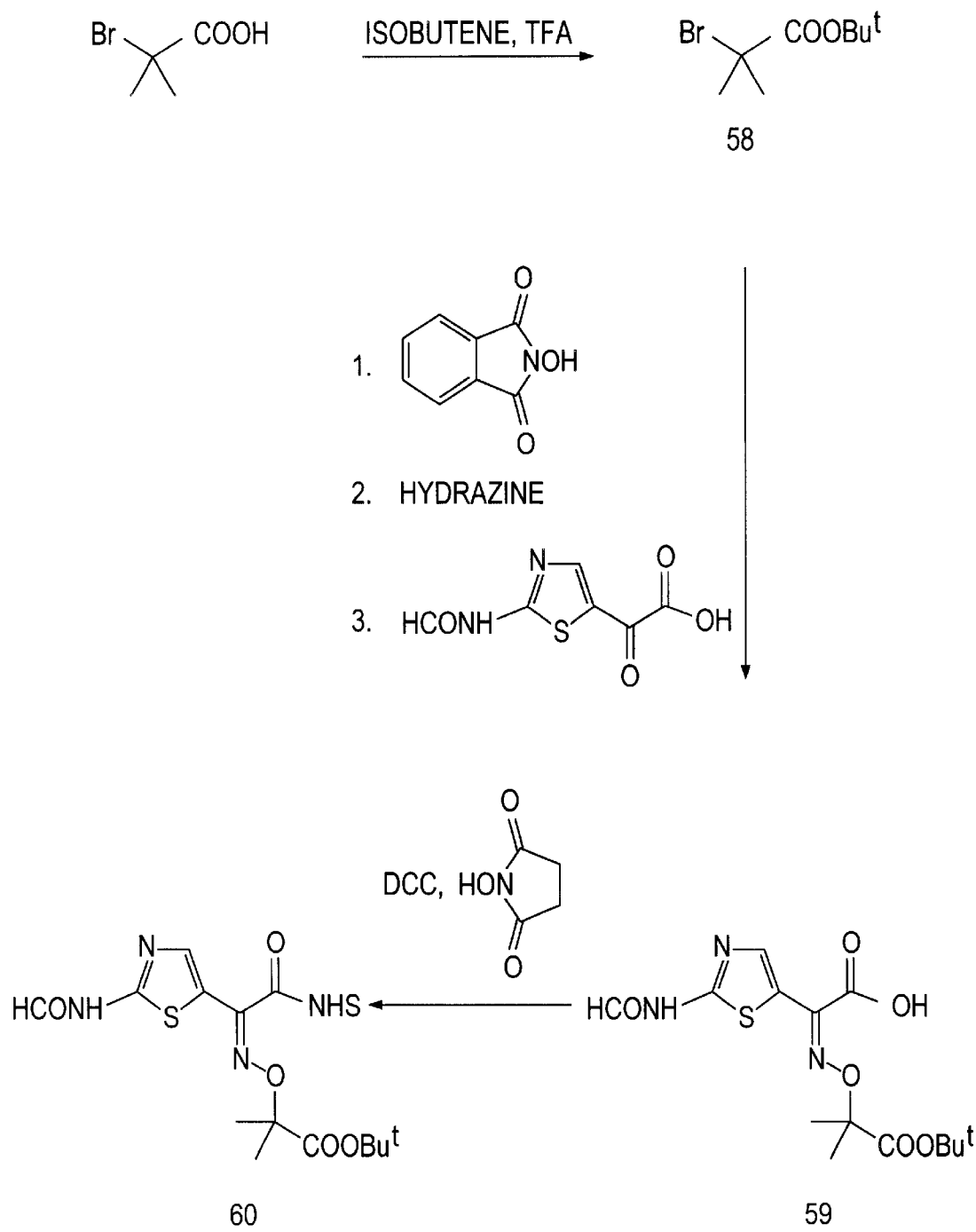
FIG. 26 shows the preparation of the intermediate of the prodrugs in Examples 16 and 20 and of the haptens of the prodrugs in Examples 18 and 22, the (thiazolyl)iminoacetic ester, Compound 60.

Refer to FIG. 26 for the bold numbered compounds in this Example.

The N-alkoxyphthalimide of bromide 58 is prepared, and then it is treated with hydrazine and 2-formamido-4-thiazolylglyoxylic acid to give acid 59. Activation of the acid carboxyl using N-hydroxysuccinimide gives N-hydroxysuccinimidyl (Z)-2-(2-formamido-4-thiazolyl)-2-(1-tert-butoxycarbonyl-1-methyl)ethoxyiminoacetate 60.

In detail, the synthesis is as follows:

tert-Butyl 2-bromo-2-methylpropanoate (58)

Isobutene is condensed into a solution of 2-bromo-2-methylpropanoic acid (10 mmol) and trifluoroacetic acid (1 mmol) in 100 mL of $CH_2Cl_2$ until the starting material is consumed, as observed by TLC. The volatile components are evaporated in vacuo, and the residue is filtered through a pad of neutral alumina using 50% ether/hexane. The filtrate is concentrated in vacuo and used without further purification.

(Z)-2-(2-Formamido-4-thiazolyl)-2-(1-tert-butoxycarbonyl-1-methyl)ethoxyiminoacetic Acid (59)

Compound 59 is synthesized using bromide 58, N-hydroxyphthalimide, and ethyl 2-(formylamino)-4-thiazoleglyoxylate following the procedure given by Takasugi, H., et al., *J. Antibiotics* 36 (1983):846–854.

N-Hydroxysuccinimidyl (Z)-2-(2-formamido-4-thiazolyl)-2-(1-tert-butoxycarbonyl-1-methyl)ethoxyiminoacetate (60)

A solution of DCC (11 mmol) in 10 mL of $CH_2Cl_2$ is added to a solution of N-hydroxysuccinimide (10 mmol) and acid 59 (10 mmol) in 90 mL of $CH_2Cl_2$ at room temperature. A precipitate forms quickly. After 1 hour, the solution is filtered and the filtrate is washed with water (40 mL), dried over anhydrous $MgSO_4$, and concentrated in vacuo to give the product as a colorless solid.

EXAMPLE 16

Preparation of the Prodrug, the 5-fluorouridine Substituted β-lactam, Compound 68

Figure 27:
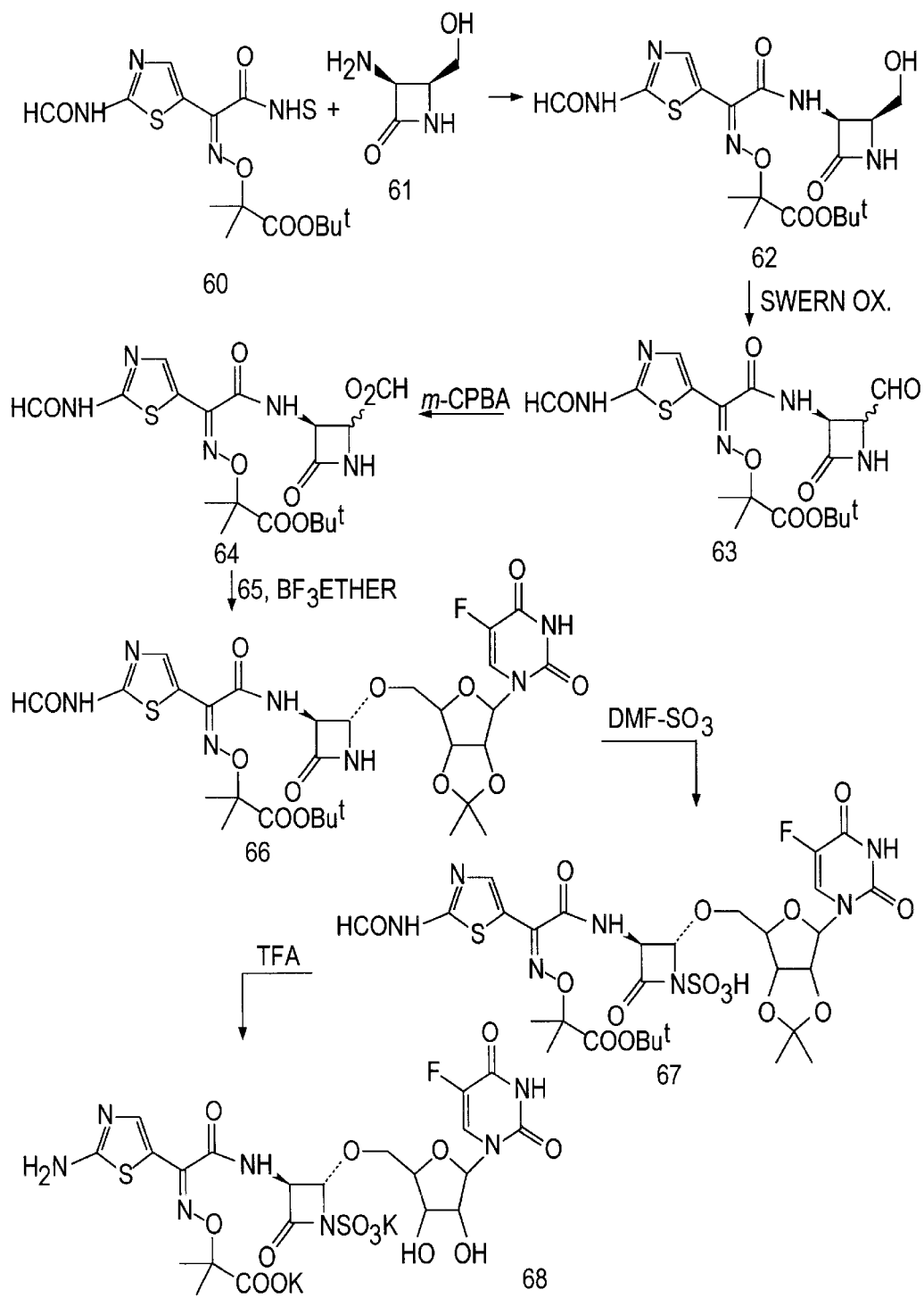
FIG. 27 shows the preparation of the prodrug, the 5-fluorouridine substituted β-lactam, Compound 68.

Refer to FIG. 27 for the bold numbered compounds in this Example.

3-(S)-Amino-4-(S)-hydroxymethylazetidinone (61), prepared following a literature procedure, is acylated with ester 60 to give amide 62, which then undergoes Swern oxidation and Baeyer-Villiger rearrangement to give ester 64. Protected 5-fluorouridine 65 is prepared and reacted with ester 64 to give azetidinone 66, where the alcohol is added to the azetidinone stereoselectively trans to the acylamino group. Azetidinone 66 is sulfonylated and deprotected to give prodrug 68.

In detail, the synthesis is as follows:

3-(S)-Amino-4-(S)-hydroxymethylazetidineone (61)

Amine 61 can be made following the procedure of Evans, D. A., et al., *Tetrahedron Lett.* (1985):3783–3786.

3-(S)-[(Z)-2-(2-Formamido-4-thiazolyl)-2-(1-tert-butoxycarbonyl-1-methyl)ethoxyiminoacetyl]amino-4-(S)-hydroxymethylazetidinone (62)

Amine 61 (1 mmol), activated ester 60 (1 mmol), and DMAP (1 mmol) are dissolved in 10 mL of DMF. After the starting material is consumed as observed by TLC, the mixture is poured into water (50 mL) and extracted with ethyl acetate (3×50 mL), the organic phases are washed with brine (50 mL) and dried over anhydrous $MgSO_4$, and the solvent is evaporated in vacuo. The residue is purified by flash chromatography to give the product as a colorless oil.

4-(R,S)-Carbonyl-3-(S)-[(Z)-2-(2-formamido-4-thiazolyl)-2-(1-tert-butoxycarbonyl-1-methyl)ethoxyiminoacetyl]aminoazetidinone (63)

A solution of oxalyl chloride (1.1 mmol) in 10 mL of $CH_2Cl_2$ is cooled to −78° C., and a solution of DMSO (1.1 mmol) in 1 mL of $CH_2Cl_2$ is added dropwise. After 15 minutes, a solution of alcohol 62 (1 mmol) in 1 mL of $CH_2Cl_2$ is added dropwise. After 30 minutes, a solution of triethylamine (1.2 mmol) in 1 mL of $CH_2Cl_2$ is added in one portion, and the mixture is allowed to warm to room temperature. The mixture is poured into water (50 mL) and extracted with $CH_2Cl_2$ (3×50 mL), the organic phases are washed with water (50 mL) and dried over anhydrous $MgSO_4$, and the solvent is evaporated in vacuo. The residue is purified by flash chromatography to give the product as a colorless oil.

4-(R,S)-Carbonyloxy-3-(S)-[(Z)-2-(2-formamido-4-thiazolyl)-2-(1-tert-butoxycarbonyl-1-methyl)ethoxyiminoacetyl]aminoazetidinone (64)

m-CPBA (1.5 mmol) is added to a solution of aldehyde 63 (1 mmol) in 10 mL of $CH_2Cl_2$ and the mixture is allowed to stand at room temperature until the starting material is consumed as observed by TLC. The mixture is poured into 1M $NaHCO_3$ (50 mL) and extracted with ethyl acetate (3×50 mL), the organic phases are dried over anhydrous $MgSO_4$, and the solvent is evaporated in vacuo. The residue is purified by flash chromatography to give the product as a colorless oil.

2',3'-O-Isopropylidene-5-fluorouridine (65)

2,2-Dimethoxypropane (2 mL) was added to a solution of 5-fluorouridine (1.05 g, 4 mmol) and TsOH (20 mg) in 5 mL of DMF. After the starting material was consumed as observed by TLC, 20 mL of methanol was added, and the reaction was allowed to stand overnight. Then the solvents were evaporated in vacuo. The resulting solid was recrystallized from hot methanol to give 864 mg of the product as a colorless solid.

Preparation of the Prodrug Precursor 66

A solution of $BF_3 \cdot OEt_2$ (0.1 mmol) in 1 mL of $CH_2Cl_2$ is added to a solution of ester 64 (1 mmol) and alcohol 65 (1 mmol) in 5 mL of $CH_2Cl_2$. After the starting material is consumed as observed by TLC, the mixture is poured into 0.1M $NaHCO_3$ (50 mL) and extracted with ethyl acetate (3×50 mL), the organic phases are dried over anhydrous $MgSO_4$, and the solvent is evaporated in vacuo. The residue is purified by flash chromatography to give the product as a colorless oil.

Preparation of the Prodrug Precursor 67

Trimethylsilyl chlorosulfonate (2 mmol) is added to DMF (4 mL). After 30 minutes, the volatile components are removed in vacuo. The residue is added to a mixture of amide 66 (1 mmol) in 4 mL of $CH_2Cl_2$ cooled by an ice bath. After 30 minutes, the solution is poured into 10 mL of 0.5M $KH_2PO_4$. The organic phase is separated, and the aqueous phase is extracted with $CH_2Cl_2$ (4 mL) and evaporated to dryness. The solid residue is triturated with methanol (40 mL), and the organic washings are concentrated in vacuo. The residue is used without further purification.

Preparation of the 5-fluorouridine-substituted β-lactam Prodrug (68)

Trifluoroacetic acid (1 mL) is added to a mixture of compound 67 (1 mmol) and anisole (0.5 mL) in 4 mL of $CH_2Cl_2$ cooled by an ice bath. The mixture is allowed to warm to room temperature, and after 1 hour, the volatile components are evaporated in vacuo. The residue is purified by reverse-phase HPLC using 0.1M triethylammonium acetate buffer (pH 7) and acetonitrile mixture as the mobile phase. The fractions containing the product are combined and dried in vacuo, the residue is redried from deionized water (2×), and the residue is then passed through a SP-Sephadex ion exchange column, potassium form, to give the product as the dipotassium salt.

EXAMPLE 17
Preparation of the Intermediate of the Hapten of the Prodrug in Example 16, the 5-alkynylated Uridine, Compound 74

Figure 28:
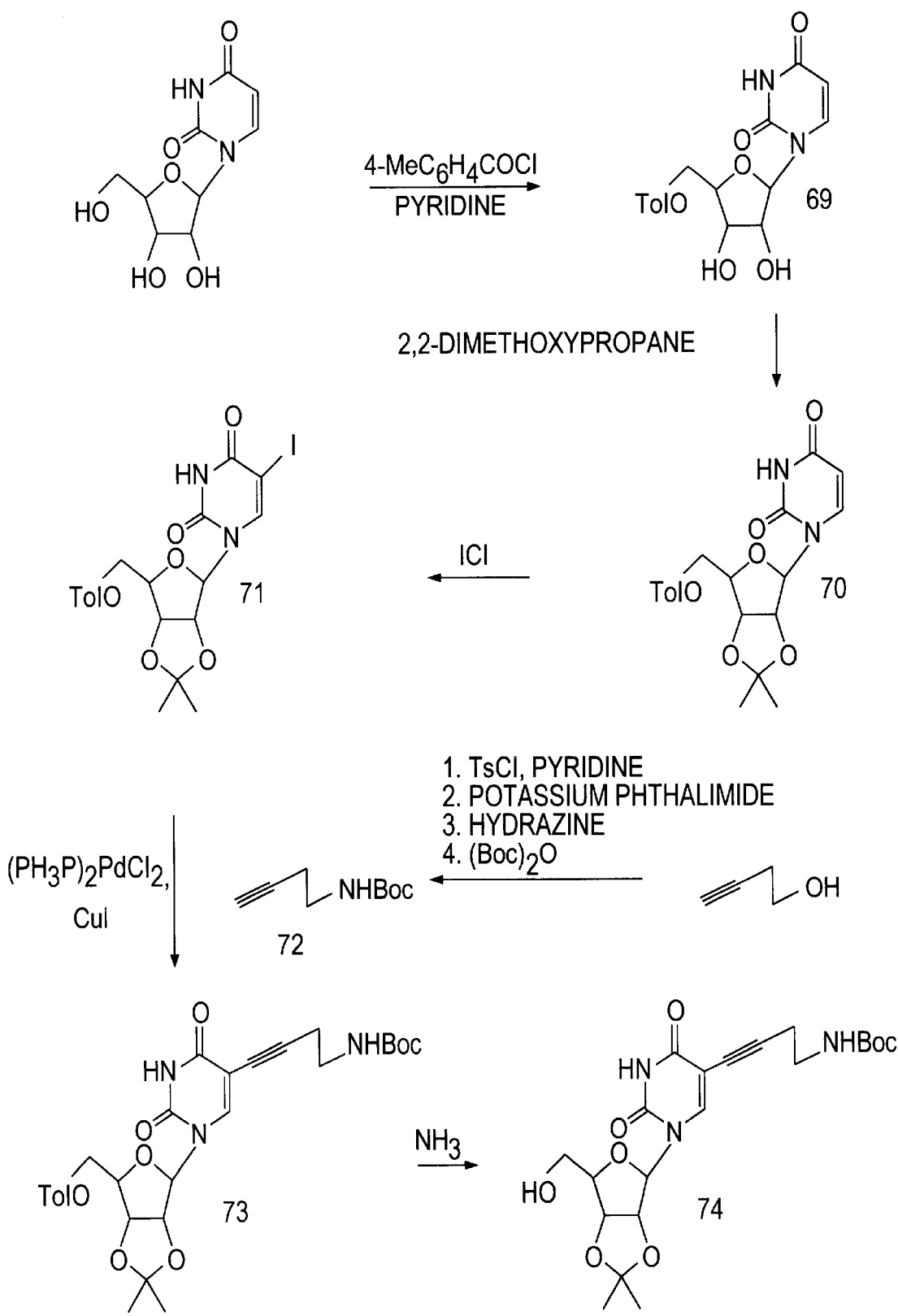
FIG. 28 shows the preparation of the intermediate of the hapten of the prodrug in Example 16, the 5-alkynylated uridine, Compound 74.

Refer to FIG. 28 for the bold numbered compounds in this Example.

The hydroxyl groups of uridine are protected to give compound 70. Compound 70 is iodinated in the 5 position to give iodide 71. A subsequent palladium-catalyzed alkynylation gives compound 73, which is selectively deprotected at the 5' hydroxyl to give the intermediate 74.

In detail, the synthesis is as follows:

5'-O-(4-Methylbenzoyl)uridine (69)

4-Methylbenzoyl chloride (10 mmol) is added to a solution of uridine (10 mmol) in 20 mL of pyridine. After no further progress occurs as observed by TLC, the volatile components are evaporated in vacuo. The residue is purified using flash chromatography to give the product as a colorless oil.

2',3'-O-Isopropylidene-5'-O-(4-methylbenzoyl) uridine (70)

A solution of diol 69 (10 mmol), dimethoxypropane (30 mmol), and TsOH (1 mmol) in 10 mL of $CH_2Cl_2$ is stirred at room temperature until the starting material is consumed as observed by TLC. Triethylamine (2 mmol) is added, and the volatile components are evaporated in vacuo. The residue is purified using flash chromatography to give the product as a colorless oil.

5-Iodo-2',3'-O-isopropylidene-5'-O-(4-methylbenzoyl)uridine (71)

A solution of compound 70 (10 mmol) and ICl (15 mmol) in 100 mL of $CH_2Cl_2$ is heated at reflux until the starting material is consumed as observed by TLC. The solution is cooled, diluted with 100 mL of $CH_2Cl_2$, and decolorized by washing with the minimum required volume of 5% $Na_2S_2O_3$. The organic phase is dried over anhydrous $MgSO_4$, and concentrated in vacuo. The residue is purified by flash chromatography to give the product as a colorless oil.

4-tert-Butoxycarbonylamino-1-butyne (72)

TsCl (10 mmol) is added to a solution of 3-butyn-1-ol (10 mmol) in 20 mL of pyridine. After the reaction is complete as observed by TLC, the volatile components are evaporated in vacuo. The residue is partitioned between 0.1M HCl (50 mL) and ethyl acetate (3×80 mL), the organic phases are dried over $MgSO_4$, and the solvent is evaporated in vacuo.

The crude product obtained above is dissolved in 20 mL of DMF, cooled by an ice bath, and potassium phthalimide (12 mmol) is added. After the reaction is complete as observed by TLC, the mixture is partitioned between 0.1M HCl (50 mL) and ethyl acetate (3×80 mL), the organic phases are dried over $MgSO_4$. and the solvent is evaporated in vacuo. The residue is purified using flash chromatography to give the product as a colorless oil.

Hydrazine (10 mmol) is added carefully to a mixture of the phthalimide obtained above and ethanol (100 mL), and the solution is heated at reflux until the starting material is consumed as observed by TLC. 1M HCl is added to dissolve the gelatinous residue in the reaction mixture and to cause the precipitation of the phthalyl hydrazide side product. The solid is filtered out and washed with water. The ethanol and water is removed in vacuo to leave a hydrochloride salt of 4-aminobutyne.

The crude amine obtained above is dissolved in 50 mL of dioxane and 2 mL of triethylamine, and a solution of di-tert-butyl dicarbonate (10 mmol) in 10 mL of dioxane is added. After the reaction is complete as observed by TLC, the mixture is partitioned between 0.05M HCl (50 mL) and ethyl acetate (3×100 mL), the organic phases are dried over $MgSO_4$, and the solvent is evaporated in vacuo. The residue is purified using flash chromatography to give the product as a colorless oil.

5-(4-tert-Butoxycarbonylamino-1-butynyl)-2',3'-O-isopropylidene-5'-O-(4-methylbenzoyl)uridine (73)

To a degassed solution of iodide 71 (5 mmol) in 150 mL of triethylamine is added 4-tert-butoxycarbonylamino-1-butyne 72 (10 mmol), $(Ph_3P)_2PdCl_2$ (0.2 mmol), and CuI (0.3 mmol). The resulting suspension is heated at 50° C. until the starting material is consumed. The volatile components are evaporated in vacuo, and the residue is taken up in $CHCl_3$ (200 mL) and washed with 5% disodium EDTA (2×100 mL) and water (100 mL), dried over $MgSO_4$, and the solvent is evaporated in vacuo. The residue is purified by flash chromatography to give the product as a colorless oil.

5-(4-tert-Butoxycarbonylamino-1-butynyl)-2',3'-O-isopropylideneuridine (74)

Concentrated ammonium hydroxide (7 mL) is added to a solution of ester 73 (5 mmol) in 90 mL of methanol. After the starting material is consumed as observed by TLC, the volatile components are evaporated in vacuo and the residue is purified by flash chromatography to give the product as a colorless oil.

EXAMPLE 18
Preparation of the Hapten of the Prodrug in Example 16, the Cyclobutanol Substituted 5-fluorouridine, Compound 81

Figure 29:
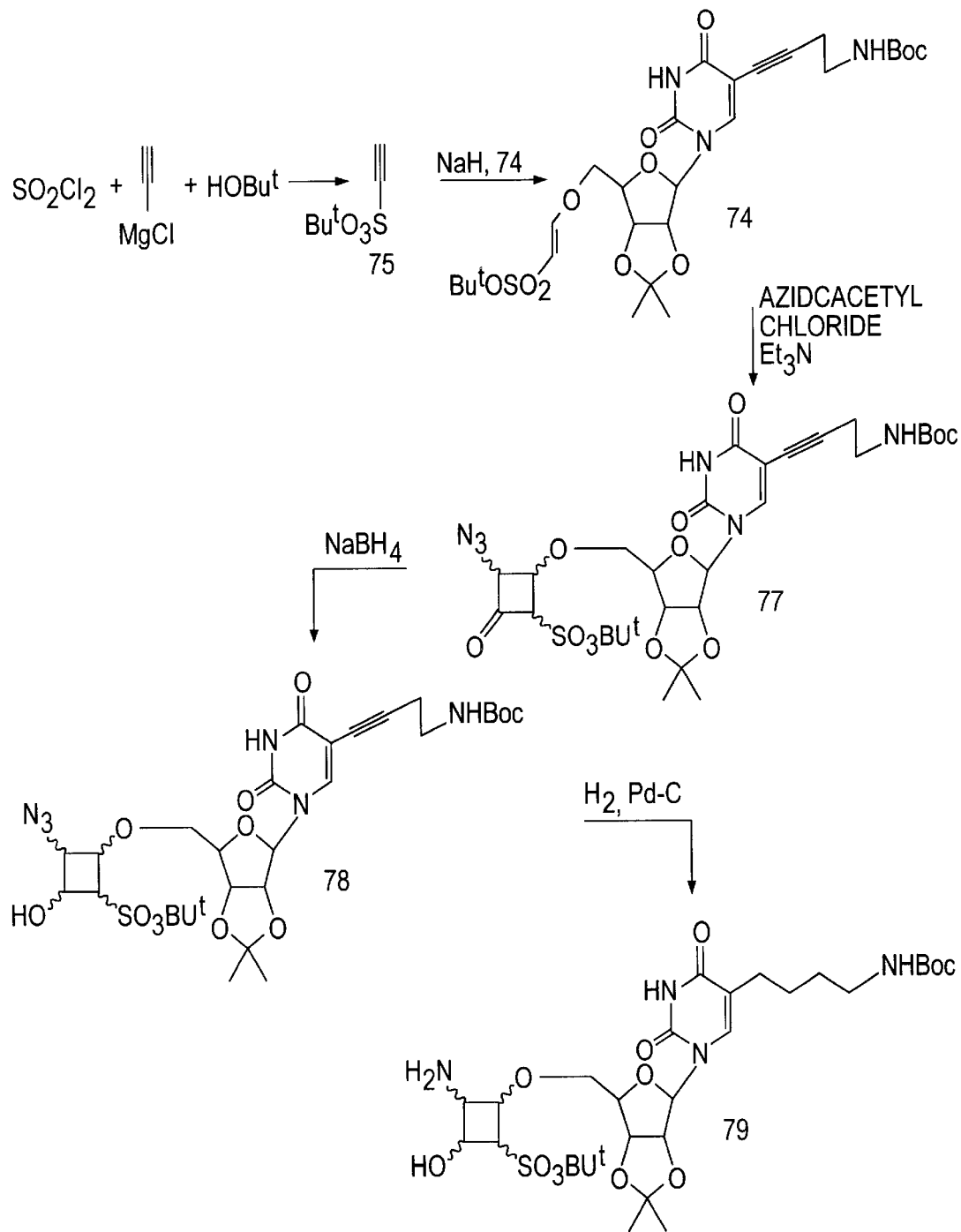
FIG. 29 shows the preparation of the intermediate of the hapten of the β-lactam prodrug, Compound 79.
Figure 30:
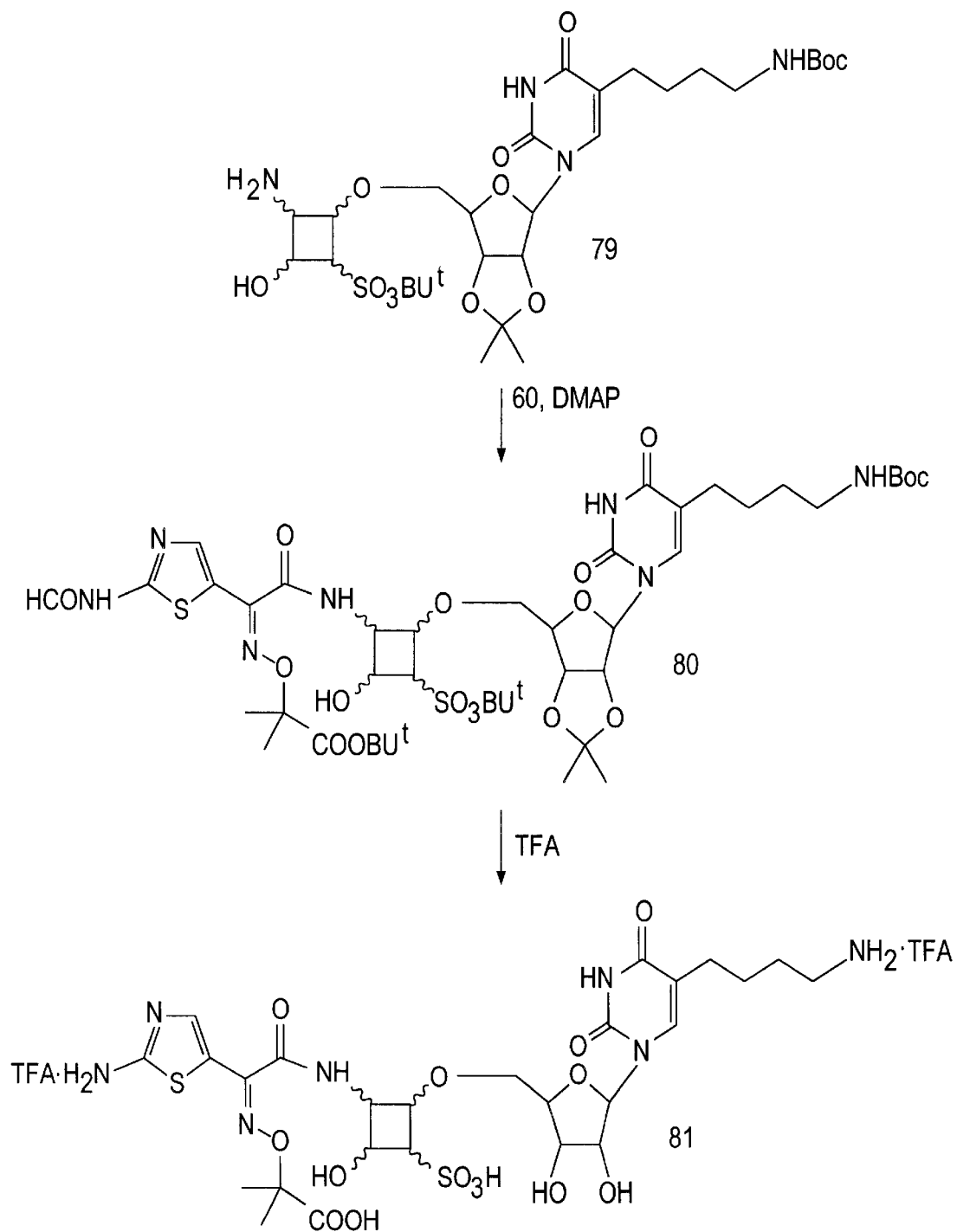
FIG. 30 shows the preparation of the hapten of the prodrug in Example 16, the cyclobutanol substituted 5-fluorouridine, Compound 81.

Refer to FIGS. 29 and 30 for the bold numbered compounds in this Example.

Alcohol 74 undergoes a conjugate addition to ethynylsulfonate 75 to give the enol ether 76. Azidoketene undergoes a [2+2] cycloaddition to enol ether 76 to give cyclobutanone 77. Reduction of the keto, azido, and alkynyl groups gives amino alcohol 79, which is N-acylated and deprotected to give compound 81, which can be linked to a carrier protein at the primary aliphatic amino group.

In detail, the synthesis is as follows:

tert-Butyl ethynsulfonate (75)

A solution of ethynylmagnesium chloride in THF (0.5M, 10 mmol) is added to a solution of sulfuryl chloride (20 mmol) in 100 mL of THF cooled to −78° C. After 1 hour, a solution of tert-butanol (60 mmol) and triethylamine (60 mmol) in 50 mL of THF is added dropwise. The solution is allowed to warm to room temperature, the volatile components are evaporated in vacuo, the residue is partitioned between ether (150 mL) and 0.05M HCl (50 mL), the organic phase is washed with brine (50 mL) and dried over $MgSO_4$, and the volatile components are evaporated in vacuo. The residue is purified by flash chromatography to give the product as a colorless oil.

Preparation of Uridine 5'-O-enol Ether 76

Sodium methoxide (0.05 mmol) is added to a solution of alkyne 75 (11 mmol) and alcohol 74 (10 mmol) in 100 mmol of THF. After the starting material is consumed as observed by TLC, acetic acid (0.1 mmol) is added, and the volatile components are evaporated in vacuo. The residue is partitioned between 5% NaHCO$_3$ (40 mL) and ethyl acetate (3×100 mL), the organic phases are dried over MgSO$_4$, and the solvent is evaporated in vacuo. The residue is purified by flash chromatography to give the product as a colorless oil.

Preparation of Cyclobutanone 77

A solution of azidoacetyl chloride (10 mmol) in 20 mL of CH$_2$Cl$_2$ is added dropwise to a solution of triethylamine (11 mmol) and enol ether 76 (5 mmol) in 50 mL of CH$_2$Cl$_2$ cooled to –78° C. The mixture is allowed to warm slowly to room temperature overnight. When no further progress in the reaction is observed by TLC, 1 mL of methanol is added and the volatile components are evaporated in vacuo. The residue is passed through a short column of silica gel using ethyl acetate as a solvent.

Preparation of Cyclobutanol 78

Sodium borohydride (10 mmol) is added to a solution of ketone 77 (2 mmol) in 20 mmol of methanol cooled by an ice bath. When no further progress in the reaction is observed by TLC, the volatile components are evaporated in vacuo. The residue is partitioned between 0.05M HCl (40 mL) and ethyl acetate (3×100 mL), the organic phases are dried over MgSO$_4$, and the solvent is evaporated in vacuo. The residue is then passed through a short column of silica gel using ethyl acetate as a solvent, concentrated in vacuo, and used without further purification.

Preparation of Amino Alcohol 79

Azide 78 (5 mmol) is dissolved in methanol (100 mL), 5% Pd-C (10% by weight) is added, and the mixture is stirred under a hydrogen atmosphere until the starting material is consumed. The catalyst is filtered out using a pad of Celite, and the catalyst is rinsed with methanol (100 mL). The solvent is evaporated in vacuo, and the product is used without further purification.

Preparation of Amide 80

Amide 80 is synthesized from amine 79 and ester 60 following the procedure used for amide 62.

Preparation of Hapten 81

Compound 80 is deprotected to give compound 81 using the procedure for compound 68. However, the trifluoroacetate salt may be used for the reaction linking compound 81 at the primary aliphatic amino group to the carrier protein.

EXAMPLE 19

Preparation of the Intermediate of the Prodrug in Example 20, the 5-fluorouridine 5'-O-aryl ester, Compound 85

Figure 31:
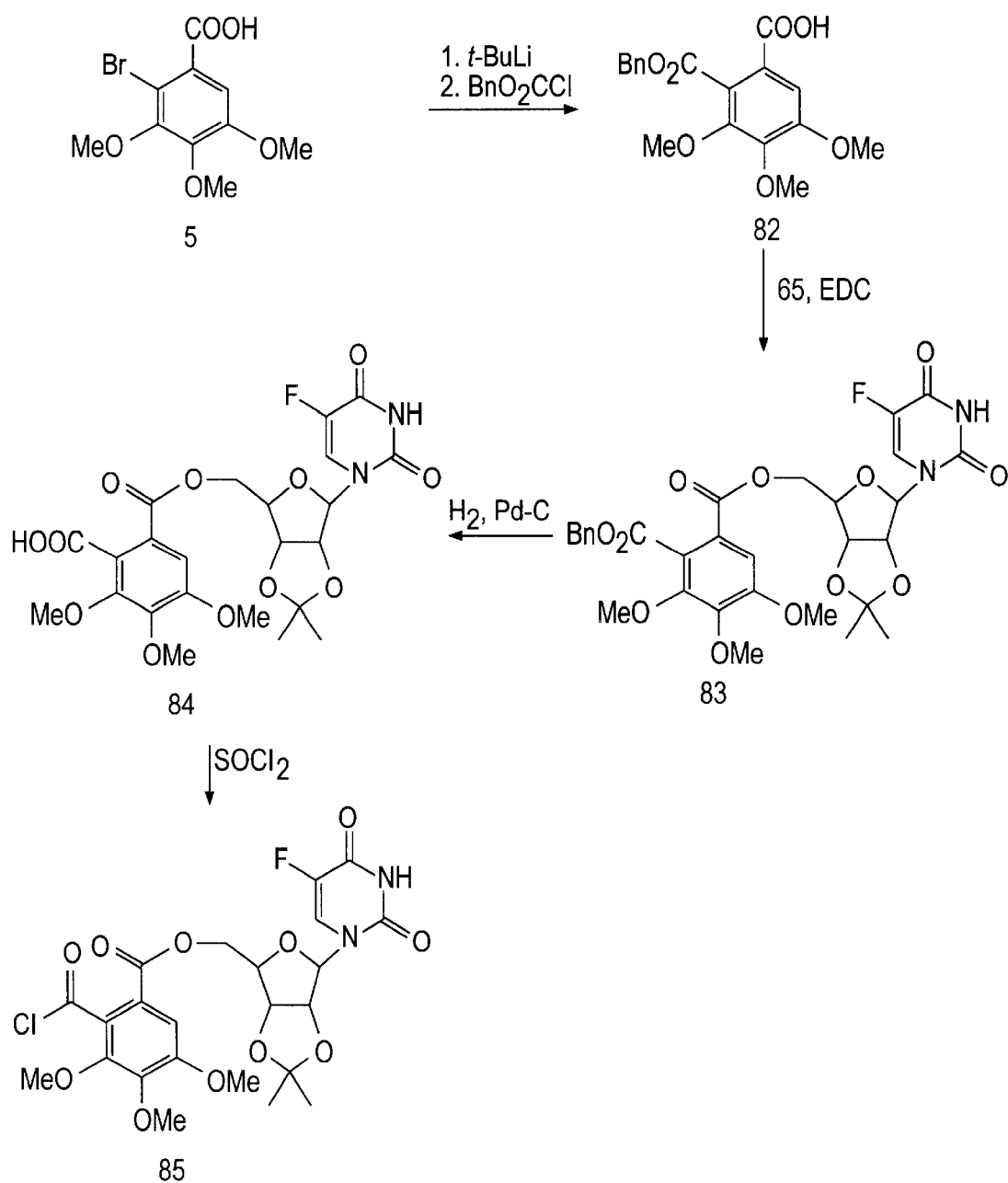
FIG. 31 shows the preparation of the intermediate of the prodrug in Example 20, the 5-fluorouridine 5'-O-aryl ester, Compound 85.

Refer to FIG. 31 for the bold numbered compounds in this Example.

Lithium-halogen exchange on bromide 5, followed by reaction with benzyl chloroformate, gives monoester 82. Esterification with 5-fluorouridine 65 gives diester 83, which is selectively deprotected and activated at the benzyl ester group to give the intermediate 85.

In detail, the synthesis is as follows:

2-Carbobenzyloxy-3,4,5-trimethoxybenzoic Acid (82)

tert-Butyllithium (1.7M solution in pentane, 15 mmol) is added to a solution of 2-bromo-3,4,5-trimethoxybenzoic acid 5 (5 mmol) in 50 mL of THF, while maintaining the temperature of the mixture below –95° C. After the addition is completed, the mixture is allowed to warm to –78° C. After 30 minutes, benzyl chloroformate (5 mmol) is added in one portion, and the mixture is allowed to warm to 0° C. Water (50 mL) is added, and then the pH of the mixture is carefully adjusted to 3 using 0.1 M HCl. The mixture is extracted with ethyl acetate (5×100 mL). The organic phases are dried over anhydrous Na$_2$SO$_4$ and concentrated in vacuo. The mixture is purified by flash chromatography to give the product as a colorless oil.

Preparation of Diester 83

A mixture of acid 82 (5 mmol), 2',3'-O-isopropylidene-5-fluorouridine 65 (5 mmol), and EDC (6 mmol) in 50 mL of CH$_2$Cl$_2$ is stirred at room temperature until the starting material is consumed. The solution is washed with water (2×30 mL), the aqueous phases are washed with CH$_2$Cl$_2$ (2×50 mL), the organic phases are dried over anhydrous MgSO$_4$. and the solvent is evaporated in vacuo. The residue is purified by flash chromatography to give the product as a colorless oil.

Preparation of Monoacid 84

Diester 83 (2 mmol) is dissolved in ethyl acetate (100 mL), 5% Pd-C (10% by weight) is added, and the mixture is stirred under a hydrogen atmosphere until the starting material is consumed. The catalyst is filtered out using a pad of Celite, and the catalyst is rinsed with ethyl acetate (100 mL). The solvent is evaporated in vacuo, and the product is used without further purification.

Preparation of Acid Chloride 85

Monoacid 84 (1 mmol) is dissolved in CH$_2$Cl$_2$ (20 mL), and thionyl chloride (5 mmol) is added. The progress of the reaction is monitored by methanolysis of aliquots and $^1$H-NMR spectroscopy. When the reaction is complete, the volatile components are evaporated in vacuo to give compound 85 as an oil.

EXAMPLE 20

Preparation of the Prodrug, the b-lactam Substituted by a 5'-O-aroyl-5-fluorouridine, Compound 90

Figure 32:
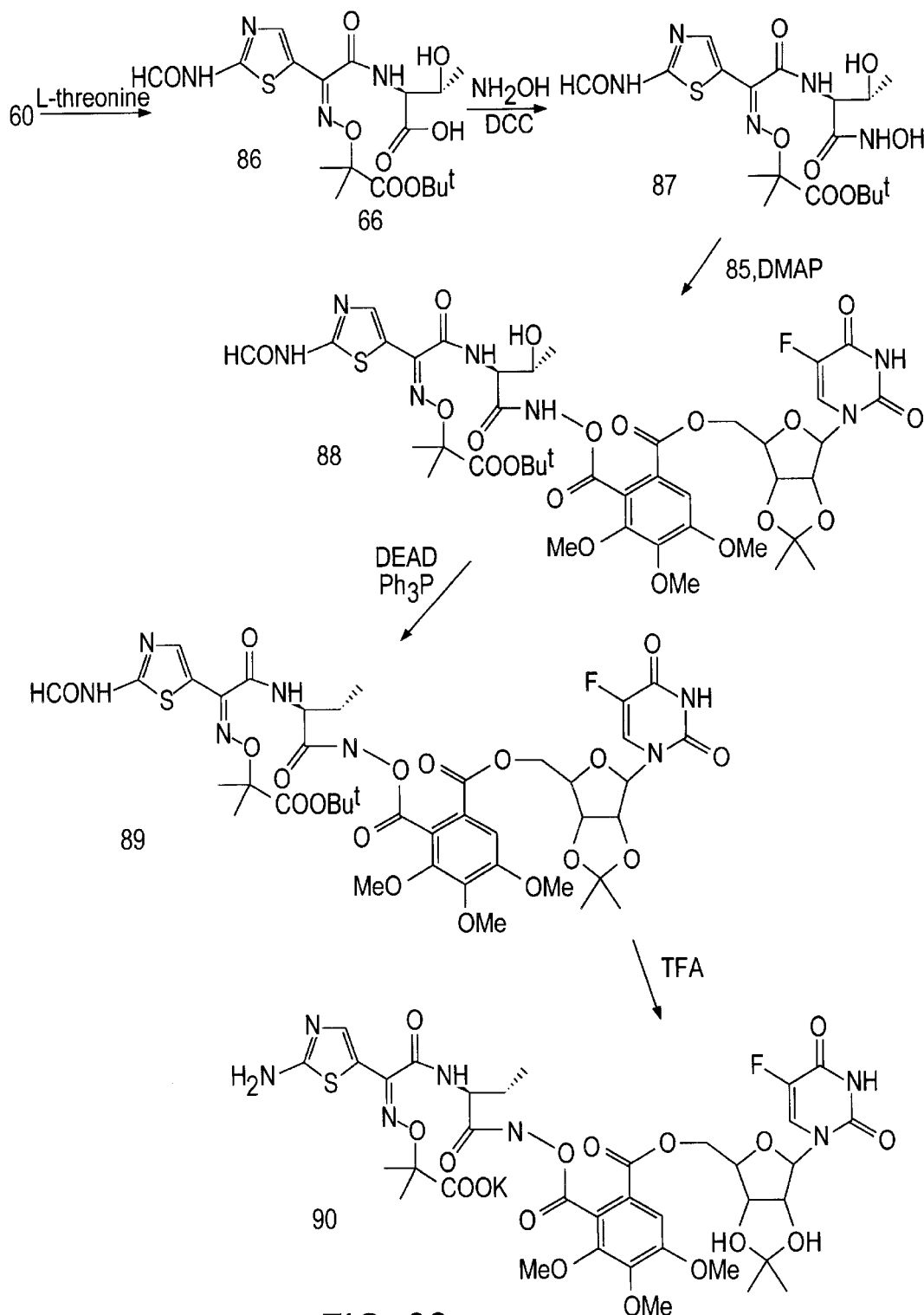
FIG. 32 shows the preparation of the prodrug, the β-lactam substituted by a 5'-O-aroyl-5-fluorouridine, Compound 90.

Refer to FIG. 32 -for the bold numbered compounds in this Example.

N-acylation and amidation, using hydroxylamine, of threonine gives hydroxamic acid 87. Reaction of compound 87 at the more acidic hydroxamic acid hydroxyl using acid chloride 85 gives amide 88, which undergoes ring closure by a Mitsunobu reaction. Subsequent deprotection gives the b-lactam prodrug 90.

In detail, the synthesis is as follows:

N-[(Z)-2-(2-Formamido-4-thiazolyl)-2-(1-tert-butoxycarbonyl-1-methyl)ethoxyiminoacetyl] threonine (86)

A mixture of L-threonine (5 mmol), ester 60 (5 mmol), and DMAP (5 mmol) in 30 mL of DMF is stirred at room temperature. After the starting material is consumed as observed by TLC, the mixture is poured into 0.05M HCl (50 mL) and extracted with ethyl acetate (3×50 mL), the organic phases are washed with brine (50 mL) and dried over anhydrous MgSO$_4$, and the solvent is evaporated in vacuo. The residue is purified by flash chromatography to give the product as a colorless oil.

Preparation of Threonine Hydroxamic Acid 87

A solution of DCC (5.5 mmol) in 5 mL of CH$_2$Cl$_2$ is added to a solution of hydroxylamine hydrochloride (5 mmol), triethylamine (5 mmol), and acid 86 (5 mmol) in 45 mL of CH$_2$Cl$_2$ at room temperature. A precipitate forms quickly. After 1 hour, the solution is filtered and the filtrate is washed with 0.05M HCl (40 mL), the aqueous phase is extracted with $CH_2Cl_2$ (50 mL), and the organic phases are dried over anhydrous $MgSO_4$, and concentrated in vacuo to give the product as a colorless solid.

Preparation of O-benzoyl Hydroxamic Acid 88

Compound 85 is taken up in 5 mL of $CH_2Cl_2$ and added dropwise to a solution of hydroxamic acid 87 (1 mmol) and DMAP (2 mmol) in 20 mL of $CH_2Cl_2$ cooled by an ice bath. After 2 hours, the mixture is poured into water (50 mL) and extracted with ethyl acetate (3×50 mL), the organic phases are washed with brine (50 mL) and dried over anhydrous $MgSO_4$, and the solvent is evaporated in vacuo. The residue is purified by flash chromatography to give the product as a colorless oil.

Preparation of b-lactam 89

A solution of DEAD (1.1 mmol) in 10 mL of THF is added dropwise to a solution of compound 88 (1 mmol) and triphenylphosphine (1.1 mmol) in 20 mL of THF at room temperature. After the reaction is complete as observed by TLC, the solvent is evaporated in vacuo. The residue is purified by flash chromatography to give the product as a colorless oil.

Preparation of b-lactam Prodrug 90

Trifluoroacetic acid (2 mL) was added to a mixture of compound 89 (1 mmol) and anisole (1 mL) in 10 mL of $CH_2Cl_2$ cooled by an ice bath. The mixture is warmed to room temperature, and, after 1 hour, the volatile components are evaporated in vacuo. The residue is purified by reverse-phase HPLC using 0.1M triethylammonium acetate buffer (pH 7) and acetonitrile mixture as the mobile phase. The fractions containing the product are combined and dried in vacuo, the residue is redried from deionized water (3×), and the residue is then passed through a SP-Sephadex ion exchange column, potassium form, to give the product as the potassium salt.

EXAMPLE 21

Preparation of the Intermediate of the Hapten in Example 22, the 5-alkynylated Uridine 5'-O-aryl ester, Compound 92

Figure 33:
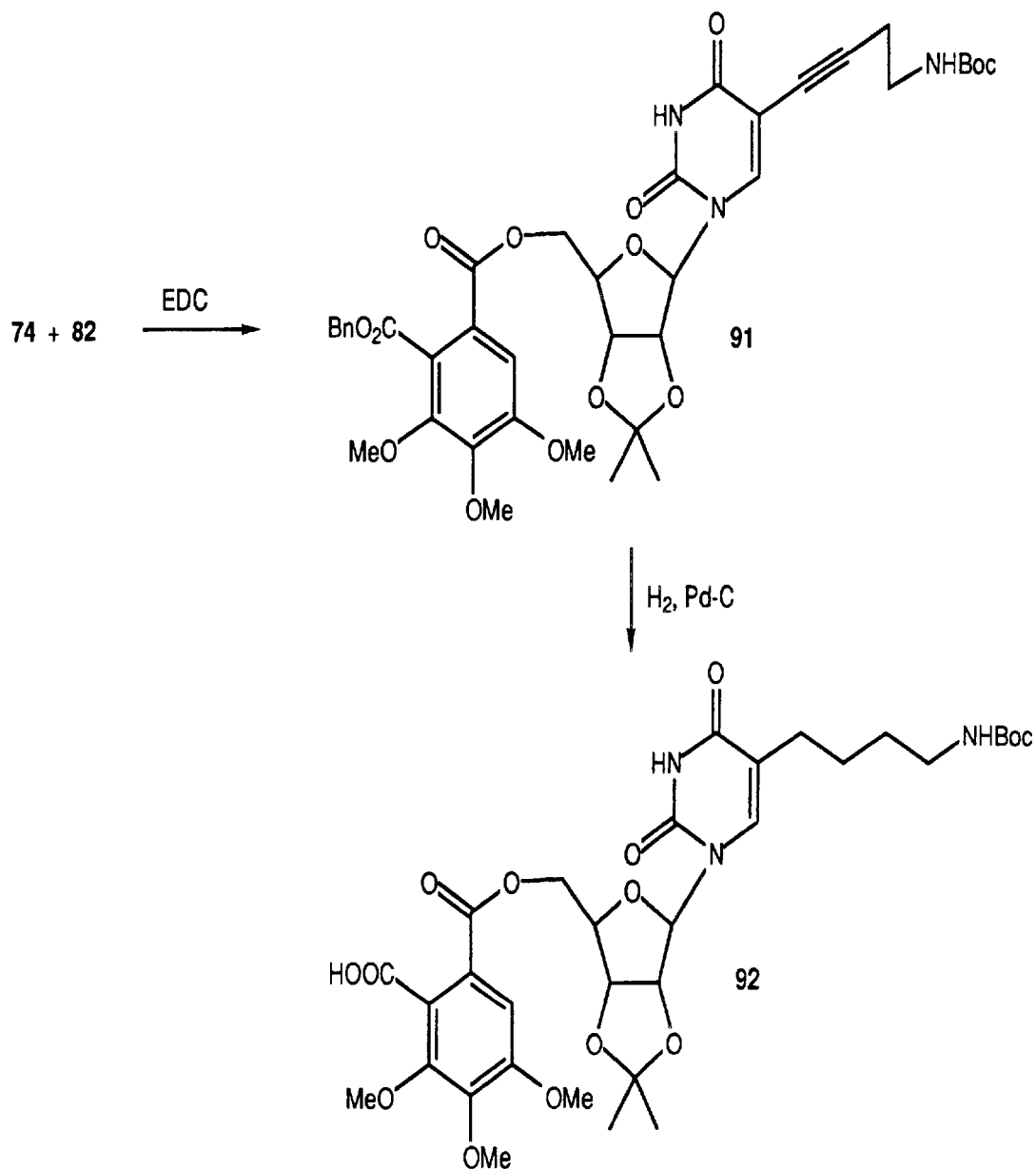
FIG. 33 shows the preparation of the intermediate of the hapten in Example 22, the 5-alkynylated uridine 5'-O-aryl ester, Compound 92.

Refer to FIG. 33 for the bold numbered compounds in this Example.

Esterification of acid 82 using alcohol 74 gives diester 91. Selective deprotection of the benzyl ester carboxyl group gives the monoacid 92.

In detail, the synthesis is as follows:

Preparation of the Uridine 5'-O-aryl Ester 91

A mixture of acid 82 (5 mmol), alcohol 74 (5 mmol), and EDC (6 mmol) in 50 mL of $CH_2Cl_2$ is stirred at room temperature until the starting material is consumed. The solution is washed with water (2×30 mL), the aqueous phases are washed with $CH_2Cl_2$ (2×50 mL), the organic phases are dried over anhydrous $MgSO_4$, and the solvent is evaporated in vacuo. The residue is purified by flash chromatography to give the product as a colorless oil.

Preparation of the Monoacid 92

Diester 91 (5 mmol) is dissolved in ethyl acetate (100 mL), 5% Pd-C (10% by weight) is added, and the mixture is stirred under a hydrogen atmosphere until the starting material is consumed. The catalyst is filtered out using a pad of Celite, and the catalyst is rinsed with ethyl acetate (100 mL). The solvent is evaporated in vacuo, and the product is used without further purification.

EXAMPLE 22

Preparation of the Hapten of the Prodrug in Example 20, the Cyclobutanol Substituted by a 5'-O-aroyl uridine, Compound 100

Figure 34:
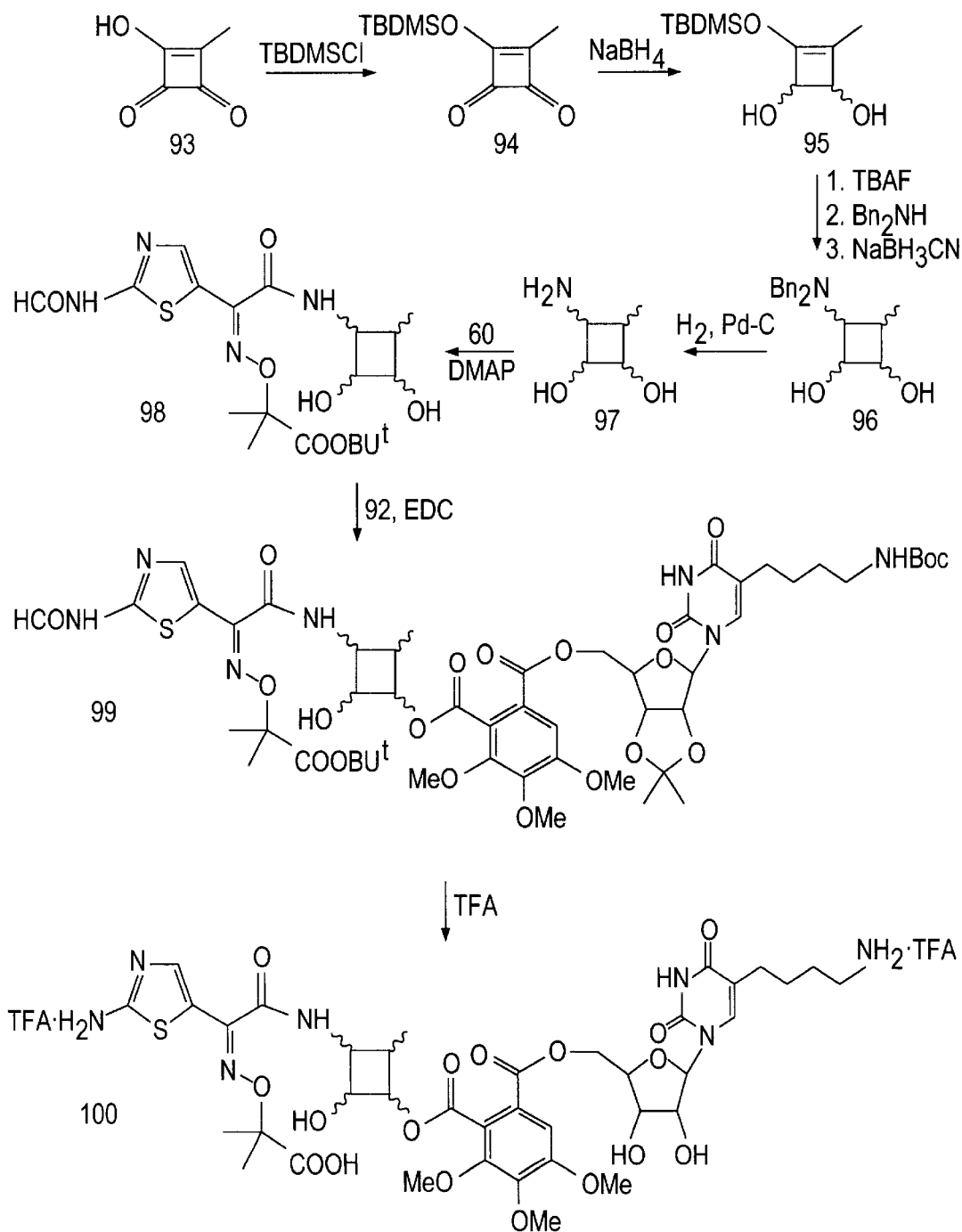
FIG. 34 shows the preparation of the hapten of the prodrug in Example 20, the cyclobutanol substituted by a 5'-O-aroyl uridine, Compound 100.
Figure 35:
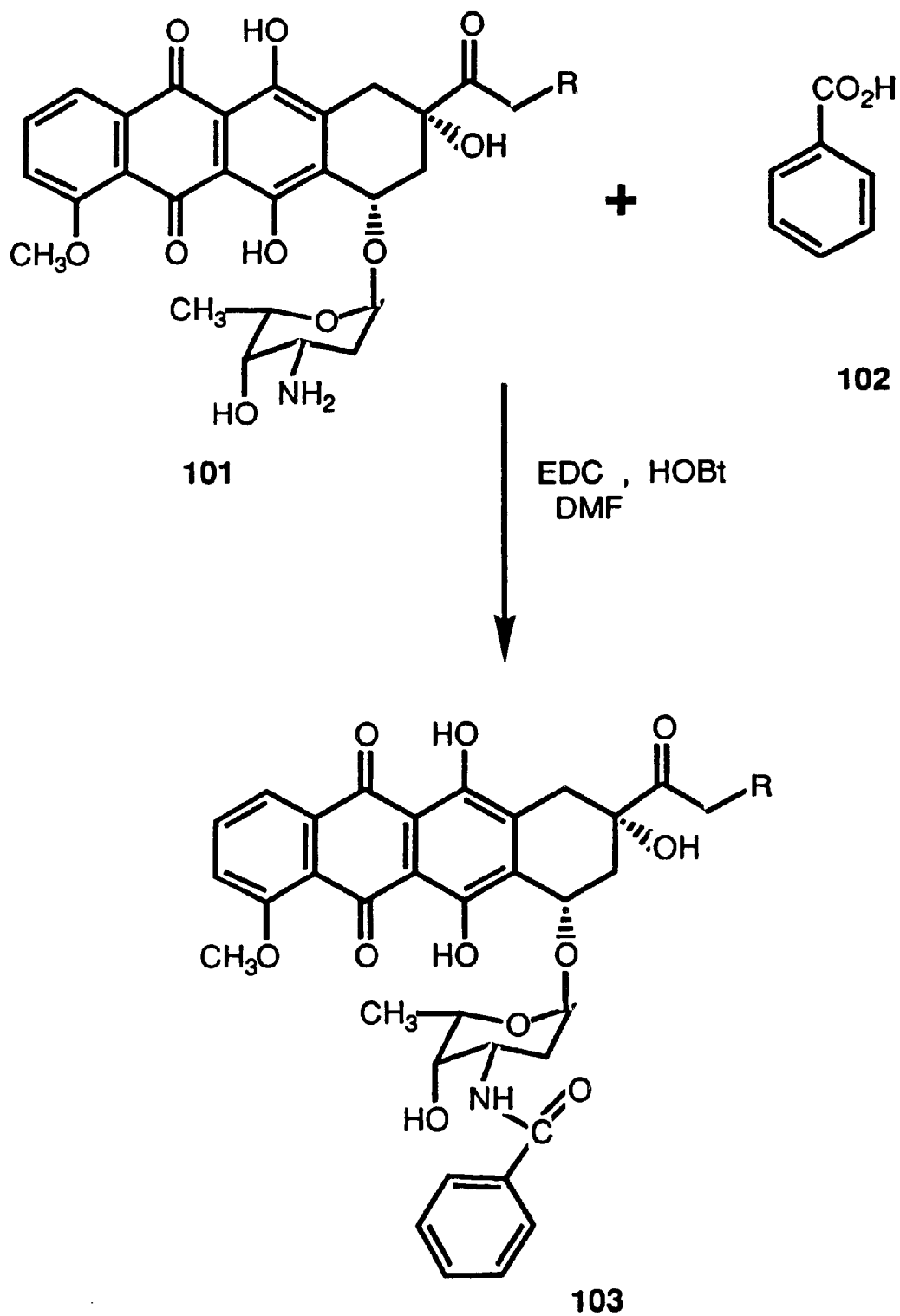
FIG. 35 shows the preparation of the adriamycin prodrug, aroylamide, Compound 103.
Figure 36:
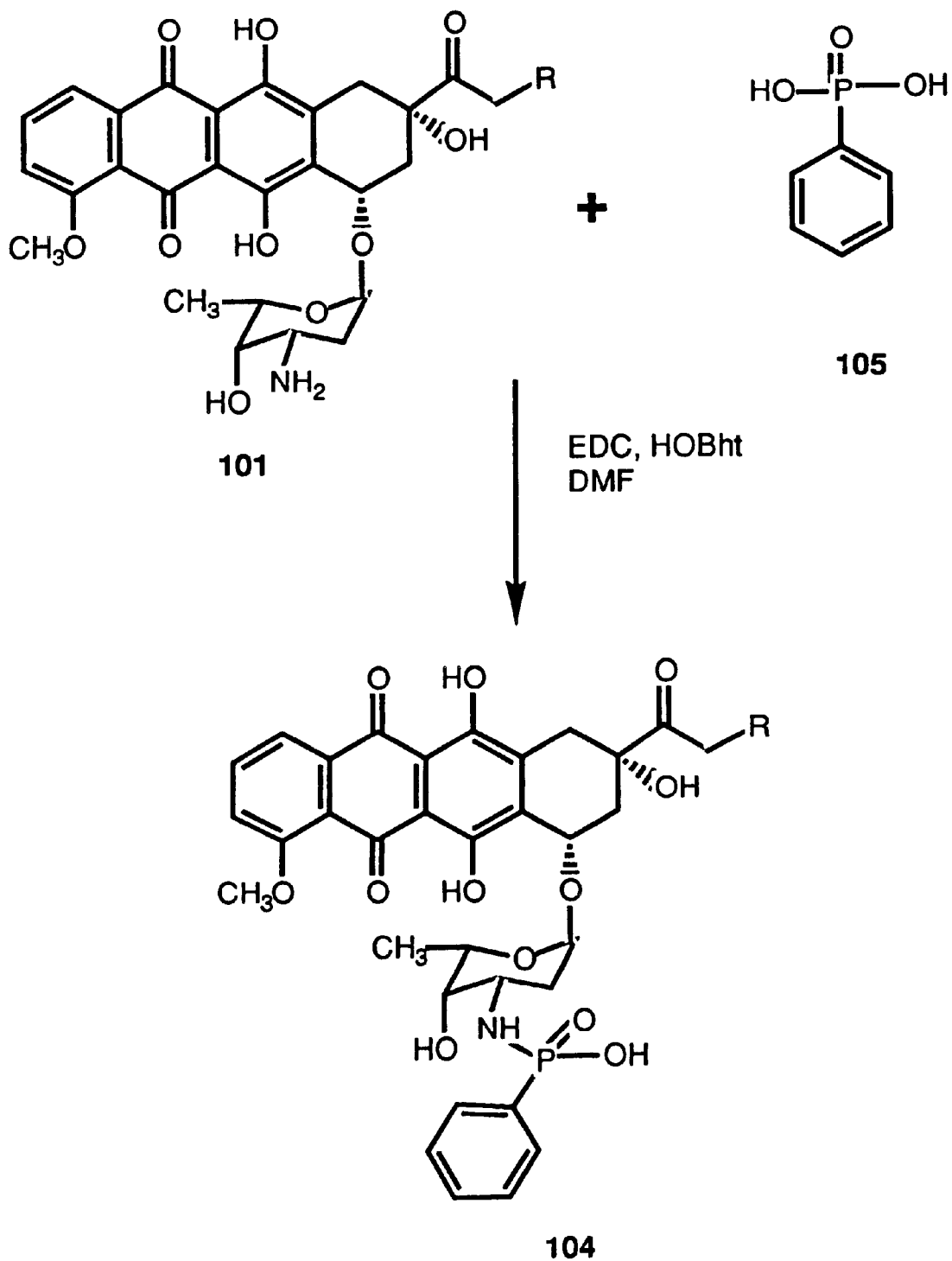
FIG. 36 shows the preparation of the hapten of the adriamycin prodrug, in Example 23, the phosphate of the aroylamide of adriamycin, Compound 104.
Figure 37:
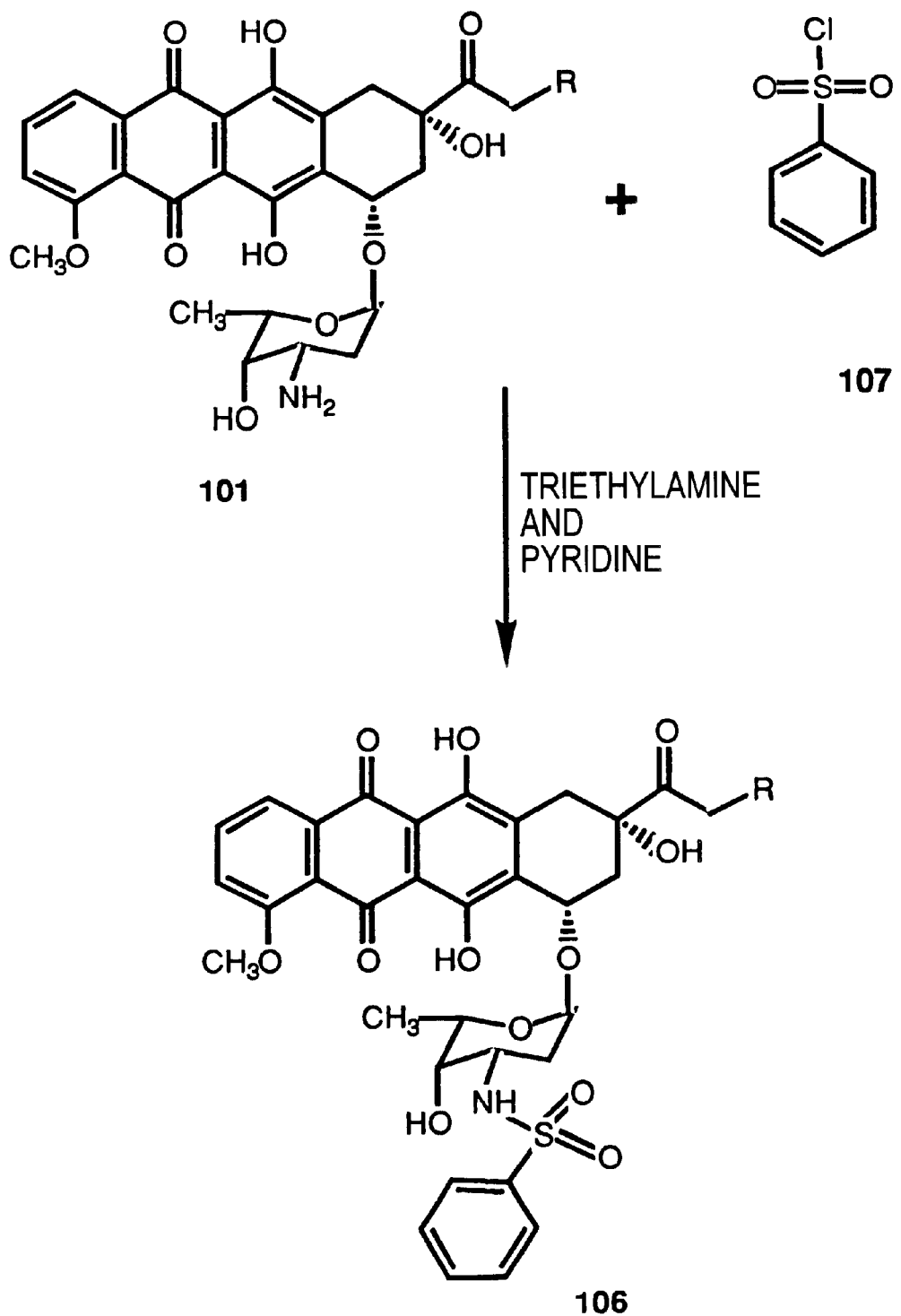
FIG. 37 shows the preparation of the hapten of the prodrug in Example 23, the aroyl sulphonamides of adriamycin, Compound 106.
Figure 38:
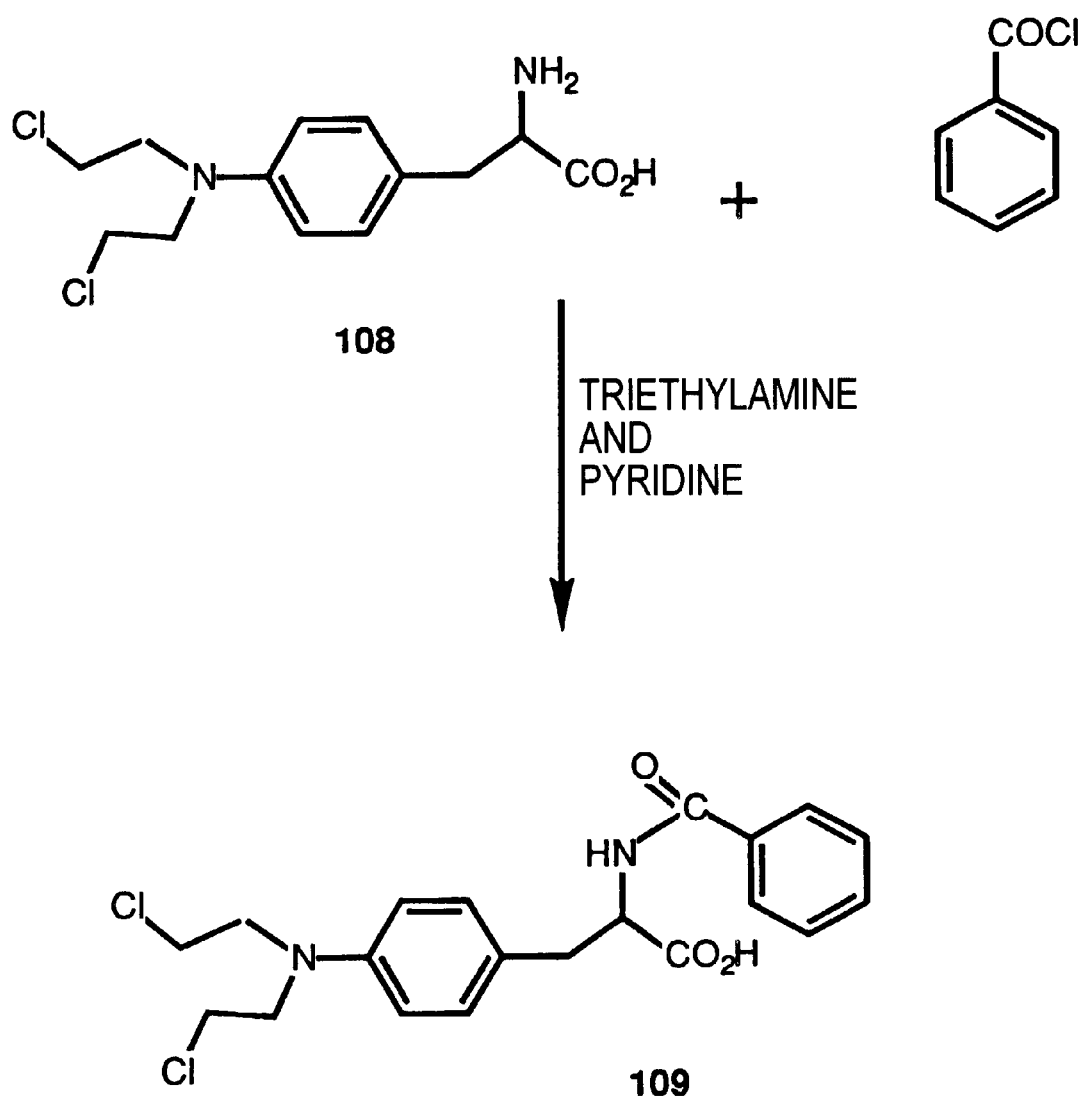
FIG. 38 shows the preparation of melphalan aroylamide prodrugs, Compound 109.
Figure 39:
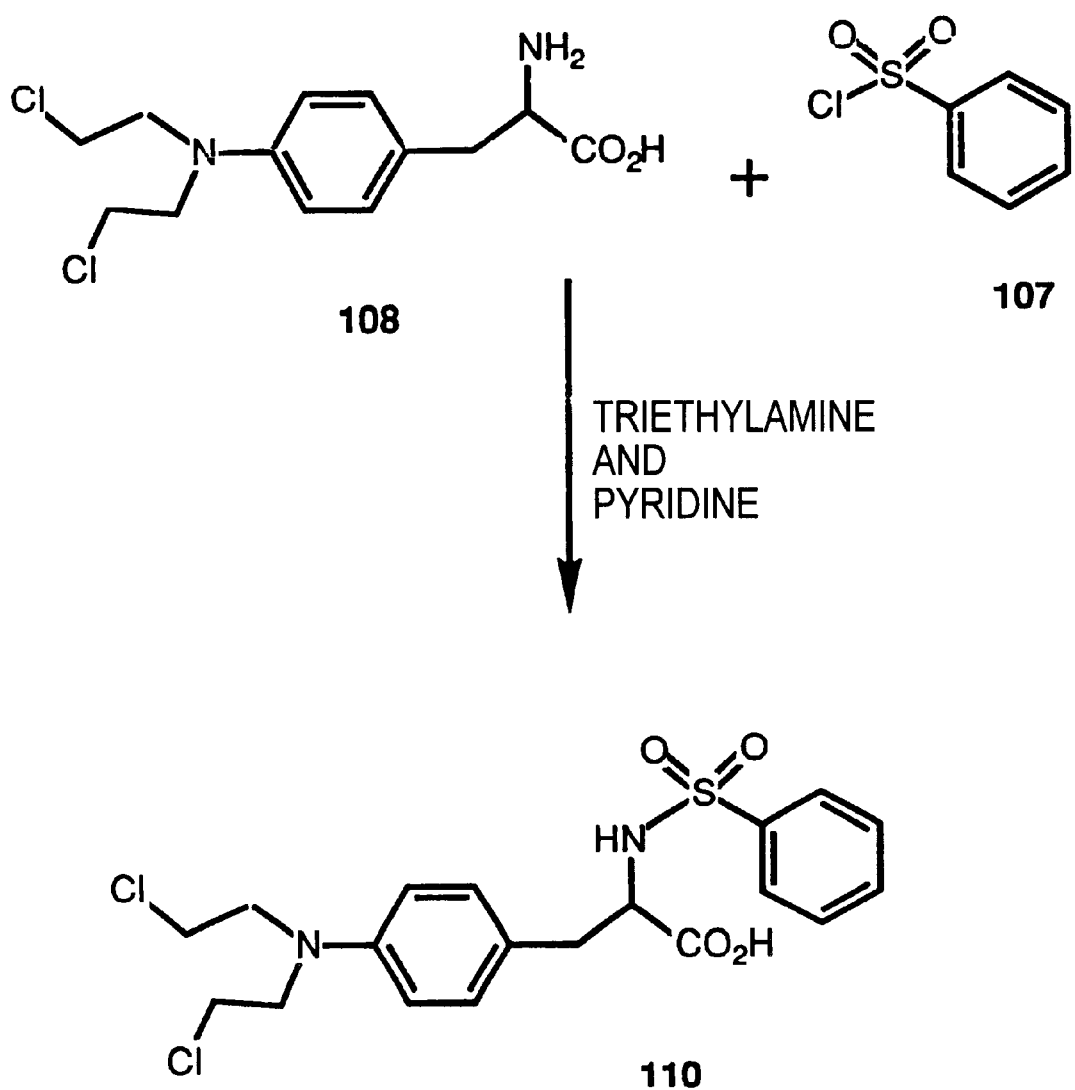
FIG. 39 shows the preparation of the hapten of the prodrug in Example 25. The sulphonamide of the aroylamide of melphalan, Compound 110.

Refer to FIG. 34 for the bold numbered compounds in this Example.

Cyclobutenedione 93, prepared following a literature procedure, is converted, after several steps, to the aminocyclobutanediol 97. Selective N- and O-acylation reactions and deprotection gives the cyclobutanol hapten 100.

In detail, the synthesis is as follows:

3-Hydroxy-4-methyl-3-cyclobutene-1,2-dione (93)

Compound 93 can be synthesized using the procedure of Bellus, D., et al., Helv. Chim. Acta 63 (1980):1130–1140.

3-tert-Butyldimethylsiloxy-4-methylcyclobutene-1, 2-dione (94)

Imidazole (11 mmol) is added to a solution of compound 93 (5 mmol) and tert-butyldimethylchlorosilane (5.5 mmol) in 5 mL of DMF cooled by an ice bath. The mixture is allowed to warm to room temperature. After 16 hours, the mixture is poured into water (50 mL) and extracted with ether (3×50 mL), the organic phases are washed with brine (50 mL) and dried over anhydrous $MgSO_4$, and the solvent is evaporated in vacuo. The residue is purified by flash chromatography to give the product as a colorless oil.

Preparation of Cyclobutenediol 95

Sodium borohydride (20 mmol) is added to a solution of compound 94 (5 mmol) in 50 mL of ethanol cooled by an ice bath. After the starting material is consumed as observed by TLC, the mixture is poured into water (100 mL) and extracted with ether (4×75 mL), the organic phases are washed with brine (50 mL) and dried over anhydrous $MgSO_4$, and the solvent is evaporated in vacuo. The residue is purified by flash chromatography to give the product as a colorless oil.

Preparation of Aminocyclobutanediol 96

Tetrabutylammonium fluoride (1.0M solution in THF, 6 mmol) is added to a solution of compound 95 (5 mmol) in 50 mL of THF cooled by an ice bath. After 30 minutes, dibenzylamine (20 mmol) is added. After an additional 15 minutes, sodium cyanoborohydride (30 mmol) is added. After an additional 2 hours, the mixture is poured into water (100 mL), the pH is adjusted to 10, the mixture is extracted with ether (4×75 mL), the organic phases are wasted with brine (50 mL) and dried over anhydrous $Na_2SO_4$, and the solvent is evaporated in vacuo. The residue is purified by flash chromatography to give the product as a colorless oil.

Preparation of Aminocyclobutanediol 97

A mixture of 5% Pd-C (10% by weight) and amine 96 (5 mmol) in 20 mL of methanol is stirred at room temperature under an atmosphere of hydrogen until the starting material is consumed as observed by TLC. The catalyst is filtered out through a pad of Celite, washing with 150 mL of additional MeOH. The solvent is evaporated in vacuo, nd the resulting oil is used without further purification.

Preparation of Amide 98

DMAP (6 mmol) is added to a solution of amine 97 (3 mmol) and thiazole ester 60 (3 mmol) in 15 mL of $CH_2Cl_2$. After no further progress in the reaction occurs as observed by TLC, the mixture is poured into water (50 mL) and extracted with ethyl acetate (3×50 mL), the organic phases are washed with brine (50 mL) and dried over anhydrous $MgSO_4$, and the solvent is evaporated in vacuo. The residue is purified by flash chromatography to give the product as a colorless oil.

Preparation of Ester 99

A mixture of acid 92 (1 mmol), alcohol 98 (1 mmol), and EDC (1.2 mmol) in 10 mL of $CH_2Cl_2$ is stirred at room temperature until the starting material is consumed. The solution is washed with water (2×20 mL), the aqueous phases are washed with $CH_2Cl_2$ (2×20 mL), the organic phases are dried over anhydrous $MgSO_4$, and the solvent is evaporated in vacuo. The residue is purified by flash chromatography to give the product as a colorless oil.

Preparation of Cyclobutanol Hapten 100

Trifluoroacetic acid (2 mL) was added to a mixture of compound 99 (1 mmol) and anisole (1 mL) in 10 mL of $CH_2Cl_2$ cooled by an ice bath. The mixture is allowed to warm to room temperature, and after 1 hour, the volatile components are evaporated in vacuo. The residue is used for linking to a carrier protein without further purification.

EXAMPLE 23
Adriamycin & Melphalan Prodrugs

Adriamycine and daunomycin are anthracycline anti-tumor antibiotics were found to inhibit DNA synthesis via intercalation (Di marco, A., et al., *Biochem. Pharmacol* 20 (1971):1323–1328). It was demonstrated that these compounds intercalate with base pair through chromophore interaction and an electrostatic interaction between the amino group of the sugar residue (daunasamine) and the phosphate group of DNA (Di marco, A., et al., *Cancer Chemoth. Rep.*, Vol 6 No 2 (1975):91–106).

It was demonstrated that derivatizing the amino group via the amide bond formation (Chandra, P., *Cancer Chemoth. Rep.* (1975):115–122), by amino acids, peptides or other carboxylic acids decreased the toxicity of these compounds (Levin, Y., *Febs Letters* 119–122).

EXAMPLE 23
Preparation of Adriamycin Pro-drug, Aroyl Amide Compound 103

Refer to FIG. 27 for the bold numbered compounds in this example

Synthesis of adriamycin pro drug 103 can be prepared starting from adriamycin 101 and benzoic acid 102 (FIG. 27). Adriamycin 101 is treated with benzoic acid 102 in the presence of 1-ethyl 3(3dimethylaminopropyl)carbodiimide (EDC) and 1-hydroxybenzotriazole (HOBT) in DMF. In detail, the synthesis is as follows:

General Procedure for the Synthesis of Benzoylamide of Adriamycin Pro-drug 103

To a solution of Adriamycin 101 (1 eq) in DMF (0.015 M) add sequentially the benzoic acid 102 (1 eq), 1-ethyl 3(3 dimethylaminopropyl)carbodiimide (EDC, 1.05 eq) and 1-hydroxy benzotriazole (HOBT 1 eq) and stir the reaction mixture under argon atmosphere at room temperature. After completion of the reaction purify the product by chromatography. Other aroylamides can be prepared using the same procedure by substituting the appropriate aroyl carboxylic acids.

EXAMPLE 24
Preparation of the Hapten of the Pro-drug in Example 23, the Phosphate of the Aroylamide of Adriamycin Compound 104

Refer to FIG. 28 for the bold numbered compounds in this example.

The synthesis of transition state analog of adriamycin, compound 104, can be prepared starting from adriamycin 101 and benzenephosphonic acid 105. Adriamycin 101 is treated with benzenephosphonic acid 105 in the presence of EDC and 1-hydroxybenzotriazole in DMF.

In detail, the synthesis is as follows:

EXAMPLE 24
General Procedure for the Preparation of the TS Analog 104 of Adriamycin To a solution of adriamycin 101 (1 eq) in DMF add sequentially the benzenephosphonic acid 105 (1 eq), 1-ethyl 3(3 dimethylaminopropyl)carbodiimide (EDC, 1 eq) and 1-hydroxybenzotriazole (1 eq) and stir the reaction mixture at room temperature. After completion of the reaction the product 104 can be purified by chromatography.

Example 24a the synthesis of another TS analog, the sulphonate compounds 106, could be accomplished by treating the adriamycin 101 with benzenesulphonyl chloride 107 in the presence of triethylamine in dry DMF (FIG. 29).

EXAMPLE 24a
Preparation of the Hapten of the Pro-drug in Example 23, the Aroyl Sulphonamides of Adriamycin Compound 106

Refer to FIG. 29 for the bold numbered compounds in this example

Aroyl sulphonamide hapten compound 106 can be prepared by treating adriamycin 101 with benzenesulfonyl chloride 107 in the presence of triethylamine in dry DMF.

In detail, the synthesis is as follows:

Synthesis of TS Analog Compound 106

To a solution of adriamycin 101 (1 eq) in DMF in the presence of triethylamine (1.5 eq) under argon atmosphere is added slowly at 0 C. benzenesulphonyl chloride 107 (1.1 eq). The reaction mixture is stirred at room temperature and after completion of the reaction, the product 106 can be purified by chromatography.

EXAMPLE 25
Preparation of Melphalan Aroylamide Pro-drugs 109

Refer to FIG. 30 for the bold numbered compounds in this example.

Synthesis of melphalan prodrug 109 could be accomplished starting from melphalan 108 and benzoyl chloride. Detail synthesis of compound 109 follows the same procedure as described for the preparation of 106 where benzoyl chloride is used instead of benzenesulphonyl chloride.

EXAMPLE 26a
Preparation of the Hapten of the Prodrug in Example 25, the Sulphonamide Compound 110

Refer to FIG. 31 for the bold numbered compounds in this example.

Synthesis of hapten of melphalan, compound 110, could be achieved starting from the melphalan 108 and benzenesulphonyl chloride 107 using the similar reaction conditions as described for the preparation 106. Detail synthesis of the compound follows the same procedure as described for the synthesis of 106.

EXAMPLE 27
Relative Toxicities of 5-fluorouridine Prodrugs

Fluorouridine is a cytotoxic antineoplastic nucleoside analog, with clinical utility in treating solid tumors in various tissues. Fluorouridine is, however, toxic to normal tissues, particularly bone marrow and gastrointestinal epithelium. Prodrugs of fluorouridine that are activated by catalytic antibodies or enzymes targeted to tumor cells may improve the therapeutic index of fluorouridine substantially. The key issue is to design prodrugs that are not activated by endogenous enzymes but which can be readily activated by catalytic antibodies.

Catalytic antibodies which cleave esters can be prepared through straight-forward methods. Ester substituents attached to the 5'-position of fluorouridine render it non-toxic and protect it from degradation by uridine phosphorylase. 5'benzoate and substituted 5'-benzoate prodrugs of fluorouridine were administered to mice to determine whether substituents on the benzoate moiety could modify deesterification by endogenous enzymes thereby resulting in prodrugs that are substantially less toxic than fluorouridine itself.

METHODS

Fluorouridine (FU) and fluorouridine prodrugs were administered to groups (n=7) of 20-gram female Balb/c mice by intraperitoneal injection, in the following doses:

1. Fluorouridine (10 mg/kg.
2. Fluorouridine 50 mg/kg.
3. Fluorouridine 100 mg/kg.
4. 5'Benzoylfluorouridine (BZFU) 139.7 mg/kg.
5. 5'-2,4,6-trimethylbenzoylfluorouridine (TMBFU) 156.9 mg/kg.
6. 5'-3,4,5-trimethoxybenzoylfluorouridine (TMOXFU) 175.2 mg/kg.

The doses of the three aromatic esters of fluorouridine are the molar equivalent of 100 mg/kg fluorouridine.

A seventh group (Control) received only the injection vehicle (0.4 ml of 10% DMSO in 0.9% saline).

Seven days after administration of fluorouridine or its prodrugs, blood samples were taken from the retro-orbital sinus for determination of differential blood cell counts, cells from one femur of each mouse were collected for counting total marrow cellularity, and spleens were collected and weighed. Body weight was also determined.

RESULTS

Fluorouracil administration resulted in dose-dependent reductions in blood cell counts and marrow cell counts.

100 mg/kg fluorouridine produced a significant reduction in body weight and spleen weight. Benzoylfluorouridine (139 mg/kg), which was expected to be cleaved by mouse esterase activity was approximately equal in toxicity to a molar equivalent of fluorouridine alone (100 mg/kg), as is reflected in all indices tested.

2,4,6-trimethylbenzoylfluorouridine (TMBFU) produced very little evidence of toxicity, with only erythrocyte counts significantly below control values. This compound produced less damage to bone marrow, as determined by marrow cell count and neutrophil counts, than did 1/10 the molar equivalent of fluorouridine (FU 10 mg/kg).

3,4,5-trimethoxybenzoylfluorouridine (TMOXFU) was slightly less toxic than ½the molar equivalent of fluorouridine (FJ 50 mg/kg).

Data are shown in Tables 1 and 2.

TABLE 1

Relative toxicities of fluorouridine and fluorouridine prodrugs--blood cell counts.

| Cellularity Groups | Body Weight (grams) | Spleen Weight (mg) | Marrow $10^6$ cells/femur |
|---|---|---|---|
| Control | 20.1 ± 0.5 | 89.9 ± 3.4 | 8.28 ± 0.69 |
| FU 10 mg/kg |  | 89.9 ± 2.0 ns | 5.83 ± 0.77* |
| FU 50 mg/kg |  | 69.6 ± 2.4* | 2.85 ± 0.16* |
| FU 100 mg/kg | 16.3 ± 0.6* | 57.7 ± 2.5* | 0.98 ± 0.19* |
| BZFU | 17.5 ± 0.6* | 61.8 ± 1.2* | 1.23 ± 0.10* |
| TMBFU | 19.6 ± 0.4 ns | 99.2 ± 4.4 ns | 7.88 ± 0.47 ns |
| TMOXFU | 20.0 ± 0.5 ns | 73.3 ± 3.5* | 3.42 ± 0.29* |

| Groups | Platelets (K/ml) | Neutrophils (K/ml) | Erythrocytes (K/ml) |
|---|---|---|---|
| Control | 741 ± 15 | 1.747 ± .737 | 9.01 ± 0.09 |
| FU 10 mg/kg | 705 ± 14 ns | .607 ± .330 ns | 8.33 ± 0.09* |
| FU 50 mg/kg | 433 ± 39* | .020 ± .036* | 7.81 ± 0.11* |
| FU 100 mg/kg | 155 ± 20* | .010 ± .019* | 7.59 ± 0.25* |
| BZFU | 209 ± 31* | .011 ± .030* | 7.76 ± 0.22* |
| TMBFU | 707 ± 23 ns | 1.300 ± .338 ns | 8.69 ± 0.07* |
| TMOXFU | 628 ± 27* | .093 ± .039* | 7.65 ± 0.11* |

Legend:
*indicates significantly lower than Control value, P < .05; ns indicates not different from Control (untreated) group.

EXAMPLE 28

Relative Toxicities of 5-fluorouridine and 5'-b-galactosyl-fluorouridine

5'-b-galactosyl-fluorouridine (Gal-Furd) is a prodrug of fluorouridine which can be activated by the non-mammalian enzyme b-galactosidase or by an appropriate catalytic antibody. A crucial issue is the degree to which a sugar attached covalently to the 5' position reduces the toxicity of fluorouridine. The primary dose-limiting toxicity for antineoplastic fluorinated pyrimidine analogs is damage to bone marrow. The toxicity of fluorouridine versus Gal-Furd was assessed in mice, using blood cell counts and bone marrow cell counts as the indices of toxicity. In addition, Gal-Furd was administered together with the enzyme b-galactosidase to determine if the prodrug could be activated by an enzyme in vivo.

Female Balb/C mice (20 grams) were divided into 6 groups, each containing 6 animals:

1. Control—Saline 0.2 ml i.p.
2. Fluorouridine—10 mg/kg i.p.
3. Fluorouridine—100 mg/kg i.p.
4. Gal-Furd—160 mg/kg i.p. (molar equivalent of 100 mg/kg fluorouridine)
5. b-galactosidase—5 mg/kg i.p.
6. Gal-Furd 160 mg/kg +b-galactosidase 5 mg/kg i.p. (Gal-Furd was administered after b-galactosidase in a separate injection).

Seven days after administration of fluorouridine or Gal-Furd, blood samples were taken from the retro-orbital sinus for determination of differential blood cell counts, and cells from one femur of each mouse were collected for counting total marrow cellularity; spleens were also collected for determination of their weight.

RESULTS

Seven days after administration of fluorouridine resulted in significant declines in all hematologic indices tested. In contrast, blood cell and bone marrow cell counts seven days after administration of Gal-Furd were within the range of normal values for Balb/C mice. Coadministration of Gal-Furd and b-galactosidase (each administered by a separate injection so that prodrug and enzyme were not in contact prior to administration) resulted in hematologic toxicity, indicating that the relatively nontoxic prodrug was converted to active cytotoxic drug by the enzyme b-galactosidae in vivo. The results are summarized in Tables 1 and 2, and in Figure ?

TABLE 1

Effects of Furd versus Gal-Furd on spleen weight and marrow cellularity

| Groups | Spleen Wt (mg) | Marrow Cellularity ($10^6$ cells/femur) |
| --- | --- | --- |
| Control | 92.8 ± 3.5 | 8.86 ± 1.09 |
| FUrd 10 mg/kg | 100.52.0 ns | — |
| FUrd 100 mg/kg | 53.5 ± 2.1* | 0.96 ± 0.25* |
| Gal-Furd 160 mg/kg | 89.9 ± 3.4 ns | 9.70 ± 0.81 ns |
| Galactosidase | 91.3 ± 1.9 ns | — |
| Gal-Furd + Galactosidase | 80.2 ± 4.3* | 4.04 ± 0.84* |

Legend:
*indicates significantly lower than Control value, $P < .05$; ns indicates not different from Control (untreated) group.

TABLE 2

Effects of Furd versus Gal-Furd on blood cell counts

| Groups | Platelets (k/ml) | Neutrophils (k/ml) | Lymphocytes (M/ml) |
| --- | --- | --- | --- |
| Control | 833 ± 30 | 2.25 ± .22 | 10.37 ± 0.68 |
| FUrd 10 mg/kg | 809 ± 28 ns | 0.75 ± .15* | 7.28 ± 0.67* |
| FUrd 100 mg/kg | 242 ± 12* | 0.08 ± .02* | 3.07 ± 0.23* |
| Gal-Furd 160 mg/kg | 770 ± 25 ns | 1.90 ± .22 nd | 7.39 ± 0.45* |
| Gal-Furd + Galactosidase | 572 ± 39* | 0.74 ± .07* | 4.78 ± 0.21* |

Legend
*indicates significantly lower than Control value, $P < .05$; ns indicates not different from Control (untreated) group.

The foregoing is intended as illustrative of the present invention but not limiting. Numerous variations and modifications may be effected without departing from the true spirit and scope of the invention.

What is claimed is:

1. A catalytic antibody raised to a hapten of formula I $$G-F-(CH_2)_n-E-D-B-A-X \qquad (I)$$

wherein:

X is
  (a) a nucleoside analog joined at the 5' and/or 3' position of the aldose ring wherein the hydroxyl groups on the sugar moiety of the nucleoside analog are unsubstituted, independently substituted with acyl, phosphate and all radicals, or replaced with H, halogen or azide, and wherein the O of the nucleoside by which it is attached can be replaced by S, NH, or $CH_2$,
  (b) $QP(O)(NH_2)NR^1R^2$, wherein Q is O or $CH_2$, or Q can be omitted, and $R^1$ and $R^2$ are the same or different but both cannot be H and each is haloalkyl, alkyl, alkyl with heteroatoms, cycloalkyl, phenyl, substituted phenyl, alkylphosphonate, alkylsulfonate, alkylcarboxylate, alkylammonium or alkene, or $R^1$ and $R^2$ are connected to each other in a ring structure such as morpholino or piperidine,
  (c) melphalan joined to the remainder of the compound at a primary amino group, or melphalan joined to the remainder of the compound at a primary amino group wherein the primary amino group can be replaced by $CH_2$ or S; or
  (d) daunomycin or other drug joined to the remainder of the compound at a hydroxy, amino or thio group which can be replaced by $CH_2$, S, or O;

A, which may be omitted, is ethylene or any isomer of propenyl;

B, which may be omitted, is O, S, $CH_2$, or $NR^3$, wherein $R^3$ is H, alkyl, alkyl with heteroatoms, cycloalkyl, phenyl, substituted phenyl, alkylphosphonate, alkylsulfonate, alkylcarboxylate, alkylammonium or alkene;

D, which may be omitted, is
  (a) C=O,
  (b) $C=NR^4$ or $R^5R^6N-C=NR^4$, wherein $R^4$ is H, alkyl, alkyl with heteroatoms, cycloalkyl, phenyl, substituted phenyl, alkylphosphonate, alkylsulfonate, alkylcarboxylate, alkylammonium or alkene, $R^4$ and $R^5$ or $R^5$ and $R^6$ can be connected to each other in a ring structure such as morpholino or piperidine, or $R^5$ and $R^6$ can be haloalkyl, alkyl, alkyl with heteroatoms, cycloalkyl, phenyl, substituted phenyl, alkylphosphonate, alkylsulfonate, alkylcarboxylate, alkylammonium or alkene,
  (c) SO or CHOH with any stereochemistry,
  (d) $SO_2$, or
  (e) $P(T)(TR^7)$ wherein T is O, N, S or $CH_2$ and $R^7$ is H, alkyl, alkyl with heteroatoms, cycloalkyl, phenyl, substituted phenyl, alkylphosphonate, alkylsulfonate, alkylcarboxylate, alkylammonium or a alkene and is unattached or attached to E at $R^8$, $R^{11}$ or $R^{13}$;

E, which may be omitted, is the radical

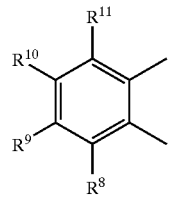

or $R^{12}R^{13}C$ wherein $R^{8-13}$ are the same or different and are H or alkyl with 1–10 carbon atoms, phenyl, substituted phenyl, alkene with 1–10 carbon atoms, hydroxyalkyl, alkoxy, aminoalkyl, alkylthio, thioalkyl, amino, aklylamino, alkylphosphonate, alkylsulfonate, alkylcarboxylate, alkylammonium, carboxylate, sulfate, phosphate, or hydroxyl, and wherein $R^{12}$ and $R^{13}$ are the same or different and are O substituted with alkyl, alkyl with heteroatoms, cycloalkyl, phenyl, substituted phenyl, alkylphosphonate, alkylsulfonate, alkylcarboxylate, alkylammonium or alkene, or $R^{8-13}$ are connected to each other in a ring structure such as a five-membered or six-membered acetal ring where the diol is derived from a sugar, cycloalkyl or phenyl moiety, and is unattached or attached to the radical D at $R^7$ through $R^8$ or $R^{11}$ or $R^{13}$;

n is an integer from 0 to 3;

F, which may be omitted, is an oxygen, carbonyloxy, or oxycarbonyl radical; and

G, which may be omitted, is
  (a) H or alkyl with 1–10 carbon atoms, alkoxy with 1–10 carbon atoms, phenyl, substituted phenyl, alkene with 1–10 carbon atoms, hydroxyalkyl, aminoalkyl, thioalkyl, amino, alkylamino, alkylphosphonate, alkylsulfonate, alkylcarboxylate, alkylammonium, carboxylate, sulfate, phosphate, or hydroxyl, or

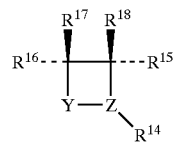

wherein Y is C=O, SO$_2$, CHOH or SO with any stereochemistry, Z is O, N, CH with any stereochemistry, or S, and R$^{14}$, R$^{15}$, R$^{16}$, R$^{17}$ or R$^{18}$ is the site of attachment to the remainder of the compound, provided that where R$^{14}$ is the site of attachment, then R$^{15}$, R$^{16}$, R$^{17}$, and R$^{18}$ are the same or different and are hydrogen, alkyl with 1–10 carbon atoms, alkenyl with 1–10 carbon atoms, phenyl, substituted phenyl, carboxylalky with 1–10 carbon atoms which is unsubstituted or substituted by a heterocyclic ring or phenyl ring, said rings being unsubstituted or substituted, alkoxy with 1–10 carbon atoms, alkylamino with 1–10 carbon atoms, aminoalkyl with 1–10 carbon atoms, acyloxy with 1–10 carbon atoms which is unsubstituted or substituted by a heterocyclic ring or a phenyl ring, said rings being unsubstituted or substituted, or acylamino with 1–10 carbon atoms which is unsubstituted or substituted by a heterocyclic ring or a phenyl ring, said rings being unsubstituted or substituted, and further provided that where one of R$^{15}$, R$^{16}$, R$^{17}$, or R$^{18}$ is the site of attachment, then R$^{14}$ and the remainder of R$^{15}$, R$^{16}$, R$^{17}$, and R$^{18}$ are the same or different and are as defined for R$^{15}$–R$^{18}$ above when R$^{14}$ is the site of attachment and R$^{14}$ is either SO$_3$H or SO$_4$H, said catalytic antibody being capable of catalytically enhancing the rate of cleavage of a drug X or B—A—X, wherein B, A, and X are defined as above, from a residue of a prodrug of formula I, wherein said catalytic antibody exhibits catalytic activity which corresponds to activities exhibited by an enzyme selected from the group consisting of an esterase, an amidase, an acetal hydrolase and a glycosidase.

2. The catalytic antibody of claim 1 wherein said hapten is

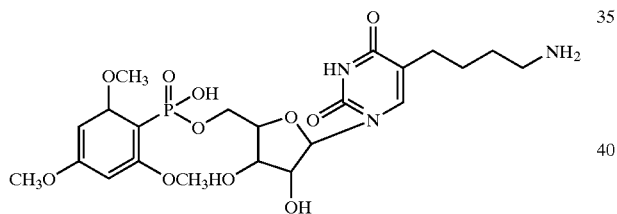

and said prodrug is

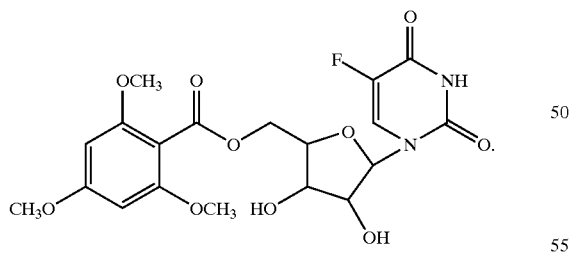

3. The catalytic antibody of claim 1 wherein said hapten has the same or substantially the same substituents as said prodrug.

4. The catalytic antibody of claim 1 wherein said prodrug has formula G—F—(CH$_2$)$_n$—E(C=O)—B—A—X, and wherein said formula, the moiety G—F—(CH$_2$)$_n$—E—(C=O) substantially reduces the toxicity of said drug X or B—A—X.

5. The catalytic antibody of claim 4 wherein the toxicity of said prodrug is less than one percent of the toxicity of said drug X or B—A—X.

6. The catalytic antibody of claim 4 wherein said prodrug has a half like in serum of at least one hour.

7. The catalytic antibody of claim 1 wherein said hapten and said prodrug have formula

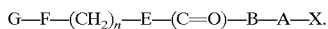

G—F—(CH$_2$)$_n$—E—(C=O)—B—A—X.

8. The catalytic antibody of claim 1 wherein in formula I of said prodrug, D is C=O, and said hapten has the same or substantially the same formula as said prodrug, except that in said hapten, D is not C=O.

9. The catalytic antibody of claim 1 wherein said hapten has formula II

G—E—D—B—A—X                                    (II)

wherein:

X is
(a) a nucleoside analog joined at the 5' and/or 3' position of the aldose ring wherein the hydroxyl groups on the sugar moiety of the nucleoside analog are unsubstituted, independently substituted with acyl, phosphate and alkyl radicals, or replaced with H, halogen or azide, and wherein the O of the nucleoside by which it is attached can be replaced by S, NH, or CH$_2$,
(b) QP(O)(NH$_2$)NR$^1$R$^2$, wherein Q is O or CH$_2$, or Q can be omitted, and R$^1$ and R$^2$ are the same or different but both cannot be H and each is haloalkyl, alkyl, alkyl with heteroatoms, cycloalkyl, phenyl, substituted phenyl, alkylphosphonate, alkylsulfonate, alkylcarboxylate, alkylammonium or alkene, or R$^1$ and R$^2$ are connected to each other in a ring structure such as morpholino or piperidine,
(c) melphalan joined to the remainder of the compound at a primary amino group, or melphalan joined to the remainder of the compound at a primary amino group wherein the primary amino group can be replaced by CH$_2$ or S; or
(d) daunomycin or other drug joined to the remainder of the compound at a hydroxy, amino or thio group which can be replaced by CH$_2$, S, or O;

A, which may be omitted, is ethylene or any isomer of propenyl;

B, which may be omitted, is O, S or CH$_2$;

D is
(a) C=O,
(b) SO or CHOH with any stereochemistry,
(c) SO$_2$, or
(d) P(T)(TR$^7$) wherein T is O, N, S or CH$_2$ and R$^7$ is A, alkyl, alkyl with heteroatoms, cycloalkyl, phenyl, substituted phenyl, alkylphosphonate, alkylsulfonate, alkylcarboxylate, alkylammonium or alkene and is unattached or attached to E at R$^8$, R$^{11}$ or R$^{13}$;

E is the radical

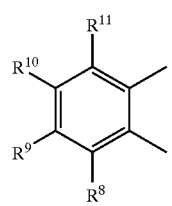

or R$^{12}$R$^{13}$C wherein R$^{8-13}$ are the same or different and are H or alkyl with 1–10 carbon atoms, phenyl, substituted phenyl, alkene with 1–10 carbon atoms, hydroxyalkyl, alkoxy, aminoalkyl, alkylthio, thioalkyl, amino, alkylamino, alkylphosphonate, alkylsulfonate, alkylcarboxylate, alkylammonium, carboxylate, sulfate, phosphate, or hydroxyl or are unattached or attached to the radical D at $R^7$ through $R^8$ or $R^{11}$ or $R^{13}$; and G, which may be omitted, is H or alkyl with 1–10 carbon atoms, alkoxy with 1–10 carbon atoms, phenyl, substituted phenyl alkene with 1–10 carbon atoms, hydroyalkyl, aminoalkyl, thioalkyl, amino, alkylamino, alkylphosphonate, alkylsulfonate, alkylcarboxylate, alkylammonium, carboxylate, sulfate, phosphate, or hydroxyl.

10. The catalytic antibody of claim 1 wherein said prodrug has formula II

  (II)

wherein

X is
(a) a nucleoside analog joined at the 5' and/or 3' position of the aldose ring wherein the hydroxyl groups on the sugar moiety of the nucleoside analog are unsubstituted, independently substituted with acyl, phosphate and alkyl radicals, or replaced with H, halogen or azide, and wherein the O of the nucleoside by which it is attached can be replaced by S, NH, or $CH_2$,
(b) $QP(O)(NH_2)NR^1R^2$, wherein Q is O or $CH_2$, or Q can be omitted, and $R^1$ and $R^2$ are the same or different but both cannot be H and each is haloalkyl, alkyl, alkyl with heteroatoms, cycloalkyl, phenyl, substituted phenyl, alkylphosphonate, alkylsulfonate, alkylcarboxylate, alkylammonium or alkene, or $R^1$ and $R^2$ are connected to each other in a ring structure such as morpholino or piperidine,
(c) melphalan joined to the remainder of the compound at a primary amino group, or melphalan joined to the remainder of the compound at a primary amino group wherein the primary amino group can be replaced by $CH_2$ or S;
(d) daunomycin or other drug joined to the remainder of the compound at a hydroxy, amino or thio group which can be replaced by $CH_2$, S, or O;

A, which may be omitted, is ethylene or any isomer of propenyl;

B, which may be omitted, is O, S or $CH_2$;

D is
(a) C=O,
(b) SO or CHOH with any stereochemistry,
(c) $SO_2$, or
(d) $P(T)(TR^7)$ wherein T is O, N, S or $CH_2$ and $R^7$ is H, alkyl, alkyl with heteroatoms, cycloalkyl, phenyl, substituted phenyl, alkylphosphonate, alkylsulfonate, alkylcarboxylate, aklylammonium or alkene and is unattached or attached to E at $R^8$, $R^{11}$ or $R^{13}$;

E is the radical

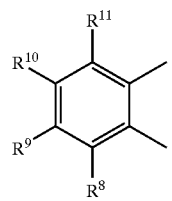

or $R^{12}R^{13}C$ wherein $R^{8-13}$ are the same or different and are H or alkyl with 1–10 carbon atoms, phenyl, substituted phenyl, alkene with 1–10 carbon atoms, hydroxyalkyl, alkoxy, aminoalkyl, alkylthio, thioalkyl, amino, alkyl amino, alkylphosphonate, alkylsulfonate, alkylcarboxylate, alkylammonium, carboxylate, sulfate, phosphate, or hydroxyl or are unattached or attached to the radical D at $R^7$ through $R^8$ or $R^{11}$ or $R^{13}$; and G is H or alkyl with 1–10 carbon atoms, alkoxy with 1–10 carbon atoms, phenyl, substituted phenyl, alkene with 1–10 carbon atoms, hydroxylalkyl, aminoalkyl, thioalkyl, amino, alkylamino, alkylphosphonate, alkylsulfonate, alkylcarboxylate, alkylammonium, carboxylate, sulfate, phosphate or hydroxyl.

11. The catalytic antibody of claim 9 wherein said prodrug has formula IIA

  (IIA)

wherein

X is a nucleoside analog joined at the 3' and/or 5' position of the aldose ring, E is substituted phenyl, and G is H, alkyl with 1–10 carbon atoms, alkoxy with 1–10 carbon atoms, phenyl, substituted phenyl, alkene with 1–10 carbon atoms or alkylthio.

12. The catalytic antibody of claim 9 wherein said hapten has formula IIB

  (IIB)

wherein

X is a nucleoside analog joined at the 3' and/or 5' position of the aldose ring wherein the O of the nucleoside by which it is attached is replaced by B, B is O, S, NH or $CH_2$, D is P(O)OH, $SO_2$, or CHOH, E is a substituted phenyl group, and G is H alkyl with 1–10 carbon atoms, alkoxyl with 1–10 carbon atoms, phenyl, substituted phenyl, alkene with 1–10 carbon atoms or alkylthio.

13. The catalytic antibody of claim 11 wherein formula IIA of said prodrug, X is a nucleoside analog joined at the 3' and/or 5' position of the aldose ring, E is phenyl with a substituent ortho to the (C=O)X and said substituent is hydroxalkyl, aminoalkyl, thioalkyl, alkylcarboxylate, alkylammonium, alkylamine or carboxylate, and G is H, alkyl with 1–10 carbon atoms, alkoxy with 1–10 carbon atoms, phenyl, substituted phenyl, alkene with 1–10 carbon atoms or alkylthio.

14. The catalytic antibody of claim 9, wherein said hapten has formula IIB

  (IIB)

wherein

X is a nucleoside analog joined at the 3' and/or 5' position of the aldose ring wherein the O of the nucleoside by which it is attached is replaced by B, B is O, S, NH or CH$_2$, D is P(T)(TR$^7$) wherein T is O, N, S, or CH$_2$ and R$^7$ is H, alkyl, alkyl with heteroatoms, cycloalkyl, phenyl, substituted phenyl, or alkene and is attached to radical E at R$^8$ or R$^{11}$, B is a substituted phenyl group where R$^8$ or R$^{11}$ is attached to the radical D at R$^7$, R$^{11}$ are the same or different and are H or alkyl with 1–10 carbon atoms, phenyl, substituted phenyl, alkene with 1–10 carbon atoms, hydroxyalkyl, alkoxy, aminoalkyl, alkylthio, thioalkyl, amino, alkylamino, alkylphosphonate, alkylsulfonate, alkycarbonxylate, alkylammonium, carboxylate, sulfate, phosphate, or hydroxalkyl, and G is H, alkyl with 1–10 carbon atoms, alkoxy with 1–10 carbon atoms, phenyl, substituted phenyl, alkene with 1–10 carbon atoms, or alkylthio.

15. The catalytic antibody of claim 10 wherein said prodrug has formula IIA

$$G—E—(C=O)—X \quad\quad (IIA)$$

wherein

X is a nucleoside analog jointed at the 3' and/or 5' position of the aldose ring, E is R$^{12}$R$^{13}$C and G is H.

16. The catalytic antibody of claim 9, wherein said hapten has formula IIC $$E—D—B—X \quad\quad (IIC)$$

wherein

X is an antineoplastic nucleoside analog joined at the 3' and/or 5' position of the aldose ring wherein the O of the nucleoside by which it is attached is replaced by B, B is O, S, NH or CH$_2$, D is P(O)OH, SO$_2$ or CHOH and E is R$^{12}$R$^{13}$C.

17. The catalytic antibody is claim 10 wherein said prodrug has formula (IIA)

$$G—E—(C=O)—X \quad\quad (IIA)$$

wherein

X is a nucleoside analog jointed at the 3' and/or 5' position of the aldose ring, E is R$^{12}$R$^{13}$C wherein R$^{12}$ is hydroxyalkyl, aminoalkyl, thioalkyl, alkylcarboxylate, alkylammonium, alkylamino or carboxylate, R$^{13}$ is the same as R$^{12}$ or different than R$^{12}$, and, if different, is alkyl, phenyl, substituted phenyl, alkene, alkylphosphonate, alkylsulfonate, or hydroxyl, and G is H, alkyl with 1–10 carbon atoms, alkoxy with 1–10 carbon atoms, phenyl, substituted phenyl, alkene with 1–10 carbon atoms or alkylthio.

18. The catalytic antibody of claim 9, wherein said hapten has formula IIB $$G—E—D—B—X \quad\quad (IIB)$$

wherein

X is a nucleoside analog joined at the 3' and/or 5' position of the aldose ring wherein the O of the nucleoside by which it is attached is replaced by B, B is O, S, NH or CH$_2$, D is P(T)(TR$^7$) wherein T is O, N, S or CH$_2$ and R$^7$ is alkyl, alkyl with heteroatoms, cycloalkyl, phenyl, substituted phenyl, or alkene and is attached to radical E at R$^{12}$ or R$^{13}$, E is R$^{12}$ or R$^{13}$C, wherein R$^{12}$ or R$^{13}$ is attached to the radical D at R$^7$, and the other of R$^{12}$ or R$^{13}$ are is alkyl, alkyl with heteroatoms, cycloalkkyl, phenyl, substituted phenyl or alkene, and G is H, alkyl with 1–10 carbon atoms, alkoxy with 1–10 carbon atoms, phenyl, substituted phenyl, alkene with 1–10 carbon atoms to alkylthio.

19. The catalytic antibody is claim 10 wherein said prodrug is an enol substituted benzoate prodrug compound of cyclophosphamide of the formula (IIA)

$$G—E—(C=O)—X \quad\quad (IIA)$$

wherein

X is

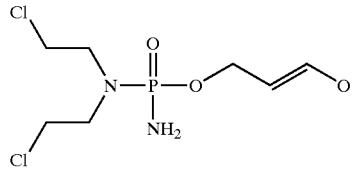

and G—E is a substituted phenyl radical.

20. The catalytic antibody of claim 19 wherein said hapten has formula IID $$G—E—P(=O)OH—X \quad\quad (IID)$$

wherein

X is B—A—Q—P(=O)NH$_2$—NR$^1$R$^2$, and wherein Q is O or CH$_2$ and R$^1$ and R$^2$ are the same or different but cannot be H, and are alkyl, alkyl with heteroatoms, haloalkyl, cycloaklyl, phenyl, substituted phenyl, alkylphosphonate, alkylsulfonate, alkylcarboxylate alkylammonium or alkene, or R$^1$ and R$^2$ are connected to each other in a ring structure such as morpholino or piperidino moieties;

A is any isomer of propenyl;

B is O, S, or CH$_2$;

E is a radical

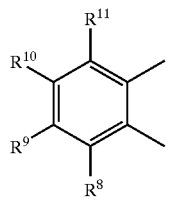

wherein where R$^8$ or R$^{11}$ is attached to the radical D at R$^7$, R$^{8-11}$ are the same or different and are H or alkyl with 1–10 carbon atoms, phenyl, substituted phenyl, alkene with 1–10 carbon atoms, hydroxyalkyl, alkoxy, aminoalkyl alkylthio, thioalkyl, amino, alkylamino, alkylphosphonate, alkylsulfonate, alkycarbonxylate, alkylammonium, carboxylate, sulfate, phosphate, or hydroxyl; and G is H, alkyl with 1–10 carbon atoms, alkoxy with 1–10 carbon atoms, phenyl, substituted phenyl, alkene with 1–10 carbon atoms, or alkylthio.

21. The catalytic antibody of claim 19 wherein said prodrug of formula IIA, E is phenyl with a substituent ortho to the (C=O)X and said substituent is hydroxyalkyl, aminoalkyl, thioalkyl alkylcarboxylate, alkylammonium, alkylamine or carboxylate, and G is H, alkyl with 1–10 carbon atoms, alkoxy with 1–10 carbon atoms, phenyl, substituted phenyl, alkene with 1–10 carbon atoms, or alkylthio.

22. The catalytic antibody of claim 9 wherein said hapten has a substituent in the ortho position to the enol ester of formula IIE $$G—E—D—X \quad\quad (IIE)$$

wherein

X is B—A—Q—P(=O)NH$_2$—NR$^1$R$^2$, and wherein Q is or CH$_2$ and R$^1$ and R$^2$ are the same or different but cannot be H, and are alkyl, alkyl with heteroatoms, haloalkyl, cycloalkyl, phenyl, substituted phenyl, alkylphosphonate, alkylsulfonate, alkycarbonxylate, alkylammonium or alkene, or R$^1$ and R$^2$ are connected to each other in a ring structure such as morpholino or piperidino moieties;

A is any isomer of propenyl;

B is O, S, or CH$_2$;

D is P(T)(TR$^7$) wherein T is O, N, S or CH$_2$ and R$^7$ is alkyl, alkyl with heteroatoms, cycloalkyl, phenyl, substituted phenyl, or alkene and is attached to radical H at R$^8$ or R$^{11}$;

E is a radical

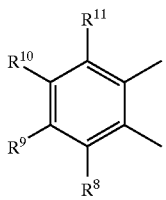

wherein where R$^8$ or R$^{11}$ is attached to the radical D at R$^7$, R$^{8-11}$ are the same or different and are H or alkyl with 1–10 carbon atoms, phenyl, substituted phenyl alkene with 1–10 carbon atoms, hydroxyalkyl, alkoxy, aminoalkyl, alkylthio, thioalkyl, amino, alkylamino, alkylphosphonate, alkylsulfonate, alkylcarbonxylate, alkylammonium, carboxylate, sulfate, phosphate, or hydroxyl; and G is H, alkyl with 1–10 carbon atoms, alkoxy with 1–10 carbon atoms, phenyl, substituted phenyl, alkene with 1–10 carbon atoms, or alkylthio, and said prodrug is an enol substituted benzoate prodrug.

23. The catalytic antibody of claim 16 wherein said prodrug has formula IIA

wherein

X is an anthracycline antineoplastic agent joined via the oxygen atom of a free hydroxyl group on either the anthracycline moiety or a aglycone moiety and E is a substituted phenyl radical.

24. The catalytic antibody of claim 23 wherein said anthracycline antineoplastic agent is selected from the group consisting of doxorubincin, daunorubicin, or epirubicin.

25. The catalytic antibody of claim 9 wherein said hapten has formula IIB

wherein

X is an anthracycline antineoplastic agent joined via the oxygen atom of a free hydroxyl group on either the anthracycline moiety or a aglycone moiety, B is O, S, NH or CH$_2$, D is P(O)OH, SO$_2$, or CHOH, and E is a substituted phenyl radical.

26. The catalytic antibody of claim 25 wherein said anthracycline antineoplastic agent is selected from the group consisting of doxorubincin, daunorubicin, or epirubicin.

27. The catalytic antibody is claim 13 wherein G is alkyl with 1–9 atoms in a linear configuration, alkyl with 1–9 atoms in a linear configuration and containing heteroatoms, alkyl with 1–9 atoms in a linear configuration and substituted with phenyl, alkyl, alkyl with heteroatom substituents, and which terminates in OH, NH$_2$, NHR, or SH.

28. The catalytic antibody of claim 27 wherein G is alkyl.

29. The catalytic antibody of claim 27 wherein G is alkyl with heteroatoms.

30. A catalytic antibody raised to a hapten of formula IA

wherein:

X is
(a) a nucleoside analog joined at the 5' and/or 3' position of the aldose ring wherein the hydroxyl groups on the sugar moiety of the nucleoside analog are unsubstituted, independently substituted with acyl, phosphate and alkyl radicals, or replaced with H, halogen or azide, and wherein the O of the nucleoside by which it is attached can be replaced by S, NH, or CH$_2$,
(b) melphalan joined to the remainder of the compound at a primary amino group, or melphalan joined to the remainder of the compound at a primary amino group wherein the primary amino group can be replaced by CH$_2$ or S; or
(c) daunomycin or other drug joined to the remainder of the compound at a hydroxy, amino or thio group which can be replaced by CH$_2$, S, or O;

D, which maybe omitted, is
(a) C=O
(b) SO or CHOH with any stereochemistry,
(c) SO$_2$, or
(e) P(T)(TR7) wherein T is O, N, S or CH$_2$ and R$^7$ is H, alkyl, alkyl with heteroatoms, cycloalkyl, phenyl, substituted phenyl, alkylphosphonate, alkylsulfonate, alkylcarboxylate, alkylammonium or alkene and is unattached or attached to E at R$^8$, R$^{11}$ or R$^{13}$;

E, which may be omitted, is the radical

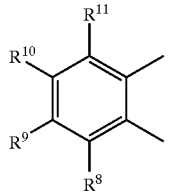

or R$^{12}$R$^{13}$C wherein R$^{8-13}$ are the same or different and are H or alkyl with 1–10 carbon atoms, phenyl, substituted phenyl, alkene with 1–10 carbon atoms, hydroxyalkyl, alkoxy, aminoalkyl, alkylthio, trioalkyl, amino, alkylamino, aklylphosphonate, alkylsulfonate, alkylcarboxylate, alkylammonium, carboxylate, sulfate, phosphate, or hydroxyl, and is unattached or attached to the radical D at R$^7$ through R$^8$ or R$^{11}$ or R$^{13}$;

n is an integer from 0 to 3;

F, which may be omitted, is an oxygen, carbonyloxy, or oxycarbonyl radical; and

G is H or the radical

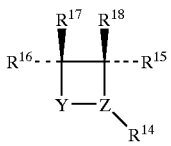

wherein Y is C=O, SO$_2$, CHOH or SO with any stereochemistry, Z is O, N, CH with any stereochemistry, or S, and R$^{14}$, R$^{15}$, R$^{16}$, R$^{17}$ or R$^{18}$ is the site of attachment to the remainder of the compound, provided that where R$^{14}$ is the site of attachment, then R$^{15}$, R$^{16}$, R$_{17}$, and R$^{18}$ are the same or different and are hydrogen, alkyl with 1–10 carbon atoms, alkenyl with 1–10 carbon atoms, phenyl, substituted phenyl, carboxylalky with 1–10 carbon atoms which is unsubstituted or substituted by a heterocyclic ring or phenyl ring, said rings being unsubstituted or substituted, alkoxy with 1–10 carbon atoms, alkylamino with 1–10 carbon atoms, aminoalkyl with 1–10 carbon atoms, acyloxy with 1–10 carbon atoms which is unsubstituted or substituted by a heterocyclic ring or a phenyl ring, said rings being unsubstituted or substituted, or acylamino with 1–10 carbon atoms which is unsubstituted or substituted by a heterocyclic ring or a phenyl ring, said rings being unsubstituted or substituted, and further provided that where one of R$^{15}$, R$^{16}$, R$^{17}$, or R$^{18}$ is the site of attachment, then R$^{14}$ and the remainder of R$^{15}$, R$^{16}$, R$^{17}$ and R$^{18}$ are the same or different and are as defined for R$^{15}$–R$^{18}$ above when R$^{14}$ is he site of attachment and R$^{14}$ is either SO$_3$H or SO$_4$H, said catalytic antibody being capable of catalytically enhancing the rate of cleavage of a drug X or B—A—X, wherein B, A, and X are defined as above, from a residue of a prodrug of formula IA, wherein said catalytic antibody exhibits catalytic activity which corresponds to activities exhibited by an enzyme selected from the group consisting of an esterase, an amidase, an acetal hydrolase and a glycosidase.

31. The catalytic antibody of claim 30 wherein said hapten has the same of substantially the same substituents as said prodrug.

32. The catalytic antibody of claim 30 wherein said prodrug has formula IB $$G—F—(CH_2)_N—E—C(=O)—X \qquad (IB)$$

wherein
X is a nucleoside analog esterified in the 5' and/or 3' position, B is a substituted phenyl radical, and G is said azetidinone radical.

33. The catalytic antibody of claim 30 wherein in formula IA of said hapten, X is a nucleoside analog esterified in the 5' and/or 3' position, E is a substituted phenyl radical, and G is said azetidinone radical wherein Y is SO$_2$, CHOH, or SO with any stereochemistry, and Z is CH.

34. The catalytic antibody of claim 30 wherein said prodrug has formula IB $$G—F—(CH_2)_n—E—C(=O)—X \qquad (IB)$$

wherein
E is R$^{12}$R$^{13}$C.

35. The catalytic antibody of claim 30 wherein in formula IA of said hapten, D is C=O, E is R$^{12}$R$^{13}$C, and G is said azetidinone radical wherein Y is SO$_2$, CHOH, or SO with any stereochemistry, and Z is CH.

36. The catalytic antibody of claim 30 wherein said prodrug has formula IC $$G—X \qquad (IC)$$

wherein
X is a nucleoside alkylated in the 5' and/or 3' position, and G is a azetidinone radical.

37. The catalytic antibody of claim 36 wherein said hapten has formula IC wherein X is a nucleoside alkylated in the 5' and/or 3' position and where the hydroxyl at the point of attachment can be replaced by CH$_2$, and G is a 2-azetidione radical wherein Y is SO$_2$, CHOH, or SO with any stereochemistry, and Z is CH.

38. The catalytic antibody of claim 30 wherein said prodrug is a prodrug compound of formula ID $$G—E—C(=O)—X \qquad (ID)$$

wherein
X is a melphalan bound at its free amino group and E is a substituted phenyl group or R$^{12}$R$^{13}$C, and G is H, alkyl, alkoxy, phenyl, substituted phenyl, alkene and a alkylthio.

39. The catalytic antibody of claim 30 wherein said hapten has formula IE $$—E—D—B—X—(I—E)$$

wherein
X is melphalan whose free amino group is replaced by B wherein B is O, S, NH, CH$_2$, D is P(O)(OH), SO$_2$ or CHOH, and E is a substituted phenyl group.

40. The catalytic antibody of claim 39 wherein B is O.

41. A catalytic antibody raised to a hapten of formula III $$G—E—D—B—A—X \qquad (III)$$

wherein:
X is
(a) a nucleoside analog joined at the 5' and/or 3' position of the aldose ring wherein the hydroxyl groups on the sugar moiety of the nucleoside analog are unsubstituted, independently substituted with acyl, phosphate and alkyl radicals, or replaced with H, halogen or azide, and wherein the O of the nucleoside by which it is attached can be replaced by S, NH, or CH$_2$,
(b) QP(O)(NH$_2$)NR$^1$R$^2$, wherein Q is O or CH$_2$, or Q can be omitted, and R$^1$ and R$^2$ are the same or different but both cannot be H and each is haloalky, alkyl, alkyl with heteroatoms, cycloalkyl, phenyl, substituted phenyl, alkylphosphonate, alkylsulfonate, alkylcarboxylate, alkylammonium or alkene, or R$^1$ and R$^2$ are connected to each other in a ring structure such as morpholino or piperidine,
(c) melphalan joined to the remainder of the compound at a primary amino group, or melphalan joined to the remainder of the compound at a primary amino group wherein the primary amino group can be replaced by CH$_2$ or S;
(d) daunomycin or other drug joined to the remainder of the compound at a hydroxy, amino or thio group which can be replaced by CH$_2$, S, or O;
A, which may be omitted, is ethylene or any isomer of propenyl;

B, which may be omitted is $NR^3$, wherein $R^3$ is H, alkyl, alkyl with heteroatoms, cycloalkyl, phenyl, substituted phenyl, alkylphosphonate, alkylsulfonate, alkylcarboxylate, alkylammonium and alkene;

D, which may be omitted, is $C=NR^4$ or $R^5R^6N=NR^4$, wherein $R^4$ is H, alkyl, alkyl with heteroatoms, cycloalkyl, phenyl, substituted phenyl, alkylphosphonate, alkylsulfonate, alkylcarboxylate, alkylammonium and alkene, $R^4$ and $R^5$ or $R^5$ and $R^6$ can be connected to each other in a ring structure such as morpholino or piperidine, or $R^5$ and $R^6$ can be hydrogen, haloalky, alkyl, alkyl with heteroatoms, cycloalkyl, phenyl, substituted phenyl, alkylphosphonate, alkylsulfonate, alkylcarboxylate, alkylammonium or alkene, E, which may be omitted, is $R^{12}R^{13}C$ wherein $R^{8-13}$ are the same or different and are O substituted with alkyl, alkyl with heteroatoms, cycloalkyl, phenyl, substituted phenyl, alkylphosphonate, alkylsulfonate, alkylcarboxylate, alkylammonium or alkene, or $R^{8-13}$ connected to each other in a ring structure such as a five-membered or six-membered acetal ring where the diol is derived from a sugar, cycloalkyl or phenyl moiety, but may be omitted;

G, which may be omitted, is H or alkyl with 1–10 carbon atoms, alkoxy with 1–10 carbon atoms, phenyl, substituted phenyl, alkylphosphonate, alkylsulfonate, or alkylcarboxylate, said catalytic antibody being capable of catalytically enhancing the rate of cleavage of a drug X or B—A—X, wherein B, A, and X are defined as above, from a residue of a prodrug of formula III, wherein said catalytic antibody exhibits catalytic activity which corresponds to activities exhibited by an anzyme selected from the group consisting of an esterase, an amidase, an acetal hydrolase and a glycosidase.

42. The catalytic antibody of claim 41 wherein said hapten has the same or substantially the same substituents as said prodrug.

43. The catalytic antibody of claim 41 wherein said prodrug has formula IIIA $$G—E—A—X \quad (IIIA)$$

wherein

X is $QP(O)(NH_2)NR^1R^2$, wherein Q is O, $R^1$ and $R^2$ are —$CH_2$—$CH_2$—Cl, A is ethylene, E is $R^{12}R^{13}C$ and G is H.

44. The catalytic antibody of claim 43 wherein $R^{12}$ and $R^{13}$ are the same or different and are alkoxy radicals and G is H.

45. The catalytic antibody of claim 43 wherein $R^{12}$ and $R^{13}$ are the same or different and are ethoxy radicals and G is H.

46. The catalytic antibody of claim 41 wherein said hapten has formula IIIB $$D—B—A—X \quad (IIIB)$$

wherein

X is $QP(O)(NH_2)NR^1R^2$, wherein Q is omitted, $R^1$ and $R^2$ are ethylene groups joined with an NH to form a piperazino moiety, A is ethylene, B is $NR^3$ wherein $R^3$ is H, D is $R^5R^6N—C=NR^4$ wherein $R^4$ and $R^5$ are alkyl and $R^6$ is H.

47. The catalytic antibody of claim 46 wherein $R^4$ and $R^5$ are ethyl.

48. The catalytic antibody of claim 41 wherein said hapten has formula IIB $$D—B—A—X \quad (IIIB)$$

wherein

X is $QP(O)(NH_2)NR^1R^2$, Q is $CH_2$, $R^1$ and $R^2$ are ethylene groups joined with an NH to form a piperazino moiety, A is ethylene, B is $NR^3$ wherein $R^3$ is H, D is $R^5R^6N—C=NR^4$ wherein $R^4$ and $R^5$ are alkyl and $R^6$ is H.

49. The catalytic antibody of claim 48 wherein $R^4$ and $R^5$ are ethyl.

50. The catalytic antibody of claim 41 wherein said hapten has formula IIIC $$G—E—X \quad (IIIC)$$

wherein

X is a nucleoside analog joined at the 5' and/or 3' position of the aldose ring and E is $R^{12}R^{12}C$ wherein $R^{12}$ and $R^{13}$ are the same or different a nd a re alkoxy radicals, and G is H.

51. The catalytic antibody of claim 50 wherein $R^{12}$ and $R^{13}$ are ethoxy radicals and G is H.

52. The catalytic antibody of claim 42 wherein said hapten has formula IIID $$D—X \quad (IIID)$$

wherein

X is a nucleoside analog joined at the 5' and 3' position of the aldose ring and D is $R^5R^6N—C=NR^4$ wherein $R^4$ and $R^5$ are and $R^6$ is H.

53. The catalytic antibody of claim 52 wherein $R^4$ and $R^5$ are ethyl.

54. The catalytic antibody of claim 1 wherein said prodrug is a prodrug of an antineoplastic nucleoside analog comprising a monosaccharide hexapyranose or hexafuranose covalently attached via the anomeric position to the 3' to 5' oxygen of the nucleoside analog.

55. The catalytic antibody of claim 54 wherein said prodrug is activated by a glycosidase.

56. The catalytic antibody of claim 55 wherein said glycosidase is beta-galactosidase.

57. The catalytic antibody of claim 54 wherein said hexapyranose or hexafuranose is selected from the group consisting of glucose, glycosamine, D-quinovopyranose, galactose, galactosamine, L-fucopyranose, L-rhamnopyranose, D-glucopyranuronic acid, D-galactoypranuronic acid, D-mannopyranuronic acid, or D-iodopyranuronic acid.

58. The catalytic antibody of claim 30 wherein said prodrug is a prodrug of an antineoplastic nucleoside analog comprising a monosaccharide hexapyranose or hexafuranose covalently attached via the anomeric position to the 3' or 5' oxygen of the nucleoside analog.

59. The catalytic antibody of claim 58 wherein said prodrug is activated by a glycosidase.

60. The catalytic antibody of claim 59 wherein said glycosidase is beta-galactosidase.

61. The catalytic antibody of claim 58 wherein said hexapyranose or hexafuranose is selected from the group consisting of glucose, glycosamine, D-quinovopyranose, galactose, galactosamine, L-fucopyranose, L-rhamnopyranose, D-glucopyranuronic acid, D-galactoypranuronic acid, D-mannopyranuronic acid, or D-iodopyranuronic acid.

62. The catalytic antibody of claim 41 wherein said prodrug is a prodrug of an antineoplastic nucleoside analog comprising a monosaccharide hexapyranose or hexafuranose covalently attached via the anomeric position to the 3' or 5' oxygen of the nucleoside analog.

63. The catalytic antibody of claim 62 wherein said prodrug is activated by a glycosidase.

64. The catalytic antibody of claim 63 wherein said glycosidase is beta-galactosidase.

65. The catalytic antibody of claim 62 wherein said hexapyranose or hexafuranose is selected from the group consisting of glucose, glycosamine, D-quinovopyranose, galactose, galactosamine, L-fucopyranose, L-rhamnopyranose, D-glucopyranuronic acid, D-galactoypranuronic acid, D-mannopyranuronic acid, or D-iodopyranuronic acid.

66. The catalytic antibody of claim 1 wherein said hapten comprises an amidine analog of a monosaccharide hexapyranose or hexafuranose in which the nucleoside oxygen of attachment is replaced by $NR^1$ and the furanose or pyranose ring oxygen is replaced by $NR^2$, and said prodrug is a glycosyl prodrug of an antineoplastic nucleoside analog.

67. The catalytic antibody of claim 66 wherein said amidine analog of a monosaccharide hexapyranose or hexafuranose is a structural analog of a sugar selected from the group consisting of glucose, glycosamine, D-quinovopyranose, galactose, galactosamine, L-galactoypranuronic acid, D-mannopyranuronic acid, or D-iodopyranuronic acid.

68. The catalytic antibody of claim 30 wherein said hapten comprises an amidine analog of a monosaccharide hexapyranose or hexafuranose in which the nucleoside oxygen of attachment is replaced by $NR^1$ and the furanose or pyranose ring oxygen is replaced by $NR^2$, and said prodrug is a glycosyl prodrug of an antineoplastic nucleoside analog.

69. The catalytic antibody of claim 68 wherein said amidine analog of a monosaccharide hexapyranose or hexafuranose is a structural analog of a sugar selected from the group consisting of glucose, glycosamine, D-quinovopyranose, galactose, galactosamine, L-galactoypranuronic acid, D-mannopyranuronic acid, or D-iodopyranuronic acid.

70. The catalytic antibody of claim 41 wherein said hapten comprises an amidine analog of a monosaccharide hexapyranose or hexafuranose in which the nucleoside oxygen of attachment is replaced by $NR^1$ and the furanose or pyranose ring oxygen is replaced by $NR^2$, and said prodrug is a glycosyl prodrug of an antineoplastic nucleoside analog.

71. The catalytic antibody of claim 70 wherein said amidine analog of a monosaccharide hexapyranose or hexafuranose is a structural analog of a sugar selected from the group consisting of glucose, glycosamine, D-quinovopyranose, galactose, galactosamine, L-galactoypranuronic acid, D-mannopyranuronic acid, or D-iodopyranuronic acid.

* * * * *